US012188018B2

(12) United States Patent
Bowen et al.

(10) Patent No.: US 12,188,018 B2
(45) Date of Patent: Jan. 7, 2025

(54) POLYPEPTIDES USEFUL FOR GENE EDITING AND METHODS OF USE

(71) Applicant: Life Edit Therapeutics, Inc., Durham, NC (US)

(72) Inventors: Tyson D. Bowen, Morrisville, NC (US); Alexandra Briner Crawley, Cary, NC (US); Tedd D. Elich, Durham, NC (US); Mark Moore, Durham, NC (US); Michael Lassner, Portland, OR (US)

(73) Assignee: Life Edit Therapeutics, Inc., Durham, NC (US)

( * ) Notice: Subject to any disclaimer, the term of this patent is extended or adjusted under 35 U.S.C. 154(b) by 0 days.

(21) Appl. No.: 18/316,698

(22) Filed: May 12, 2023

(65) Prior Publication Data

US 2023/0272398 A1 Aug. 31, 2023

Related U.S. Application Data

(63) Continuation of application No. 17/418,498, filed as application No. PCT/US2019/068079 on Dec. 20, 2019.

(60) Provisional application No. 62/932,169, filed on Nov. 7, 2019, provisional application No. 62/790,262, filed on Jan. 9, 2019, provisional application No. 62/790,261, filed on Jan. 9, 2019, provisional application No. 62/790,256, filed on Jan. 9, 2019, provisional application No. 62/790,266, filed on Jan. 9, 2019, provisional application No. 62/790,258, filed on Jan. 9, 2019, provisional application No. 62/785,391, filed on Dec. 27, 2018.

(51) Int. Cl.
  *C12N 15/113* (2010.01)
  *C12N 9/22* (2006.01)
  *C12N 9/78* (2006.01)

(52) U.S. Cl.
  CPC .............. *C12N 15/113* (2013.01); *C12N 9/22* (2013.01); *C12N 9/78* (2013.01); *C12N 2310/20* (2017.05); *C12Y 305/04004* (2013.01)

(58) Field of Classification Search
  None
  See application file for complete search history.

(56) References Cited

U.S. PATENT DOCUMENTS

2014/0186919 A1* 7/2014 Zhang ................... C12N 15/86
 435/320.1
2024/0174995 A1 5/2024 Li et al.

FOREIGN PATENT DOCUMENTS

| AU | 2015101792 A4 | 1/2016 | | |
|---|---|---|---|---|
| CN | 108513575 A | 9/2018 | | |
| WO | WO 2011/075627 A1 | 6/2011 | | |
| WO | WO 2013/138644 A2 | 9/2013 | | |
| WO | WO 2017/062855 A1 * | 4/2017 | ............... | C12N 9/22 |
| WO | WO 2017/070632 A2 | 4/2017 | | |
| WO | WO 2018/213726 A1 | 11/2018 | | |
| WO | WO 2019/120310 A1 * | 6/2019 | ............... | C12N 9/22 |

OTHER PUBLICATIONS

Yang et al., "Engineering and optimising deaminase fusions for genome editing" 7 Nature Communications 13330 1-12 (Year: 2016).*
Henry et al., "Evolution of the Primate APOBEC3A Cytidine Deaminase Gene and Idenfiticaiton of Related Coding Regions" 7(1) PLoS ONE e30036 1-7 (Year: 2012).*
Hayward et al., "Differential Evolution of Antiretroviral Restriction Factors in Pteropid Bats as Revealed by APOBEC3 Gene Complexity" 35(7) Molecular Biology and Evolution 1626-1637 (Year: 2018).*
Chylinski, K., et al., "Survey and Summary—Classification and evolution of type II CRISPR-Cas systems," *Nucleic Acids Research*, 2014, vol. 42(10), pp. 6091-6105.
Y. Bulliard, et al., "Structure-Function Analyses Point to a Polynucleotide-Accommodating Groove Essential for APOBEC3A Restriction Activities", *Journal of Virology*, vol. 85(4), pp. 1765-1776, Feb. 15, 2011.
RecName: Full=DNA dC->dU-editing enzyme APOBEC-3G {ECO:0000256 RuleBase: RU367054}; EC=3.5.4.—{ECO:0000256 RuleBase: RU367054}; AltName: Full=Deoxycytidine deaminase {ECO: 0000256 ARBA:ARBA00032972, ECO: 0000256 RuleBase: RU367054};, XP002811398, retrieved from EBI accession No. UNIPROT: G8GPV9, Jan. 25, 2012.

(Continued)

*Primary Examiner* — Nancy J Leith
(74) *Attorney, Agent, or Firm* — Womble Bond Dickinson (US) LLP

(57) ABSTRACT

Compositions and methods for binding to a target sequence of interest are provided. Compositions include fusion proteins between DNA binding proteins or protein domains and nucleic acid modifying proteins or protein domains. The compositions find use in cleaving or modifying a target sequence of interest, visualization of a target sequence of interest, and modifying the expression of a sequence of interest. Compositions comprise RNA-guided nuclease polypeptides, CRISPR RNAs, trans-activating CRISPR RNAs, guide RNAs, deaminases, and nucleic acid molecules encoding the same. Vectors and host cells comprising the nucleic acid molecules are also provided. Further provided are CRISPR systems for binding a target sequence of interest, wherein the CRISPR system comprises an RNA-guided nuclease polypeptide and one or more guide RNAs. Also provided are deaminases which may be fused to a DNA-binding polypeptide and may be useful for gene editing.

28 Claims, No Drawings

Specification includes a Sequence Listing.

(56) References Cited

OTHER PUBLICATIONS

Bernat, V., et al., "RNA Structures as Mediators of Neurological Diseases and as Drug Targets," *Neuron*, 2015, vol. 87, pp. 28-46.
Lin, L., et al., "Engineering the Direct Repeat Sequence of crRNA for Optimization of FnCpf1-Mediated Genome Editing in Human Cells," *Molecular Therapy*, 2018, vol. 26(11), pp. 2650-2657.
Nowak, C., et al., "Guide RNA engineering for versatile Cas9 functionality," *Nucleic Acids Research*, 2016, vol. 44(20), pp. 9555-9564.
Pace, B., et al., "Sickle Cell Disease: Genetics, Cellular and Molecular Mechanisms, and Therapies," *Anemia*, 2012, Article ID 143594, pp. 1-2.

\* cited by examiner

POLYPEPTIDES USEFUL FOR GENE EDITING AND METHODS OF USE

CROSS REFERENCE TO RELATED APPLICATIONS

This application is a continuation of U.S. application Ser. No. 17/418,498, filed Jun. 25, 2021, which is a National Stage application of International Application PCT/US2019/068079, filed Dec. 20, 2019, which was published by the International Bureau in English on Jul. 2, 2020, and which claims priority from U.S. Provisional Application Nos. 62/785,391, filed Dec. 27, 2018, 62/790,256, filed Jan. 9, 2019, 62/790,258, filed Jan. 9, 2019, 62/790,261, filed Jan. 9, 2019, 62/790,262, filed Jan. 9, 2019, 62/790,266, filed Jan. 9, 2019, and 62/932,169, filed Nov. 7, 2019, each of which is hereby incorporated in its entirety by reference in this application.

FIELD OF THE INVENTION

The present invention relates to the field of molecular biology and gene editing.

REFERENCE TO A SEQUENCE LISTING SUBMITTED AS AN XML (ST.26) FILE VIA USPTO PATENT CENTER

The instant application contains a Sequence Listing which has been submitted in xml (ST.26) format via USPTO Patent Center and is hereby incorporated by reference in its entirety. Said xml (ST.26) copy, created on May 12, 2023, is named L103438 1150US.CIT1 0156.1 Seq List, and is 805,103 bytes in size.

BACKGROUND OF THE INVENTION

Targeted genome editing or modification is rapidly becoming an important tool for basic and applied research. Initial methods involved engineering nucleases such as meganucleases, zinc finger fusion proteins or TALENs, requiring the generation of chimeric nucleases with engineered, programmable, sequence-specific DNA-binding domains specific for each particular target sequence. RNA-guided nucleases (RGNs), such as the Clustered Regularly Interspaced Short Palindromic Repeats (CRISPR)-associated (cas) proteins of the CRISPR-cas bacterial system, allow for the targeting of specific sequences by complexing the nucleases with guide RNA that specifically hybridizes with a particular target sequence. Producing target-specific guide RNAs is less costly and more efficient than generating chimeric nucleases for each target sequence. Such RNA-guided nucleases can be used to edit genomes through the introduction of a sequence-specific, double-stranded break that is repaired via error-prone non-homologous end-joining (NHEJ) to introduce a mutation at a specific genomic location. Alternatively, heterologous DNA may be introduced into the genomic site via homology-directed repair.

Additionally, RGNs are useful for DNA editing approaches. Targeted editing of nucleic acid sequences, for example targeted cleavage to allow for introduction of a specific modification into genomic DNA, enables a highly nuanced approach to studying gene function and gene expression. Such targeted editing also may be deployed for targeting genetic diseases in humans or for introducing agronomically beneficial mutations in the genomes of crop plants. The development of genome editing tools provides new approaches to gene editing-based mammalian therapeutics and agrobiotechnology.

BRIEF SUMMARY OF THE INVENTION

Compositions and methods for binding a target nucleic acid sequence of interest are provided. The compositions find use in cleaving or modifying a target sequence of interest, detection of a target sequence of interest, and modifying the expression of a sequence of interest. Compositions comprise RNA-guided nuclease (RGN) polypeptides and variants thereof, CRISPR RNAs (crRNAs), trans-activating CRISPR RNAs (tracrRNAs), guide RNAs (gRNAs), deaminase polypeptides, nucleic acid molecules encoding the same, and vectors and host cells comprising the nucleic acid molecules. Also provided are CRISPR systems for binding a target sequence of interest, wherein the CRISPR system comprises an RNA-guided nuclease polypeptide and one or more guide RNAs. Also provided are fusion polypeptides comprising an RNA-guided, DNA binding polypeptide, and a deaminase polypeptide. Methods disclosed herein are drawn to binding a target nucleic acid sequence of interest, and in some embodiments, cleaving or modifying the target nucleic acid sequence of interest. The target sequence of interest can be modified, for example, as a result of non-homologous end joining or homology-directed repair with an introduced donor sequence, or as a result of base editing.

DETAILED DESCRIPTION

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended embodiments. Although specific terms are employed herein, they are used in a generic and descriptive sense only and not for purposes of limitation.

I. Overview

RNA-guided nucleases (RGNs) allow for the targeted manipulation of a single site within a genome and are useful in the context of gene targeting for therapeutic and research applications. In a variety of organisms, including mammals, RNA-guided nucleases have been used for genome engineering by stimulating non-homologous end joining and homologous recombination, for example. The compositions and methods described herein are useful for creating single- or double-stranded breaks in polynucleotides, modifying polynucleotides, detecting a particular site within a polynucleotide, or modifying the expression of a particular gene.

The RNA-guided nucleases disclosed herein can alter gene expression by modifying a target sequence. In specific embodiments, the RNA-guided nucleases are directed to the target sequence by a guide RNA (also referred to as gRNA or sgRNA) as part of a Clustered Regularly Interspaced Short Palindromic Repeats (CRISPR) RNA-guided nuclease system. Guide RNAs form a complex with the RNA-guided nucleases to direct the RNA-guided nuclease to bind to a target sequence and in some embodiments, introduce a single-stranded or double-stranded break at the target sequence. After the target sequence has been cleaved, the break can be repaired such that the DNA sequence of the target sequence is modified during the repair process. Thus, provided herein are methods for using the RNA-guided nucleases to modify a target sequence in the DNA of host cells. For example, RNA-guided nucleases can be used to modify a target sequence at a genomic locus of eukaryotic cells or prokaryotic cells.

This disclosure further provides deaminase polypeptides and nucleic acid molecules encoding the same, as well as fusion proteins that comprise a DNA-binding polypeptide and a deaminase polypeptide. In some embodiments, the DNA-binding polypeptide is or is derived from a meganuclease, zinc finger fusion protein, or TALEN. In some embodiments, the fusion protein comprises an RNA-guided DNA-binding polypeptide and a deaminase polypeptide. In some embodiments, the RNA-guided DNA-binding polypeptide is an RGN. In some embodiments, the RGN is a Type II CRISPR-Cas polypeptide. In other embodiments, the RGN is a Type V CRISPR-Cas polypeptide. In further embodiments, the RGN is a Cas9 polypeptide domain that binds to a gRNA, which, in turn, binds a target nucleic acid sequence via strand hybridization.

The deaminase polypeptide comprises a deaminase domain that can deaminate a nucleobase, such as, for example, cytidine. The deamination of a nucleobase by a deaminase can lead to a point mutation at the respective residue, which is referred to herein as "nucleic acid editing" or "base editing". Fusion proteins comprising an RGN polypeptide variant or domain and a deaminase domain can thus be used for the targeted editing of nucleic acid sequences.

Such fusion proteins are useful for targeted editing of DNA in vitro, e.g., for the generation of mutant cells. These mutant cells may be in plants or animals. Such fusion proteins may also be useful for the introduction of targeted mutations, e.g., for the correction of genetic defects in mammalian cells ex vivo, e.g., in cells obtained from a subject that are subsequently re-introduced into the same or another subject; and for the introduction of targeted mutations, e.g., the correction of genetic defects or the introduction of deactivating mutations in disease-associated genes in a mammalian subject. Such fusion proteins may also be useful for the introduction of targeted mutations in plant cells, e.g., for the introduction of beneficial or agronomically valuable traits or alleles.

The terms "protein," "peptide," and "polypeptide" are used interchangeably herein, and refer to a polymer of amino acid residues linked together by peptide (amide) bonds. The terms refer to a protein, peptide, or polypeptide of any size, structure, or function. Typically, a protein, peptide, or polypeptide will be at least three amino acids long. A protein, peptide, or polypeptide may refer to an individual protein or a collection of proteins. One or more of the amino acids in a protein, peptide, or polypeptide may be modified, for example, by the addition of a chemical entity such as a carbohydrate group, a hydroxyl group, a phosphate group, a farnesyl group, an isofarnesyl group, a fatty acid group, a linker for conjugation, functionalization, or other modification, etc. A protein, peptide, or polypeptide may also be a single molecule or may be a multi-molecular complex. A protein, peptide, or polypeptide may be just a fragment of a naturally occurring protein or peptide. A protein, peptide, or polypeptide may be naturally occurring, recombinant, or synthetic, or any combination thereof.

The term "fusion protein" as used herein refers to a hybrid polypeptide which comprises protein domains from at least two different proteins. One protein may be located at the amino-terminal (N-terminal) portion of the fusion protein or at the carboxyterminal (C-terminal) protein thus forming an "amino-terminal fusion protein" or a "carboxy-terminal fusion protein," respectively. A protein may comprise different domains, for example, a nucleic acid binding domain (e.g., the gRNA binding domain of Cas9 that directs the binding of the protein to a target site) and a nucleic acid cleavage domain or a catalytic domain of a recombinase. In some embodiments, a protein comprises a proteinaceous part, e.g., an amino acid sequence constituting a nucleic acid binding domain, and an organic compound, e.g., a compound that can act as a nucleic acid cleavage agent. In some embodiments, a protein is in a complex with, or is in association with, a nucleic acid, e.g., RNA. Any of the proteins provided herein may be produced by any method known in the art. For example, the proteins provided herein may be produced via recombinant protein expression and purification, which is especially suited for fusion proteins comprising a peptide linker. Methods for recombinant protein expression and purification are well known, and include those described by Green and Sambrook, *Molecular Cloning: A Laboratory Manual* (4th ed., Cold Spring Harbor Laboratory Press, Cold Spring Harbor, N.Y. (2012)), the entire contents of which are incorporated herein by reference.

II. RNA-Guided Nucleases

Provided herein are RNA-guided nucleases. The term RNA-guided nuclease (RGN) refers to a polypeptide that binds to a particular target nucleotide sequence in a sequence-specific manner and is directed to the target nucleotide sequence by a guide RNA molecule that is complexed with the polypeptide and hybridizes with the target sequence. Although an RNA-guided nuclease can be capable of cleaving the target sequence upon binding, the term RNA-guided nuclease also encompasses nuclease-dead RNA-guided nucleases that are capable of binding to, but not cleaving, a target sequence. Cleavage of a target sequence by an RNA-guided nuclease can result in a single- or double-stranded break. RNA-guided nucleases only capable of cleaving a single strand of a double-stranded nucleic acid molecule are referred to herein as nickases.

The RNA-guided nucleases disclosed herein include the APG00969, APG03128, APG09748, APG00771, and APG02789 RNA-guided nucleases, the amino acid sequences of which are set forth, respectively, as SEQ ID NOs: 1, 16, 24, 35, 43, or 50, and active fragments or variants thereof that retain the ability to bind to a target nucleotide sequence in an RNA-guided sequence-specific manner. In some of these embodiments, the active fragment or variant of the APG00969, APG03128, APG09748, APG00771, and APG02789 RGN is capable of cleaving a single- or double-stranded target sequence. In some embodiments, an active variant of the APG00969, APG03128, APG09748, APG00771, or APG02789 RGN comprises an amino acid sequence having at least 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence set forth as SEQ ID NOs: 1, 16, 24, 35, 43, or 50. In certain embodiments, an active fragment of the APG00969, APG03128, APG09748, APG00771, or APG02789 RGN comprises at least 50, 100, 150, 200, 250, 300, 350, 400, 450, 500, 550, 600, 650, 700, 750, 800, 850, 900, 950, 1000, 1050 or more contiguous amino acid residues of the amino acid sequence set forth as SEQ ID NOs:

1, 16, 24, 35, 43, or 50. RNA-guided nucleases provided herein can comprise at least one nuclease domain (e.g., DNase, RNase domain) and at least one RNA recognition and/or RNA binding domain to interact with guide RNAs. Further domains that can be found in RNA-guided nucleases provided herein include, but are not limited to: DNA binding domains, helicase domains, protein-protein interaction domains, and dimerization domains. In specific embodiments, the RNA-guided nucleases provided herein can comprise at least 70%, 75%, 80%, 85%, 90%, 91%, 92%, 93%, 94%, 95%, 96%, 97%, 98%, 99% to one or more of a DNA binding domains, helicase domains, protein-protein interaction domains, and dimerization domains.

A target nucleotide sequence is bound by an RNA-guided nuclease provided herein and hybridizes with the guide RNA associated with the RNA-guided nuclease. The target sequence can then be subsequently cleaved by the RNA-guided nuclease if the polypeptide possesses nuclease activity. The terms "cleave" or "cleavage" refer to the hydrolysis of at least one phosphodiester bond within the backbone of a target nucleotide sequence that can result in either single-stranded or double-stranded breaks within the target sequence. The presently disclosed RGNs can cleave nucleotides within a polynucleotide, functioning as an endonuclease or can be an exonuclease, removing successive nucleotides from the end (the 5' and/or the 3' end) of a polynucleotide. In other embodiments, the disclosed RGNs can cleave nucleotides of a target sequence within any position of a polynucleotide and thus function as both an endonuclease and exonuclease. The cleavage of a target polynucleotide by the presently disclosed RGNs can result in staggered breaks or blunt ends.

The presently disclosed RNA-guided nucleases can be wild-type sequences derived from bacterial or archaeal species. Alternatively, the RNA-guided nucleases can be variants or fragments of wild-type polypeptides. The wild-type RGN can be modified to alter nuclease activity or alter PAM specificity, for example. In some embodiments, the RNA-guided nuclease is not naturally-occurring.

In certain embodiments, the RNA-guided nuclease functions as a nickase, only cleaving a single strand of the target nucleotide sequence. Such RNA-guided nucleases have a single functioning nuclease domain. In some of these embodiments, additional nuclease domains have been mutated such that the nuclease activity is reduced or eliminated. The nuclease inactive RGN or nickase RGN may be referred to as an RNA-guided, DNA-binding polypeptide, or an RNA-guided, DNA-binding protein, or an RNA-guided, DNA-binding domain of a fusion protein.

In other embodiments, the RNA-guided nuclease lacks nuclease activity altogether or exhibits reduced nuclease activity, and is referred to herein as nuclease-dead. Any method known in the art for introducing mutations into an amino acid sequence, such as PCR-mediated mutagenesis and site-directed mutagenesis, can be used for generating nickases or nuclease-dead RGNs. See, e.g., U.S. Publ. No. 2014/0068797 and U.S. Pat. No. 9,790,490; each of which is incorporated by reference in its entirety.

RNA-guided nucleases that lack nuclease activity can be used to deliver a fused polypeptide, polynucleotide, or small molecule payload to a particular genomic location. In some of these embodiments, the RGN polypeptide or guide RNA can be fused to a detectable label to allow for detection of a particular sequence. As a non-limiting example, a nuclease-dead RGN can be fused to a detectable label (e.g., fluorescent protein) and targeted to a particular sequence associated with a disease to allow for detection of the disease-associated sequence.

Alternatively, nuclease-dead RGNs can be targeted to particular genomic locations to alter the expression of a desired sequence. In some embodiments, the binding of a nuclease-dead RNA-guided nuclease to a target sequence results in the repression of expression of the target sequence or a gene under transcriptional control by the target sequence by interfering with the binding of RNA polymerase or transcription factors within the targeted genomic region. In other embodiments, the RGN (e.g., a nuclease-dead RGN) or its complexed guide RNA further comprises an expression modulator that, upon binding to a target sequence, serves to either repress or activate the expression of the target sequence or a gene under transcriptional control by the target sequence. In some of these embodiments, the expression modulator modulates the expression of the target sequence or regulated gene through epigenetic mechanisms.

In other embodiments, the nuclease-dead RGNs or a RGN with only nickase activity can be targeted to particular genomic locations to modify the sequence of a target polynucleotide through fusion to a base-editing polypeptide, for example a deaminase polypeptide or active variant or fragment thereof that deaminates a nucleotide base, resulting in conversion from one nucleotide base to another. The base-editing polypeptide can be fused to the RGN at its N-terminal or C-terminal end. Additionally, the base-editing polypeptide may be fused to the RGN via a peptide linker. A non-limiting example of a deaminase polypeptide that is useful for such compositions and methods include cytidine deaminase or the adenosine deaminase base editor described in Gaudelli et al. (2017) *Nature* 551:464-471, U.S. Publ. Nos. 2017/0121693 and 2018/0073012, and International Publ. No. WO/2018/027078, each of which is herein incorporated by reference in its entirety.

RNA-guided nucleases that are fused to a polypeptide or domain can be separated or joined by a linker. The term "linker," as used herein, refers to a chemical group or a molecule linking two molecules or moieties, e.g., a binding domain and a cleavage domain of a nuclease. In some embodiments, a linker joins a gRNA binding domain of an RNA guided nuclease and a base-editing polypeptide, such as a deaminase. In some embodiments, a linker joins a nuclease-dead RGN and a deaminase. Typically, the linker is positioned between, or flanked by, two groups, molecules, or other moieties and connected to each one via a covalent bond, thus connecting the two. In some embodiments, the linker is an amino acid or a plurality of amino acids (e.g., a peptide or protein). In some embodiments, the linker is an organic molecule, group, polymer, or chemical moiety. In some embodiments, the linker is 5-100 amino acids in length, for example, 5, 6, 7, 8, 9, 10, 11, 12, 13, 14, 15, 16, 17, 18, 19, 20, 21, 22, 23, 24, 25, 26, 27, 28, 29, 30, 30-35, 35-40, 40-45, 45-50, 50-60, 60-70, 70-80, 80-90, 90-100, 100-150, or 150-200 amino acids in length. Longer or shorter linkers are also contemplated.

The presently disclosed RNA-guided nucleases can comprise at least one nuclear localization signal (NLS) to enhance transport of the RGN to the nucleus of a cell. Nuclear localization signals are known in the art and generally comprise a stretch of basic amino acids (see, e.g., Lange et al., *J Biol. Chem.* (2007) 282:5101-5105). In particular embodiments, the RGN comprises 2, 3, 4, 5, 6 or more nuclear localization signals. The nuclear localization signal(s) can be a heterologous NLS. Non-limiting examples of nuclear localization signals useful for the presently disclosed RGNs are the nuclear localization signals of SV40 Large T-antigen, nucleopasmin, and c-Myc (see, e.g., Ray et al. (2015) *Bioconjug Chem* 26(6):1004-7). In particular embodiments, the RGN comprises the NLS sequence set forth as SEQ ID NO: 10. The RGN can comprise one or more NLS sequences at its N-terminus, C-terminus, or both the N-terminus and C-terminus. For example, the RGN can comprise two NLS sequences at the N-terminal region and four NLS sequences at the C-terminal region.

Other localization signal sequences known in the art that localize polypeptides to particular subcellular location(s) can also be used to target the RGNs, including, but not limited to, plastid localization sequences, mitochondrial localization sequences, and dual-targeting signal sequences that target to both the plastid and mitochondria (see, e.g., Nassoury and Morse (2005) *Biochim Biophys Acta* 1743:5-19; Kunze and Berger (2015) *Front Physiol* dx.doi.org/10.3389/fphys.2015.00259; Herrmann and Neupert (2003) *IUBMB Life* 55:219-225; Soll (2002) *Curr Opin Plant Biol* 5:529-535; Carrie and Small (2013) *Biochim Biophys Acta* 1833:253-259; Carrie et al. (2009) *FEBS J* 276:1187-1195; Silva-Filho (2003) *Curr Opin Plant Biol* 6:589-595; Peeters and Small (2001) *Biochim Biophys Acta* 1541:54-63; Murcha et al. (2014) *J Exp Bot* 65:6301-6335; Mackenzie (2005) *Trends Cell Biol* 15:548-554; Glaser et al. (1998) *Plant Mol Biol* 38:311-338).

In certain embodiments, the presently disclosed RNA-guided nucleases comprise at least one cell-penetrating domain that facilitates cellular uptake of the RGN. Cell-penetrating domains are known in the art and generally comprise stretches of positively charged amino acid residues (i.e., polycationic cell-penetrating domains), alternating polar amino acid residues and non-polar amino acid residues (i.e., amphipathic cell-penetrating domains), or hydrophobic amino acid residues (i.e., hydrophobic cell-penetrating domains) (see, e.g., Milletti F. (2012) *Drug Discov Today* 17:850-860). A non-limiting example of a cell-penetrating domain is the trans-activating transcriptional activator (TAT) from the human immunodeficiency virus 1.

The nuclear localization signal, plastid localization signal, mitochondrial localization signal, dual-targeting localization signal, and/or cell-penetrating domain can be located at the amino-terminus (N-terminus), the carboxyl-terminus (C-terminus), or in an internal location of the RNA-guided nuclease.

The presently disclosed RGNs can be fused to an effector domain, such as a cleavage domain, a deaminase domain, or an expression modulator domain, either directly or indirectly via a linker peptide. Such a domain can be located at the N-terminus, the C-terminus, or an internal location of the RNA-guided nuclease. In some of these embodiments, the RGN component of the fusion protein is a nuclease-dead RGN.

In some embodiments, the RGN fusion protein comprises a cleavage domain, which is any domain that is capable of cleaving a polynucleotide (i.e., RNA, DNA, or RNA/DNA hybrid) and includes, but is not limited to, restriction endonucleases and homing endonucleases, such as Type IIS endonucleases (e.g., FokI) (see, e.g., Belfort et al. (1997) *Nucleic Acids Res.* 25:3379-3388; Linn et al. (eds.) Nucleases, Cold Spring Harbor Laboratory Press, 1993).

In other embodiments, the RGN fusion protein comprises a deaminase domain that deaminates a nucleotide base, resulting in conversion from one nucleotide base to another, and includes, but is not limited to, a cytidine deaminase or an adenosine deaminase base editor (see, e.g., Gaudelli et al. (2017) *Nature* 551:464-471, U.S. Publ. Nos. 2017/0121693 and 2018/0073012, U.S. Pat. No. 9,840,699, and International Publ. No. WO/2018/027078). In further embodiments, the RGN fusion protein may comprise a deaminase of the invention, which comprises the amino acid sequence of any one of SEQ ID NO: 374-545 or 572-584, or an active variant thereof.

In other embodiments, a deaminase of the invention, which comprises the amino acid sequence of any one of SEQ ID NO: 374-545 or 572-584, or an active variant thereof, may be fused to any DNA-binding protein. In some embodiments, the deaminase is fused to an RGN of the invention. In other embodiments, the deaminase is fused to an RGN known in the art. In other embodiments, the deaminase is fused to a DNA-binding protein that is not an RGN, such as for example a meganuclease, TALEN, or zinc finger nuclease. In some embodiments, the deaminase has an amino acid sequence of at least 50%, at least 55%, at least 60%, at least 65%, at least 70%, at least 75%, at least 80%, at least 85%, at least 90%, at least 95%, at least 96%, at least 97%, at least 98%, or at least 99% identity to the amino acid sequence of any of SEQ ID NOs: 374-545 and 572-584. In certain embodiments, the deaminase has an amino acid sequence of at least 50%, at least 55%, at least 60%, at least 65%, at least 70%, at least 75%, at least 80%, at least 85%, at least 90%, at least 95%, at least 96%, at least 97%, at least 98%, or at least 99% identity to the amino acid sequence of any of SEQ ID NOs: 374, 383, 397, 399, 407, 408, 411, 414, 416, 420, 514, and 572-584. In some of these embodiments, the variant deaminase polypeptide has a certain level of sequence identity to any one of SEQ ID NOs: 572-584, wherein specific amino acid residues are unchanged from the parent sequence. For example, in some embodiments, a variant SEQ ID NO: 572 comprises a lysine at a position corresponding to position 102, a tyrosine at a position corresponding to position 104, and a threonine at a position corresponding to position 106 of SEQ ID NO: 572. In particular embodiments, a variant SEQ ID NO: 574 comprises a glutamic acid at a position corresponding to position 101, a serine at a position corresponding to position 103, and a lysine at a position corresponding to position 105 of SEQ ID NO: 574. In certain embodiments, a variant SEQ ID NO: 575 comprises a lysine at a position corresponding to position 101, a leucine at a position corresponding to position 103, and a glutamic acid at a position corresponding to position 105 of SEQ ID NO: 575. In some embodiments, a variant SEQ ID NO: 576 comprises an alanine at a position corresponding to position 105 and an arginine at a position corresponding to position 107 of SEQ ID NO: 576. In particular embodiments, a variant SEQ ID NO: 577 comprises a glycine at a position corresponding to position 102, a serine at a position corresponding to position 104, and an arginine at a position corresponding to position 106 of SEQ ID NO: 577. In certain embodiments, a variant SEQ ID NO: 578 comprises a serine at a position corresponding to position 105 and a threonine at a position corresponding to position 107 of SEQ ID NO: 578. In some embodiments, a variant SEQ ID NO: 579 comprises a serine at a position corresponding to position 102, a glutamine at a position corresponding to position 104, and a glycine at a position corresponding to position 106 of SEQ ID NO: 579. In particular embodiments, a variant SEQ ID NO: 580 comprises a glycine at a position corresponding to position 111 of SEQ ID NO: 580. In some embodiments, a variant SEQ ID NO: 581 comprises a glutamine at a position corresponding to position 104, a glycine at a position corresponding to position 106, and a glutamic acid at a position corresponding to position 108 of SEQ ID NO: 581. In certain embodiments, a variant SEQ ID NO: 582 comprises an arginine at a position corresponding to position 102, a tryptophan at a position corresponding to position 104, and a glutamic acid at a position corresponding to position 106 of SEQ ID NO: 582. In certain embodiments, a variant SEQ ID NO: 583 comprises an arginine at a position corresponding to position 104 and a serine at a position corresponding to position 106 of SEQ ID NO: 583. In particular embodiments, a variant SEQ ID NO: 584 comprises a phenylalanine at a position corresponding to position 110, a serine at a position corresponding to position 112, and a threonine at a position corresponding to position 114 of SEQ ID NO: 584.

The term "deaminase" refers to an enzyme that catalyzes a deamination reaction (i.e., the removal of an amino group from an amino acid or other compound). In some embodiments, the deaminase is a cytidine deaminase, catalyzing the hydrolytic deamination of cytidine or deoxycytidine to uracil or deoxyuracil, respectively. In other embodiments, the deaminase is an adenine deaminase. Deamination of adenine yields inosine, which is treated as guanine by polymerases. Cytidine deaminases and adenine deaminases may work on either DNA or RNA, although to date there are no known naturally occurring adenine deaminases that deaminate adenine in DNA. Disclosed herein, however, is APG07458 (SEQ ID NO: 514) that is a naturally occurring protein with significant adenosine deaminase activity on DNA. The deaminases of the invention may be used for editing of DNA or RNA molecules. The deaminases of the invention, as a group, enable the programmable installation of all four transitions (C to T, A to G, T to C, and G to A) in DNA molecules and C to U, A to G, and G to A transitions in RNA molecules.

The deaminases of the invention operate on single-stranded nucleic acid molecules. An RGN which has nickase activity on the target strand nicks the target strand, while the complementary, non-target strand is modified by the deaminase. Cellular DNA-repair machinery may repair the nicked, target strand using the modified non-target strand as a template, thereby introducing a mutation in the DNA.

In some embodiments, a nuclease inactive RGN or nickase RGN fused to a deaminase can be targeted to particular genomic locations to alter the expression of a desired sequence. In some embodiments, the nuclease inactive RGN or nickase RGN may be referred to as an RNA-guided, DNA-binding polypeptide or protein or protein domain of a fusion protein. In some embodiments, the binding of this fusion protein to a target sequence results in deamination of a nucleotide base, resulting in conversion from one nucleotide base to another. In some embodiments, the effector domain of the RGN fusion protein can be an expression modulator domain, which is a domain that either serves to upregulate or downregulate transcription. The expression modulator domain can be an epigenetic modification domain, a transcriptional repressor domain or a transcriptional activation domain.

In some of these embodiments, the expression modulator of the RGN fusion protein comprises an epigenetic modification domain that covalently modifies DNA or histone proteins to alter histone structure and/or chromosomal structure without altering the DNA sequence, leading to changes in gene expression (i.e., upregulation or downregulation). Non-limiting examples of epigenetic modifications include acetylation or methylation of lysine residues, arginine methylation, serine and threonine phosphorylation, and lysine ubiquitination and sumoylation of histone proteins, and methylation and hydroxymethylation of cytosine residues in DNA. Non-limiting examples of epigenetic modification domains include histone acetyltransferase domains, histone deacetylase domains, histone methyltransferase domains, histone demethylase domains, DNA methyltransferase domains, and DNA demethylase domains.

In other embodiments, the expression modulator of the fusion protein comprises a transcriptional repressor domain, which interacts with transcriptional control elements and/or transcriptional regulatory proteins, such as RNA polymerases and transcription factors, to reduce or terminate transcription of at least one gene. Transcriptional repressor domains are known in the art and include, but are not limited to, Sp1-like repressors, IκB, and Krüppel associated box (KRAB) domains.

In yet other embodiments, the expression modulator of the fusion protein comprises a transcriptional activation domain, which interacts with transcriptional control elements and/or transcriptional regulatory proteins, such as RNA polymerases and transcription factors, to increase or activate transcription of at least one gene. Transcriptional activation domains are known in the art and include, but are not limited to, a herpes simplex virus VP16 activation domain and an NFAT activation domain.

The presently disclosed RGN and deaminase polypeptides, or fusion polypeptides thereof, can comprise a detectable label or a purification tag. The detectable label or purification tag can be located at the N-terminus, the C-terminus, or an internal location of the RNA-guided nuclease, either directly or indirectly via a linker peptide. In some of these embodiments, the RGN component of the fusion protein is a nuclease-dead RGN. In other embodiments, the RGN component of the fusion protein is an RGN with nickase activity.

A detectable label is a molecule that can be visualized or otherwise observed. The detectable label may be fused to the RGN as a fusion protein (e.g., fluorescent protein) or may be a small molecule conjugated to the RGN polypeptide that can be detected visually or by other means. Detectable labels that can be fused to the presently disclosed RGNs or deaminases as a fusion protein include any detectable protein domain, including but not limited to, a fluorescent protein or a protein domain that can be detected with a specific antibody. Non-limiting examples of fluorescent proteins include green fluorescent proteins (e.g., GFP, EGFP, ZsGreen1) and yellow fluorescent proteins (e.g., YFP, EYFP, ZsYellow1). Non-limiting examples of small molecule detectable labels include radioactive labels, such as $^3$H and $^{35}$S.

RGN and deaminase polypeptides of the invention, or fusion polypeptides thereof, can also comprise a purification tag, which is any molecule that can be utilized to isolate a protein or fused protein from a mixture (e.g., biological sample, culture medium). Non-limiting examples of purification tags include biotin, myc, maltose binding protein (MBP), and glutathione-S-transferase (GST).

II. Guide RNA

The present disclosure provides guide RNAs and polynucleotides encoding the same. The term "guide RNA" refers to a nucleotide sequence having sufficient complementarity with a target nucleotide sequence to hybridize with the target sequence and direct sequence-specific binding of an associated RNA-guided nuclease to the target nucleotide sequence. Thus, a RGN's respective guide RNA is one or more RNA molecules (generally, one or two), that can bind to the RGN and guide the RGN to bind to a particular target nucleotide sequence, and in those instances wherein the RGN has nickase or nuclease activity, also cleave the target nucleotide sequence. In general, a guide RNA comprises a CRISPR RNA (crRNA) and a trans-activating CRISPR RNA (tracrRNA). Native guide RNAs that comprise both a crRNA and a tracrRNA generally comprise two separate RNA molecules that hybridize to each other through the repeat sequence of the crRNA and the anti-repeat sequence of the tracrRNA.

Native direct repeat sequences within a CRISPR array generally range in length from 28 to 37 base pairs, although the length can vary between about 23 bp to about 55 bp. Spacer sequences within a CRISPR array generally range from about 32 to about 38 bp in length, although the length can be between about 21 bp to about 72 bp. Each CRISPR array generally comprises less than 50 units of the CRISPR repeat-spacer sequence. The CRISPRs are transcribed as part of a long transcript termed the primary CRISPR transcript, which comprises much of the CRISPR array. The primary CRISPR transcript is cleaved by Cas proteins to produce crRNAs or in some cases, to produce pre-crRNAs that are further processed by additional Cas proteins into mature crRNAs. Mature crRNAs comprise a spacer sequence and a CRISPR repeat sequence. In some embodiments in which pre-crRNAs are processed into mature (or processed) crRNAs, maturation involves the removal of about one to about six or more 5', 3', or 5' and 3' nucleotides. For the purposes of genome editing or targeting a particular target nucleotide sequence of interest, these nucleotides that are removed during maturation of the pre-crRNA molecule are not necessary for generating or designing a guide RNA.

A CRISPR RNA (crRNA) comprises a spacer sequence and a CRISPR repeat sequence. The "spacer sequence" is the nucleotide sequence that directly hybridizes with the target nucleotide sequence of interest. The spacer sequence is engineered to be fully or partially complementary with the target sequence of interest. In various embodiments, the spacer sequence can comprise from about 8 nucleotides to about 30 nucleotides, or more. For example, the spacer sequence can be about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, or more nucleotides in length. In some embodiments, the spacer sequence is about 10 to about 26 nucleotides in length, or about 12 to about 30 nucleotides in length. In particular embodiments, the spacer sequence is about 30 nucleotides in length. In some embodiments, the degree of complementarity between a spacer sequence and its corresponding target sequence, when optimally aligned using a suitable alignment algorithm, is about or more than about 50%, about 60%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or more. In particular embodiments, the spacer sequence is free of secondary structure, which can be predicted using any suitable polynucleotide folding algorithm known in the art, including but not limited to mFold (see, e.g., Zuker and Stiegler (1981) *Nucleic Acids Res.* 9:133-148) and RNAfold (see, e.g., Gruber et al. (2008) *Cell* 106(1):23-24).

RGN proteins can have varying sensitivity to mismatches between a spacer sequence in a gRNA and its target sequence that affects the efficiency of cleavage.

The CRISPR RNA repeat sequence comprises a nucleotide sequence that comprises a region with sufficient complementarity to hybridize to a tracrRNA. In various embodiments, the CRISPR RNA repeat sequence can comprise from about 8 nucleotides to about 30 nucleotides, or more. For example, the CRISPR repeat sequence can be about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, or more nucleotides in length. In some embodiments, the CRISPR repeat sequence is about 21 nucleotides in length. In some embodiments, the degree of complementarity between a CRISPR repeat sequence and its corresponding tracrRNA sequence, when optimally aligned using a suitable alignment algorithm, is about or more than about 50%, about 60%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or more. In particular embodiments, the CRISPR repeat sequence comprises the nucleotide sequence of SEQ ID NOs: 2, 17, 25, 36, 44, 51, or 63, or an active variant or fragment thereof that when comprised within a guide RNA, is capable of directing the sequence-specific binding of an associated RNA-guided nuclease provided herein to a target sequence of interest. In certain embodiments, an active CRISPR repeat sequence variant of a wild-type sequence comprises a nucleotide sequence having at least 40%, 45%, 50%, 55%, 60%, 65%, 70%, 75%, 80%, 85%, 90%, 91%, 92%, 93%, 94%, 95%, 96%, 97%, 98%, 99% or more sequence identity to the nucleotide sequence set forth as SEQ ID NOs: 2, 17, 25, 36, 44, 51, or 63. In certain embodiments, an active CRISPR repeat sequence fragment of a wild-type sequence comprises at least 5, 6, 7, 8, 9, 10, 11, 12, 13, 14, 15, 16, 17, 18, 19, or 20 contiguous nucleotides of the nucleotide sequence set forth as SEQ ID NOs: 2, 17, 25, 36, 44, or 51.

In certain embodiments, the crRNA is not naturally-occurring. In some of these embodiments, the specific CRISPR repeat sequence is not linked to the engineered spacer sequence in nature and the CRISPR repeat sequence is considered heterologous to the spacer sequence. In certain embodiments, the spacer sequence is an engineered sequence that is not naturally occurring.

A trans-activating CRISPR RNA or tracrRNA molecule comprises a nucleotide sequence comprising a region that has sufficient complementarity to hybridize to a CRISPR repeat sequence of a crRNA, which is referred to herein as the anti-repeat region. In some embodiments, the tracrRNA molecule further comprises a region with secondary structure (e.g., stem-loop) or forms secondary structure upon hybridizing with its corresponding crRNA. In particular embodiments, the region of the tracrRNA that is fully or partially complementary to a CRISPR repeat sequence is at the 5' end of the molecule and the 3' end of the tracrRNA comprises secondary structure. For Type II RGNs, this region of secondary structure generally comprises several hairpin structures, including the nexus hairpin, which is found adjacent to the anti-repeat sequence. The nexus hairpin often has a conserved nucleotide sequence in the base of the hairpin stem, with the motif UNANNC (SEQ ID NO: 13; for APG00969), ANGNNU (SEQ ID NO: 23; for APG03128), or UNANNA (SEQ ID NO: 42; for APG00771) found in the nexus hairpins of tracrRNAs. There are often terminal hairpins at the 3' end of the tracrRNA that can vary in structure and number, but often comprise a GC-rich Rho-independent transcriptional terminator hairpin followed by a string of U's at the 3' end. See, for example, Briner et al. (2014) *Molecular Cell* 56:333-

339, Briner and Barrangou (2016) *Cold Spring Harb Protoc*; doi: 10.1101/pdb.top090902, and U.S. Publication No. 2017/0275648, each of which is herein incorporated by reference in its entirety.

In various embodiments, the anti-repeat region of the tracrRNA that is fully or partially complementary to the CRISPR repeat sequence comprises from about 8 nucleotides to about 30 nucleotides, or more. For example, the region of base pairing between the tracrRNA anti-repeat sequence and the CRISPR repeat sequence can be about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, or more nucleotides in length. In particular embodiments, the anti-repeat region of the tracrRNA that is fully or partially complementary to a CRISPR repeat sequence is about 20 nucleotides in length. In some embodiments, the degree of complementarity between a CRISPR repeat sequence and its corresponding tracrRNA anti-repeat sequence, when optimally aligned using a suitable alignment algorithm, is about or more than about 50%, about 60%, about 70%, about 75%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, or more.

In various embodiments, the entire tracrRNA can comprise from about 60 nucleotides to more than about 140 nucleotides. For example, the tracrRNA can be about 60, about 65, about 70, about 75, about 80, about 85, about 90, about 95, about 100, about 105, about 110, about 115, about 120, about 125, about 130, about 135, about 140, or more nucleotides in length. In particular embodiments, the tracrRNA is about 80 to about 90 nucleotides in length, including about 80, about 81, about 82, about 83, about 84, about 85, about 86, about 87, about 88, about 89, and about 90 nucleotides in length. In certain embodiments, the tracrRNA is about 85 nucleotides in length.

In particular embodiments, the tracrRNA comprises the nucleotide sequence of SEQ ID NOs: 3, 18, 26, 37, 45, 52, or 62, or an active variant or fragment thereof that when comprised within a guide RNA is capable of directing the sequence-specific binding of an associated RNA-guided nuclease provided herein to a target sequence of interest. In certain embodiments, an active tracrRNA sequence variant of a wild-type sequence comprises a nucleotide sequence having at least 40%, 45%, 50%, 55%, 60%, 65%, 70%, 75%, 80%, 85%, 90%, 91%, 92%, 93%, 94%, 95%, 96%, 97%, 98%, 99% or more sequence identity to the nucleotide sequence set forth as SEQ ID NOs: 3, 18, 26, 37, 45, 52, or 62. In certain embodiments, an active tracrRNA sequence fragment of a wild-type sequence comprises at least 5, 10, 15, 20, 25, 30, 35, 40, 45, 50, 55, 60, 65, 70, 75, 80, or more contiguous nucleotides of the nucleotide sequence set forth as SEQ ID NOs: 3, 18, 26, 37, 45, or 52.

Two polynucleotide sequences can be considered to be substantially complementary when the two sequences hybridize to each other under stringent conditions. Likewise, an RGN is considered to bind to a particular target sequence within a sequence-specific manner if the guide RNA bound to the RGN binds to the target sequence under stringent conditions. By "stringent conditions" or "stringent hybridization conditions" is intended conditions under which the two polynucleotide sequences will hybridize to each other to a detectably greater degree than to other sequences (e.g., at least 2-fold over background). Stringent conditions are sequence-dependent and will be different in different circumstances. Typically, stringent conditions will be those in which the salt concentration is less than about 1.5 M Na ion, typically about 0.01 to 1.0 M Na ion concentration (or other salts) at pH 7.0 to 8.3, and the temperature is at least about 30° C. for short sequences (e.g., 10 to 50 nucleotides) and at least about 60° C. for long sequences (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C., and a wash in 0.5× to 1×SSC at 55 to 60° C. Exemplary high stringency conditions include hybridization in 50% formamide, 1 M NaCl, 1% SDS at 37° C., and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

The Tm is the temperature (under defined ionic strength and pH) at which 50% of a complementary target sequence hybridizes to a perfectly matched sequence. For DNA-DNA hybrids, the Tm can be approximated from the equation of Meinkoth and Wahl (1984) Anal. Biochem. 138:267-284: $Tm=81.5° C.+16.6 (\log M)+0.41 (\% GC)-0.61 (\% form)-500/L$; where M is the molarity of monovalent cations, % GC is the percentage of guanosine and cytosine nucleotides in the DNA, % form is the percentage of formamide in the hybridization solution, and L is the length of the hybrid in base pairs. Generally, stringent conditions are selected to be about 5° C. lower than the thermal melting point (Tm) for the specific sequence and its complement at a defined ionic strength and pH. However, severely stringent conditions can utilize a hybridization and/or wash at 1, 2, 3, or 4° C. lower than the thermal melting point (Tm); moderately stringent conditions can utilize a hybridization and/or wash at 6, 7, 8, 9, or 10° C. lower than the thermal melting point (Tm); low stringency conditions can utilize a hybridization and/or wash at 11, 12, 13, 14, 15, or 20° C. lower than the thermal melting point (Tm). Using the equation, hybridization and wash compositions, and desired Tm, those of ordinary skill will understand that variations in the stringency of hybridization and/or wash solutions are inherently described. An extensive guide to the hybridization of nucleic acids is found in Tijssen (1993) Laboratory Techniques in Biochemistry and Molecular Biology-Hybridization with Nucleic Acid Probes, Part I, Chapter 2 (Elsevier, New York); and Ausubel et al., eds. (1995) Current Protocols in Molecular Biology, Chapter 2 (Greene Publishing and Wiley-Interscience, New York). See Sambrook et al. (1989) Molecular Cloning: A Laboratory Manual (2d ed., Cold Spring Harbor Laboratory Press, Plainview, New York).

The guide RNA can be a single guide RNA or a dual-guide RNA system. A single guide RNA comprises the crRNA and tracrRNA on a single molecule of RNA, whereas a dual-guide RNA system comprises a crRNA and a tracrRNA present on two distinct RNA molecules, hybridized to one another through at least a portion of the CRISPR repeat sequence of the crRNA and at least a portion of the tracrRNA, which may be fully or partially complementary to the CRISPR repeat sequence of the crRNA. In some of those embodiments wherein the guide RNA is a single guide RNA, the crRNA and tracrRNA are separated by a linker nucleotide sequence. In general, the linker nucleotide sequence is one that does not include complementary bases in order to avoid the formation of secondary structure within or comprising nucleotides of the linker nucleotide sequence. In some embodiments, the linker nucleotide sequence between the crRNA and tracrRNA is at least 3, at least 4, at least 5, at least 6, at least 7, at least 8, at least 9, at least 10, at least 11, at least 12, or more nucleotides in length. In particular embodiments, the linker nucleotide sequence of a single guide RNA is at least 4 nucleotides in length. In certain embodiments, the linker nucleotide sequence is the nucleotide sequence set forth as SEQ ID NO: 8 or 31. In other embodiments, the linker nucleotide sequence is at least 6 nucleotides in length.

The single guide RNA or dual-guide RNA can be synthesized chemically or via in vitro transcription. Assays for determining sequence-specific binding between a RGN and a guide RNA are known in the art and include, but are not limited to, in vitro binding assays between an expressed RGN and the guide RNA, which can be tagged with a detectable label (e.g., biotin) and used in a pull-down detection assay in which the guide RNA:RGN complex is captured via the detectable label (e.g., with streptavidin beads). A control guide RNA with an unrelated sequence or structure to the guide RNA can be used as a negative control for non-specific binding of the RGN to RNA. In certain embodiments, the guide RNA is SEQ ID NO: 4, 19, 27, 38, 46, 53, 64, 65, or 66, wherein the spacer sequence can be any sequence and is indicated as a poly-N sequence.

In certain embodiments, the guide RNA can be introduced into a target cell, organelle, or embryo as an RNA molecule. The guide RNA can be transcribed in vitro or chemically synthesized. In other embodiments, a nucleotide sequence encoding the guide RNA is introduced into the cell, organelle, or embryo. In some of these embodiments, the nucleotide sequence encoding the guide RNA is operably linked to a promoter (e.g., an RNA polymerase III promoter). The promoter can be a native promoter or heterologous to the guide RNA-encoding nucleotide sequence.

In various embodiments, the guide RNA can be introduced into a target cell, organelle, or embryo as a ribonucleoprotein complex, as described herein, wherein the guide RNA is bound to an RNA-guided nuclease polypeptide.

The guide RNA directs an associated RNA-guided nuclease to a particular target nucleotide sequence of interest through hybridization of the guide RNA to the target nucleotide sequence. A target nucleotide sequence can comprise DNA, RNA, or a combination of both and can be single-stranded or double-stranded. A target nucleotide sequence can be genomic DNA (i.e., chromosomal DNA), plasmid DNA, or an RNA molecule (e.g., messenger RNA, ribosomal RNA, transfer RNA, micro RNA, small interfering RNA). The target nucleotide sequence can be bound (and in some embodiments, cleaved) by an RNA-guided nuclease in vitro or in a cell. The chromosomal sequence targeted by the RGN can be a nuclear, plastid or mitochondrial chromosomal sequence. In some embodiments, the target nucleotide sequence is unique in the target genome.

The target nucleotide sequence is adjacent to a protospacer adjacent motif (PAM). A protospacer adjacent motif is generally within about 1 to about 10 nucleotides from the target nucleotide sequence, including about 1, about 2, about 3, about 4, about 5, about 6, about 7, about 8, about 9, or about 10 nucleotides from the target nucleotide sequence. The PAM can be 5' or 3' of the target sequence. In some embodiments, the PAM is 3' of the target sequence for the presently disclosed RGNs. Generally, the PAM is a consensus sequence of about 3-4 nucleotides, but in particular embodiments, can be 2, 3, 4, 5, 6, 7, 8, 9, or more nucleotides in length. In various embodiments, the PAM sequence recognized by the presently disclosed RGNs comprises the consensus sequence set forth as SEQ ID NOs: 7, 22, 30, 41, or 49.

In particular embodiments, an RNA-guided nuclease having SEQ ID NOs: 1, 16, 24, 35, 43, or 50 or an active variant or fragment thereof binds respectively a target nucleotide sequence adjacent to a PAM sequence set forth as SEQ ID NOs: 7, 22, 30, 41, or 49. In some of these embodiments, the RGN binds to a guide sequence comprising a CRISPR repeat sequence set forth in SEQ ID NOs: 2, 17, 25, 36, 44, 51, or 63, respectively, or an active variant or fragment thereof, and a tracrRNA sequence set forth in SEQ ID NOs: 3, 18, 26, 37, 45, 52, or 62, respectively, or an active variant or fragment thereof. The RGN systems are described further in Example 1 and Table 1 of the present specification.

It is well-known in the art that PAM sequence specificity for a given nuclease enzyme is affected by enzyme concentration (see, e.g., Karvelis et al. (2015) *Genome Biol* 16:253), which may be modified by altering the promoter used to express the RGN, or the amount of ribonucleoprotein complex delivered to the cell, organelle, or embryo.

Upon recognizing its corresponding PAM sequence, the RGN can cleave the target nucleotide sequence at a specific cleavage site. As used herein, a cleavage site is made up of the two particular nucleotides within a target nucleotide sequence between which the nucleotide sequence is cleaved by an RGN. The cleavage site can comprise the $1^{st}$ and $2^{nd}$, $2^{nd}$ and $3^{rd}$, $3^{rd}$ and $4^{th}$, $4^{th}$ and $5^{th}$, $5^{th}$ and $6^{th}$, $7^{th}$ and $8^{th}$, or $8^{th}$ and $9^{th}$ nucleotides from the PAM in either the 5' or 3' direction. In some embodiments, the cleavage site may be over 10, 11, 12, 13, 14, 15, 16, 17, 18, 19, or 20 nucleotides from the PAM in either the 5' or 3' direction. In some embodiments, the cleavage site is 4 nucleotides away from the PAM. In other embodiments, the cleavage site is at least 15 nucleotides away from the PAM. As RGNs can cleave a target nucleotide sequence resulting in staggered ends, in some embodiments, the cleavage site is defined based on the distance of the two nucleotides from the PAM on the positive (+) strand of the polynucleotide and the distance of the two nucleotides from the PAM on the negative (−) strand of the polynucleotide.

III. Fusion Proteins

The term "linker," as used herein, refers to a chemical group or a molecule linking two molecules or moieties, e.g., a binding domain and a cleavage domain of a nuclease. In some embodiments, a linker joins an RNA guided nuclease and a deaminase. In some embodiments, a linker joins a dCas9 and a deaminase. Typically, the linker is positioned between, or flanked by, two groups, molecules, or other moieties and connected to each one via a covalent bond, thus connecting the two. In some embodiments, the linker is an amino acid or a plurality of amino acids (e.g., a peptide or protein). In some embodiments, the linker is an organic molecule, group, polymer, or chemical moiety. In some embodiments, the linker is 5-100 amino acids in length, for example, 5, 6, 7, 8, 9, 10, 11, 12, 13, 14, 15, 16, 17, 18, 19, 20, 21, 22, 23, 24, 25, 26, 27, 28, 29, 30, 30-35, 35-40, 40-45, 45-50, 50-60, 60-70, 70-80, 80-90, 90-100, 100-150, or 150-200 amino acids in length. Longer or shorter linkers are also contemplated.

Some aspects of this disclosure provide fusion proteins that comprise a DNA-binding polypeptide and a deaminase polypeptide. The DNA-binding polypeptide may be any protein or protein domain which binds to DNA. In some embodiments, the DNA-binding polypeptide of the fusion protein is a meganuclease, zinc finger fusion protein, or TALEN. Some aspects of this disclosure provide fusion proteins that comprise an RNA-guided DNA-binding polypeptide and a deaminase polypeptide. In some embodiments, the RNA-guided DNA-binding polypeptide is an RNA-guided nuclease. In some embodiments, the RNA-guided nuclease is an RGN of the invention. In some embodiments, the RGN is not an RGN of the invention. In further embodiments, the RNA-guided nuclease is a CRISPR-Cas protein. In still further embodiments, the CRISPR-Cas protein is a Type II CRISPR-Cas protein. In other embodiments, the CRISPR-Cas protein is a Type V CRISPR-Cas protein. In other embodiments, the CRISPR-Cas protein is a Type VI CRISPR-Cas protein. In some embodiments, the RNA-guided nuclease is a Cas9 domain that binds to a guide RNA, which, in turn, binds a target nucleic acid sequence via strand hybridization. In some embodiments, the deaminase polypeptide may be a deaminase domain that can deaminate a nucleobase, such as, for example, cytidine or adenine. In some embodiments, the deaminase polypeptide comprises an amino acid sequence selected from any of SEQ ID NO: 374-545 or 572-584, or a variant thereof. In some of these embodiments, the deaminase polypeptide comprises an amino acid sequence selected from any one of SEQ ID NOs: 374, 383, 397, 399, 407, 408, 411, 414, 416, 420, 514, and 572-584, or a variant thereof. The deamination of a nucleobase by a deaminase can lead to a point mutation at the respective residue, thereby modifying the DNA molecule. This act of modification is also referred to herein as nucleic acid editing, or base editing. Fusion proteins comprising a Cas9 variant or domain and a deaminase domain can thus be used for the targeted editing of nucleic acid sequences.

Such fusion proteins are useful for targeted editing of DNA in vitro, e.g., for the generation of mutant cells. These mutant cells may be in plants or animals. Such fusion proteins may also be useful for the introduction of targeted mutations, e.g., for the correction of genetic defects in mammalian cells ex vivo, e.g., in cells obtained from a subject that are subsequently re-introduced into the same or another subject; and for the introduction of targeted mutations, e.g., the correction of genetic defects or the introduction of deactivating mutations in disease-associated genes in a mammalian subject. Such fusion proteins may also be useful for the introduction of targeted mutations in plant cells, e.g., for the introduction of beneficial or agronomically important traits or alleles.

The term "uracil glycosylase inhibitor" or "UGI," as used herein, refers to a protein that is capable of inhibiting an uracil-DNA glycosylase base-excision repair enzyme. In some embodiments, the fusion protein comprises a nuclease-inactive RGN, such as Cas9 (dCas9) fused to a deaminase. In some embodiments, the fusion protein comprises a nickase RGN, such as Cas9 (nCas9), fused to a deaminase. In some embodiments, the fusion protein comprises a nuclease inactive RGN or a nickase RGN fused to a deaminase and further fused to a UGI domain.

In some embodiments, the nickase RGN of the fusion protein comprises a D10A mutation or a homologously equivalent mutation (SEQ ID NO: 569; or similarly SEQ ID NO: 553) which renders the RGN capable of cleaving only the target strand (the strand which comprises the PAM) of a nucleic acid duplex. In some embodiments, the nuclease-inactive ("dead") RGN of the fusion protein comprises a D10A mutation and a H840A mutation or homologously equivalent mutations (SEQ ID NO: 568; or similarly SEQ ID NO: 547), which renders the RGN incapable to cleave the DNA target. In some embodiments, the nickase RGN of the fusion protein comprises a H840A mutation, which renders the RGN capable of cleaving only the non-target strand (the strand which does not comprise the PAM) of a nucleic acid duplex. A nickase RGN comprising an H840A mutation, or an equivalent mutation, has an inactivated HNH domain. A nickase RGN comprising a D10A mutation, or an equivalent mutation, has an inactivated RuvC domain. The deaminase acts on the non-target strand. A nickase comprising a D10A mutation, or an equivalent mutation, has an inactive RuvC nuclease domain and is not able to cleave the non-targeted strand of the DNA, i.e., the strand where base editing is desired.

In some embodiments, the RGN of the fusion proteins described herein have nickase activity, wherein the nickase may be a fragment of an RGN or a nickase variant of an RGN. In some embodiments, the RGN domain of the fusion proteins described herein have at least partially deactivated nuclease activity, and may be referred to as RNA-guided, DNA-binding polypeptides. Methods for the use of said fusion proteins as described herein are also provided. In some embodiments, the RGN is a Cas9 protein. Non-limiting, exemplary nuclease-inactive and nickase Cas9 domains are provided herein. One exemplary suitable nuclease-inactive RGN domains is the D10A/H840A Cas9 domain mutant (see, e.g., Qi et al., Cell. 2013; 152(5): 1173-83, the entire contents of which are incorporated herein by reference). Additional suitable nuclease-inactive Cas9 domains will be apparent to those of skill in the art based on this disclosure. Such additional exemplary suitable nuclease inactive Cas9 domains include, but are not limited to, D10A, D10A/D839A/H840A, and D10A/D839A/H840A/N863A mutant domains (See, e.g., Mali et al., Nature Biotechnology. 2013; 31(9): 833-838, the entire contents of which are incorporated herein by reference). Additionally, suitable nuclease-inactive RGN domains of other known RGNs can be determined (for example, SEQ ID NO: 547, a nuclease-inactive variant of the RGN APG08290.1; see U.S. patent application Ser. No. 16/432, 321, the entire contents of which are incorporated herein by reference herein).

Some aspects of this disclosure provide fusion proteins comprising (i) a nuclease-inactive or nickase RGN or domain; and (ii) a deaminase enzyme or domain. In some embodiments, the deaminase enzyme or domain is a DNA-editing enzyme or domain. In some embodiments, the deaminase enzyme possesses deaminase activity. In some embodiments, the deaminase enzyme or domain comprises or is a deaminase domain. In some embodiments, the deaminase is a cytidine deaminase. In some embodiments, the deaminase is an apolipoprotein B mRNA-editing complex (APOBEC) family deaminase. In some embodiments, the deaminase is an APOBEC1 family deaminase. In other embodiments, the deaminase is an APOBEC3 family deaminase. In some embodiments, the deaminase is an activation-induced cytidine deaminase (AID). In some embodiments, the deaminase is an ACF1/ASE deaminase. In some embodiments, the deaminase is an adenosine deaminase. In some embodiments, the deaminase is an ADAT family deaminase. Some nucleic-acid deaminase enzymes and domains are described in detail herein (see Table 17). Additional suitable deaminase enzymes or domains will be apparent to the skilled artisan based on this disclosure. In some of these embodiments, the deaminase polypeptide comprises an amino acid sequence selected from any one of SEQ ID NOs:

374, 383, 397, 399, 407, 408, 411, 414, 416, 420, 514, and 572-584, or a variant thereof.

The instant disclosure provides fusion proteins of various configurations. In some embodiments, the deaminase enzyme or domain is fused to the N-terminus of the RGN domain. In some embodiments, the deaminase enzyme or domain is fused to the C-terminus of the RGN domain. In some embodiments, the linker comprises a (GGGGS)$_n$ (SEQ ID NO: 585), a (G)$_n$ (SEQ ID NO: 586), an (EAAAK)$_n$ (SEQ ID NO: 587), or an (XP)$_n$ (SEQ ID NO: 588) motif, or a combination of any of these, wherein n is independently an integer between 1 and 30. In some embodiments, n is independently 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30, or, if more than one linker or more than one linker motif is present, any combination thereof. Additional suitable linker motifs and linker configurations will be apparent to those of skill in the art. In some embodiments, suitable linker motifs and configurations include those described in Chen et al., Fusion protein linkers: property, design and functionality (*Adv Drug Deliv Rev.* 2013; 65(10):1357-69, the entire contents of which are incorporated herein by reference). Additional suitable linker sequences will be apparent to those of skill in the art based on the instant disclosure.

In some embodiments, the general architecture of exemplary fusion proteins provided herein comprises the structure: [NH$_2$]-[deaminase enzyme or domain]-[RGN protein or domain][COOH] or [NH$_2$]-[RGN protein or domain]-[deaminase enzyme or domain][COOH], wherein NH$_2$ is the N-terminus of the fusion protein, and COOH is the C-terminus of the fusion protein. Additional features may be present, for example, one or more linker sequences between the NLS and the rest of the fusion protein and/or between the deaminase enzyme or domain and the RGN protein or domain. Other exemplary features that may be present are localization sequences, such as nuclear localization sequences, cytoplasmic localization sequences, export sequences, such as nuclear export sequences, or other localization sequences, as well as sequence tags that are useful for solubilization, purification or detection of the fusion proteins. Suitable localization signal sequences and sequences of protein tags that are provided herein, and include, but are not limited to, biotin carboxylase carrier protein (BCCP) tags, myc-tags, calmodulin-tags, FLAG-tags, hemagglutinin (HA)-tags, polyhistidine tags, also referred to as histidine tags or His-tags, maltose binding protein (MBP)-tags, nus-tags, glutathione-S-transferase (GST)-tags, green fluorescent protein (GFP)-tags, thioredoxin-tags, S-tags, Softags (e.g., Softag 1, Softag 3), streptags, biotin ligase tags, FlAsH tags, V5 tags, and SBP-tags. Additional suitable sequences will be apparent to those of skill in the art.

In some embodiments, the deaminase enzyme or the general architecture of exemplary fusion proteins with a deaminase enzyme or domain comprises the structure: [NH$_2$]-[NLS]-[RGN protein or domain]-[deaminase]-[COOH], [NH$_2$]-[NLS]-[deaminase]-[RGN protein or domain]-[COOH], [NH$_2$]-[RGN protein or domain]-[deaminase]-[COOH], or [NH$_2$]-[deaminase]-[RGN protein or domain]-[COOH] wherein NLS is a nuclear localization signal, NH$_2$ is the N-terminus of the fusion protein, and COOH is the C-terminus of the fusion protein. In some embodiments, a linker is inserted between the RGN protein or domain and the deaminase. In some embodiments, the NLS is located C-terminal of the deaminase and/or the RGN protein or domain. In some embodiments, the NLS is located between the deaminase and the RGN protein or domain.

Additional features, such as sequence tags, may also be present. "RGN protein or domain" here represents any RNA-guided nuclease, including CRISPR-Cas proteins and variants and mutants thereof, which can be used to create a fusion protein of the invention. The RGN protein may be a nuclease-inactive RGN or CRISPR-Cas, such as for example dCas9 (SEQ ID NO: 568) or alternatively SEQ ID NO: 547, or a RGN or Cas9 nickase, such as for example SEQ ID NO: 569 (or SEQ ID NO: 553). In some embodiments, a fusion protein of the invention comprises a RNA-guided, DNA-binding polypeptide and a deaminase, wherein the deaminase has an amino acid sequence of at least 50%, at least 55%, at least 60%, at least 65%, at least 70%, at least 75%, at least 80%, at least 85%, at least 90%, at least 95%, at least 96%, at least 97%, at least 98%, at least 99%, or 100% identical to any of SEQ ID NO: 374-545 or 572-584, or an active variant thereof. In some of these embodiments, the fusion protein comprises a deaminase polypeptide comprising an amino acid sequence selected from any one of SEQ ID NOs: 374, 383, 397, 399, 407, 408, 411, 414, 416, 420, 514, and 572-584, or a variant thereof. Examples of such fusion proteins are described in the Examples section here.

One exemplary suitable type of deaminase enzymes and domains are cytosine deaminases, for example, of the APOBEC family. The apolipoprotein B mRNA editing complex (APOBEC) family of cytosine deaminase enzymes encompasses eleven proteins that serve to initiate mutagenesis in a controlled and beneficial manner (Conticello et al., 2008. Genome Biology, 9(6): 229). One family member, activation-induced cytidine deaminase (AID), is responsible for the maturation of antibodies by converting cytosines in ssDNA to uracils in a transcription dependent, strand-biased fashion (Reynaud et al., 2003. Nature Immunology, 4(7): 631-638). The apolipoprotein B editing complex 3 (APOBEC3) enzyme provides protection to human cells against a certain HIV-1 strain via the deamination of cytosines in reverse-transcribed viral ssDNA (Bhagwat et al., 2004, 3(1): 85-9). These proteins all require a $Zn^{2+}$-coordinating motif (HisX-Glu-X$_{23-26}$-Pro-Cys-X$_{2-4}$-Cys; SEQ ID NO: 589) and bound water molecule for catalytic activity. The Glu residue acts to activate the water molecule to a zinc hydroxide for nucleophilic attack in the deamination reaction. Each family member preferentially deaminates at its own particular "hotspot", ranging from WRC (W is A or T, R is A or G) for hAID, to TTC for hAPOBEC3F (Navaratnam et al., 2006. Intl J Hematol 83(3): 195-200). A recent crystal structure of the catalytic domain of APOBEC3G revealed a secondary structure comprised of a five-stranded β-sheet core flanked by six α-helices, which is believed to be conserved across the entire family (Holden et al., 2008. Nature 456(7218): 121-124). The active center loops have been shown to be responsible for both ssDNA binding and in determining "hotspot" identity (Chelico et al., 2009. J Biol Chem 284(41): 27761-27765). Overexpression of these enzymes has been linked to genomic instability and cancer, thus highlighting the importance of sequence-specific targeting (Pham et al., 2005. Biochem 44(8): 2703-2715).

Another exemplary suitable type of deaminase enzymes and domains are adenosine deaminases. An ADAT family adenosine deaminase can be fused to an RGN or fragment or a domain of an RGN or a variant thereof, such as for example a nuclease-inactive Cas9 domain, thus yielding a Cas9-ADAT fusion protein. This disclosure includes a systematic series of fusions between an RGN or fragment or a domain of an RGN or a variant thereof and a deaminase enzyme, for example a cytosine deaminase such as an APOBEC enzyme, or an adenosine deaminase enzyme such as an ADAT enzyme, so that the RGN-deaminase fusion directs the enzymatic activity of the deaminase to a specific site in genomic DNA. The advantages of using an RGN as the recognition agent are twofold: (1) the sequence specificity of the fusion protein can be easily altered by simply changing the sgRNA sequence; and (2) RGNs such as Cas9 bind to its target sequence by denaturing the dsDNA, resulting in a stretch of DNA that is single-stranded and therefore a viable substrate for the deaminase. Successful fusion proteins have been generated with human and mouse deaminase domains, e.g., AID domains (WO 2010132092, incorporated by reference herein). A variety of other fusion proteins between deaminases recited herein and an RGN are also contemplated.

The portion of DNA that is single stranded in the RGN-DNA complex (the size of the RGN-DNA bubble) has not been delineated. However, it has been shown in a dCas9 system with a sgRNA specifically designed for the complex to interfere with transcription that transcriptional interference only occurs when the sgRNA binds to the non-template strand. This result suggests that certain portions of the DNA in the DNA-Cas9 complex are unguarded by Cas9 and could potentially be targeted by a deaminase in the fusion protein (Qi et al., 2013. Cell 152(15): 1173-83). Accordingly, both N-terminal and C-terminal fusions of Cas9, or generically an RGN, with a deaminase domain are useful according to aspects of this disclosure.

In some embodiments, the deaminase domain and the RNA-guided, DNA-binding domain of an RGN are fused to each other via a linker. Various linker lengths and flexibilities between the deaminase domain (e.g., AID) and the RGN domain can be employed (e.g., ranging from very flexible linkers of the form $(GGGGS)_n$ (SEQ ID NO 590) and $(G)_n$ to more rigid linkers of the form $(EAAAK)_n$ (SEQ ID NO: 591) and $(XP)_n$ in order to achieve the optimal length for deaminase activity for the specific applications.

Some exemplary suitable nucleic-acid editing enzymes and domains, e.g., deaminases and deaminase domains, that can be fused to RNA-guided, DNA-binding domains according to aspects of this disclosure are provided (SEQ ID NOs: 374-545 and 572-584). It will be understood that, in some embodiments, the active domain of the respective sequence can be used, e.g., the domain without a localizing signal (nuclear localizing signal, without nuclear export signal, cytoplasmic localizing signal).

In some embodiments, fusion proteins as provided herein comprise the full-length amino acid of a deaminase enzyme, e.g., any one of SEQ ID NO: 374-545 or 572-584. In other embodiments, however, fusion proteins as provided herein do not comprise a full-length sequence of a nucleic acid editing enzyme, but only a fragment thereof. For example, in some embodiments, a fusion protein provided herein comprises an RNA-guided, DNA-binding domain and a fragment of a deaminase enzyme, e.g., wherein the fragment comprises a deaminase domain. Exemplary amino acid sequences of deaminase domains are described in Table 17, and additional suitable sequences of such domains will be apparent to those of skill in the art.

Additional suitable nucleic-acid editing enzyme sequences, e.g., deaminase enzyme and domain sequences, that can be used according to aspects of this invention, e.g., that can be fused to a nuclease-inactive or nickase RGN domain, will be apparent to those of skill in the art based on this disclosure. In some embodiments, such additional enzyme sequences include deaminase enzyme or deaminase domain sequences that are at least 70%, at least 75%, at least 80%, at least 85%, at least 90%, at least 95%, at least 96%, at least 97%, at least 98%, or at least 99% similar to the sequences provided herein. Additional suitable RGN domains, variants, and sequences will also be apparent to those of skill in the art. Examples of such additional suitable RGN domains include, but are not limited to, D10A, D10A/D839A/H840A, and D10A/D839A/H840A/N863A mutant domains (See, e.g., Mali et al., Cas9 transcriptional activators for target specificity screening and paired nickases for cooperative genome engineering. *Nature Biotechnology*. 2013; 31(9): 833-838 the entire contents of which are incorporated herein by reference).

Additional suitable strategies for generating fusion proteins comprising an RNA-guided, DNA-binding domain and a deaminase domain will be apparent to those of skill in the art based on this disclosure in combination with the general knowledge in the art. Suitable strategies for generating fusion proteins according to aspects of this disclosure using linkers or without the use of linkers will also be apparent to those of skill in the art view of the instant disclosure and the knowledge in the art.

In some embodiments, the RNA-guided, DNA-binding domain is an RGN protein variant that has nickase activity. In some embodiments, the RNA-guided, DNA-binding domain is a RGN nickase. In some embodiments, the RGN is an RGN of the invention. In other embodiments, the RGN is not an RGN of the invention. The RGN nickase may be a Cas9 protein that is capable of cleaving only one strand of a duplexed nucleic acid molecule (e.g., a duplexed DNA molecule, also referred to as a double-stranded DNA molecule). In some embodiments the RGN nickase cleaves the target strand of a duplexed nucleic acid molecule, meaning that the RGN nickase cleaves the strand that is base paired to (complementary to) a gRNA that is bound to the RGN. In some embodiments, the RGN nickase comprises a D10A mutation, or the equivalent mutation. In other embodiments, the RGN nickase comprises a H840A mutation, or the equivalent mutation. For example, an RGN nickase may comprise the amino acid sequence as set forth in SEQ ID NO: 569. In some embodiments the RGN nickase is a D10A Cas9 nickase, which inactivates the RuvC domain of the Cas9 and results in cleavage of the target, non-base edited strand of a duplexed nucleic acid molecule, meaning that the D10A Cas9 nickase cleaves the strand that is base paired to a gRNA (e.g., an sgRNA) that is bound to the Cas9. In some embodiments, a Cas9 nickase comprises an H840A mutation, which inactivates the HNH domain of the Cas9 polypeptide. The H840A Cas9 nickase will cleave the non-target, based-edited strand. In some embodiments the RGN nickase comprises an amino acid sequence that is at least 60%, at least 65%, at least 70%, at least 75%, at least 80%, at least 85%, at least 90%, at least 95%, at least 96%, at least 97%, at least 98%, at least 99%, or at least 99.5% identical to SEQ ID NO: 568, 569, 547, or 553. Additional suitable RGN proteins mutated to be nickases will be apparent to those of skill in the art based on this disclosure and knowledge in the field (such as for example the RGNs disclosed in U.S. patent application Ser. No. 16/432,321) and are within the scope of this disclosure.

Some aspects of the disclosure relate to fusion proteins that comprise a uracil glycosylase inhibitor (UGI) domain. In some embodiments, any of the fusion proteins provided herein that comprise an RNA-guided, DNA-binding domain (e.g., a nuclease active RGN domain, or an RGN variant that is nuclease inactive or functions as a nickase) may be further fused to at least one UGI domain either directly or via a linker. In some embodiments, the fusion protein is further fused to at least two UGI domains, either directly or via a linker. Some aspects of this disclosure provide deaminase-RGN fusion proteins, deaminase-nuclease inactive RGN fusion proteins and deaminase-nickase RGN fusion proteins, further fused to at least one UGI domain and with increased C→T nucleobase editing efficiency as compared to a similar fusion protein that does not comprise a UGI domain. Without wishing to be bound by any particular theory, cellular DNA-repair response to the presence of U:G heteroduplex DNA may be responsible for the decrease in nucleobase editing efficiency in cells. For example, uracil DNA glycosylase (UDG) catalyzes removal of U from DNA in cells, which may initiate base excision repair, with reversion of the U:G pair to a C:G pair as the most common outcome.

This disclosure contemplates a fusion protein comprising a deaminase of the invention and an RNA-guided, DNA-binding polypeptide further fused to a UGI domain. This disclosure also contemplates a fusion protein comprising a deaminase, an RGN nickase or a nuclease inactive RGN polypeptide, further fused to a UGI domain. It should be understood that the use of a UGI domain may increase the editing efficiency of a nucleic acid editing domain that is capable of catalyzing a C to U change. For example, fusion proteins comprising a UGI domain may be more efficient in deaminating C residues. In some embodiments, the fusion protein comprises the structure: [deaminase]-[optional linker sequence]-[nuclease-inactive RGN]-[optional linker sequence]-[UGI]; [deaminase]-[optional linker sequence]-[UGI]-[optional linker sequence]-[nuclease-inactive RGN]; [UGI]-[optional linker sequence]-[deaminase]-[optional linker sequence]-[nuclease-inactive RGN]; [UGI]-[optional linker sequence]-[nuclease-inactive RGN]-[optional linker sequence]-[deaminase]; [nuclease-inactive RGN]-[optional linker sequence]-[deaminase]-[optional linker sequence]-[UGI]; or [nuclease-inactive RGN]-[optional linker sequence]-[UGI]-[optional linker sequence]-[deaminase]. It should be understood that "nuclease-inactive RGN" represents any RGN, including any CRISPR-Cas protein, which has been mutated to be nuclease-inactive. It should also be understood that "UGI" represents one or more UGI domains.

In other embodiments, the fusion protein comprises the structure: [deaminase]-[optional linker sequence]-[RGN nickase]-[optional linker sequence]-[UGI]; [deaminase]-[optional linker sequence]-[UGI]-[optional linker sequence]-[RGN nickase]; [UGI]-[optional linker sequence]-[deaminase][optional linker sequence]-[RGN nickase]; [UGI]-[optional linker sequence]-[RGN nickase]-[optional linker sequence]-[deaminase]; [RGN nickase]-[optional linker sequence][deaminase]-[optional linker sequence]-[UGI]; or [RGN nickase]-[optional linker sequence]-[UGI]-[optional linker sequence]-[deaminase]. It should be understood that "RGN nickase" represents any RGN, including any CRISPR-Cas protein, which has been mutated to be active as a nickase. It should also be understood that "UGI" represents one or more UGI domains.

In some embodiments, the fusion proteins provided herein do not comprise a linker sequence. In some embodiments, one or both of the optional linker sequences are present.

In some embodiments, the "-" used in the general architecture above indicates the presence of an optional linker sequence. In some embodiments, the fusion proteins comprising a UGI further comprise a nuclear targeting sequence, for example a nuclear localization sequence. In some embodiments, fusion proteins provided herein further comprise a nuclear localization sequence (NLS). In some embodiments, the NLS is fused to the N-terminus of the fusion protein. In some embodiments, the NLS is fused to the C-terminus of the fusion protein. In some embodiments, the NLS is fused to the N-terminus of the UGI protein. In some embodiments, the NLS is fused to the C-terminus of the UGI protein. In some embodiments, the NLS is fused to the N-terminus of the RGN protein. In some embodiments, the NLS is fused to the C-terminus of the RGN protein. In some embodiments, the NLS is fused to the N-terminus of the deaminase. In some embodiments, the NLS is fused to the C-terminus of the deaminase. In some embodiments, the NLS is fused to the N-terminus of the second RGN. In some embodiments, the NLS is fused to the C-terminus of the second RGN. In some embodiments, the NLS is fused to the fusion protein via one or more linkers. In some embodiments, the NLS is fused to the fusion protein without a linker. In some embodiments, the NLS comprises an amino acid sequence of any one of the NLS sequences provided or referenced herein. In some embodiments, the NLS comprises an amino acid sequence as set forth in SEQ ID NO: 10.

In some embodiments, a UGI domain comprises a wild-type UGI or a UGI as set forth in SEQ ID NO: 570. In some embodiments, the UGI proteins provided herein include fragments of UGI and proteins homologous to a UGI or a UGI fragment. For example, in some embodiments, a UGI domain comprises a fragment of the amino acid sequence set forth in SEQ ID NO: 570. In some embodiments, a UGI fragment comprises an amino acid sequence that comprises at least 60%, at least 65%, at least 70%, at least 75%, at least 80%, at least 85%, at least 90%, at least 95%, at least 96%, at least 97%, at least 98%, at least 99%, or at least 99.5% of the amino acid sequence as set forth in SEQ ID NO: 570. In some embodiments, a UGI comprises an amino acid sequence homologous to the amino acid sequence set forth in SEQ ID NO: 570 or an amino acid sequence homologous to a fragment of the amino acid sequence set forth in SEQ ID NO: 570. In some embodiments, proteins comprising UGI or fragments of UGI or homologs of UGI or UGI fragments are referred to as "UGI variants." A UGI variant shares homology to UGI, or a fragment thereof. For example, a UGI variant is at least 70% identical, at least 75% identical, at least 80% identical, at least 85% identical, at least 90% identical, at least 95% identical, at least 96% identical, at least 97% identical, at least 98% identical, at least 99% identical, at least 99.5% identical, or at least 99.9% identical to a wild type UGI or a UGI as set forth in SEQ ID NO: 570. In some embodiments, the UGI variant comprises a fragment of UGI, such that the fragment is at least 70% identical, at least 80% identical, at least 90% identical, at least 95% identical, at least 96% identical, at least 97% identical, at least 98% identical, at least 99% identical, at least 99.5% identical, or at least 99.9% to the corresponding fragment of wild-type UGI or a UGI as set forth in SEQ ID NO: 570.

Suitable UGI protein and nucleotide sequences are provided herein and additional suitable UGI sequences are known to those in the art, and include, for example, those published in Wang et al., 1989. J. Biol. Chem. 264: 1163-1171; Lundquist et al., 1997. J. Biol. Chem. 272:21408-21419; Ravishankar et al., 1998. Nucleic Acids Res. 26:4880-4887; and Putnam et al., 1999. J. Mol. Biol. 287: 331-346(1999), the entire contents of each are incorporated herein by reference.

It should be appreciated that additional proteins may be uracil glycosylase inhibitors. For example, other proteins that are capable of inhibiting (e.g., sterically blocking) a uracil-DNA glycosylase base-excision repair enzyme are within the scope of this disclosure. Additionally, any proteins that block or inhibit base-excision repair as also within the scope of this disclosure. In some embodiments, a protein that binds DNA is used. In another embodiment, a substitute for UGI is used. In some embodiments, a uracil glycosylase inhibitor is a protein that binds single-stranded DNA. For example, a uracil glycosylase inhibitor may be a *Erwinia tasmaniensis* single-stranded binding protein. In some embodiments, a uracil glycosylase inhibitor is a protein that binds uracil. In some embodiments, a uracil glycosylase inhibitor is a protein that binds uracil in DNA. In some embodiments, a uracil glycosylase inhibitor is a catalytically inactive uracil DNA-glycosylase protein. In some embodiments, a uracil glycosylase inhibitor is a catalytically inactive uracil DNA-glycosylase protein that does not excise uracil from the DNA. It should be appreciated that other uracil glycosylase inhibitors would be apparent to the skilled artisan and are within the scope of this disclosure. A suitable UGI protein sequence is provided herein (SEQ ID NO: 570) and additional suitable UGI sequences are known to those in the art, and include, for example, those published in Wang et al., 1989. J. Biol. Chem. 264: 1163-1171; Lundquist et al., 1997. J. Biol. Chem. 272:21408-21419; Ravishankar et al 1998. Nucleic Acids Res. 26:4880-4887; and Putnam et al., 1999. J. Mol. Biol. 287:331-346, the entire contents of which are incorporated herein by reference. In some embodiments, the optional linker comprises a (SGGS)$_n$ (SEQ ID NO: 592) motif, wherein n is 1, 2, 3, 4, 5, 6, 7, 8, 9, 19, 11, 12, 13, 14, 15, 16, 17, 18, 19, or 20. In some embodiments, the optional linker comprises the amino acid sequence as set forth in SEQ ID NO: 546

In certain embodiments, the presently disclosed fusion proteins comprise at least one cell-penetrating domain that facilitates cellular uptake of the RGN. Cell-penetrating domains are known in the art and generally comprise stretches of positively charged amino acid residues (i.e., polycationic cell-penetrating domains), alternating polar amino acid residues and non-polar amino acid residues (i.e., amphipathic cell-penetrating domains), or hydrophobic amino acid residues (i.e., hydrophobic cell-penetrating domains) (see, e.g., Milletti F. (2012) *Drug Discov Today* 17:850-860). A non-limiting example of a cell-penetrating domain is the trans-activating transcriptional activator (TAT) from the human immunodeficiency virus 1.

The nuclear localization signal, plastid localization signal, mitochondrial localization signal, dual-targeting localization signal, and/or cell-penetrating domain can be located at the amino-terminus (N-terminus), the carboxyl-terminus (C-terminus), or in an internal location of the fusion protein.

Another embodiment of the invention is a ribonucleoprotein complex comprising the fusion protein and the guide RNA, either as a single guide or as a dual guide RNA (collectively referred to as gRNA).

IV. Nucleotides Encoding RNA-Guided Nucleases, RNA-Guided DNA Binding Polypeptides, Deaminases, CRISPR RNA, tracrRNA, and gRNA The present disclosure provides polynucleotides comprising the presently disclosed RGNs, RNA-guided, DNA-binding polypeptide-deaminase fusions, deaminases, CRISPR RNAs, tracrRNAs, and/or sgRNAs. Presently disclosed polynucleotides include those comprising or encoding a CRISPR repeat sequence comprising the nucleotide sequence of SEQ ID NOs: 2, 17, 25, 36, 44, 51, or 63, or an active variant or fragment thereof that when comprised within a guide RNA is capable of directing the sequence-specific binding of an associated RNA-guided nuclease to a target sequence of interest. Also disclosed are polynucleotides comprising or encoding a tracrRNA comprising the nucleotide sequence of SEQ ID NOs: 3, 18, 26, 37, 45, 52, or 62, or an active variant or fragment thereof that when comprised within a guide RNA is capable of directing the sequence-specific binding of an associated RNA-guided nuclease to a target sequence of interest. Polynucleotides are also provided that encode an RGN comprising the amino acid sequence set forth as SEQ ID NOs: 1, 16, 24, 35, 43, or 50, and active fragments or variants thereof that retain the ability to bind to a target nucleotide sequence in an RNA-guided sequence-specific manner.

The present disclosure further provides polynucleotides encoding for fusion proteins which comprise a deaminase recited herein (SEQ ID NOs: 374-545 and 572-584, or an active variant thereof) and a DNA binding polypeptide, for example a meganuclease, a zinc finger fusion protein, or a TALEN. The present disclosure further provides polynucleotides encoding for fusion proteins which comprise a deaminase recited herein and an RNA-guided, DNA-binding polypeptide. Such an RNA-guided, DNA-binding polypeptide may be an RGN of the invention, an RGN known in the art, a CRISPR-Cas protein, or a protein variant of any thereof. The protein variant may be nuclease-inactive or a nickase. Examples of such RGN variants include a nuclease-inactive RGN (SEQ ID NO: 568 or SEQ ID NO: 547) or a RGN nickase mutant (SEQ ID NO: 569 or SEQ ID NO: 553). Other examples of RGN nucleases are well-known in the art, and similar corresponding mutations can create mutant variants which are also nuclease inactive or nickases.

The use of the term "polynucleotide" is not intended to limit the present disclosure to polynucleotides comprising DNA. Those of ordinary skill in the art will recognize that polynucleotides can comprise ribonucleotides (RNA) and combinations of ribonucleotides and deoxyribonucleotides. Such deoxyribonucleotides and ribonucleotides include both naturally occurring molecules and synthetic analogues. These include peptide nucleic acids (PNAs), PNA-DNA chimers, locked nucleic acids (LNAs), and phosphothiorate linked sequences. The polynucleotides disclosed herein also encompass all forms of sequences including, but not limited to, single-stranded forms, double-stranded forms, DNA-RNA hybrids, triplex structures, stem-and-loop structures, and the like.

The nucleic acid molecules encoding RGNs, deaminases, or fusion proteins can be codon optimized for expression in an organism of interest. A "codon-optimized" coding sequence is a polynucleotide coding sequence having its frequency of codon usage designed to mimic the frequency of preferred codon usage or transcription conditions of a particular host cell. Expression in the particular host cell or organism is enhanced as a result of the alteration of one or more codons at the nucleic acid level such that the translated amino acid sequence is not changed. Nucleic acid molecules can be codon optimized, either wholly or in part. Codon tables and other references providing preference information for a wide range of organisms are available in the art (see, e.g., Campbell and Gowri (1990) *Plant Physiol.* 92:1-11 for a discussion of plant-preferred codon usage). Methods are available in the art for synthesizing plant-preferred genes. See, for example, U.S. Pat. Nos. 5,380,831, and 5,436,391, and Murray et al. (1989) *Nucleic Acids Res.* 17:477-498, herein incorporated by reference.

Polynucleotides encoding the RGNs, RNA-guided, DNA-binding polypeptide-deaminase fusions, deaminases, crRNAs, tracrRNAs, and/or sgRNAs provided herein can be provided in expression cassettes for in vitro expression or expression in a cell, organelle, embryo, or organism of interest. The cassette will include 5' and 3' regulatory sequences operably linked to a polynucleotide encoding an RGN, RNA-guided, DNA-binding polypeptide-deaminase fusion, deaminase, crRNA, tracrRNAs, and/or sgRNAs provided herein that allows for expression of the polynucleotide. The cassette may additionally contain at least one additional gene or genetic element to be cotransformed into the organism. Where additional genes or elements are included, the components are operably linked. The term "operably linked" is intended to mean a functional linkage between two or more elements. For example, an operable linkage between a promoter and a coding region of interest (e.g., region coding for an RGN, RNA-guided, DNA-binding polypeptide-deaminase fusion, deaminase, crRNA, tracrRNAs, and/or sgRNAs) is a functional link that allows for expression of the coding region of interest. Operably linked elements may be contiguous or non-contiguous. When used to refer to the joining of two protein coding regions, by operably linked is intended that the coding regions are in the same reading frame. Alternatively, the additional gene(s) or element(s) can be provided on multiple expression cassettes. For example, the nucleotide sequence encoding a presently disclosed RGN can be present on one expression cassette, whereas the nucleotide sequence encoding a crRNA, tracrRNA, or complete guide RNA can be on a separate expression cassette. Such an expression cassette is provided with a plurality of restriction sites and/or recombination sites for insertion of the polynucleotides to be under the transcriptional regulation of the regulatory regions. The expression cassette may additionally contain a selectable marker gene.

The expression cassette will include in the 5'-3' direction of transcription, a transcriptional (and, in some embodiments, translational) initiation region (i.e., a promoter), an RGN-, RNA-guided, DNA-binding polypeptide-deaminase fusion-, deaminase-, crRNA-, tracrRNA- and/or sgRNA-encoding polynucleotide of the invention, and a transcriptional (and in some embodiments, translational) termination region (i.e., termination region) functional in the organism of interest. The promoters of the invention are capable of directing or driving expression of a coding sequence in a host cell. The regulatory regions (e.g., promoters, transcriptional regulatory regions, and translational termination regions) may be endogenous or heterologous to the host cell or to each other. As used herein, "heterologous" in reference to a sequence is a sequence that originates from a foreign species, or, if from the same species, is substantially modified from its native form in composition and/or genomic locus by deliberate human intervention. As used herein, a chimeric gene comprises a coding sequence operably linked to a transcription initiation region that is heterologous to the coding sequence.

Convenient termination regions are available from the Ti-plasmid of *A. tumefaciens*, such as the octopine synthase and nopaline synthase termination regions. See also Guerineau et al. (1991) *Mol. Gen. Genet.* 262:141-144; Proudfoot (1991) *Cell* 64:671-674; Sanfacon et al. (1991) *Genes Dev.* 5:141-149; Mogen et al. (1990) *Plant Cell* 2:1261-1272; Munroe et al. (1990) *Gene* 91:151-158; Ballas et al. (1989) *Nucleic Acids Res.* 17:7891-7903; and Joshi et al. (1987) *Nucleic Acids Res.* 15:9627-9639.

Additional regulatory signals include, but are not limited to, transcriptional initiation start sites, operators, activators, enhancers, other regulatory elements, ribosomal binding sites, an initiation codon, termination signals, and the like. See, for example, U.S. Pat. Nos. 5,039,523 and 4,853,331; EPO 0480762A2; Sambrook et al. (1992) Molecular Cloning: A Laboratory Manual, ed. Maniatis et al. (Cold Spring Harbor Laboratory Press, Cold Spring Harbor, N.Y.), hereinafter "Sambrook 11"; Davis et al., eds. (1980) *Advanced Bacterial Genetics* (Cold Spring Harbor Laboratory Press), Cold Spring Harbor, N.Y., and the references cited therein.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites, or the like. For this purpose, in vitro mutagenesis, primer repair, restriction, annealing, resubstitutions, e.g., transitions and transversions, may be involved.

A number of promoters can be used in the practice of the invention. The promoters can be selected based on the desired outcome. The nucleic acids can be combined with constitutive, inducible, growth stage-specific, cell type-specific, tissue-preferred, tissue-specific, or other promoters for expression in the organism of interest. See, for example, promoters set forth in WO 99/43838 and in U.S. Pat. Nos. 8,575,425; 7,790,846; 8,147,856; 8,586832; 7,772,369; 7,534,939; 6,072,050; 5,659,026; 5,608,149; 5,608,144; 5,604,121; 5,569,597; 5,466,785; 5,399,680; 5,268,463; 5,608,142; and 6,177,611; herein incorporated by reference.

For expression in plants, constitutive promoters also include CaMV 35S promoter (Odell et al. (1985) *Nature* 313:810-812); rice actin (McElroy et al. (1990) *Plant Cell* 2:163-171); ubiquitin (Christensen et al. (1989) *Plant Mol. Biol.* 12:619-632 and Christensen et al. (1992) *Plant Mol. Biol.* 18:675-689); pEMU (Last et al. (1991) *Theor. Appl. Genet.* 81:581-588); and MAS (Velten et al. (1984) *EMBO J* 3:2723-2730).

Examples of inducible promoters are the AdhI promoter which is inducible by hypoxia or cold stress, the Hsp70 promoter which is inducible by heat stress, the PPDK promoter and the pepcarboxylase promoter which are both inducible by light. Also useful are promoters which are chemically inducible, such as the In2-2 promoter which is safener induced (U.S. Pat. No. 5,364,780), the Axig1 promoter which is auxin induced and tapetum specific but also active in callus (PCT US01/22169), the steroid-responsive promoters (see, for example, the ERE promoter which is estrogen induced, and the glucocorticoid-inducible promoter in Schena et al. (1991) *Proc. Natl. Acad. Sci. USA* 88:10421-10425 and McNellis et al. (1998) *Plant J.* 14(2):247-257) and tetracycline-inducible and tetracycline-repressible promoters (see, for example, Gatz et al. (1991)*Mol. Gen. Genet.* 227:229-237, and U.S. Pat. Nos. 5,814,618 and 5,789,156), herein incorporated by reference.

Tissue-specific or tissue-preferred promoters can be utilized to target expression of an expression construct within a particular tissue. In certain embodiments, the tissue-specific or tissue-preferred promoters are active in plant tissue. Examples of promoters under developmental control in plants include promoters that initiate transcription preferentially in certain tissues, such as leaves, roots, fruit, seeds, or flowers. A "tissue specific" promoter is a promoter that initiates transcription only in certain tissues. Unlike constitutive expression of genes, tissue-specific expression is the result of several interacting levels of gene regulation. As such, promoters from homologous or closely related plant species can be preferable to use to achieve efficient and reliable expression of transgenes in particular tissues. In some embodiments, the expression comprises a tissue-preferred promoter. A "tissue preferred" promoter is a promoter that initiates transcription preferentially, but not necessarily entirely or solely in certain tissues.

In some embodiments, the nucleic acid molecules encoding a RGN, RNA-guided, DNA-binding polypeptide-deaminase fusion, deaminase, crRNA, and/or tracrRNA comprise a cell type-specific promoter. A "cell type specific" promoter is a promoter that primarily drives expression in certain cell types in one or more organs. Some examples of plant cells in which cell type specific promoters functional in plants may be primarily active include, for example, BETL cells, vascular cells in roots, leaves, stalk cells, and stem cells. The nucleic acid molecules can also include cell type preferred promoters. A "cell type preferred" promoter is a promoter that primarily drives expression mostly, but not necessarily entirely or solely in certain cell types in one or more organs. Some examples of plant cells in which cell type preferred promoters functional in plants may be preferentially active include, for example, BETL cells, vascular cells in roots, leaves, stalk cells, and stem cells.

The nucleic acid sequences encoding the RGNs, RNA-guided, DNA-binding polypeptide-deaminase fusions, deaminases, crRNAs, tracrRNAs, and/or sgRNAs can be operably linked to a promoter sequence that is recognized by a phage RNA polymerase for example, for in vitro mRNA synthesis. In such embodiments, the in vitro-transcribed RNA can be purified for use in the methods described herein. For example, the promoter sequence can be a T7, T3, or SP6 promoter sequence or a variation of a T7, T3, or SP6 promoter sequence. In such embodiments, the expressed protein and/or RNAs can be purified for use in the methods of genome modification described herein.

In certain embodiments, the polynucleotide encoding the RGN, RNA-guided, DNA-binding polypeptide-deaminase fusion, deaminase, crRNA, tracrRNA, and/or sgRNA also can be linked to a polyadenylation signal (e.g., SV40 polyA signal and other signals functional in plants) and/or at least one transcriptional termination sequence. Additionally, the sequence encoding the RGN, RNA-guided, DNA-binding polypeptide-deaminase fusion, or deaminase also can be linked to sequence(s) encoding at least one nuclear localization signal, at least one cell-penetrating domain, and/or at least one signal peptide capable of trafficking proteins to particular subcellular locations, as described elsewhere herein.

The polynucleotide encoding the RGN, RNA-guided, DNA-binding polypeptide-deaminase fusion, deaminase, crRNA, tracrRNA, and/or sgRNA can be present in a vector or multiple vectors. A "vector" refers to a polynucleotide composition for transferring, delivering, or introducing a nucleic acid into a host cell. Suitable vectors include plasmid vectors, phagemids, cosmids, artificial/mini-chromosomes, transposons, and viral vectors (e.g., lentiviral vectors, adeno-associated viral vectors, baculoviral vector). The vector can comprise additional expression control sequences (e.g., enhancer sequences, Kozak sequences, polyadenylation sequences, transcriptional termination sequences), selectable marker sequences (e.g., antibiotic resistance genes), origins of replication, and the like. Additional information can be found in "Current Protocols in Molecular Biology" Ausubel et al., John Wiley & Sons, New York, 2003 or "Molecular Cloning: A Laboratory Manual" Sambrook & Russell, Cold Spring Harbor Press, Cold Spring Harbor, N.Y., 3rd edition, 2001.

The vector can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D).

In some embodiments, the expression cassette or vector comprising the sequence encoding the RGN polypeptide, RNA-guided, DNA-binding polypeptide-deaminase fusion, or deaminase can further comprise a sequence encoding a crRNA and/or a tracrRNA, or the crRNA and tracrRNA combined to create a guide RNA. The sequence(s) encoding the crRNA and/or tracrRNA can be operably linked to at least one transcriptional control sequence for expression of the crRNA and/or tracrRNA in the organism or host cell of interest. For example, the polynucleotide encoding the crRNA and/or tracrRNA can be operably linked to a promoter sequence that is recognized by RNA polymerase III (Pol III). Examples of suitable Pol III promoters include, but are not limited to, mammalian U6, U3, H1, and 7SL RNA promoters and rice U6 and U3 promoters.

As indicated, expression constructs comprising nucleotide sequences encoding the RGN, RNA-guided, DNA-binding polypeptide-deaminase fusion, deaminase, crRNA, tracrRNA, and/or sgRNA can be used to transform organisms of interest. Methods for transformation involve introducing a nucleotide construct into an organism of interest. By "introducing" is intended to introduce the nucleotide construct to the host cell in such a manner that the construct gains access to the interior of the host cell. The methods of the invention do not require a particular method for introducing a nucleotide construct to a host organism, only that the nucleotide construct gains access to the interior of at least one cell of the host organism. The host cell can be a eukaryotic or prokaryotic cell. In particular embodiments, the eukaryotic host cell is a plant cell, a mammalian cell, or an insect cell. Methods for introducing nucleotide constructs into plants and other host cells are known in the art including, but not limited to, stable transformation methods, transient transformation methods, and virus-mediated methods.

The methods result in a transformed organism, such as a plant, including whole plants, as well as plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, pollen).

"Transgenic organisms" or "transformed organisms" or "stably transformed" organisms or cells or tissues refers to organisms that have incorporated or integrated a polynucleotide encoding a RGN, RNA-guided, DNA-binding polypeptide-deaminase fusion, deaminase, crRNA, and/or tracrRNA of the invention. It is recognized that other exogenous or endogenous nucleic acid sequences or DNA fragments may also be incorporated into the host cell. *Agrobacterium*- and biolistic-mediated transformation remain the two predominantly employed approaches for transformation of plant cells. However, transformation of a host cell may be performed by infection, transfection, microinjection, electroporation, microprojection, biolistics or particle bombardment, electroporation, silica/carbon fibers, ultrasound mediated, PEG mediated, calcium phosphate co-precipitation, polycation DMSO technique, DEAE dextran procedure, and viral mediated, liposome mediated and the like. Viral-mediated introduction of a polynucleotide encoding an RGN, RNA-guided, DNA-binding polypeptide-deaminase fusion, deaminase, crRNA, and/or tracrRNA includes retroviral, lentiviral, adenoviral, and adeno-associated viral mediated introduction and expression, as well as the use of Caulimoviruses, Geminiviruses, and RNA plant viruses.

Transformation protocols as well as protocols for introducing polypeptides or polynucleotide sequences into plants may vary depending on the type of host cell (e.g., monocot or dicot plant cell) targeted for transformation. Methods for transformation are known in the art and include those set forth in U.S. Pat. Nos. 8,575,425; 7,692,068; 8,802,934; 7,541,517; each of which is herein incorporated by reference. See, also, Rakoczy-Trojanowska, M. (2002) *Cell Mol Biol Lett.* 7:849-858; Jones et al. (2005) *Plant Methods* 1:5; Rivera et al. (2012) *Physics of Life Reviews* 9:308-345; Bartlett et al. (2008) *Plant Methods* 4:1-12; Bates, G. W. (1999) *Methods in Molecular Biology* 111:359-366; Binns and Thomashow (1988) *Annual Reviews in Microbiology* 42:575-606; Christou, P. (1992) *The Plant Journal* 2:275-281; Christou, P. (1995) *Euphytica* 85:13-27; Tzfira et al. (2004) *TRENDS in Genetics* 20:375-383; Yao et al. (2006) *Journal of Experimental Botany* 57:3737-3746; Zupan and Zambryski (1995) *Plant Physiology* 107:1041-1047; Jones et al. (2005) *Plant Methods* 1:5;

Transformation may result in stable or transient incorporation of the nucleic acid into the cell. "Stable transformation" is intended to mean that the nucleotide construct introduced into a host cell integrates into the genome of the host cell and is capable of being inherited by the progeny thereof. "Transient transformation" is intended to mean that a polynucleotide is introduced into the host cell and does not integrate into the genome of the host cell.

Methods for transformation of chloroplasts are known in the art. See, for example, Svab et al. (1990) *Proc. Nail. Acad. Sci. USA* 87:8526-8530; Svab and Maliga (1993) *Proc. Natl. Acad. Sci. USA* 90:913-917; Svab and Maliga (1993) *EMBO J* 12:601-606. The method relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) *Proc. Natl. Acad. Sci. USA* 91:7301-7305.

The cells that have been transformed may be grown into a transgenic organism, such as a plant, in accordance with conventional ways. See, for example, McCormick et al. (1986) *Plant Cell Reports* 5:81-84. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a nucleotide construct of the invention, for example, an expression cassette of the invention, stably incorporated into their genome.

Alternatively, cells that have been transformed may be introduced into an organism. These cells could have originated from the organism, wherein the cells are transformed in an ex vivo approach.

The sequences provided herein may be used for transformation of any plant species, including, but not limited to, monocots and dicots. Examples of plants of interest include, but are not limited to, corn (maize), sorghum, wheat, sunflower, tomato, crucifers, peppers, potato, cotton, rice, soybean, sugarbeet, sugarcane, tobacco, barley, and oilseed rape, *Brassica* sp., alfalfa, rye, millet, safflower, peanuts, sweet potato, cassaya, coffee, coconut, pineapple, citrus trees, cocoa, tea, banana, avocado, fig, guava, mango, olive, *papaya*, cashew, macadamia, almond, oats, vegetables, ornamentals, and conifers.

Vegetables include, but are not limited to, tomatoes, lettuce, green beans, lima beans, peas, and members of the genus *Curcumis* such as cucumber, cantaloupe, and musk melon. Ornamentals include, but are not limited to, azalea, *hydrangea*, hibiscus, roses, tulips, daffodils, petunias, carnation, poinsettia, and *chrysanthemum*. Preferably, plants of the present invention are crop plants (for example, maize, sorghum, wheat, sunflower, tomato, crucifers, peppers, potato, cotton, rice, soybean, sugarbeet, sugarcane, tobacco, barley, oilseed rape, etc.).

As used herein, the term plant includes plant cells, plant protoplasts, plant cell tissue cultures from which plants can be regenerated, plant calli, plant clumps, and plant cells that are intact in plants or parts of plants such as embryos, pollen, ovules, seeds, leaves, flowers, branches, fruit, kernels, ears, cobs, husks, stalks, roots, root tips, anthers, and the like. Grain is intended to mean the mature seed produced by commercial growers for purposes other than growing or reproducing the species. Progeny, variants, and mutants of the regenerated plants are also included within the scope of the invention, provided that these parts comprise the introduced polynucleotides. Further provided is a processed plant product or byproduct that retains the sequences disclosed herein, including for example, soymeal.

The polynucleotides encoding the RGNs, RNA-guided, DNA-binding polypeptide-deaminase fusions, deaminases, crRNAs, and/or tracrRNAs can also be used to transform any prokaryotic species, including but not limited to, archaea and bacteria (e.g., *Bacillus* sp., *Klebsiella* sp. *Streptomyces* sp., *Rhizobium* sp., *Escherichia* sp., *Pseudomonas* sp., *Salmonella* sp., *Shigella* sp., *Vibrio* sp., *Yersinia* sp., *Mycoplasma* sp., *Agrobacterium*, *Lactobacillus* sp.).

The polynucleotides encoding the RGNs, RNA-guided, DNA-binding polypeptide-deaminase fusions, deaminases, crRNAs, and/or tracrRNAs can be used to transform any eukaryotic species, including but not limited to animals (e.g., mammals, insects, fish, birds, and reptiles), fungi, amoeba, algae, and yeast. Conventional viral and non-viral based gene transfer methods can be used to introduce nucleic acids in mammalian cells or target tissues. Such methods can be used to administer nucleic acids encoding components of a CRISPR system to cells in culture, or in a host organism. Non-viral vector delivery systems include DNA plasmids, RNA (e.g. a transcript of a vector described herein), naked nucleic acid, and nucleic acid complexed with a delivery vehicle, such as a liposome. Viral vector delivery systems include DNA and RNA viruses, which have either episomal or integrated genomes after delivery to the cell. For a review of gene therapy procedures, see Anderson, *Science* 256: 808-813 (1992); Nabel & Feigner, *TIBTECH* 11:211-217 (1993); Mitani & Caskey, *TIBTECH* 11:162-166 (1993); Dillon, *TIBTECH* 11:167-175 (1993); Miller, *Nature* 357:455-460 (1992); Van Brunt, *Biotechnology* 6(10): 1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology*, Doerfler and Bohm (eds) (1995); and Yu et al., *Gene Therapy* 1:13-26 (1994).

Methods of non-viral delivery of nucleic acids include lipofection, nucleofection, microinjection, biolistics, virosomes, liposomes, immunoliposomes, polycation or lipid:nucleic acid conjugates, naked DNA, artificial virions, and agent-enhanced uptake of DNA. Lipofection is described in e.g., U.S. Pat. Nos. 5,049,386, 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Feigner, WO 91/17424; WO 91/16024. Delivery can be to cells (e.g. in vitro or ex vivo administration) or target tissues (e.g. in vivo administration). The preparation of lipid:nucleic acid complexes, including targeted liposomes such as immunolipid complexes, is well known to one of skill in the art (see, e.g., Crystal, Science 270:404-410 (1995); Blaese et al., Cancer Gene Ther. 2:291-297 (1995); Behr et al., Bioconjugate Chem. 5:382-389 (1994); Remy et al., Bioconjugate Chem. 5:647-654 (1994); Gao et al., Gene Therapy 2:710-722 (1995); Ahmad et al., Cancer Res. 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids takes advantage of highly evolved processes for targeting a virus to specific cells in the body and trafficking the viral payload to the nucleus. Viral vectors can be administered directly to patients (in vivo) or they can be used to treat cells in vitro, and the modified cells may optionally be administered to patients (ex vivo). Conventional viral based systems could include retroviral, lentivirus, adenoviral, adeno-associated and herpes simplex virus vectors for gene transfer. Integration in the host genome is possible with the retrovirus, lentivirus, and adeno-associated virus gene transfer methods, often resulting in long term expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system would therefore depend on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immuno deficiency virus (SIV), human immuno deficiency virus (HIV), and combinations thereof (see, e.g., Buchscher et al., J. Viral. 66:2731-2739 (1992); Johann et al., J. Viral. 66:1635-1640 (1992); Sommnerfelt et al., Viral. 176:58-59 (1990); Wilson et al., J. Viral. 63:2374-2378 (1989); Miller et al., 1. Viral. 65:2220-2224 (1991); PCT/US94/05700).

In applications where transient expression is preferred, adenoviral based systems may be used. Adenoviral based vectors are capable of very high transduction efficiency in many cell types and do not require cell division. With such vectors, high titer and levels of expression have been obtained. This vector can be produced in large quantities in a relatively simple system. Adeno-associated virus ("AAV") vectors may also be used to transduce cells with target nucleic acids, e.g., in the in vitro production of nucleic acids and peptides, and for in vivo and ex vivo gene therapy procedures (see, e.g., West et al., Virology 160:38-47 (1987); U.S. Pat. No. 4,797,368; WO 93/24641; Katin, Human Gene Therapy 5:793-801 (1994); Muzyczka, J. Clin. Invest. 94:1351 (1994). Construction of recombinant AAV vectors are described in a number of publications, including U.S. Pat. No. 5,173,414; Tratschin et al., Mol. Cell. Biol. 5:3251-3260 (1985); Tratschin, et al., Mol. Cell. Biol. 4:2072-2081 (1984); Hermonat & Muzyczka, PNAS 81:6466-6470 (1984); and Samulski et al., J. Viral. 63:03822-3828 (1989). Packaging cells are typically used to form virus particles that are capable of infecting a host cell. Such cells include 293 cells, which package adenovirus, and ψJ2 cells or PA317 cells, which package retrovirus.

Viral vectors used in gene therapy are usually generated by producing a cell line that packages a nucleic acid vector into a viral particle. The vectors typically contain the minimal viral sequences required for packaging and subsequent integration into a host, other viral sequences being replaced by an expression cassette for the polynucleotide(s) to be expressed. The missing viral functions are typically supplied in trans by the packaging cell line. For example, AAV vectors used in gene therapy typically only possess ITR sequences from the AAV genome which are required for packaging and integration into the host genome. Viral DNA is packaged in a cell line, which contains a helper plasmid encoding the other AAV genes, namely rep and cap, but lacking ITR sequences.

The cell line may also be infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV. Additional methods for the delivery of nucleic acids to cells are known to those skilled in the art. See, for example, US20030087817, incorporated herein by reference.

In some embodiments, a host cell is transiently or non-transiently transfected with one or more vectors described herein. In some embodiments, a cell is transfected as it naturally occurs in a subject. In some embodiments, a cell that is transfected is taken from a subject. In some embodiments, the cell is derived from cells taken from a subject, such as a cell line. A wide variety of cell lines for tissue culture are known in the art. Examples of cell lines include, but are not limited to, C8161, CCRF-CEM, MOLT, mIMCD-3, NHDF, HeLaS3, Huh1, Huh4, Huh7, HUVEC, HASMC, HEKn, HEKa, MiaPaCell, Panel, PC-3, TF1, CTLL-2, CIR, Rat6, CVI, RPTE, AlO, T24, 182, A375, ARH-77, Calul, SW480, SW620, SKOV3, SK-UT, CaCo2, P388Dl, SEM-K2, WEHI-231, HB56, TIB55, lurkat, 145.01, LRMB, Bcl-1, BC-3, IC21, DLD2, Raw264.7, NRK, NRK-52E, MRC5, MEF, Hep G2, HeLa B, HeLa T4. COS, COS-1, COS-6, COS-M6A, BS-C-1 monkey kidney epithelial, BALB/3T3 mouse embryo fibroblast, 3T3 Swiss, 3T3-L1, 132-d5 human fetal fibroblasts; 10.1 mouse fibroblasts, 293-T, 3T3, 721, 9L, A2780, A2780ADR, A2780cis, A172, A20, A253, A431, A-549, ALC, B16, B35, BCP-I cells, BEAS-2B, bEnd.3, BHK-21, BR 293, BxPC3, C3H-10T1/2, C6/36, Cal-27, CHO, CHO-7, CHO-IR, CHO-K1, CHO-K2, CHO–T, CHO Dhfr–/–, COR-L23, COR-L23/CPR, COR-L235010, CORL23/R23, COS-7, COV-434, CML Tl, CMT, CT26, D17, DH82, DU145, DuCaP, EL4, EM2, EM3, EMT6/AR1, EMT6/AR10.0, FM3, H1299, H69, HB54, HB55, HCA2, HEK-293, HeLa, Hepalclc7, HL-60, HMEC, HT-29, lurkat, lY cells, K562 cells, Ku812, KCL22, KG1, KYO1, LNCap, Ma-Mel 1-48, MC-38, MCF-7, MCF-10A, MDA-MB-231, MDA-MB-468, MDA-MB-435, MDCKII, MDCKII, MOR/0.2R, MONO-MAC 6, MTD-1A, MyEnd, NCI-H69/CPR, NCI-H69/LX10, NCI-H69/LX20, NCI-H69/LX4, NIH-3T3, NALM-1, NW-145, OPCN/OPCT cell lines, Peer, PNT-1A/PNT 2, RenCa, RIN-5F, RMA/RMAS, Saos-2 cells, Sf-9, SkBr3, T2, T-47D, T84, THP1 cell line, U373, U87, U937, VCaP, Vero cells, WM39, WT-49, X63, YAC-1, YAR, and transgenic varieties thereof. Cell lines are available from a variety of sources known to those with skill in the art (see, e.g., the American Type Culture Collection (ATCC) (Manassas, Va.)).

In some embodiments, a cell transfected with one or more vectors described herein is used to establish a new cell line comprising one or more vector-derived sequences. In some embodiments, a cell transiently transfected with the components of a CRISPR system or deaminase or fusion thereof as described herein (such as by transient transfection of one or more vectors, or transfection with RNA), and modified through the activity of a CRISPR complex or deaminase, is used to establish a new cell line comprising cells containing the modification but lacking any other exogenous sequence. In some embodiments, cells transiently or non-transiently transfected with one or more vectors described herein, or cell lines derived from such cells are used in assessing one or more test compounds.

In some embodiments, one or more vectors described herein are used to produce a non-human transgenic animal or transgenic plant. In some embodiments, the transgenic animal is a mammal, such as a mouse, rat, or rabbit. In some embodiments, transgenic human cells are produced.

V. Variants and Fragments of Polypeptides and Polynucleotides

The present disclosure provides active variants and fragments of naturally-occurring (i.e., wild-type) RNA-guided nucleases and deaminases, the amino acid sequences of which are set forth as SEQ ID NOs: 1, 16, 24, 35, 43, 50, 374-545, 572-590, and active variants thereof, as well as active variants and fragments of naturally-occurring CRISPR repeats, such as the sequence set forth as SEQ ID NOs: 2, 17, 25, 36, 44, 51, or 63, and active variant and fragments of naturally-occurring tracrRNAs, such as the sequence set forth as SEQ ID NOs: 3, 18, 26, 37, 45, 52, or 62, and polynucleotides encoding the same. Also provided are active variants and fragments of deaminases, such as the sequences set forth as SEQ ID NOs: 374-545 and 572-584.

While the activity of a variant or fragment may be altered compared to the polynucleotide or polypeptide of interest, the variant and fragment should retain the functionality of the polynucleotide or polypeptide of interest. For example, a variant or fragment may have increased activity, decreased activity, different spectrum of activity or any other alteration in activity when compared to the polynucleotide or polypeptide of interest.

Fragments and variants of naturally-occurring RGN polypeptides, such as those disclosed herein, will retain sequence-specific, RNA-guided DNA-binding activity. In particular embodiments, fragments and variants of naturally-occurring RGN polypeptides, such as those disclosed herein, will retain nuclease activity (single-stranded or double-stranded). In other embodiments, fragments and variants of naturally-occurring deaminases, such as those disclosed herein, will retain deaminase activity. In some embodiments, the deaminase variants have altered activity, such as for example activity on DNA templates, or activity on nucleotides different from the native deaminase, such as for example activity on adenosine.

Fragments and variants of naturally-occurring CRISPR repeats, such as those disclosed herein, will retain the ability, when part of a guide RNA (comprising a tracrRNA), to bind to and guide an RNA-guided nuclease (complexed with the guide RNA) to a target nucleotide sequence in a sequence-specific manner.

Fragments and variants of naturally-occurring tracrRNAs, such as those disclosed herein, will retain the ability, when part of a guide RNA (comprising a CRISPR RNA), to guide an RNA-guided nuclease (complexed with the guide RNA) to a target nucleotide sequence in a sequence-specific manner.

The term "fragment" refers to a portion of a polynucleotide or polypeptide sequence of the invention. "Fragments" or "biologically active portions" include polynucleotides comprising a sufficient number of contiguous nucleotides to retain the biological activity (i.e., binding to and directing an RGN in a sequence-specific manner to a target nucleotide sequence when comprised within a guideRNA). "Fragments" or "biologically active portions" include polypeptides comprising a sufficient number of contiguous amino acid residues to retain the biological activity (i.e., binding to a target nucleotide sequence in a sequence-specific manner when complexed with a guide RNA). Fragments of the RGN proteins include those that are shorter than the full-length sequences due to the use of an alternate downstream start site. A biologically active portion of an RGN protein can be a polypeptide that comprises, for example, 10, 25, 50, 100, 150, 200, 250, 300, 350, 400, 450, 500, 550, 600, 650, 700, 750, 800, 850, 900, 950, 1000, 1050 or more contiguous amino acid residues of SEQ ID NOs: 1, 16, 24, 35, 43, or 50. Such biologically active portions can be prepared by recombinant techniques and evaluated for sequence-specific, RNA-guided DNA-binding activity. A biologically active fragment of a CRISPR repeat sequence can comprise at least 8 contiguous nucleic acids of SEQ ID NOs: 2, 17, 25, 36, 44, 51, or 63. A biologically active portion of a CRISPR repeat sequence can be a polynucleotide that comprises, for example, 8, 9, 10, 11, 12, 13, 14, 15, 16, 17, 18, 19, or 20 contiguous nucleotides of SEQ ID NOs: 2, 17, 25, 36, 44, 51, or 63. A biologically active portion of a tracrRNA can be a polynucleotide that comprises, for example, 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80 or more contiguous nucleotides of SEQ ID NOs: 3, 18, 26, 37, 45, 52, or 62. A biologically active portion of a deaminase can be a polypeptide that comprises, for example, 10, 25, 50, 100, 150, 200 or more contiguous amino acid residues of any one of SEQ ID NOs: 374-545 and 572-584.

In general, "variants" is intended to mean substantially similar sequences. For polynucleotides, a variant comprises a deletion and/or addition of one or more nucleotides at one or more internal sites within the native polynucleotide and/or a substitution of one or more nucleotides at one or more sites in the native polynucleotide. As used herein, a "native" or "wild type" polynucleotide or polypeptide comprises a naturally occurring nucleotide sequence or amino acid sequence, respectively. For polynucleotides, conservative variants include those sequences that, because of the degeneracy of the genetic code, encode the native amino acid sequence of the gene of interest. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotides, such as those generated, for example, by using site-directed mutagenesis but which still encode the polypeptide or the polynucleotide of interest. Generally, variants of a particular polynucleotide disclosed herein will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide disclosed herein (i.e., the reference polynucleotide) can also be evaluated by comparison of the percent sequence identity between the polypeptide encoded by a variant polynucleotide and the polypeptide encoded by the reference polynucleotide. Percent sequence identity between any two polypeptides can be calculated using sequence alignment programs and parameters described elsewhere herein. Where any given pair of polynucleotides disclosed herein is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

In particular embodiments, the presently disclosed polynucleotides encode a deaminase polypeptide comprising an amino acid sequence having at least 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or greater identity to an amino acid sequence of any of SEQ ID NOs: 374-545 or 572-584. In certain embodiments, the deaminase has an amino acid sequence of at least 50%, at least 55%, at least 60%, at least 65%, at least 70%, at least 75%, at least 80%, at least 85%, at least 90%, at least 95%, at least 96%, at least 97%, at least 98%, or at least 99% identity to the amino acid sequence of any of SEQ ID NOs: 374, 383, 397, 399, 407, 408, 411, 414, 416, 420, 514, and 572-584. In some of these embodiments, the variant deaminase polypeptide has a certain level of sequence identity to any one of SEQ ID NOs: 572-584, wherein specific amino acid residues are unchanged from the parent sequence. For example, in some embodiments, a variant SEQ ID NO: 572 comprises a lysine at a position corresponding to position 102, a tyrosine at a position corresponding to position 104, and a threonine at a position corresponding to position 106 of SEQ ID NO: 572. In particular embodiments, a variant SEQ ID NO: 574 comprises a glutamic acid at a position corresponding to position 101, a serine at a position corresponding to position 103, and a lysine at a position corresponding to position 105 of SEQ ID NO: 574. In certain embodiments, a variant SEQ ID NO: 575 comprises a lysine at a position corresponding to position 101, a leucine at a position corresponding to position 103, and a glutamic acid at a position corresponding to position 105 of SEQ ID NO: 575. In some embodiments, a variant SEQ ID NO: 576 comprises an alanine at a position corresponding to position 105 and an argnine at a position corresponding to position 107 of SEQ ID NO: 576. In particular embodiments, a variant SEQ ID NO: 577 comprises a glycine at a position corresponding to position 102, a serine at a position corresponding to position 104, and an arginine at a position corresponding to position 106 of SEQ ID NO: 577. In certain embodiments, a variant SEQ ID NO: 578 comprises a serine at a position corresponding to position 105 and a threonine at a position corresponding to position 107 of SEQ ID NO: 578. In some embodiments, a variant SEQ ID NO: 579 comprises a serine at a position corresponding to position 102, a glutamine at a position corresponding to position 104, and a glycine at a position corresponding to position 106 of SEQ ID NO: 579. In particular embodiments, a variant SEQ ID NO: 580 comprises a glycine at a position corresponding to position 111 of SEQ ID NO: 580. In some embodiments, a variant SEQ ID NO: 581 comprises a glutamine at a position corresponding to position 104, a glycine at a position corresponding to position 106, and a glutamic acid at a position corresponding to position 108 of SEQ ID NO: 581. In certain embodiments, a variant SEQ ID NO: 582 comprises an arginine at a position corresponding to position 102, a tryptophan at a position corresponding to position 104, and a glutamic acid at a position corresponding to position 106 of SEQ ID NO: 582. In certain embodiments, a variant SEQ ID NO: 583 comprises an arginine at a position corresponding to position 104 and a serine at a position corresponding to position 106 of SEQ ID NO: 583. In particular embodiments, a variant SEQ ID NO: 584 comprises a phenylalanine at a position corresponding to position 110, a serine at a position corresponding to position 112, and a threonine at a position corresponding to position 114 of SEQ ID NO: 584.

A biologically active variant of a deaminase polypeptide of the invention may differ by as few as about 1-15 amino acid residues, as few as about 1-10, such as about 6-10, as few as 5, as few as 4, as few as 3, as few as 2, or as few as 1 amino acid residue. In specific embodiments, the polypeptides can comprise an N-terminal or a C-terminal truncation, which can comprise at least a deletion of 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, 1050 amino acids or more from either the N or C terminus of the polypeptide.

In other particular embodiments, the presently disclosed polynucleotides encode an RNA-guided nuclease polypeptide comprising an amino acid sequence having at least 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or greater identity to an amino acid sequence of SEQ ID NOs: 1, 16, 24, 35, 43, or 50.

A biologically active variant of an RGN or deaminase polypeptide of the invention may differ by as few as about 1-15 amino acid residues, as few as about 1-10, such as about 6-10, as few as 5, as few as 4, as few as 3, as few as 2, or as few as 1 amino acid residue. In specific embodiments, the polypeptides can comprise an N-terminal or a C-terminal truncation, which can comprise at least a deletion of 10, 15, 20, 25, 30, 35, 40, 45, 50, 55, 60, 65, 70, 75, 80, 85, 90, 95, 100, 150, 200, 250, 300, 350, 400, 450, 500, 550, 600, 650, 700, 750, 800, 850, 900, 950, 1000, 1050 amino acids or more from either the N or C terminus of the polypeptide.

In certain embodiments, the presently disclosed polynucleotides comprise or encode a CRISPR repeat comprising a nucleotide sequence having at least 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or greater identity to the nucleotide sequence set forth as SEQ ID NOs: 2, 17, 25, 36, 44, 51, or 63.

The presently disclosed polynucleotides can comprise or encode a tracrRNA comprising a nucleotide sequence having at least 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99%, or greater identity to the nucleotide sequence set forth as SEQ ID NOs: 3, 18, 26, 37, 45, 52, or 62.

Biologically active variants of a CRISPR repeat or tracrRNA of the invention may differ by as few as about 1-25 nucleotides, as few as about 1-20, as few as about 1-10, as few as about 6-10, as few as 5, as few as 4, as few as 3, as few as 2, or as few as 1 nucleotide. In some embodiments, the polynucleotides can comprise a 5' or 3' truncation, which can comprise at least a deletion of 10, 15, 20, 25, 30, 35, 40, 45, 50, 55, 60, 65, 70, 75, 80 nucleotides or more from either the 5' or 3' end of the polynucleotide. In some embodiments, a CRISPR repeat or a tracrRNA may be altered by both deletion and/or insertion and also by mutation or substitution of nucleotides.

It is recognized that modifications may be made to the RGN polypeptides, DNA-binding polypeptide-deaminase fusion polypeptides, deaminase polypeptides, CRISPR repeats, and tracrRNAs provided herein creating variant proteins and polynucleotides. Changes designed by man may be introduced through the application of site-directed mutagenesis techniques. Alternatively, native, as yet-unknown or as yet unidentified polynucleotides and/or polypeptides structurally and/or functionally-related to the sequences disclosed herein may also be identified that fall within the scope of the present invention. Conservative amino acid substitutions may be made in nonconserved regions that do not alter the function of the RGN or deaminase proteins. Alternatively, modifications may be made that improve or alter the activity of the RGN or deaminase.

Variant polynucleotides and proteins also encompass sequences and proteins derived from a mutagenic and recombinogenic procedure such as DNA shuffling. With such a procedure, one or more different RGN or deaminase proteins disclosed herein (e.g., SEQ ID NOs: 1, 16, 24, 35, 43, 50, 374-545, and 572-584) is manipulated to create a new RGN or deaminase protein possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the RGN sequences provided herein and other known RGN genes to obtain a new gene coding for a protein with an improved property of interest, such as an increased $K_m$ in the case of an enzyme. The deaminases provided herein may also be shuffled in a similar strategy. Strategies for such DNA shuffling are known in the art. See, for example, Stemmer (1994) *Proc. Natl. Acad. Sci. USA* 91:10747-10751; Stemmer (1994) *Nature* 370:389-391; Crameri et al. (1997) *Nature Biotech.* 15:436-438; Moore et al. (1997) *J. Mol. Biol.* 272:336-347; Zhang et al. (1997) *Proc. Natl. Acad. Sci. USA* 94:4504-4509; Crameri et al. (1998) *Nature* 391:288-291; and U.S. Pat. Nos. 5,605,793 and 5,837,458. A "shuffled" nucleic acid is a nucleic acid produced by a shuffling procedure such as any shuffling procedure set forth herein. Shuffled nucleic acids are produced by recombining (physically or virtually) two or more nucleic acids (or character strings), for example in an artificial, and optionally recursive, fashion. Generally, one or more screening steps are used in shuffling processes to identify nucleic acids of interest; this screening step can be performed before or after any recombination step. In some (but not all) shuffling embodiments, it is desirable to perform multiple rounds of recombination prior to selection to increase the diversity of the pool to be screened. The overall process of recombination and selection are optionally repeated recursively. Depending on context, shuffling can refer to an overall process of recombination and selection, or, alternately, can simply refer to the recombinational portions of the overall process.

As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically, this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, California).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

Two sequences are "optimally aligned" when they are aligned for similarity scoring using a defined amino acid substitution matrix (e.g., BLOSUM62), gap existence penalty and gap extension penalty so as to arrive at the highest score possible for that pair of sequences. Amino acid substitution matrices and their use in quantifying the similarity between two sequences are well-known in the art and described, e.g., in Dayhoff et al. (1978) "A model of evolutionary change in proteins." In "Atlas of Protein Sequence and Structure," Vol. 5, Suppl. 3 (ed. M. O. Dayhoff), pp. 345-352. Natl. Biomed. Res. Found., Washington, D.C. and Henikoff et al. (1992) *Proc. Natl. Acad. Sci. USA* 89:10915-10919. The BLOSUM62 matrix is often used as a default scoring substitution matrix in sequence alignment protocols. The gap existence penalty is imposed for the introduction of a single amino acid gap in one of the aligned sequences, and the gap extension penalty is imposed for each additional empty amino acid position inserted into an already opened gap. The alignment is defined by the amino acids positions of each sequence at which the alignment begins and ends, and optionally by the insertion of a gap or multiple gaps in one or both sequences, so as to arrive at the highest possible score. While optimal alignment and scoring can be accomplished manually, the process is facilitated by the use of a computer-implemented alignment algorithm, e.g., gapped BLAST 2.0, described in Altschul et al. (1997) *Nucleic Acids Res.* 25:3389-3402, and made available to the public at the National Center for Biotechnology Information Website (www.ncbi.nlm.nih.gov). Optimal alignments, including multiple alignments, can be prepared using, e.g., PSI-BLAST, available through www.ncbi.nlm.nih.gov and described by Altschul et al. (1997) *Nucleic Acids Res.* 25:3389-3402.

With respect to an amino acid sequence that is optimally aligned with a reference sequence, an amino acid residue "corresponds to" the position in the reference sequence with which the residue is paired in the alignment. The "position" is denoted by a number that sequentially identifies each amino acid in the reference sequence based on its position relative to the N-terminus. Owing to deletions, insertion, truncations, fusions, etc., that must be taken into account when determining an optimal alignment, in general the amino acid residue number in a test sequence as determined by simply counting from the N-terminal will not necessarily be the same as the number of its corresponding position in the reference sequence. For example, in a case where there is a deletion in an aligned test sequence, there will be no amino acid that corresponds to a position in the reference sequence at the site of deletion. Where there is an insertion in an aligned reference sequence, that insertion will not correspond to any amino acid position in the reference sequence. In the case of truncations or fusions there can be stretches of amino acids in either the reference or aligned sequence that do not correspond to any amino acid in the corresponding sequence.

VI. Antibodies

Antibodies to the RGN polypeptides, ribonucleoproteins comprising the RGN polypeptides of the present invention, deaminases, or DNA-binding deaminase fusion proteins, including those comprising the amino acid sequence set forth as SEQ ID NOs: 1, 16, 24, 35, 43, 50, 374-545, and 572-584, or active variants or fragments thereof, are also encompassed. Methods for producing antibodies are well known in the art (see, for example, Harlow and Lane (1988) Antibodies: A Laboratory Manual, Cold Spring Harbor Laboratory, Cold Spring Harbor, N.Y.; and U.S. Pat. No. 4,196,265). These antibodies can be used in kits for the detection and isolation of RGN polypeptides or ribonucleoproteins. Thus, this disclosure provides kits comprising antibodies that specifically bind to the polypeptides or ribonucleoproteins described herein, including, for example, polypeptides having the sequence of any one of SEQ ID NOs: 1, 16, 24, 35, 43, 50, 374-545, and 572-584.

VII. Systems and Ribonucleoprotein Complexes for Binding a Target Sequence of Interest and Methods of Making the Same The present disclosure provides a system for binding a target sequence of interest, wherein the system comprises at least one guide RNA or a nucleotide sequence encoding the same, and at least one RNA-guided nuclease or a nucleotide sequence encoding the same. The guide RNA hybridizes to the target sequence of interest and also forms a complex with the RGN polypeptide, thereby directing the RGN polypeptide to bind to the target sequence. In some of these embodiments, the RGN comprises an amino acid sequence of SEQ ID NOs: 1, 16, 24, 35, 43, or 50, or an active variant or fragment thereof. In various embodiments, the guide RNA comprises a CRISPR repeat sequence comprising the nucleotide sequence of SEQ ID NOs: 2, 17, 25, 36, 44, 51, or 63, or an active variant or fragment thereof. In particular embodiments, the guide RNA comprises a tracrRNA comprising a nucleotide sequence of SEQ ID NOs: 3, 18, 26, 37, 45, 52, or 62, or an active variant or fragment thereof. The guide RNA of the system can be a single guide RNA or a dual-guide RNA. In particular embodiments, the system comprises a RNA-guided nuclease that is heterologous to the guideRNA, wherein the RGN and guideRNA are not naturally complexed in nature.

The present disclosure also provides a system which targets to a nucleic acid sequence and modifies the target nucleic acid sequence. The RNA-guided, DNA-binding polypeptide, such as an RGN, and the gRNA are responsible for targeting the ribonucleopolypeptide complex to a nucleic acid sequence of interest; the deaminase polypeptide is responsible for modifying the targeted nucleic acid sequence. The guide RNA hybridizes to the target sequence of interest and also forms a complex with the RNA-guided, DNA-binding polypeptide, thereby directing the RNA-guided, DNA-binding polypeptide to bind to the target sequence. The RNA-guided, DNA-binding polypeptide is one domain of a fusion protein; the other domain is a deaminase described herein. In some embodiments, the RNA-guided, DNA-binding polypeptide is an RGN, such as a Cas9. In further embodiments, the RNA-guided, DNA-binding polypeptide comprises an amino acid sequence of SEQ ID NO: 568, 569, 547, 553, or an active variant or fragment thereof. Other examples of RNA-guided, DNA-binding polypeptides include RGNs such as those described in U.S. patent application Ser. No. 16/432,321 (herein incorporated in its entirety by reference). In some embodiments, the RNA-guided, DNA-binding polypeptide is a Type II CRISPR-Cas polypeptide, or an active variant or fragment thereof. In some embodiments, the RNA-guided, DNA-binding polypeptide is a Type V CRISPR-Cas polypeptide, or an active variant or fragment thereof. In other embodiments, the RNA-guided, DNA-binding polypeptide is a Type VI CRISPR-Cas polypeptide. In other embodiments, the DNA-binding domain of the fusion protein does not require an RNA guide, such as a Zn finger nuclease, TALEN, or meganuclease polypeptide, wherein the nuclease activity of each has been inactivated.

The system for binding a target sequence of interest provided herein can be a ribonucleoprotein complex, which is at least one molecule of an RNA bound to at least one protein. In some embodiments, the ribonucleoprotein complexes provided herein comprise at least one guide RNA as the RNA component and an RNA-guided nuclease as the protein component. Such ribonucleoprotein complexes can be purified from a cell or organism that naturally expresses an RGN polypeptide and has been engineered to express a particular guide RNA that is specific for a target sequence of interest. In other embodiments, the ribonucleoprotein complexes provided herein comprise at least one guide RNA as the RNA component and a fusion protein comprising a deaminase of the invention and an RNA-guided, DNA-binding polypeptide as the protein component. In the case of fusion proteins, or in the case of an RGN of the invention, the ribonucleoprotein complex can be purified from a cell or organism that has been transformed with polynucleotides that encode the fusion protein (or an RGN of the invention alone) and a guide RNA and cultured under conditions to allow for the expression of the fusion protein (or an RGN of the invention alone) and guide RNA. Thus, methods are provided for making an RGN of the invention, a deaminase of the invention, a ribonucleoprotein complex comprising an RGN of the invention, a fusion protein of the invention, or a fusion protein ribonucleoprotein complex. Such methods comprise culturing a cell comprising a nucleotide sequence encoding a polypeptide of the invention, and in some embodiments a nucleotide sequence encoding a guide RNA, under conditions in which the polypeptide (and in some embodiments, the guide RNA) is expressed. The RGN of the invention, a ribonucleoprotein complex comprising an RGN of the invention, a fusion protein of the invention, or a fusion protein ribonucleoprotein complex can then be purified from a lysate of the cultured cells.

Methods for purifying an RGN of the invention, a deaminase of the invention, a ribonucleoprotein complex comprising an RGN of the invention, a fusion protein of the invention, or a fusion protein ribonucleoprotein complex from a lysate of a biological sample are known in the art (e.g., size exclusion and/or affinity chromatography, 2D-PAGE, HPLC, reversed-phase chromatography, immunoprecipitation). In particular methods, the polypeptide of the invention is recombinantly produced and comprises a purification tag to aid in its purification, including but not limited to, glutathione-S-transferase (GST), chitin binding protein (CBP), maltose binding protein, thioredoxin (TRX), poly(NANP), tandem affinity purification (TAP) tag, myc, AcV5, AU1, AU5, E, ECS, E2, FLAG, HA, nus, Softag 1, Softag 3, Strep, SBP, Glu-Glu, HSV, KT3, S, S1, T7, V5, VSV-G, 6×His (SEQ ID NO: 593), 10×His (SEQ ID NO: 594), biotin carboxyl carrier protein (BCCP), and calmodulin. Generally, the tagged polypeptide or ribonucleoprotein complex of the invention is purified using immobilized metal affinity chromatography. It will be appreciated that other similar methods known in the art may be used, including other forms of chromatography or for example immunoprecipitation, either alone or in combination.

An "isolated" or "purified" polypeptide, or biologically active portion thereof, is substantially or essentially free from components that normally accompany or interact with the polypeptide as found in its naturally occurring environment. Thus, an isolated or purified polypeptide is substantially free of other cellular material, or culture medium when produced by recombinant techniques, or substantially free of chemical precursors or other chemicals when chemically synthesized. A protein that is substantially free of cellular material includes preparations of protein having less than about 30%, 20%, 10%, 5%, or 1% (by dry weight) of contaminating protein. When the protein of the invention or biologically active portion thereof is recombinantly produced, optimally culture medium represents less than about 30%, 20%, 10%, 5%, or 1% (by dry weight) of chemical precursors or non-protein-of-interest chemicals.

Particular methods provided herein for binding and/or cleaving a target sequence of interest involve the use of an in vitro assembled RGN ribonucleoprotein complex. In vitro assembly of an RGN ribonucleoprotein complex can be performed using any method known in the art in which an RGN polypeptide is contacted with a guide RNA under conditions to allow for binding of the RGN polypeptide to the guide RNA. As used herein, "contact", contacting", "contacted," refer to placing the components of a desired reaction together under conditions suitable for carrying out the desired reaction. The RGN polypeptide can be purified from a biological sample, cell lysate, or culture medium, produced via in vitro translation, or chemically synthesized. The guide RNA can be purified from a biological sample, cell lysate, or culture medium, transcribed in vitro, or chemically synthesized. The RGN polypeptide and guide RNA can be brought into contact in solution (e.g., buffered saline solution) to allow for in vitro assembly of the RGN ribonucleoprotein complex.

VII. Methods of Binding, Cleaving, or Modifying a Target Sequence

The present disclosure provides methods for binding, cleaving, and/or modifying a target nucleotide sequence of interest. In some embodiments, the methods include delivering a system comprising at least one guide RNA or a polynucleotide encoding the same, and at least one RGN polypeptide or a polynucleotide encoding the same to the target sequence or a cell, organelle, or embryo comprising the target sequence. In some of these embodiments, the RGN comprises the amino acid sequence of SEQ ID NOs: 1, 16, 24, 35, 43, or 50, or an active variant or fragment thereof. In various embodiments, the guide RNA comprises a CRISPR repeat sequence comprising the nucleotide sequence of SEQ ID NOs: 2, 17, 25, 36, 44, 51, or 63, or an active variant or fragment thereof. In particular embodiments, the guide RNA comprises a tracrRNA comprising the nucleotide sequence of SEQ ID NOs: 3, 18, 26, 37, 45, 52, or 62, or an active variant or fragment thereof. The guide RNA of the system can be a single guide RNA or a dual-guide RNA. The RGN of the system may be nuclease dead RGN, have nickase activity, or may be a fusion polypeptide. In some embodiments, the fusion polypeptide comprises a base-editing polypeptide, for example a cytidine deaminase or an adenosine deaminase. In particular embodiments, the RGN and/or guide RNA is heterologous to the cell, organelle, or embryo to which the RGN and/or guide RNA (or polynucleotide(s) encoding at least one of the RGN and guide RNA) are introduced.

In other embodiments, the methods include delivering a system comprising at least one guide RNA or a polynucleotide encoding the same, and at least one fusion protein comprising a deaminase of the invention and an RNA-guided, DNA-binding polypeptide or a polynucleotide encoding the same to the target sequence or a cell, organelle, or embryo comprising the target sequence. In some of these embodiments, the fusion protein comprises any one of the amino acid sequences of SEQ ID NO: 374-545 or 572-584, or an active variant or fragment thereof.

In some embodiments, the methods comprise contacting a target polynucleotide with a deaminase disclosed herein. In some embodiments, the methods comprise contacting a target polynucleotide with a fusion protein comprising a deaminase domain and DNA-binding domain. In some of these embodiments, the methods comprise contacting a DNA molecule with (a) a fusion protein comprising a deaminase domain and a RNA-guided, DNA-binding polypeptide, such as for example a nuclease-inactive RGN domain; and (b) a gRNA targeting the fusion protein of (a) to a target nucleotide sequence of the DNA strand; wherein the DNA molecule is contacted with the fusion protein and the gRNA in an amount effective and under conditions suitable for the deamination of a nucleotide base. In some of those embodiments wherein a deaminase is utilized in the method, the deaminase has the amino acid sequence of any one of SEQ ID NOs: 374, 383, 397, 399, 407, 408, 411, 414, 416, 420, 514, and 572-584 or is a variant thereof, wherein the variant has an amino acid sequence of at least 50%, at least 55%, at least 60%, at least 65%, at least 70%, at least 75%, at least 80%, at least 85%, at least 90%, at least 95%, at least 96%, at least 97%, at least 98%, or at least 99% identity to the amino acid sequence of any of SEQ ID NOs: 374, 383, 397, 399, 407, 408, 411, 414, 416, 420, 514, and 572-584. In some of these embodiments, the variant deaminase polypeptide has a certain level of sequence identity to any one of SEQ ID NOs: 572-584, wherein specific amino acid residues are unchanged from the parent sequence. For example, in some embodiments, a variant SEQ ID NO: 572 comprises a lysine at a position corresponding to position 102, a tyrosine at a position corresponding to position 104, and a threonine at a position corresponding to position 106 of SEQ ID NO: 572. In particular embodiments, a variant SEQ ID NO: 574 comprises a glutamic acid at a position corresponding to position 101, a serine at a position corresponding to position 103, and a lysine at a position corresponding to position 105 of SEQ ID NO: 574. In certain embodiments, a variant SEQ ID NO: 575 comprises a lysine at a position corresponding to position 101, a leucine at a position corresponding to position 103, and a glutamic acid at a position corresponding to position 105 of SEQ ID NO: 575. In some embodiments, a variant SEQ ID NO: 576 comprises an alanine at a position corresponding to position 105 and an arginine at a position corresponding to position 107 of SEQ ID NO: 576. In particular embodiments, a variant SEQ ID NO: 577 comprises a glycine at a position corresponding to position 102, a serine at a position corresponding to position 104, and an arginine at a position corresponding to position 106 of SEQ ID NO: 577. In certain embodiments, a variant SEQ ID NO: 578 comprises a serine at a position corresponding to position 105 and a threonine at a position corresponding to position 107 of SEQ ID NO: 578. In some embodiments, a variant SEQ ID NO: 579 comprises a serine at a position corresponding to position 102, a glutamine at a position corresponding to position 104, and a glycine at a position corresponding to position 106 of SEQ ID NO: 579. In particular embodiments, a variant SEQ ID NO: 580 comprises a glycine at a position corresponding to position 111 of SEQ ID NO: 580. In some embodiments, a variant SEQ ID NO: 581 comprises a glutamine at a position corresponding to position 104, a glycine at a position corresponding to position 106, and a glutamic acid at a position corresponding to position 108 of SEQ ID NO: 581. In certain embodiments, a variant SEQ ID NO: 582 comprises an arginine at a position corresponding to position 102, a tryptophan at a position corresponding to position 104, and a glutamic acid at a position corresponding to position 106 of SEQ ID NO: 582. In certain embodiments, a variant SEQ ID NO: 583 comprises an arginine at a position corresponding to position 104 and a serine at a position corresponding to position 106 of SEQ ID NO: 583. In particular embodiments, a variant SEQ ID NO: 584 comprises a phenylalanine at a position corresponding to position 110, a serine at a position corresponding to position 112, and a threonine at a position corresponding to position 114 of SEQ ID NO: 584.

In some embodiments, the methods comprise contacting a DNA molecule with (a) a fusion protein comprising a deaminase domain and a RNA-guided, DNA-binding polypeptide, such as for example a nuclease-inactive RGN domain; and (b) a gRNA targeting the fusion protein of (a) to a target nucleotide sequence of the DNA strand; wherein the DNA molecule is contacted with the fusion protein and the gRNA in an amount effective and under conditions suitable for the deamination of a nucleotide base. In some embodiments, the target DNA sequence comprises a sequence associated with a disease or disorder, and wherein the deamination of the nucleotide base results in a sequence that is not associated with a disease or disorder. In some embodiments, the target DNA sequence resides in an allele of a crop plant, wherein the particular allele of the trait of interest results in a plant of lesser agronomic value. The deamination of the nucleotide base results in an allele that improves the trait and increases the agronomic value of the plant.

In some embodiments, the DNA sequence comprises a T→C or A→G point mutation associated with a disease or disorder, and wherein the deamination of the mutant C or G base results in a sequence that is not associated with a disease or disorder. In some embodiments, the deamination corrects a point mutation in the sequence associated with the disease or disorder.

In some embodiments, the sequence associated with the disease or disorder encodes a protein, and wherein the deamination introduces a stop codon into the sequence associated with the disease or disorder, resulting in a truncation of the encoded protein. In some embodiments, the contacting is performed in vivo in a subject susceptible to having, having, or diagnosed with the disease or disorder. In some embodiments, the disease or disorder is a disease associated with a point mutation, or a single-base mutation, in the genome. In some embodiments, the disease is a genetic disease, a cancer, a metabolic disease, or a lysosomal storage disease.

In those embodiments wherein the method comprises delivering a polynucleotide encoding a guide RNA and/or an RGN polypeptide or a fusion polypeptide comprising a deaminase of the invention and an RNA-guided, DNA-binding polypeptide, the cell or embryo can then be cultured under conditions in which the guide RNA and/or RGN polypeptide are expressed. In various embodiments, the method comprises contacting a target sequence with an RGN ribonucleoprotein complex. The RGN ribonucleoprotein complex may comprise an RGN that is nuclease dead or has nickase activity. In some embodiments, the RGN of the ribonucleoprotein complex is a fusion polypeptide comprising a base-editing polypeptide, such as for example a deaminase disclosed herein. In other embodiments, the ribonucleoprotein complex comprises a fusion polypeptide comprising a deaminase of the invention and an RNA-guided, DNA-binding polypeptide. In certain embodiments, the method comprises introducing into a cell, organelle, or embryo comprising a target sequence an RGN ribonucleoprotein complex. The RGN ribonucleoprotein complex can be one that has been purified from a biological sample, recombinantly produced and subsequently purified, or in vitro-assembled as described herein. In those embodiments wherein the RGN ribonucleoprotein complex that is contacted with the target sequence or a cell organelle, or embryo has been assembled in vitro, the method can further comprise the in vitro assembly of the complex prior to contact with the target sequence, cell, organelle, or embryo.

A purified or in vitro assembled RGN ribonucleoprotein complex can be introduced into a cell, organelle, or embryo using any method known in the art, including, but not limited to electroporation. Alternatively, an RGN polypeptide, a fusion polypeptide comprising a deaminase of the invention and an RNA-guided, DNA-binding polypeptide, and/or polynucleotide encoding or comprising the guide RNA can be introduced into a cell, organelle, or embryo using any method known in the art (e.g., electroporation).

Upon delivery to or contact with the target sequence or cell, organelle, or embryo comprising the target sequence, the guide RNA directs the RGN polypeptide or the fusion polypeptide to bind to the target sequence in a sequence-specific manner. In those embodiments wherein the RGN has nuclease activity, the RGN polypeptide cleaves the target sequence of interest upon binding. The target sequence can subsequently be modified via endogenous repair mechanisms, such as non-homologous end joining, or homology-directed repair with a provided donor polynucleotide.

Methods to measure binding of an RNA-guided, DNA-binding polypeptide to a target sequence are known in the art and include chromatin immunoprecipitation assays, gel mobility shift assays, DNA pull-down assays, reporter assays, microplate capture and detection assays. Likewise, methods to measure cleavage or modification of a target sequence are known in the art and include in vitro or in vivo cleavage assays wherein cleavage is confirmed using PCR, sequencing, or gel electrophoresis, with or without the attachment of an appropriate label (e.g., radioisotope, fluorescent substance) to the target sequence to facilitate detection of degradation products. Alternatively, the nicking triggered exponential amplification reaction (NTEXPAR) assay can be used (see, e.g., Zhang et al. (2016) *Chem. Sci.* 7:4951-4957). In vivo cleavage can be evaluated using the Surveyor assay (Guschin et al. (2010) *Methods Mol Biol* 649:247-256).

In some embodiments, the methods involve the use of a single type of RGN complexed with more than one guide RNA. The more than one guide RNA can target different regions of a single gene or can target multiple genes. In other embodiments, the methods involve the use of a single type of RNA-binding, DNA-guided domain, as part of the fusion protein, complexed with more than one guide RNA. This multiple targeting enables the deaminase domain of the fusion protein to modify nucleic acids, thereby introducing multiple mutations in the genome of interest.

In those embodiments wherein a donor polynucleotide is not provided, a double-stranded break introduced by an RGN polypeptide can be repaired by a non-homologous end-joining (NHEJ) repair process. Due to the error-prone nature of NHEJ, repair of the double-stranded break can result in a modification to the target sequence. As used herein, a "modification" in reference to a nucleic acid molecule refers to a change in the nucleotide sequence of the nucleic acid molecule, which can be a deletion, insertion, or substitution of one or more nucleotides, or a combination thereof. Modification of the target sequence can result in the expression of an altered protein product or inactivation of a coding sequence.

In those embodiments wherein a donor polynucleotide is present, the donor sequence in the donor polynucleotide can be integrated into or exchanged with the target nucleotide sequence during the course of repair of the introduced double-stranded break, resulting in the introduction of the exogenous donor sequence. A donor polynucleotide thus comprises a donor sequence that is desired to be introduced into a target sequence of interest. In some embodiments, the donor sequence alters the original target nucleotide sequence such that the newly integrated donor sequence will not be recognized and cleaved by the RGN. Integration of the donor sequence can be enhanced by the inclusion within the donor polynucleotide of flanking sequences that have substantial sequence identity with the sequences flanking the target nucleotide sequence, allowing for a homology-directed repair process. In those embodiments wherein the RGN polypeptide introduces double-stranded staggered breaks, the donor polynucleotide can comprise a donor sequence flanked by compatible overhangs, allowing for direct ligation of the donor sequence to the cleaved target nucleotide sequence comprising overhangs by a non-homologous repair process during repair of the double-stranded break.

In those embodiments wherein the method involves the use of an RGN of the invention that is a nickase (i.e., is only able to cleave a single strand of a double-stranded polynucleotide), the method can comprise introducing two RGN nickases that target identical or overlapping target sequences and cleave different strands of the polynucleotide. For example, an RGN nickase that only cleaves the positive (+) strand of a double-stranded polynucleotide can be introduced along with a second RGN nickase that only cleaves the negative (−) strand of a double-stranded polynucleotide. Similarly, in some embodiments, the method involves the use of a fusion polypeptide comprising a deaminase of the invention and an RNA-guided, DNA-binding polypeptide, such as for example and RGN, wherein the RGN is a nickase (for example SEQ ID NO: 569).

In various embodiments, a method is provided for binding a target nucleotide sequence and detecting the target sequence, wherein the method comprises introducing into a cell, organelle, or embryo at least one guide RNA or a polynucleotide encoding the same, and at least one RGN polypeptide or a polynucleotide encoding the same, expressing the guide RNA and/or RGN polypeptide (if coding sequences are introduced), wherein the RGN polypeptide is a nuclease-dead RGN and further comprises a detectable label, and the method further comprises detecting the detectable label. The detectable label may be fused to the RGN as a fusion protein (e.g., fluorescent protein) or may be a small molecule conjugated to or incorporated within the RGN polypeptide that can be detected visually or by other means.

Also provided herein are methods for modulating the expression of a target sequence or a gene of interest under the regulation of a target sequence. The methods comprise introducing into a cell, organelle, or embryo at least one guide RNA or a polynucleotide encoding the same, and at least one RGN polypeptide or a polynucleotide encoding the same, expressing the guide RNA and/or RGN polypeptide (if coding sequences are introduced), wherein the RGN polypeptide is a nuclease-dead RGN. In some of these embodiments, the nuclease-dead RGN is a fusion protein comprising an expression modulator domain (i.e., epigenetic modification domain, transcriptional activation domain or a transcriptional repressor domain) as described herein. In some embodiments, the nuclease-dead RGN is a fusion protein comprising a deaminase described herein.

The present disclosure also provides methods for binding and/or modifying a target nucleotide sequence of interest. The methods include delivering a system comprising at least one guide RNA or a polynucleotide encoding the same, and at least one fusion polypeptide comprises an RGN of the invention and a base-editing polypeptide, for example a deaminase described herein, or a polynucleotide encoding the fusion polypeptide, to the target sequence or a cell, organelle, or embryo comprising the target sequence.

One of ordinary skill in the art will appreciate that any of the presently disclosed methods can be used to target a single target sequence or multiple target sequences. Thus, methods comprise the use of a single RGN polypeptide in combination with multiple, distinct guide RNAs, which can target multiple, distinct sequences within a single gene and/or multiple genes. Also encompassed herein are methods wherein multiple, distinct guide RNAs are introduced in combination with multiple, distinct RGN polypeptides. These guide RNAs and guide RNA/RGN polypeptide systems can target multiple, distinct sequences within a single gene and/or multiple genes.

In one aspect, the invention provides kits containing any one or more of the elements disclosed in the above methods and compositions. In some embodiments, the kit comprises a vector system and instructions for using the kit. In some embodiments, the vector system comprises (a) a first regulatory element operably linked to a tracr mate sequence and one or more insertion sites for inserting a guide sequence upstream of the tracr mate sequence, wherein when expressed, the guide sequence directs sequence-specific binding of a CRISPR complex to a target sequence in a eukaryotic cell, wherein the CRISPR complex comprises a CRIS PR enzyme complexed with (1) the guide sequence that is hybridized to the target sequence, and (2) the tracr mate sequence that is hybridized to the tracr sequence; and/or (b) a second regulatory element operably linked to an enzyme coding sequence encoding said CRISPR enzyme comprising a nuclear localization sequence.

In some embodiments, the kit comprises a fusion protein comprising an RNA-guided, DNA-binding polypeptide, such as an RGN polypeptide, for example a nuclease-inactive Cas9 domain, and a deaminase of the invention, and, optionally, a linker positioned between the Cas9 domain and the deaminase. In addition, in some embodiments, the kit comprises suitable reagents, buffers, and/or instructions for using the fusion protein, e.g., for in vitro or in vivo DNA or RNA editing. Elements may be provided individually or in combinations, and may be provided in any suitable container, such as a vial, a bottle, or a tube. In some embodiments, the kit comprises instructions regarding the design and use of suitable gRNAs for targeted editing of a nucleic acid sequence.

In some embodiments, the kit includes instructions in one or more languages. In some embodiments, a kit comprises one or more reagents for use in a process utilizing one or more of the elements described herein. Reagents may be provided in any suitable container. For example, a kit may provide one or more reaction or storage buffers. Reagents may be provided in a form that is usable in a particular assay, or in a form that requires addition of one or more other components before use (e.g. in concentrate or lyophilized form). A buffer can be any buffer, including but not limited to a sodium carbonate buffer, a sodium bicarbonate buffer, a borate buffer, a Tris buffer, a MOPS buffer, a HEPES buffer, and combinations thereof. In some embodiments, the buffer is alkaline. In some embodiments, the buffer has a pH from about 7 to about 10.

In some embodiments, the kit comprises one or more oligonucleotides corresponding to a guide sequence for insertion into a vector so as to operably link the guide sequence and a regulatory element. In some embodiments, the kit comprises a homologous recombination template polynucleotide. In one aspect, the invention provides methods for using one or more elements of a CRISPR system. The CRISPR complex of the invention provides an effective means for modifying a target polynucleotide. The CRISPR complex of the invention has a wide variety of utility including modifying (e.g., deleting, inserting, translocating, inactivating, activating) a target polynucleotide in a multiplicity of cell types. As such the CRISPR complex of the invention has a broad spectrum of applications in, e.g., gene therapy, drug screening, disease diagnosis, and prognosis. An exemplary CRISPR complex comprises a CRISPR enzyme complexed with a guide sequence hybridized to a target sequence within the target polynucleotide.

VII. Target Polynucleotides

In one aspect, the invention provides for methods of modifying a target polynucleotide in a eukaryotic cell, which may be in vivo, ex vivo or in vitro. In some embodiments, the method comprises sampling a cell or population of cells from a human or non-human animal or plant (including microalgae) and modifying the cell or cells. Culturing may occur at any stage ex vivo. The cell or cells may even be re-introduced into the non-human animal or plant (including micro-algae).

Using natural variability, plant breeders combine most useful genes for desirable qualities, such as yield, quality, uniformity, hardiness, and resistance against pests. These desirable qualities also include growth, day length preferences, temperature requirements, initiation date of floral or reproductive development, fatty acid content, insect resistance, disease resistance, nematode resistance, fungal resistance, herbicide resistance, tolerance to various environmental factors including drought, heat, wet, cold, wind, and adverse soil conditions including high salinity The sources of these useful genes include native or foreign varieties, heirloom varieties, wild plant relatives, and induced mutations, e.g., treating plant material with mutagenic agents. Using the present invention, plant breeders are provided with a new tool to induce mutations. Accordingly, one skilled in the art can analyze the genome for sources of useful genes, and in varieties having desired characteristics or traits employ the present invention to induce the rise of useful genes, with more precision than previous mutagenic agents and hence accelerate and improve plant breeding programs.

The target polynucleotide of an RGN system can be any polynucleotide endogenous or exogenous to the eukaryotic cell. For example, the target polynucleotide can be a polynucleotide residing in the nucleus of the eukaryotic cell. The target polynucleotide can be a sequence coding a gene product (e.g., a protein) or a non-coding sequence (e.g., a regulatory polynucleotide or a junk DNA). Without wishing to be bound by theory, it is believed that the target sequence should be associated with a PAM (protospacer adjacent motif); that is, a short sequence recognized by the CRISPR complex. The precise sequence and length requirements for the PAM differ depending on the CRISPR enzyme used, but PAMs are typically 2-5 base pair sequences adjacent the protospacer (that is, the target sequence).

The target polynucleotide of a CRISPR complex may include a number of disease-associated genes and polynucleotides as well as signaling biochemical pathway-associated genes and polynucleotides. Examples of target polynucleotides include a sequence associated with a signaling biochemical pathway, e.g., a signaling biochemical pathway-associated gene or polynucleotide. Examples of target polynucleotides include a disease associated gene or polynucleotide. A "disease-associated" gene or polynucleotide refers to any gene or polynucleotide which is yielding transcription or translation products at an abnormal level or in an abnormal form in cells derived from a disease-affected tissues compared with tissues or cells of a non-disease control. It may be a gene that becomes expressed at an abnormally high level; it may be a gene that becomes expressed at an abnormally low level, where the altered expression correlates with the occurrence and/or progression of the disease. A disease-associated gene also refers to a gene possessing mutation(s) or genetic variation that is directly responsible or is in linkage disequilibrium with a gene(s) that is responsible for the etiology of a disease (e.g., a causal mutation). The transcribed or translated products may be known or unknown, and further may be at a normal or abnormal level. Examples of disease-associated genes and polynucleotides are available from McKusick-Nathans Institute of Genetic Medicine, Johns Hopkins University (Baltimore, Md.) and National Center for Biotechnology Information, National Library of Medicine (Bethesda, Md.), available on the World Wide Web.

Although CRISPR systems are particularly useful for their relative ease in targeting to genomic sequences of interest, there still remains an issue of what the RGN can do to address a causal mutation. One approach is to produce a fusion protein between an RGN (preferably an inactive or nickase variant of the RGN) and a base-editing enzyme or the active domain of a base editing enzyme, such as a cytidine deaminase or an adenosine deaminase base editor (U.S. Pat. No. 9,840,699, herein incorporated by reference). In some embodiments, the methods comprise contacting a DNA molecule with (a) a fusion protein comprising an RGN of the invention and a base-editing polypeptide such as a deaminase; and (b) a gRNA targeting the fusion protein of (a) to a target nucleotide sequence of the DNA strand; wherein the DNA molecule is contacted with the fusion protein and the gRNA in an amount effective and under conditions suitable for the deamination of a nucleotide base. In some embodiments, the target DNA sequence comprises a sequence associated with a disease or disorder, and wherein the deamination of the nucleotide base results in a sequence that is not associated with a disease or disorder. In some embodiments, the target DNA sequence resides in an allele of a crop plant, wherein the particular allele of the trait of interest results in a plant of lesser agronomic value. The deamination of the nucleotide base results in an allele that improves the trait and increases the agronomic value of the plant.

In some embodiments, the DNA sequence comprises a T4C or A4G point mutation associated with a disease or disorder, and wherein the deamination of the mutant C or G base results in a sequence that is not associated with a disease or disorder. In some embodiments, the deamination corrects a point mutation in the sequence associated with the disease or disorder.

In some embodiments, the sequence associated with the disease or disorder encodes a protein, and wherein the deamination introduces a stop codon into the sequence associated with the disease or disorder, resulting in a truncation of the encoded protein. In some embodiments, the contacting is performed in vivo in a subject susceptible to having, having, or diagnosed with the disease or disorder. In some embodiments, the disease or disorder is a disease associated with a point mutation, or a single-base mutation, in the genome. In some embodiments, the disease is a genetic disease, a cancer, a metabolic disease, or a lysosomal storage disease.

Further examples of loci which are causal for certain genetic diseases, particularly loci which can be readily targeted by RGNs or RGN-base editor fusion proteins of the invention, can be found in Example 7 and corresponding Table 8.

Hurler Syndrome

An example of a genetically inherited disease which could be corrected using an approach that relies on an RGN-base editor fusion protein of the invention is Hurler Syndrome. Hurler Syndrome, also known as MPS-1, is the result of a deficiency of α-L-iduronidase (IDUA) resulting in a lysosomal storage disease characterized at the molecular level by the accumulation of dermatan sulfate and heparan sulfate in lysosomes. This disease is generally an inherited genetic disorder caused by mutations in the IDUA gene encoding α-L-iduronidase. Common IDUA mutations are W402X and Q70X, both nonsense mutations resulting in premature termination of translation. Such mutations are well addressed by precise genome editing (PGE) approaches, since reversion of a single nucleotide, for example by a base-editing approach, would restore the wild-type coding sequence and result in protein expression controlled by the endogenous regulatory mechanisms of the genetic locus. Additionally, since heterozygotes are known to be asymptomatic, a PGE therapy that targets one of these mutations would be useful to a large proportion of patients with this disease, as only one of the mutated alleles needs to be corrected (Bunge et al. (1994) Hum. Mol. Genet. 3(6): 861-866, herein incorporated by reference).

Current treatments for Hurler Syndrome include enzyme replacement therapy and bone marrow transplants (Vellodi et al. (1997) Arch. Dis. Child. 76(2): 92-99; Peters et al. (1998) Blood 91(7): 2601-2608, herein incorporated by reference). While enzyme replacement therapy has had a dramatic effect on the survival and quality of life of Hurler Syndrome patients, this approach requires costly and time-consuming weekly infusions. Additional approaches include the delivery of the IDUA gene on an expression vector or the insertion of the gene into a highly expressed locus such as that of serum albumin (U.S. Pat. No. 9,956,247, herein incorporated by reference). However, these approaches do not restore the original IDUA locus to the correct coding sequence. A genome-editing strategy would have a number of advantages, most notably that regulation of gene expression would be controlled by the natural mechanisms present in healthy individuals. Additionally, using base editing does not necessitate causing a double stranded DNA breaks, which could lead to large chromosomal rearrangements, cell death, or oncogenecity by the disruption of tumor suppression mechanisms. An enabling description of a method to correct the causal mutation of this disease is provided in Example 8. The described methods are an example of a general strategy directed toward using RGN-base editor fusion proteins of the invention to target and correct certain disease-causing mutations in the human genome. It will be appreciated that similar approaches to target diseases such as those described in Table 8 may also be pursued. It will be further appreciated that similar approaches to target disease-causing mutations in other species, particularly common household pets or livestock, can also be deployed using the RGNs of the invention. Common household pets and livestock include dogs, cats, horses, pigs, cows, sheep, chickens, donkeys, snakes, ferrets, fish including salmon, and shrimp.

Friedreich's Ataxia

RGNs of the invention could also be useful in human therapeutic approaches where the causal mutation is more complicated. For example, some diseases such as Friedreich's Ataxia and Huntington's Disease are the result of a significant increase in repeats of a three nucleotide motif at a particular region of a gene, which affects the ability of the expressed protein to function or to be expressed. Friedreich's Ataxia (FRDA) is an autosomal recessive disease resulting in progressive degeneration of nervous tissue in the spinal cord. Reduced levels of the frataxin (FXN) protein in the mitochondria cause oxidative damages and iron deficiencies at the cellular level. The reduced FXN expression has been linked to a GAA triplet expansion within the intron 1 of the somatic and germline FXN gene. In FRDA patients, the GAA repeat frequently consists of more than 70, sometimes even more than 1000 (most commonly 600-900) triplets, whereas unaffected individuals have about 40 repeats or less (Pandolfo et al. (2012) Handbook of Clinical Neurology 103: 275-294; Campuzano et al. (1996) Science 271: 1423-1427; Pandolfo (2002) Adv. Exp. Med. Biol. 516: 99-118; all herein incorporated by reference).

The expansion of the trinucleotide repeat sequence causing Friedreich's Ataxia (FRDA) occurs in a defined genetic locus within the FXN gene, referred to as the FRDA instability region. RNA guided nucleases (RGNs) may be used for excising the instability region in FRDA patient cells. This approach requires 1) an RGN and guide RNA sequence that can be programmed to target the allele in the human genome; and 2) a delivery approach for the RGN and guide sequence. Many nucleases used for genome editing, such as the commonly used Cas9 nuclease from *S. pyogenes* (SpCas9), are too large to be packaged into adeno-associated viral (AAV) vectors, especially when considering the length of the SpCas9 gene and the guide RNA in addition to other genetic elements required for functional expression cassettes. This makes an approach using SpCas9 more difficult.

The compact RNA guided nucleases of the invention are uniquely well suited for the excision of the FRDA instability region. Each RGN has a PAM requirement that is in the vicinity of the FRDA instability region. Additionally, each of these RGNs can be packaged into an AAV vector along with a guide RNA. Packing two guide RNAs may require a second vector, but this approach still compares favorably to what would be required of a larger nuclease such as SpCas9, which may require splitting the protein sequence between two vectors. An enabling description of a method to correct the causal mutation of this disease is provided in Example 9. The described methods encompass a strategy using RGNs of the invention in which a region of genomic instability is removed. Such a strategy is applicable to other diseases and disorders which have a similar genetic basis, such as Huntington's Disease. Similar strategies using RGNs of the invention may also be applicable to similar diseases and disorders in non-human animals of agronomic or economic importance, including dogs, cats, horses, pigs, cows, sheep, chickens, donkeys, snakes, ferrets, fish including salmon, and shrimp. Hemoglobinopathies RGNs of the invention could also be used to introduce disruptive mutations that may result in a beneficial effect. Genetic defects in the genes encoding hemoglobin, particularly the beta globin chain (the HBB gene), can be responsible for a number of diseases known as hemoglobinopathies, including sickle cell anemia and thalassemias.

In adult humans, hemoglobin is a heterotetramer comprising two alpha (a)-like globin chains and two beta ($\beta$)-like globin chains and 4 heme groups. In adults the $\alpha 2\beta 2$ tetramer is referred to as Hemoglobin A (HbA) or adult hemoglobin. Typically, the alpha and beta globin chains are synthesized in an approximate 1:1 ratio and this ratio seems to be critical in terms of hemoglobin and red blood cell (RBC) stabilization. In a developing fetus, a different form of hemoglobin, fetal hemoglobin (HbF), is produced which has a higher binding affinity for oxygen than Hemoglobin A such that oxygen can be delivered to the baby's system via the mother's blood stream. Fetal hemoglobin also contains two a globin chains, but in place of the adult $\beta$-globin chains, it has two fetal gamma ($\gamma$)-globin chains (i.e., fetal hemoglobin is $\alpha 2\gamma 2$). The regulation of the switch from production of gamma- to beta-globin is quite complex, and primarily involves a down-regulation of gamma globin transcription with a simultaneous up-regulation of beta globin transcription. At approximately 30 weeks of gestation, the synthesis of gamma globin in the fetus starts to drop while the production of beta globin increases. By approximately 10 months of age, the newborn's hemoglobin is nearly all $\alpha 2\beta 2$ although some HbF persists into adulthood (approximately 1-3% of total hemoglobin). In the majority of patients with hemoglobinopathies, the genes encoding gamma globin remain present, but expression is relatively low due to normal gene repression occurring around parturition as described above.

Sickle cell disease is caused by a V6E mutation in the $\beta$ globin gene (HBB) (a GAG to GTG at the DNA level), where the resultant hemoglobin is referred to as "hemoglobinS" or "HbS." Under lower oxygen conditions, HbS molecules aggregate and form fibrous precipitates. These aggregates cause the abnormality or 'sickling' of the RBCs, resulting in a loss of flexibility of the cells. The sickling RBCs are no longer able to squeeze into the capillary beds and can result in vaso-occlusive crisis in sickle cell patients. In addition, sickled RBCs are more fragile than normal RBCs, and tend towards hemolysis, eventually leading to anemia in the patient.

Treatment and management of sickle cell patients is a life-long proposition involving antibiotic treatment, pain management and transfusions during acute episodes. One approach is the use of hydroxyurea, which exerts its effects in part by increasing the production of gamma globin. Long term side effects of chronic hydroxyurea therapy are still unknown, however, and treatment gives unwanted side effects and can have variable efficacy from patient to patient. Despite an increase in the efficacy of sickle cell treatments, the life expectancy of patients is still only in the mid to late 50's and the associated morbidities of the disease have a profound impact on a patient's quality of life.

Thalassemias (alpha thalassemias and beta thalassemia) are also diseases relating to hemoglobin and typically involve a reduced expression of globin chains. This can occur through mutations in the regulatory regions of the genes or from a mutation in a globin coding sequence that results in reduced expression or reduced levels or functional globin protein. Treatment of thalassemias usually involves blood transfusions and iron chelation therapy. Bone marrow transplants are also being used for treatment of people with severe thalassemias if an appropriate donor can be identified, but this procedure can have significant risks.

One approach that has been proposed for the treatment of both SCD and beta thalassemias is to increase the expression of gamma globin so that HbF functionally replaces the aberrant adult hemoglobin As mentioned above, treatment of SCD patients with hydroxyurea is thought to be successful in part due to its effect on increasing gamma globin expression (DeSimone (1982) Proc Nat'l Acad Sci USA 79(14):

4428-31; Ley, et al., (1982) N. Engl. J. Medicine, 307: 1469-1475; Ley, et al., (1983) Blood 62: 370-380; Constantoulakis et al., (1988) Blood 72(6):1961-1967, all herein incorporated by reference). Increasing the expression of HbF involves identification of genes whose products play a role in the regulation of gamma globin expression. One such gene is BCL11A. BCL11A encodes a zinc finger protein that expressed in adult erythroid precursor cells, and down-regulation of its expression leads to an increase in gamma globin expression (Sankaran et at (2008) Science 322: 1839, herein incorporated by reference). Use of an inhibitory RNA targeted to the BCL11A gene has been proposed (e.g., U.S. Patent Publication 2011/0182867, herein incorporated by reference) but this technology has several potential drawbacks, including that complete knock down may not be achieved, delivery of such RNAs may be problematic, and the RNAs must be present continuously, requiring multiple treatments for life.

RGNs of the invention may be used to target the BCL11A enhancer region to disrupt expression of BCL11A, thereby increasing gamma globin expression. This targeted disruption can be achieved by non-homologous end joining (NHEJ), whereby an RGN of the invention targets to a particular sequence within the BCL11A enhancer region, makes a double-stranded break, and the cell's machinery repairs the break, typically simultaneously introducing deleterious mutations. Similar to what is described for other disease targets, the RGNs of the invention have advantages over other known RGNs due to their relatively small size, which enables packaging expression cassettes for the RGN and its guide RNA into a single AAV vector for in vivo delivery. An enabling description of this method is provided in Example 10. Similar strategies using RGNs of the invention may also be applicable to similar diseases and disorders in both humans and in non-human animals of agronomic or economic importance.

IX. Cells Comprising a Polynucleotide Genetic Modification

Provided herein are cells and organisms comprising a target sequence of interest that has been modified using a process mediated by an RGN, crRNA, tracrRNA, and/or deaminase as described herein. In some of these embodiments, the RGN comprises the amino acid sequence of SEQ ID NOs: 1, 16, 24, 35, 43, or 50, or an active variant or fragment thereof. In various embodiments, the guide RNA comprises a CRISPR repeat sequence comprising the nucleotide sequence of SEQ ID NOs: 2, 17, 25, 36, 44, 51, or 63, or an active variant or fragment thereof. In particular embodiments, the guide RNA comprises a tracrRNA comprising the nucleotide sequence of SEQ ID NOs: 3, 18, 26, 37, 45, 52, or 62, or an active variant or fragment thereof. The guide RNA of the system can be a single guide RNA or a dual-guide RNA. In some embodiments, the deaminase comprises the amino acid sequence of any one of SEQ ID NOs: 374-545 and 572-584 or an active variant or fragment thereof.

The modified cells can be eukaryotic (e.g., mammalian, plant, insect cell) or prokaryotic. Also provided are organelles and embryos comprising at least one nucleotide sequence that has been modified by a process utilizing an RGN, crRNA, and/or tracrRNA as described herein. The genetically modified cells, organisms, organelles, and embryos can be heterozygous or homozygous for the modified nucleotide sequence.

The chromosomal modification of the cell, organism, organelle, or embryo can result in altered expression (up-regulation or down-regulation), inactivation, or the expression of an altered protein product or an integrated sequence. In those instances wherein the chromosomal modification results in either the inactivation of a gene or the expression of a non-functional protein product, the genetically modified cell, organism, organelle, or embryo is referred to as a "knock out". The knock out phenotype can be the result of a deletion mutation (i.e., deletion of at least one nucleotide), an insertion mutation (i.e., insertion of at least one nucleotide), or a nonsense mutation (i.e., substitution of at least one nucleotide such that a stop codon is introduced).

Alternatively, the chromosomal modification of a cell, organism, organelle, or embryo can produce a "knock in", which results from the chromosomal integration of a nucleotide sequence that encodes a protein. In some of these embodiments, the coding sequence is integrated into the chromosome such that the chromosomal sequence encoding the wild-type protein is inactivated, but the exogenously introduced protein is expressed.

In other embodiments, the chromosomal modification results in the production of a variant protein product. The expressed variant protein product can have at least one amino acid substitution and/or the addition or deletion of at least one amino acid. The variant protein product encoded by the altered chromosomal sequence can exhibit modified characteristics or activities when compared to the wild-type protein, including but not limited to altered enzymatic activity or substrate specificity.

In yet other embodiments, the chromosomal modification can result in an altered expression pattern of a protein. As a non-limiting example, chromosomal alterations in the regulatory regions controlling the expression of a protein product can result in the overexpression or downregulation of the protein product or an altered tissue or temporal expression pattern.

The article "a" and "an" are used herein to refer to one or more than one (i.e., to at least one) of the grammatical object of the article. By way of example, "a polypeptide" means one or more polypeptides.

All publications and patent applications mentioned in the specification are indicative of the level of those skilled in the art to which this disclosure pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended embodiments.

Non-limiting embodiments include:

1. A nucleic acid molecule comprising a polynucleotide encoding an RNA-guided nuclease (RGN) polypeptide, wherein said polynucleotide comprises a nucleotide sequence encoding an RGN polypeptide comprising an amino acid sequence having at least 95% sequence identity to SEQ ID NOs: 1, 16, 24, 35, 43, or 50;
   wherein said RGN polypeptide binds a target DNA sequence in an RNA-guided sequence specific manner when bound to a guide RNA (gRNA) capable of hybridizing to said target DNA sequence, and
   wherein said polynucleotide encoding an RGN polypeptide is operably linked to a promoter heterologous to said polynucleotide.

2. The nucleic acid molecule of embodiment 1, wherein said RGN polypeptide is capable of cleaving said target DNA sequence upon binding.
3. The nucleic acid molecule of embodiment 2, wherein cleavage by said RGN polypeptide generates a double-stranded break.
4. The nucleic acid molecule of embodiment 2, wherein cleavage by said RGN polypeptide generates a single-stranded break.
5. The nucleic acid molecule of embodiment 1, wherein said RGN polypeptide is nuclease dead or functions as a nickase.
6. The nucleic acid molecule of embodiment 5, wherein the RGN polypeptide is operably fused to a base-editing polypeptide.
7. The nucleic acid molecule of embodiment 6, wherein said base-editing polypeptide is a deaminase.
8. The nucleic acid molecule of embodiment 7, wherein said deaminase has at least 90% sequence identity to any one of SEQ ID NOs: 374, 383, 397, 399, 407, 408, 411, 414, 416, 420, 514, and 572-584.
9. The nucleic acid molecule of any one of embodiments 1-8, wherein the RGN polypeptide comprises one or more nuclear localization signals.
10. The nucleic acid molecule of any one of embodiments 1-9, wherein the RGN polypeptide is codon optimized for expression in a eukaryotic cell.
11. The nucleic acid molecule of any one of embodiments 1-10, wherein said target DNA sequence is located adjacent to a protospacer adjacent motif (PAM).
12. A vector comprising the nucleic acid molecule of any one of embodiments 1-11.
13. The vector of embodiment 12, further comprising at least one nucleotide sequence encoding said gRNA capable of hybridizing to said target DNA sequence.
14. The vector of embodiment 13, where said gRNA is a single guide RNA.
15. The vector of embodiment 13, wherein said gRNA is a dual-guide RNA.
16. The vector of any one of embodiments 13-15, wherein the guide RNA comprises a CRISPR RNA comprising a CRISPR repeat sequence having at least 95% sequence identity to SEQ ID NOs: 2, 17, 25, 36, 44, 51, or 63.
17. The vector of any one of embodiments 13-16, wherein the guide RNA comprises a tracrRNA having at least 95% sequence identity to SEQ ID NOs: 3, 18, 26, 37, 45, 52, or 62.
18. A cell comprising the nucleic acid molecule of any one of embodiments 1-11 or the vector of any one of embodiments 12-17.
19. A method for making an RGN polypeptide comprising culturing the cell of embodiment 18 under conditions in which the RGN polypeptide is expressed.
20. A method for making an RGN polypeptide comprising introducing into a cell a heterologous nucleic acid molecule comprising a nucleotide sequence encoding an RNA-guided nuclease (RGN) polypeptide comprising an amino acid sequence having at least 95% sequence identity to SEQ ID NOs: 1, 16, 24, 35, 43, or 50;
wherein said RGN polypeptide binds a target DNA sequence in an RNA-guided sequence specific manner when bound to a guide RNA (gRNA) capable of hybridizing to said target DNA sequence;
and culturing said cell under conditions in which the RGN polypeptide is expressed.

21. The method of embodiment 19 or 20, further comprising purifying said RGN polypeptide.
22. The method of embodiment 19 or 20, wherein said cell further expresses one or more guide RNAs that binds to said RGN polypeptide to form an RGN ribonucleoprotein complex.
23. The method of embodiment 22, further comprising purifying said RGN ribonucleoprotein complex.
24. A nucleic acid molecule comprising a polynucleotide encoding a CRISPR RNA (crRNA), wherein said crRNA comprises a spacer sequence and a CRISPR repeat sequence, wherein said CRISPR repeat sequence comprises a nucleotide sequence having at least 95% sequence identity to SEQ ID NOs: 2, 17, 25, 36, 44, 51, or 63;
wherein a guide RNA comprising:
  a) said crRNA; and
  b) a trans-activating CRISPR RNA (tracrRNA) hybridized to said CRISPR repeat sequence of said crRNA;
is capable of hybridizing to a target DNA sequence in a sequence specific manner through the spacer sequence of said crRNA when said guide RNA is bound to an RNA-guided nuclease (RGN) polypeptide, and
wherein said polynucleotide encoding a crRNA is operably linked to a promoter heterologous to said polynucleotide.
25. A vector comprising the nucleic acid molecule of embodiment 24.
26. The vector of embodiment 25, wherein said vector further comprises a polynucleotide encoding said tracrRNA.
27. The vector of embodiment 26, wherein said tracrRNA comprises a nucleotide sequence having at least 95% sequence identity to SEQ ID NOs: 3, 18, 26, 37, 45, 52, or 62.
28. The vector of embodiment 26 or 27, wherein said polynucleotide encoding said crRNA and said polynucleotide encoding said tracrRNA are operably linked to the same promoter and are encoded as a single guide RNA.
29. The vector of embodiment 26 or 27, wherein said polynucleotide encoding said crRNA and said polynucleotide encoding said tracrRNA are operably linked to separate promoters.
30. The vector of any one of embodiments 25-29, wherein said vector further comprises a polynucleotide encoding said RGN polypeptide, wherein said RGN polypeptide comprises an amino acid sequence having at least 95% sequence identity to SEQ ID NOs: 1, 16, 24, 35, 43, or 50.
31. A nucleic acid molecule comprising a polynucleotide encoding a trans-activating CRISPR RNA (tracrRNA) comprising a nucleotide sequence having at least 95% sequence identity to SEQ ID NOs: 3, 18, 26, 37, 45, 52, or 62;
wherein a guide RNA comprising:
  a) said tracrRNA; and
  b) a crRNA comprising a spacer sequence and a CRISPR repeat sequence, wherein said tracrRNA hybridizes with said CRISPR repeat sequence of said crRNA;
is capable of hybridizing to a target DNA sequence in a sequence specific manner through the spacer sequence of said crRNA when said guide RNA is bound to an RNA-guided nuclease (RGN) polypeptide, and wherein said polynucleotide encoding a tracrRNA is operably linked to a promoter heterologous to said polynucleotide.

32. A vector comprising the nucleic acid molecule of embodiment 31.

33. The vector of embodiment 32, wherein said vector further comprises a polynucleotide encoding said crRNA.

34. The vector of embodiment 33, wherein the CRISPR repeat sequence of said crRNA comprises a nucleotide sequence having at least 95% sequence identity to SEQ ID NOs: 2, 17, 25, 36, 44, 51, or 63.

35. The vector of embodiment 33 or 34, wherein said polynucleotide encoding said crRNA and said polynucleotide encoding said tracrRNA are operably linked to the same promoter and are encoded as a single guide RNA.

36. The vector of embodiment 33 or 34, wherein said polynucleotide encoding said crRNA and said polynucleotide encoding said tracrRNA are operably linked to separate promoters.

37. The vector of any one of embodiments 32-36, wherein said vector further comprises a polynucleotide encoding said RGN polypeptide, wherein said RGN polypeptide comprises an amino acid sequence having at least 95% sequence identity to SEQ ID NOs: 1, 16, 24, 35, 43, or 50.

38. A system for binding a target DNA sequence, said system comprising:
  a) one or more guide RNAs capable of hybridizing to said target DNA sequence or one or more nucleotide sequences encoding the one or more guide RNAs (gRNAs); and
  b) an RNA-guided nuclease (RGN) polypeptide comprising an amino acid sequence having at least 95% sequence identity to SEQ ID NOs: 1, 16, 24, 35, 43, or 50 or a nucleotide sequence encoding the RGN polypeptide;
wherein said nucleotide sequences encoding the one or more guide RNAs and encoding the RGN polypeptide are each operably linked to a promoter heterologous to said nucleotide sequence;
wherein the one or more guide RNAs hybridize to the target DNA sequence, and
wherein the one or more guide RNAs form a complex with the RGN polypeptide, thereby directing said RGN polypeptide to bind to said target DNA sequence.

39. The system of embodiment 38, wherein said gRNA is a single guide RNA (sgRNA).

40. The system of embodiment 38, wherein said gRNA is a dual-guide RNA.

41. The system of any one of embodiments 38-40, wherein said gRNA comprises a CRISPR repeat sequence comprising a nucleotide sequence having at least 95% sequence identity to SEQ ID NOs: 2, 17, 25, 36, 44, 51, or 63.

42. The system of any one of embodiments 38-41, wherein said gRNA comprises a tracrRNA comprising a nucleotide sequence having at least 95% sequence identity to SEQ ID NOs: 3, 18, 26, 37, 45, 52, or 62.

43. The system of any one of embodiments 38-42, wherein said target DNA sequence is located adjacent to a protospacer adjacent motif (PAM).

44. The system of any one of embodiments 38-43, wherein the target DNA sequence is within a cell.

45. The system of embodiment 44, wherein the cell is a eukaryotic cell.

46. The system of embodiment 45, wherein the eukaryotic cell is a plant cell.

47. The system of embodiment 45, wherein the eukaryotic cell is a mammalian cell.

48. The system of embodiment 45, wherein the eukaryotic cell is an insect cell.

49. The system of embodiment 44, wherein the cell is a prokaryotic cell.

50. The system of any one of embodiments 38-49, wherein when transcribed the one or more guide RNAs hybridize to the target DNA sequence and the guide RNA forms a complex with the RGN polypeptide which causes cleavage of the target DNA sequence.

51. The system of embodiment 50, wherein the cleavage generates a double-stranded break.

52. The system of embodiment 50, wherein cleavage by said RGN polypeptide generates a single-stranded break.

53. The system of any one of embodiments 38-49, wherein said RGN polypeptide is nuclease dead or functions as a nickase.

54. The system of embodiment 53, wherein the RGN polypeptide is operably linked to a base-editing polypeptide.

55. The system of embodiment 54, wherein said base-editing polypeptide is a deaminase.

56. The system of embodiment 55, wherein said deaminase has at least 90% sequence identity to any one of SEQ ID NOs: 374, 383, 397, 399, 407, 408, 411, 414, 416, 420, 514, and 572-584.

57. The system of any one of embodiments 38-56, wherein the RGN polypeptide comprises one or more nuclear localization signals.

58. The system of any one of embodiments 38-57, wherein the RGN polypeptide is codon optimized for expression in a eukaryotic cell.

59. The system of any one of embodiments 38-58, wherein nucleotide sequences encoding the one or more guide RNAs and the nucleotide sequence encoding an RGN polypeptide are located on one vector.

60. The system of any one of embodiments 38-59, wherein said system further comprises one or more donor polynucleotides or one or more nucleotide sequences encoding the one or more donor polynucleotides.

61. A method for binding a target DNA sequence comprising delivering a system according to any one of embodiments 38-60, to said target DNA sequence or a cell comprising the target DNA sequence.

62. The method of embodiment 61, wherein said RGN polypeptide or said guide RNA further comprises a detectable label, thereby allowing for detection of said target DNA sequence.

63. The method of embodiment 61, wherein said guide RNA or said RGN polypeptide further comprises an expression modulator, thereby modulating expression of said target DNA sequence or a gene under transcriptional control by said target DNA sequence.

64. A method for cleaving or modifying a target DNA sequence comprising delivering a system according to any one of embodiments 38-60, to said target DNA sequence or a cell comprising the target DNA sequence.

65. The method of embodiment 64, wherein said modified target DNA sequence comprises insertion of heterologous DNA into the target DNA sequence.

66. The method of embodiment 64, wherein said modified target DNA sequence comprises deletion of at least one nucleotide from the target DNA sequence.
67. The method of embodiment 64, wherein said modified target DNA sequence comprises mutation of at least one nucleotide in the target DNA sequence.
68. A method for binding a target DNA sequence comprising:
   a) assembling a RNA-guided nuclease (RGN) ribonucleotide complex in vitro by combining:
      i) one or more guide RNAs capable of hybridizing to the target DNA sequence; and
      ii) an RGN polypeptide comprising an amino acid sequence having at least 95% sequence identity to SEQ ID NOs: 1, 16, 24, 35, 43, or 50; under conditions suitable for formation of the RGN ribonucleotide complex; and
   b) contacting said target DNA sequence or a cell comprising said target DNA sequence with the in vitro-assembled RGN ribonucleotide complex;
   wherein the one or more guide RNAs hybridize to the target DNA sequence, thereby directing said RGN polypeptide to bind to said target DNA sequence.
69. The method of embodiment 68, wherein said RGN polypeptide or said guide RNA further comprises a detectable label, thereby allowing for detection of said target DNA sequence.
70. The method of embodiment 68, wherein said guide RNA or said RGN polypeptide further comprises an expression modulator, thereby allowing for the modulation of expression of said target DNA sequence.
71. A method for cleaving and/or modifying a target DNA sequence, comprising contacting the DNA molecule with:
   a) an RNA-guided nuclease (RGN) polypeptide, wherein said RGN comprises an amino acid sequence having at least 95% sequence identity to SEQ ID NOs: 1, 16, 24, 35, 43, or 50; and
   b) one or more guide RNAs capable of targeting the RGN of (a) to the target DNA sequence;
   wherein the one or more guide RNAs hybridize to the target DNA sequence, thereby directing said RGN polypeptide to bind to said target DNA sequence and cleavage and/or modification of said target DNA sequence occurs.
72. The method of embodiment 71, wherein said modified target DNA sequence comprises insertion of heterologous DNA into the target DNA sequence.
73. The method of embodiment 71, wherein said modified target DNA sequence comprises a deletion of at least one nucleotide from the target DNA sequence.
74. The method of embodiment 71, wherein said modified target DNA sequence comprises a mutation of at least one nucleotide in the target DNA sequence.
75. The method of any one of embodiments 71-74, wherein said RGN polypeptide is a nickase.
76. The method of embodiment 73 or 74, wherein said RGN polypeptide is nuclease dead and is operably linked to a base-editing polypeptide.
77. The method of any one of embodiments 68-76, wherein said gRNA is a single guide RNA (sgRNA).
78. The method of any one of embodiments 68-76, wherein said gRNA is a dual-guide RNA.
79. The method of any one of embodiments 68-78, wherein said gRNA comprises a CRISPR repeat sequence comprising a nucleotide sequence having at least 95% sequence identity to SEQ ID NOs: 2, 17, 25, 36, 44, 51, or 63.
80. The method of any one of embodiments 68-79, wherein said gRNA comprises a tracrRNA comprising a nucleotide sequence having at least 95% sequence identity to SEQ ID NOs: 3, 18, 26, 37, 45, 52, or 62.
81. The method of any one of embodiments 68-80, wherein said target DNA sequence is located adjacent to a protospacer adjacent motif (PAM).
82. The method of any one of embodiments 61-81, wherein the target DNA sequence is within a cell.
83. The method of embodiment 82, wherein the cell is a eukaryotic cell.
84. The method of embodiment 83, wherein the eukaryotic cell is a plant cell.
85. The method of embodiment 83, wherein the eukaryotic cell is a mammalian cell.
86. The method of embodiment 83, wherein the eukaryotic cell is an insect cell.
87. The method of embodiment 82, wherein the cell is a prokaryotic cell.
88. The method of any one of embodiments 82-87, further comprising culturing the cell under conditions in which the RGN polypeptide is expressed and cleaves the target DNA sequence to produce a modified DNA sequence; and selecting a cell comprising said modified DNA sequence.
89. A cell comprising a modified target DNA sequence according to the method of embodiment 88.
90. The cell of embodiment 89, wherein the cell is a eukaryotic cell.
91. The cell of embodiment 90, wherein the eukaryotic cell is a plant cell.
92. A plant comprising the cell of embodiment 91.
93. A seed comprising the cell of embodiment 91.
94. The cell of embodiment 90, wherein the eukaryotic cell is a mammalian cell.
95. The cell of embodiment 90, wherein the eukaryotic cell is an insect cell.
96. The cell of embodiment 89, wherein the cell is a prokaryotic cell.
97. A method for producing a genetically modified cell with a correction in a causal mutation for a genetically inherited disease, the method comprising introducing into the cell:
   a) an RNA-guided nuclease (RGN) polypeptide, wherein the RGN polypeptide comprises an amino acid sequence having at least 95% sequence identity to SEQ ID NOs: 1, 16, 24, 35, 43, or 50, or a polynucleotide encoding said RGN polypeptide, wherein said polynucleotide encoding the RGN polypeptide is operably linked to a promoter to enable expression of the RGN polypeptide in the cell; and
   b) a guide RNA (gRNA), wherein the gRNA comprises a CRISPR repeat sequence comprising a nucleotide sequence having at least 95% sequence identity to SEQ ID NOs: 2, 17, 25, 36, 44, 51, or 63, or a polynucleotide encoding said gRNA, wherein said polynucleotide encoding the gRNA is operably linked to a promoter to enable expression of the gRNA in the cell
   whereby the RGN and gRNA target to the genomic location of the causal mutation and modify the genomic sequence to remove the causal mutation.
98. The method of embodiment 97, wherein said RGN polypeptide is nuclease dead or functions as a nickase.

99. The method of embodiment 98, wherein the RGN polypeptide is operably linked to a base-editing polypeptide.
100. The method of embodiment 99, wherein said base-editing polypeptide is a deaminase.
101. The method of embodiment 100, wherein the deaminase comprises an amino acid sequence having at least 90% sequence identity to any one of SEQ ID NOs: 374, 383, 397, 399, 407, 408, 411, 414, 416, 420, 514, and 572-584.
102. The method of any one of embodiments 97-101, wherein the cell is an animal cell.
103. The method of embodiment 102, wherein the animal cell is a mammalian cell.
104. The method of embodiment 103, wherein the cell is derived from a dog, cat, mouse, rat, rabbit, horse, cow, pig, or human.
105. The method of embodiment 102, wherein the genetically inherited disease is a disease listed in Table 8.
106. The method of embodiment 102, wherein the genetically inherited disease is Hurler Syndrome.
107. The method of embodiment 106, wherein the gRNA comprises a spacer sequence that targets SEQ ID NO: 337.
108. A method for producing a genetically modified cell with a deletion in a disease-causing genomic region of instability, the method comprising introducing into the cell:
a) an RNA-guided nuclease (RGN) polypeptide, wherein the RGN polypeptide comprises an amino acid sequence having at least 95% sequence identity to SEQ ID NOs: 1, 16, 24, 35, 43, or 50, or a polynucleotide encoding said RGN polypeptide, wherein said polynucleotide encoding the RGN polypeptide is operably linked to a promoter to enable expression of the RGN polypeptide in the cell; and
b) a first guide RNA (gRNA), wherein the gRNA comprises a CRISPR repeat sequence comprising a nucleotide sequence having at least 95% sequence identity to SEQ ID NOs: 2, 17, 25, 36, 44, 51, or 63, or a polynucleotide encoding said gRNA, wherein said polynucleotide encoding the gRNA is operably linked to a promoter to enable expression of the gRNA in the cell, and further wherein the gRNA comprises a spacer sequence that targets the 5'flank of the genomic region of instability; and
c) a second guide RNA (gRNA), wherein the gRNA comprises a CRISPR repeat sequence comprising a nucleotide sequence having at least 95% sequence identity to SEQ ID NOs: 2, 17, 25, 36, 44, 51, or 63, or a polynucleotide encoding said gRNA, wherein said polynucleotide encoding the gRNA is operably linked to a promoter to enable expression of the gRNA in the cell, and further wherein said second gRNA comprises a spacer sequence that targets the 3'flank of the genomic region of instability;
whereby the RGN and the two gRNAs target to the genomic region of instability and at least a portion of the genomic region of instability is removed.
109. The method of embodiment 108, wherein the cell is an animal cell.
110. The method of embodiment 108, wherein the cell is a mammalian cell.
111. The method of embodiment 110, wherein the cell is derived from a dog, cat, mouse, rat, rabbit, horse, cow, pig, or human.
112. The method of embodiment 109, wherein the genetically inherited disease is Friedrich's Ataxia or Huntington's Disease.
113. The method of embodiment 112, wherein the first gRNA comprises a spacer sequence that targets SEQ ID NO: 340, 341, 342, or 343.
114. The method of embodiment 113, wherein the second gRNA comprises a spacer sequence that targets SEQ ID NO: 340, 341, 342, or 343.
115. A method for producing a genetically modified mammalian hematopoietic progenitor cell having decreased BCL11A mRNA and protein expression, the method comprising introducing into an isolated human hematopoietic progenitor cell:
a) an RNA-guided nuclease (RGN) polypeptide, wherein the RGN polypeptide comprises an amino acid sequence having at least 95% sequence identity to SEQ ID NOs: 1, 16, 24, 35, 43, or 50, or a polynucleotide encoding said RGN polypeptide, wherein said polynucleotide encoding the RGN polypeptide is operably linked to a promoter to enable expression of the RGN polypeptide in the cell; and
b) a guide RNA (gRNA), wherein the gRNA comprises a CRISPR repeat sequence comprising a nucleotide sequence having at least 95% sequence identity to SEQ ID NOs: 2, 17, 25, 36, 44, 51, or 63, or a polynucleotide encoding said gRNA, wherein said polynucleotide encoding the gRNA is operably linked to a promoter to enable expression of the gRNA in the cell,
whereby the RGN and gRNA are expressed in the cell and cleave at the BCL11A enhancer region, resulting in genetic modification of the human hematopoietic progenitor cell and reducing the mRNA and/or protein expression of BCL11A.
116. The method of embodiment 115, wherein the gRNA further comprises a spacer sequence that targets SEQ ID NO: 350, 351, or 352.
117. A system for binding a target DNA sequence, said system comprising:
a) one or more guide RNAs capable of hybridizing to said target DNA sequence or one or more nucleotide sequences encoding the one or more guide RNAs (gRNAs); and
b) an RNA-guided nuclease (RGN) polypeptide comprising an amino acid sequence having at least 95% sequence identity to SEQ ID NOs: 1, 16, 24, 35, 43, or 50;
wherein the one or more guide RNAs hybridize to the target DNA sequence, and
wherein the one or more guide RNAs forms a complex with the RGN polypeptide, thereby directing said RGN polypeptide to bind to said target DNA sequence.
118. The system of embodiment 117, wherein said RGN polypeptide is nuclease dead or functions as a nickase.
119. The system of embodiment 117 or 118, wherein said RGN polypeptide is operably fused to a base-editing polypeptide.
120. The system of embodiment 119, wherein the base-editing polypeptide is a deaminase.
121. The system of embodiment 120, wherein the deaminase polypeptide comprises an amino acid sequence having at least 95% sequence identity to any one of SEQ ID NOs: 374, 383, 397, 399, 407, 408, 411, 414, 416, 420, 514, and 572-584.
122. A nucleic acid molecule comprising a polynucleotide encoding a deaminase polypeptide, wherein said polynucleotide comprises a nucleotide sequence encoding a deaminase polypeptide comprising an amino acid sequence having at least 90% sequence identity to SEQ ID NOs: 374, 383, 397, 399, 407, 408, 411, 414, 416, or 420;

wherein said deaminase polypeptide deaminates at least one nucleotide in a target polynucleotide; and wherein said polynucleotide encoding a deaminase polypeptide is operably linked to a promoter heterologous to said polynucleotide.

123. The nucleic acid molecule of embodiment 122, wherein the deaminase polypeptide is codon optimized for expression in a eukaryotic cell.

124. The nucleic acid molecule of embodiment 122 or 123, wherein the deaminase polypeptide is operably linked to a DNA-binding polypeptide that localizes said deaminase polypeptide to said target polynucleotide.

125. The nucleic acid molecule of embodiment 124, wherein the DNA-binding polypeptide is a meganuclease, zinc finger fusion protein, or a TALEN.

126. The nucleic acid molecule of embodiment 124, wherein the DNA-binding polypeptide acts in complex with an RNA guide and is therefore RNA-guided.

127. The nucleic acid molecule of embodiment 126, wherein the RNA-guided, DNA-binding polypeptide is or is derived from an RNA-guided nuclease polypeptide.

128. The nucleic acid molecule of embodiment 127, wherein the RNA-guided nuclease polypeptide is a Type II CRISPR-Cas polypeptide.

129. The nucleic acid molecule of embodiment 127, wherein the RNA-guided nuclease polypeptide is a Type V CRISPR-Cas polypeptide.

130. The nucleic acid molecule of any one of embodiments 126-129, wherein the RNA-guided, DNA-binding polypeptide is a nickase.

131. The nucleic acid molecule of embodiment 127, wherein the RNA-guided nuclease polypeptide has at least 95% sequence identity to SEQ ID NOs: 1, 16, 24, 35, 43, or 50.

132. The nucleic acid molecule of any one of embodiments 124-131, wherein the deaminase polypeptide is operably linked to a uracil glycosylase inhibitor (UGI) polypeptide.

133. The nucleic acid molecule of embodiment 132, wherein the UGI polypeptide is at least 85% identical to the amino acid sequence of SEQ ID NO: 570.

134. The nucleic acid molecule of any one of embodiments 122-133, wherein the deaminase polypeptide further comprises a nuclear localization signal (NLS).

135. A vector comprising the nucleic acid molecule of any one of embodiments 122-134.

136. A vector comprising the nucleic acid molecule of any one of embodiments 126-134, wherein said vector further comprises at least one nucleotide sequence encoding a guide RNA (gRNA) capable of hybridizing to said target polynucleotide and acting in complex with said RNA-guided, DNA-binding polypeptide.

137. The vector of embodiment 136, where said gRNA is a single guide RNA.

138. The vector of embodiment 136, wherein said gRNA is a dual-guide RNA.

139. A cell comprising the nucleic acid molecule of any one of embodiments 122-134 or the vector of any one of embodiments 135-138.

140. A method for making a deaminase polypeptide comprising culturing the cell of embodiment 139 under conditions in which the deaminase polypeptide is expressed.

141. A nucleic acid molecule comprising a polynucleotide encoding an adenosine deaminase polypeptide, wherein said polynucleotide comprises a nucleotide sequence encoding an adenosine deaminase polypeptide comprising an amino acid sequence selected from the group consisting of:

a) an amino acid sequence having at least 90% sequence identity to SEQ ID NO: 514;

b) an amino acid sequence having at least 90% sequence identity to SEQ ID NO: 572, and comprising a lysine at a position corresponding to position 102 of SEQ ID NO: 572, a tyrosine at a position corresponding to position 104 of SEQ ID NO: 572, and a threonine at a position corresponding to position 106 of SEQ ID NO: 572;

c) an amino acid sequence having at least 90% sequence identity to SEQ ID NO: 573;

d) an amino acid sequence having at least 90% sequence identity to SEQ ID NO: 574, and comprising a glutamic acid at a position corresponding to position 101 of SEQ ID NO: 574, a serine at a position corresponding to position 103 of SEQ ID NO: 574, and a lysine at a position corresponding to position 105 of SEQ ID NO: 574;

e) an amino acid sequence having at least 90% sequence identity to SEQ ID NO: 575, and comprising a lysine at a position corresponding to position 101 of SEQ ID NO: 575, a leucine at a position corresponding to position 103 of SEQ ID NO: 575, and a glutamic acid at a position corresponding to position 105 of SEQ ID NO: 575;

f) an amino acid sequence having at least 90% sequence identity to SEQ ID NO: 576, and comprising an alanine at a position corresponding to position 105 of SEQ ID NO: 576 and an arginine at a position corresponding to position 107 of SEQ ID NO: 576;

g) an amino acid sequence having at least 90% sequence identity to SEQ ID NO: 577, and comprising a glycine at a position corresponding to position 102 of SEQ ID NO: 577, a serine at a position corresponding to position 104 of SEQ ID NO: 577, and an arginine at a position corresponding to position 106 of SEQ ID NO: 577;

h) an amino acid sequence having at least 90% sequence identity to SEQ ID NO: 578, and comprising a serine at a position corresponding to position 105 of SEQ ID NO: 578 and a threonine at a position corresponding to position 107 of SEQ ID NO: 578;

i) an amino acid sequence having at least 90% sequence identity to SEQ ID NO: 579, and comprising a serine at a position corresponding to position 102 of SEQ ID NO: 579, a glutamine at a position corresponding to position 104 of SEQ ID NO: 579, and a glycine at a position corresponding to position 106 of SEQ ID NO: 579;

j) an amino acid sequence having at least 90% sequence identity to SEQ ID NO: 580, and comprising a glycine at a position corresponding to position 111 of SEQ ID NO: 580;

k) an amino acid sequence having at least 90% sequence identity to SEQ ID NO: 581, and comprising a glutamine at a position corresponding to position 104 of SEQ ID NO: 581, a glycine at a position corresponding to position 106 of SEQ ID NO: 581, and a glutamic acid at a position corresponding to position 108 of SEQ ID NO: 581;
l) an amino acid sequence having at least 90% sequence identity to SEQ ID NO: 582, and comprising an arginine at a position corresponding to position 102 of SEQ ID NO: 582, a tryptophan at a position corresponding to position 104 of SEQ ID NO: 582, and a glutamic acid at a position corresponding to position 106 of SEQ ID NO: 582;
m) an amino acid sequence having at least 90% sequence identity to SEQ ID NO: 583, and comprising an arginine at a position corresponding to position 104 of SEQ ID NO: 583 and a serine at a position corresponding to position 106 of SEQ ID NO: 583; and
n) an amino acid sequence having at least 90% sequence identity to SEQ ID NO: 584, and comprising a phenylalanine at a position corresponding to position 110 of SEQ ID NO: 584, a serine at a position corresponding to position 112 of SEQ ID NO: 584, and a threonine at a position corresponding to position 114 of SEQ ID NO: 584;
wherein said adenosine deaminase polypeptide deaminates at least one adenosine in a target polynucleotide; and
wherein said polynucleotide encoding an adenosine deaminase polypeptide is operably linked to a promoter heterologous to said polynucleotide.

142. The nucleic acid molecule of embodiment 141, wherein said adenosine deaminase polypeptide is codon optimized for expression in a eukaryotic cell.
143. The nucleic acid molecule of embodiment 141 or 142, wherein the adenosine deaminase polypeptide is operably linked to a DNA-binding polypeptide that localizes said adenosine deaminase polypeptide to said target polynucleotide.
144. The nucleic acid molecule of embodiment 143, wherein the DNA-binding polypeptide is a meganuclease, zinc finger fusion protein, or a TALEN.
145. The nucleic acid molecule of embodiment 143, wherein the DNA-binding polypeptide acts in complex with an RNA guide and is therefore RNA-guided.
146. The nucleic acid molecule of embodiment 145, wherein the RNA-guided, DNA-binding polypeptide is or is derived from an RNA-guided nuclease polypeptide.
147. The nucleic acid molecule of embodiment 146, wherein the RNA-guided nuclease polypeptide is a Type II CRISPR-Cas polypeptide.
148. The nucleic acid molecule of embodiment 146, wherein the RNA-guided nuclease polypeptide is a Type V CRISPR-Cas polypeptide.
149. The nucleic acid molecule of any one of embodiments 145-148, wherein the RNA-guided, DNA-binding polypeptide is a nickase.
150. The nucleic acid molecule of embodiment 146, wherein the RNA-guided nuclease polypeptide has at least 95% sequence identity to SEQ ID NOs: 1, 16, 24, 35, 43, or 50.
151. The nucleic acid molecule of any one of embodiments 141-150, wherein the adenosine deaminase polypeptide is operably linked to a uracil glycosylase inhibitor (UGI) polypeptide.
152. The nucleic acid molecule of embodiment 151, wherein the UGI polypeptide is at least 85% identical to the amino acid sequence of SEQ ID NO: 570.
153. The nucleic acid molecule of any one of embodiments 141-152, wherein the adenosine deaminase polypeptide further comprises a nuclear localization signal (NLS).
154. A vector comprising the nucleic acid molecule of any one of embodiments 141-153.
155. A vector comprising the nucleic acid molecule of any one of embodiments 145-153, wherein said vector further comprises at least one nucleotide sequence encoding a guide RNA (gRNA) capable of hybridizing to said target polynucleotide and acting in complex with said RNA-guided, DNA-binding polypeptide.
156. The vector of embodiment 155, where said gRNA is a single guide RNA.
157. The vector of embodiment 155, wherein said gRNA is a dual-guide RNA.
158. A cell comprising the nucleic acid molecule of any one of embodiments 141-153 or the vector of any one of embodiments 154-157.
159. A method for making an adenosine deaminase polypeptide comprising culturing the cell of embodiment 158 under conditions in which the adenosine deaminase polypeptide is expressed.
160. A fusion protein comprising:
a) a DNA-binding polypeptide that binds to a target polynucleotide; and
b) a deaminase polypeptide, wherein said deaminase polypeptide comprises an amino acid sequence having at least 90% sequence identity to SEQ ID NOs: 374, 383, 397, 399, 407, 408, 411, 414, 416, or 420, and wherein said deaminase polypeptide deaminates at least one nucleotide in said target polynucleotide.
161. The fusion protein of embodiment 160, wherein the DNA-binding polypeptide is a meganuclease, zinc finger fusion protein, or a TALEN.
162. The fusion protein of embodiment 160, wherein the DNA-binding polypeptide acts in complex with an RNA guide and is therefore RNA-guided.
163. The fusion protein of embodiment 162, wherein the RNA-guided, DNA-binding polypeptide is or is derived from an RNA-guided nuclease polypeptide.
164. The fusion protein of embodiment 163, wherein the RNA-guided nuclease polypeptide is a Type II CRISPR-Cas polypeptide.
165. The fusion protein of embodiment 163, wherein the RNA-guided nuclease polypeptide is a Type V CRISPR-Cas polypeptide.
166. The fusion protein of any one of embodiments 162-165, wherein the RNA-guided, DNA-binding polypeptide is a nickase.
167. The fusion protein of embodiment 163, wherein the RNA-guided nuclease polypeptide has at least 95% sequence identity to SEQ ID NOs: 1, 16, 24, 35, 43, or 50.
168. The fusion protein of any one of embodiments 160-167, wherein the fusion protein further comprises a uracil glycosylase inhibitor (UGI) polypeptide.
169. The fusion protein of embodiment 168, wherein the UGI polypeptide is at least 85% identical to the amino acid sequence of SEQ ID NO: 570.
170. The fusion protein of any one of embodiments 160-169, wherein the fusion protein further comprises a nuclear localization signal (NLS).
171. A fusion protein comprising:
a) a DNA-binding polypeptide that binds to a target polynucleotide; and b) an adenosine deaminase polypeptide comprising an amino acid sequence selected from the group consisting of:
  i) an amino acid sequence having at least 90% sequence identity to SEQ ID NO: 514;
  ii) an amino acid sequence having at least 90% sequence identity to SEQ ID NO: 572, and comprising a lysine at a position corresponding to position 102 of SEQ ID NO: 572, a tyrosine at a position corresponding to position 104 of SEQ ID NO: 572, and a threonine at a position corresponding to position 106 of SEQ ID NO: 572;
  iii) an amino acid sequence having at least 90% sequence identity to SEQ ID NO: 573;
  iv) an amino acid sequence having at least 90% sequence identity to SEQ ID NO: 574, and comprising a glutamic acid at a position corresponding to position 101 of SEQ ID NO: 574, a serine at a position corresponding to position 103 of SEQ ID NO: 574, and a lysine at a position corresponding to position 105 of SEQ ID NO: 574;
  v) an amino acid sequence having at least 90% sequence identity to SEQ ID NO: 575, and comprising a lysine at a position corresponding to position 101 of SEQ ID NO: 575, a leucine at a position corresponding to position 103 of SEQ ID NO: 575, and a glutamic acid at a position corresponding to position 105 of SEQ ID NO: 575;
  vi) an amino acid sequence having at least 90% sequence identity to SEQ ID NO: 576, and comprising an alanine at a position corresponding to position 105 of SEQ ID NO: 576 and an argnine at a position corresponding to position 107 of SEQ ID NO: 576;
  vii) an amino acid sequence having at least 90% sequence identity to SEQ ID NO: 577, and comprising a glycine at a position corresponding to position 102 of SEQ ID NO: 577, a serine at a position corresponding to position 104 of SEQ ID NO: 577, and an arginine at a position corresponding to position 106 of SEQ ID NO: 577;
  viii) an amino acid sequence having at least 90% sequence identity to SEQ ID NO: 578, and comprising a serine at a position corresponding to position 105 of SEQ ID NO: 578 and a threonine at a position corresponding to position 107 of SEQ ID NO: 578;
  ix) an amino acid sequence having at least 90% sequence identity to SEQ ID NO: 579, and comprising a serine at a position corresponding to position 102 of SEQ ID NO: 579, a glutamine at a position corresponding to position 104 of SEQ ID NO: 579, and a glycine at a position corresponding to position 106 of SEQ ID NO: 579;
  x) an amino acid sequence having at least 90% sequence identity to SEQ ID NO: 580, and comprising a glycine at a position corresponding to position 111 of SEQ ID NO: 580;
  xi) an amino acid sequence having at least 90% sequence identity to SEQ ID NO: 581, and comprising a glutamine at a position corresponding to position 104 of SEQ ID NO: 581, a glycine at a position corresponding to position 106 of SEQ ID NO: 581, and a glutamic acid at a position corresponding to position 108 of SEQ ID NO: 581;
  xii) an amino acid sequence having at least 90% sequence identity to SEQ ID NO: 582, and comprising an arginine at a position corresponding to position 102 of SEQ ID NO: 582, a tryptophan at a position corresponding to position 104 of SEQ ID NO: 582, and a glutamic acid at a position corresponding to position 106 of SEQ ID NO: 582;
  xiii) an amino acid sequence having at least 90% sequence identity to SEQ ID NO: 583, and comprising an arginine at a position corresponding to position 104 of SEQ ID NO: 583 and a serine at a position corresponding to position 106 of SEQ ID NO: 583; and
  xiv) an amino acid sequence having at least 90% sequence identity to SEQ ID NO: 584, and comprising a phenylalanine at a position corresponding to position 110 of SEQ ID NO: 584, a serine at a position corresponding to position 112 of SEQ ID NO: 584, and a threonine at a position corresponding to position 114 of SEQ ID NO: 584;
wherein said adenosine deaminase polypeptide deaminates at least one adeonisine in a target polynucleotide.

172. The fusion protein of embodiment 171, wherein the DNA-binding polypeptide is a meganuclease, zinc finger fusion protein, or a TALEN.
173. The fusion protein of embodiment 171, wherein the DNA-binding polypeptide acts in complex with an RNA guide and is therefore RNA-guided.
174. The fusion protein of embodiment 173, wherein the RNA-guided, DNA-binding polypeptide is or is derived from an RNA-guided nuclease polypeptide.
175. The fusion protein of embodiment 174, wherein the RNA-guided nuclease polypeptide is a Type II CRISPR-Cas polypeptide.
176. The fusion protein of embodiment 174, wherein the RNA-guided nuclease polypeptide is a Type V CRISPR-Cas polypeptide.
177. The fusion protein of any one of embodiments 173-176, wherein the RNA-guided, DNA-binding polypeptide is a nickase.
178. The fusion protein of embodiment 174, wherein the RNA-guided nuclease polypeptide has at least 95% sequence identity to SEQ ID NOs: 1, 16, 24, 35, 43, or 50.
179. The fusion protein of any one of embodiments 171-178, wherein the fusion protein further comprises a uracil glycosylase inhibitor (UGI) polypeptide.
180. The fusion protein of embodiment 179, wherein the UGI polypeptide is at least 85% identical to the amino acid sequence of SEQ ID NO: 570.
181. The fusion protein of any one of embodiments 171-180, wherein the fusion protein further comprises a nuclear localization signal (NLS).
182. A system for modifying a target polynucleotide sequence, said system comprising:
  a) one or more guide RNAs capable of hybridizing to said target polynucleotide sequence or one or more nucleotide sequences encoding the one or more guide RNAs (gRNAs); and
  b) a fusion protein of any one of embodiments 162-170 and 173-181 or a nucleotide sequence encoding said fusion protein;
wherein said nucleotide sequences encoding the one or more guide RNAs and encoding the fusion protein are each operably linked to a promoter heterologous to said nucleotide sequence;
wherein the one or more guide RNAs hybridize to the target polynucleotide sequence, and
wherein the one or more guide RNAs form a complex with the RNA-guided DNA-binding polypeptide of the fusion protein, thereby directing said fusion protein to bind to and modify said target polynucleotide sequence.

183. The system of embodiment 182, wherein said gRNA is a single guide RNA (sgRNA).

184. The system of embodiment 182, wherein said gRNA is a dual-guide RNA.

185. The system of any one of embodiments 182-184, wherein said target polynucleotide sequence is located adjacent to a protospacer adjacent motif (PAM).

186. The system of any one of embodiments 182-185, wherein the target polynucleotide sequence is within a cell.

187. The system of embodiment 186, wherein the cell is a eukaryotic cell.

188. The system of embodiment 187, wherein the eukaryotic cell is a plant cell.

189. The system of embodiment 187, wherein the eukaryotic cell is a mammalian cell.

190. The system of embodiment 187, wherein the eukaryotic cell is an insect cell.

191. The system of embodiment 186, wherein the cell is a prokaryotic cell.

192. A method for deaminating a target polynucleotide, said method comprising contacting said target polynucleotide with a deaminase comprising an amino acid sequence having at least 90% sequence identity to SEQ ID NOs: 374, 383, 397, 399, 407, 408, 411, 414, 416, or 420, wherein said deaminase polypeptide deaminates at least one nucleotide in said target polynucleotide.

193. A method for deaminating at least one adenosine in a target polynucleotide, said method comprising contacting said target polynucleotide with an adenosine deaminase polypeptide comprising an amino acid sequence selected from the group consisting of:
a) an amino acid sequence having at least 90% sequence identity to SEQ ID NO: 514;
b) an amino acid sequence having at least 90% sequence identity to SEQ ID NO: 572, and comprising a lysine at a position corresponding to position 102 of SEQ ID NO: 572, a tyrosine at a position corresponding to position 104 of SEQ ID NO: 572, and a threonine at a position corresponding to position 106 of SEQ ID NO: 572;
c) an amino acid sequence having at least 90% sequence identity to SEQ ID NO: 573;
d) an amino acid sequence having at least 90% sequence identity to SEQ ID NO: 574, and comprising a glutamic acid at a position corresponding to position 101 of SEQ ID NO: 574, a serine at a position corresponding to position 103 of SEQ ID NO: 574, and a lysine at a position corresponding to position 105 of SEQ ID NO: 574;
e) an amino acid sequence having at least 90% sequence identity to SEQ ID NO: 575, and comprising a lysine at a position corresponding to position 101 of SEQ ID NO: 575, a leucine at a position corresponding to position 103 of SEQ ID NO: 575, and a glutamic acid at a position corresponding to position 105 of SEQ ID NO: 575;
f) an amino acid sequence having at least 90% sequence identity to SEQ ID NO: 576, and comprising an alanine at a position corresponding to position 105 of SEQ ID NO: 576 and an argnine at a position corresponding to position 107 of SEQ ID NO: 576;
g) an amino acid sequence having at least 90% sequence identity to SEQ ID NO: 577, and comprising a glycine at a position corresponding to position 102 of SEQ ID NO: 577, a serine at a position corresponding to position 104 of SEQ ID NO: 577, and an arginine at a position corresponding to position 106 of SEQ ID NO: 577;
h) an amino acid sequence having at least 90% sequence identity to SEQ ID NO: 578, and comprising a serine at a position corresponding to position 105 of SEQ ID NO: 578 and a threonine at a position corresponding to position 107 of SEQ ID NO: 578;
i) an amino acid sequence having at least 90% sequence identity to SEQ ID NO: 579, and comprising a serine at a position corresponding to position 102 of SEQ ID NO: 579, a glutamine at a position corresponding to position 104 of SEQ ID NO: 579, and a glycine at a position corresponding to position 106 of SEQ ID NO: 579;
j) an amino acid sequence having at least 90% sequence identity to SEQ ID NO: 580, and comprising a glycine at a position corresponding to position 111 of SEQ ID NO: 580;
k) an amino acid sequence having at least 90% sequence identity to SEQ ID NO: 581, and comprising a glutamine at a position corresponding to position 104 of SEQ ID NO: 581, a glycine at a position corresponding to position 106 of SEQ ID NO: 581, and a glutamic acid at a position corresponding to position 108 of SEQ ID NO: 581;
l) an amino acid sequence having at least 90% sequence identity to SEQ ID NO: 582, and comprising an arginine at a position corresponding to position 102 of SEQ ID NO: 582, a tryptophan at a position corresponding to position 104 of SEQ ID NO: 582, and a glutamic acid at a position corresponding to position 106 of SEQ ID NO: 582;
m) an amino acid sequence having at least 90% sequence identity to SEQ ID NO: 583, and comprising an arginine at a position corresponding to position 104 of SEQ ID NO: 583 and a serine at a position corresponding to position 106 of SEQ ID NO: 583; and
n) an amino acid sequence having at least 90% sequence identity to SEQ ID NO: 584, and comprising a phenylalanine at a position corresponding to position 110 of SEQ ID NO: 584, a serine at a position corresponding to position 112 of SEQ ID NO: 584, and a threonine at a position corresponding to position 114 of SEQ ID NO: 584;

wherein said adenosine deaminase polypeptide deaminates at least one adeonisine in a target polynucleotide.

194. A method for modifying a target polynucleotide, said method comprising contacting said target polynucleotide with a fusion protein of any one of embodiments 160, 161, 171, and 172, wherein said DNA-binding polypeptide binds to said target polynucleotide and said deaminase deaminates at least one nucleotide in said target polynucleotide.

195. A method for modifying a target polynucleotide, said method comprising contacting said target polynucleotide with a fusion protein of any one of embodiments 162-170 and 173-181, and introducing one or more guide RNAs (gRNAs) or one or more nucleotide sequences encoding the one or more gRNAs;
wherein the one or more gRNAs hybridize to said target polynucleotide and form a complex with the RNA-guided DNA-binding polypeptide of the fusion protein, thereby directing said fusion protein to bind to said target polynucleotide sequence and said deaminase polypeptide of the fusion protein deaminates at least one nucleotide in said target polynucleotide, thereby modifying said target polynucleotide.

196. The method of embodiment 195, wherein the target polynucleotide is within a cell.

197. The method of embodiment 196, wherein the cell is a eukaryotic cell.

198. The method of embodiment 197, wherein the eukaryotic cell is a mammalian cell.

199. The method of embodiment 197, wherein the eukaryotic cell is a plant cell.

200. The method of any one of embodiments 195 to 199, wherein the modification of the target polynucleotide comprises a C to T point mutation.

201. The method of embodiment 200, wherein the deamination of the C base results in correcting a sequence that is associated with a disease or disorder.

202. The method of embodiment 200, wherein the modification of the target polynucleotide comprises a C to T change in the genome of a crop plant, and wherein deamination of the C base results in a sequence which improves the agronomic qualities of the crop plant.

203. The method of any one of embodiments 195 to 199, wherein the modification of the target polynucleotide comprises an A to G point mutation.

204. The method of embodiment 203, wherein the deamination of the A base results in correcting a sequence that is associated with a disease or disorder.

205. The method of embodiment 203, wherein the modification of the target polynucleotide comprises an A to G change in the genome of a crop plant, and wherein deamination of the A base results in a sequence which improves the agronomic qualities of the crop plant.

The following examples are offered by way of illustration and not by way of limitation.

EXPERIMENTAL

Example 1. Identification of RNA-Guided Nucleases

Six distinct CRISPR-associated RNA-guided nucleases (RGN's) were identified and are described in Table 1 below. APG00969, APG03128, and APG00771 are Type II-C RGNs. APG09748, APG02789 and APG09106 are Type V-B RGNs. Table 1 provides the name of each RGN, its amino acid sequence, the source from which it was derived, and processed crRNA repeat sequences, and tracrRNA sequences. Table 1 further provides a generic single guide RNA (sgRNA) sequence which determines the nucleic acid target sequence of the sgRNA. The location of the spacer sequence is indicated by a poly-N sequence. This poly-N sequence is only to indicate the location of the spacer sequence in the sgRNA, and does not indicate length required for a functional spacer sequence. Type II-C RGN systems each have a conserved sequence in the base of the hairpin stem of the tracrRNA: APG00969 has UNANNC (SEQ ID NO: 13); APG03128 has ANGNNU (SEQ ID NO: 23); and APG00771 has UNANNA (SEQ ID NO: 42).

TABLE 1

Summary of SEQ IDs and CRISPR associated systems

| RGN ID | SEQ ID NO. | Source | crRNA repeat seq (SEQ ID NO.) | tracrRNA (SEQ ID NO.) | sgRNA (SEQ ID NO) |
|---|---|---|---|---|---|
| APG00969 | 1 | *Bacillus* sp. | 2 | 3 | 4 |
| APG03128 | 16 | *Rhizobium* sp. | 17 | 18 | 19 |
| APG09748 | 24 | *Brevibacillus* sp. | 25 | 26 | 27 |
| APG00771 | 35 | *Chryseobacterium* sp. | 36 | 37 | 38 |
| APG02789 | 43 | *Bacillus* sp. | 44 | 45 | 46 |
| APG09106 | 50 | *Brevibacillus* sp. | 51 | 52 | 53 |

Example 2: Guide RNA Identification and sgRNA Construction

Cultures of bacteria that natively express the RNA-guided nuclease system under investigation were grown to mid-log phase (OD600 of ~0.600), pelleted, and flash frozen. RNA was isolated from the pellets using a mirVANA miRNA Isolation Kit (Life Technologies, Carlsbad, CA), and sequencing libraries were prepared from the isolated RNA using an NEBNext Small RNA Library Prep kit (NEB, Beverly, MA). The library prep was fractionated on a 6% polyacrylamide gel into 2 size fractions corresponding to 18-65 nt and 90-200 nt RNA species to detect crRNAs and tracrRNAs, respectively. Deep sequencing (40 bp paired-end for the smaller fraction and 80 bp paired-end for the larger fraction) was performed on a Next Seq 500 (High Output kit) by a service provider (MoGene, St. Louis, MO). Reads were quality trimmed using Cutadapt and mapped to reference genomes using Bowtie2. A custom RNAseq pipeline was written in Python to detect the crRNA and tracrRNA transcripts. Processed crRNA boundaries were determined by sequence coverage of the native repeat spacer array. The anti-repeat portion of the tracrRNA was identified using permissive BLASTn parameters. RNA sequencing depth confirmed the boundaries of the processed tracrRNA by identifying the transcript containing the anti-repeat. Manual curation of RNAs was performed using secondary structure prediction by NUPACK, an RNA folding software. Alternatively, the tracrRNA for APG02789 was determined bioinformatically by the anti-repeat sequence and not through small RNA sequencing. Generally, sgRNA cassettes were prepared by DNA synthesis and were generally designed as follows for APG00771, APG03128, and APG00969: (5'->3') 20-30 bp spacer sequence—processed repeat portion of the crRNA—4 bp noncomplementary linker (AAAG; SEQ ID NO: 8)—processed tracrRNA. For APG09748, APG09106, and APG02789, the sgRNA cassettes were designed as the following (5'->3'): processed tracrRNA—4 bp noncomplementary linker (AAAG; SEQ ID NO: 8)—processed repeat portion of the crRNA)—20-30 bp target spacer sequence. Other 4 bp or 6 bp noncomplementary linkers known in the art may also be used for sgRNA design. For in vitro assays, sgRNAs were synthesized by in vitro transcription of the sgRNA cassettes with a GeneArt™ Precision gRNA Synthesis Kit (ThermoFisher). Processed crRNA and tracrRNA sequences for each of the RGN polypeptides are identified and are set forth in Table 1. See below for the sgRNAs constructed for PAM libraries 1 and 2.

Example 3: Determination of PAM Requirements for Each RGN

PAM requirements for each RGN were determined using a PAM depletion assay essentially adapted from Kleinstiver et al. (2015) *Nature* 523:481-485 and Zetsche et al. (2015) *Cell* 163:759-771. Briefly, two plasmid libraries (L1 and L2) were generated in a pUC18 backbone (ampR), with each containing a distinct 30 bp protospacer (target) sequence flanked by 8 random nucleotides (i.e., the PAM region). The target sequence and flanking PAM region of library 1 and library 2 for RGNs APG00969, APG03128, and APG00771 are SEQ ID NOs: 14 and 15, respectively. The target sequence and flanking PAM region of library 1 and library 2 for RGNs AP09748, APG02789, and APG09106 are SEQ ID NOs: 32 and 33, respectively.

The libraries were separately electroporated into *E. coli* BL21(DE3) cells harboring pRSF-1b expression vectors containing an RGN of the invention (codon optimized for *E. coli*) along with a cognate sgRNA containing a spacer sequence corresponding to the protospacer in L1 or L2. Sufficient library plasmid was used in the transformation reaction to obtain >10^CFU. Both the RGN and sgRNA in the pRSF-1b backbone were under the control of T7 promoters. The transformation reaction was allowed to recover for 1 hr after which it was diluted into LB media containing carbenicillin and kanamycin and grown overnight. The following day the mixture was diluted into self-inducing Overnight Express™ Instant TB Medium (Millipore Sigma) to allow expression of the RGN and sgRNA, and grown for an additional 4 h or 20 h after which the cells were spun down and plasmid DNA was isolated with a Mini-prep kit (Qiagen, Germantown, MD). In the presence of the appropriate sgRNA, plasmids containing a PAM that is recognizable by the RGN will be cleaved resulting in their removal from the population. Plasmids containing PAMs that are not recognizable by the RGN, or that are transformed into bacteria not containing an appropriate sgRNA, will survive and replicate. The PAM and protospacer regions of uncleaved plasmids were PCR-amplified and prepared for sequencing following published protocols (16s-metagenomic library prep guide 15044223B, Illumina, San Diego, CA). Deep sequencing (80 bp single end reads) was performed on a MiSeq (Illumina) by a service provider (Mo-Gene, St. Louis, MO). Typically, 1-4M reads were obtained per amplicon. PAM regions were extracted, counted, and normalized to total reads for each sample. PAMs that lead to plasmid cleavage were identified by being underrepresented when compared to controls (i.e., when the library is transformed into *E. coli* containing the RGN but lacking an appropriate sgRNA). To represent PAM requirements for a novel RGN, the depletion ratios (frequency in sample/frequency in control) for all sequences in the region in question were converted to enrichment values with a –log base 2 transformation. Sufficient PAMs were defined as those with enrichment values >2.3 (which corresponds to depletion ratios <~0.2). PAMs above this threshold in both libraries were collected and used to generate web logos, which for example can be generated using a web-based service on the internet known as "weblogo". PAM sequences were identified and reported when there was a consistent pattern in the top enriched PAMs. A PAM (having an enrichment factor (EF)>2.3) for each RGN is provided in Table 2. For some RGNs, non-limiting exemplary PAMs (having an EF>3.3) were also identified. The PAM orientation is 5'-target-PAM-3' for APG00969, APG03128, APG00771, and 5'-PAM-target-3' for APG09748, APG09106, and APG02789.

TABLE 2

| | PAM determination | | |
|---|---|---|---|
| RGN ID | sgRNA L1 (SEQ ID NO.) | sgRNA L2 (SEQ ID NO.) | PAM (SEQ ID NO.) |
| APG00969 | 5 | 6 | 7 |
| APG03128 | 20 | 21 | 22 |
| APG09748 | 28 | 29 | 30 |
| APG00771 | 39 | 40 | 41 |
| APG02789 | 47 | 48 | 49 |
| APG09106 | 54 | 55 | 30 |

Example 4: Engineering the Guide RNA to Increase Nuclease Activity

For RGNs APG09748 and APG09106, which have very high sequence identity and have the same PAM, RNA folding predictions were used to determine regions in the guide RNA that can be altered to optimize nuclease activity. The stability of the crRNA:tracrRNA base pairing in the repeat:antirepeat region was increased by shortening the repeat:antirepeat region, adding G-C base pairs, and removing G-U wobble pairs. "Optimized" guide variants were tested and compared to the wild-type gRNA using the RGN APG09748 in in vitro cleavage assays.

To produce RGNs for RNP formation, expression plasmids containing an RGN fused to a C-terminal His6 (SEQ ID NO: 593) or His10 (SEQ ID NO: 594) tag were constructed and transformed into BL21 (DE3) strains of *E. coli*. Expression was performed using Magic Media (Thermo Fisher) supplemented with 50 µg/mL kanamycin. After lysis and clarification, the protein was purified by immobilized metal affinity chromatography and quantified using the Qubit protein quantitation kit (Thermo Fisher) or by UV-vis using a calculated extinction coefficient.

Ribonucleoprotein (RNP) was prepared by incubating the purified RGN with sgRNA at a ~2:1 ratio for 20 min at room temperature. For in vitro cleavage reactions, RNPs were incubated with plasmids or linear dsDNA containing the targeted protospacer flanked by a preferred PAM sequence for >30 min at room temperature. Two target nucleic acid sequences within the TRAC locus, TRAC11 (SEQ ID NO: 60) and TRAC14 (SEQ ID NO: 61), were tested. gRNAs were assayed both for targeted activity with the correct target nucleic acid sequence (for example, the gRNA has TRAC11 spacer sequence and the assayed target is TRAC11) and without the correct target nucleic acid sequence (for example, the gRNA has TRAC11 spacer sequence and the assayed target is TRAC14). Activity determined by plasmid cleavage is assessed by agarose gel electrophoresis. Results are shown in Table 3. Guide variants are listed as SEQ ID NOs: 56-59, and are provided with spacer sequences. These guide sequences use a noncomplementary nucleotide linker of AAAA (SEQ ID NO: 31). The optimized gRNA (SEQ ID NO: 64; poly-N indicates location of spacer sequence), with increased repeat:antirepeat binding, has optimized tracrRNA (SEQ ID NO: 62) and optimized crRNA (SEQ ID NO: 63) components. The optimized guide variant was able to cleave two loci where previously no cleavage was detected using the wild-type guide RNA. Through optimization of hybridization in the repeat:antirepeat region, in vitro cleavage of APG09748 increased from 0% cleavage to 100% cleavage for multiple targets in the TRAC locus.

TABLE 3

Editing efficiency of APG09748 with engineered guide variants

| gRNA variant (SEQ ID NO.) | Guide Design | Assayed Target | Gel 1 - 2 µL load | | Gel 2 - 1 µL load | |
|---|---|---|---|---|---|---|
| | | | % intact | % cleaved | % intact | % cleaved |
| 56 | Optimized | TRAC11 | 68 | 32 | 57 | 43 |
| 56 | Optimized | TRAC14 | 100 | 0 | 100 | 0 |
| 57 | Optimized | TRAC11 | 100 | 0 | 100 | 0 |
| 57 | Optimized | TRAC14 | 70 | 30 | 69 | 31 |
| 58 | WT | TRAC11 | 100 | 0 | 100 | 0 |
| 58 | WT | TRAC14 | 100 | 0 | 100 | 0 |
| 59 | WT | TRAC11 | 100 | 0 | 100 | 0 |
| 59 | WT | TRAC14 | 100 | 0 | 100 | 0 |
| None | | TRAC11 | 100 | 0 | 100 | 0 |
| None | | TRAC14 | 100 | 0 | 100 | 0 |

Additional optimized gRNA variants were designed and assayed. Further, different lengths of spacer sequence were also tested to determine how spacer length might affect cleavage efficiency. The sgRNA outside of the spacer sequence is referred to as the "backbone" in this assay. In Table 4, these are denoted as "WT" (SEQ ID NO: 53, the wild type sequence), and the three optimized sgRNAs: V1 (SEQ ID NO: 65), V2 (SEQ ID NO: 66) and V3 (SEQ ID NO: 64). All of these sequences have a poly-N to indicate the location of the spacer sequence. Guides were expressed as sgRNAs by in vitro transcription (IVT). Compared to the wild-type sgRNA backbone, V1 is 87.8% identical, V2 is 92.4% identical, and V3 is 85.5% identical. Synthetic tracrRNA:crRNA duplexes ("synthetic") representing dual-guide RNAs but otherwise similar to the wild type and optimized sgRNAs recited above were also produced and tested.

For this set of assays, RGN APG09106 was used; otherwise, methods for in vitro cleavage reactions were similar to what is described above. The targeted nucleic acid sequences were Target 1 (SEQ ID NO: 67) and Target 2 (SEQ ID NO: 68). The results are shown in Table 4.

TABLE 4

Editing efficiency of APG09106 with engineered guide variants

| RNA Source | Target | Spacer Length | Backbone | Spacer SEQ ID NO. | Cleavage % |
|---|---|---|---|---|---|
| Synthetic | 2 | 18 | WT | 69 | 12.3 |
| Synthetic | 1 | 20 | WT | 70 | 0 |
| Synthetic | 2 | 20 | WT | 71 | 55.0 |
| Synthetic | 1 | 25 | WT | 72 | 0 |
| Synthetic | 2 | 25 | WT | 73 | 61.4 |
| IVT | 2 | 25 | V1 | 74 | 1.1 |
| IVT | 2 | 25 | V2 | 75 | 0.9 |
| IVT | 2 | 25 | V3 | 76 | 0.7 |
| IVT | 2 | 20 | V3 | 77 | 21.0 |
| IVT | 1 | 25 | V3 | 78 | 2.0 |

Example 5: Demonstration of Gene Editing Activity in Mammalian Cells

Example 5.1: Activity of APG02789 in Mammalian Cells

RGN nucleotide sequences codon optimized for human expression were synthesized with an N-terminal nuclear localization tag and cloned into the pcDNA3.1 CMV expression plasmid. The final construct of the RGN polypeptide is as follows: N-terminus—SV40 NLS (SEQ ID NO: 10)—3×FLAG Tag (SEQ ID NO: 11)—RGN sequence (SEQ ID NOs: 1, 16, 24, 35, 43 or 50)—Nucleoplasmin NLS (SEQ ID NO: 12)—C-terminus. PCR amplicons comprising a U6 promoter driving expression of sgRNA sequences are generated using Herculase II (Agilent Technologies). 400 ng of RGN expression plasmids and 100 ng of the sgRNA PCR products are transfected into 24-well plates of HEK293FT cells at 75-90% confluency using Lipofectamine 2000 reagent (Life Technologies). Cells are incubated at 37° C. for 72 h post-transfection before genomic DNA extraction. Genomic DNA is extracted using the QuickExtract DNA Extraction Solution (Epicentre) following the manufacturer's protocol. The genomic region flanking the RGN target site is PCR amplified, and products are purified using QiaQuick Spin Column (Qiagen) following the manufacturer's protocol. 200-500 ng total of the purified PCR products are mixed with 1 µl 10×Taq DNA Polymerase PCR buffer (Enzymatics) and ultrapure water to a final volume of 10 µl, and subjected to a re-annealing process to enable heteroduplex formation: 95° C. for 10 min, 95° C. to 85° C. ramping at −2° C./s, 85° C. to 25° C. at −0.25° C./s, and 25° C. hold for 1 min. After reannealing, products are treated with SURVEYOR nuclease and SURVEYOR enhancer S (Integrated DNA Technologies) following the manufacturer's recommended protocol and analyzed on 4-20% Novex TBE polyacrylamide gels (Life Technologies). Gels are stained with SYBR Gold DNA stain (Life Technologies) for 10 min and imaged with a Gel Doc gel imaging system (Bio-rad). Quantification is based on relative band intensities. Indel percentage was determined by the formula, $100 \times (1-(1-(b+c)/(a+b+c))^{1/2})$, where a is the integrated intensity of the undigested PCR product, and b and c are the integrated intensities of each cleavage product.

For RGN APG02789, methods were carried out as described above. A number of different genes in the human genome were targeted for RNA-guided cleavage. These loci are included in Table 5 below, along with the reference to the SEQ ID NO of the sgRNA. The indel percentage, which is an indication of RGN activity, is also shown.

TABLE 5

Activity of APG02789 in mammalian cells

| sgRNA | Gene target | % INDEL |
|---|---|---|
| 79 | DNMT1 | N.D. |
| 80 | VEGFA | N.D. |
| 81 | EMX1 | 45.6 |
| 82 | AurkB | 44.3 |
| 83 | AurkB | 31.6 |
| 84 | AurkB | 25.5 |
| 85 | HPRT1 | N.D. |
| 86 | HPRT1 | 15.7 |

TABLE 5-continued

Activity of APG02789 in mammalian cells

| sgRNA | Gene target | % INDEL |
|---|---|---|
| 87 | HPRT1 | N.D. |
| 88 | RelA | N.D. |
| 89 | RelA | N.D. |
| 90 | RelA | N.D. |

Example 5.2: Activity of APG09106 in Mammalian Cells

RGN expression cassettes were produced and introduced into vectors for mammalian expression. RGNs APG00969, APG03128, APG09748, APG09106, and APG02789 were each codon-optimized for human expression (SEQ ID NOs: 357-361, respectively), and the expressed proteins were operably fused at the N-terminal end to an SV40 nuclear localization sequence (NLS; SEQ ID NO: 10) and to 3×FLAG tags (SEQ ID NO: 11), and operably fused at the C-terminal end to nucleoplasmin NLS sequences (SEQ ID NO: 12). Two copies of the NLS sequence were used, operably fused in tandem. Each expression cassette was under control of a cytomegalovirus (CMV) promoter (SEQ ID NO: 334). It is known in the art that the CMV transcription enhancer (SEQ ID NO: 335) may also be included in constructs comprising the CMV promoter. Guide RNA expression constructs encoding a single gRNA each under the control of a human RNA polymerase III U6 promoter (SEQ ID NO: 336) were produced and introduced into an expression vector. Guides targeted regions of the AurkB gene. For one RNA-guided nuclease, specific residues were mutated to increase nuclease activity of the protein, specifically the T849 residue of APG09106 was mutated to arginine (SEQ ID NO: 362). This point mutation increased editing rates in mammalian cells.

The constructs described above were introduced into mammalian cells. One day prior to transfection, 1×10$^5$ HEK293T cells (Sigma) were plated in 24-well dishes in Dulbecco's modified Eagle medium (DMEM) plus 10% (vol/vol) fetal bovine serum (Gibco) and 1% Penicillin-Streptomycin (Gibco). The next day when the cells were at 50-60% confluency, 500 ng of a RGN expression plasmid plus 500 ng of a single gRNA expression plasmid were co-transfected using 1.5 µL of Lipofectamine 3000 (Thermo Scientific) per well, following the manufacturer's instructions. After 48 hours of growth, total genomic DNA was harvested using a genomic DNA isolation kit (Machery-Nagel) according to the manufacturer's instructions.

The total genomic DNA was then analyzed to determine the rate of editing in the AurkB target. Oligonucleotides were produced to be used for PCR amplification and subsequent analysis of the amplified genomic target site (SEQ ID NOs: 363 and 364). All PCR reactions were performed using 10 µL of 2× Master Mix Phusion High-Fidelity DNA polymerase (Thermo Scientific) in a 20 µL reaction including 0.5 M of each primer. Large genomic regions encompassing each target gene were first amplified using PCR #1 primers (SEQ ID NOs: 363 and 364), using a program of: 98° C., 1 min; 30 cycles of [98° C., 10 sec; 62° C., 15 sec; 72° C., 5 min]; 72° C., 5 min; 12° C., forever.

One microliter of this PCR reaction was then further amplified using primers specific for each guide (PCR #2 primers; SEQ ID NOs: 365-370), using a program of: 98° C., 1 min; 35 cycles of [98° C., 10 sec; 67° C., 15 sec; 72° C., 30 sec]; 72° C., 5 min; 12° C., forever. Primers for PCR #2 include Nextera Read 1 and Read 2 Transposase Adapter overhang sequences for Illumina sequencing.

Following the second PCR amplification, DNA was cleaned using a PCR cleanup kit (Zymo) according to the manufacturer's instructions and eluted in water. 200-500 ng of purified PCR #2 product was combined with 2 µL of 10×NEB Buffer 2 and water in a 20 µL reaction and annealed to form heteroduplex DNA using a program of: 95° C., 5 min; 95-85° C., cooled at a rate of 2° C./sec; 85-25° C., cooled at a rate of 0.1° C./sec.; 12° C., forever. Following annealing, 5 µL of DNA was removed as a no enzyme control, and 1 µL of T7 Endonuclease I (NEB) was added and the reaction incubated at 37° C. for 1 hr. After incubation, 5×FlashGel loading dye (Lonza) was added and 5 µL of each reaction and controls were analyzed by a 2.2% agarose FlashGel (Lonza) using gel electrophoresis. Following visualization of the gel, the percentage of non-homologous end joining (NHEJ) was determined using the following equation: % NHEJ events=100×[1−(1-fraction cleaved)($\frac{1}{2}$)], where (fraction cleaved) is defined as: (density of digested products)/(density of digested products+undigested parental band).

For some samples, SURVEYOR® was used to analyze the results following expression in mammalian cells. Cells were incubated at 37° C. for 72 h post-transfection before genomic DNA extraction. Genomic DNA was extracted using the QuickExtract DNA Extraction Solution (Epicentre) following the manufacturer's protocol. The genomic region flanking the RGN target site was PCR amplified, and products were purified using QiaQuick Spin Column (Qiagen) following the manufacturer's protocol. 200-500 ng total of the purified PCR products were mixed with 1 µl 10×Taq DNA Polymerase PCR buffer (Enzymatics) and ultrapure water to a final volume of 10 µl, and subjected to a re-annealing process to enable heteroduplex formation: 95° C. for 10 min, 95° C. to 85° C. ramping at −2° C./s, 85° C. to 25° C. at −0.25° C./s, and 25° C. hold for 1 min.

After reannealing, products were treated with SURVEYOR® nuclease and SURVEYOR® enhancer S (Integrated DNA Technologies) following the manufacturer's recommended protocol and analyzed on 4-20% Novex TBE polyacrylamide gels (Life Technologies). Gels were stained with SYBR Gold DNA stain (Life Technologies) for 10 min and imaged with a Gel Doc gel imaging system (Bio-rad). Quantification was based on relative band intensities. Indel percentage was determined by the formula, 100×(1−(1−(b+c)/(a+b+c))$\frac{1}{2}$), where a is the integrated intensity of the undigested PCR product, and b and c are the integrated intensities of each cleavage product.

Additionally, products from PCR #2 containing Illumina overhang sequences underwent library preparation following the Illumina 16S Metagenomic Sequencing Library protocol. Deep sequencing was performed on an Illumina Mi-Seq platform by a service provider (MOGene). Typically, 200,000 of 250 bp paired-end reads (2×100,000 reads) are generated per amplicon. The reads were analyzed using CRISPResso (Pinello, et al. 2016 Nature Biotech, 34:695-697) to calculate the rates of editing. Output alignments were hand-curated to confirm insertion and deletion sites as well as identify microhomology sites at the recombination sites. The rates of editing are shown in Table 6. All experiments were performed in human cells. The "target sequence" is the targeted sequence within the gene target. For each target sequence, the guide RNA comprised the complementary RNA spacer sequence and the appropriate sgRNA depending on the RGN used. A selected breakdown of experiments by guide RNA is shown in Tables 7.1 and 7.2.

TABLE 6

Overall rates of editing for AurkB gene target

| RGN | Guide RNA ID | Target Sequence (SEQ ID NO.) | Overall Editing Rate in Sample | Deletion Rate in Sample | Insertion Rate in Sample |
|---|---|---|---|---|---|
| APG09106 | 830 | 371 | 0.55% | 100% | |
| APG09106 | 831 | 372 | 0.60% | 54% | 46% |

TABLE 6-continued

Overall rates of editing for AurkB gene target

| RGN | Guide RNA ID | Target Sequence (SEQ ID NO.) | Overall Editing Rate in Sample | Deletion Rate in Sample | Insertion Rate in Sample |
|---|---|---|---|---|---|
| APG09106 T849R | 830 | 371 | 2.97% | 98% | 2.00% |
| APG09106 T849R | 831 | 372 | 2.36% | 100% | |

Specific insertions and deletions for respective guides are shown in Tables 7.1 and 7.2. In these tables, the target sequence is identified by bold upper case letters. The κmer PAM regions are double underlined, with the main recognized nucleotides in bold. Insertions are identified by lowercase letters. Deletions are indicated with dashes (---). The INDEL location is calculated from the PAM proximal edge of the target sequence, with the edge being location 0. The location is positive (+) if the location is on the target side of the edge; the location is negative (−) if the location is on the PAM side of the edge.

TABLE 7.1

Specific insertions and deletions for Guide 831 using RGN APG09106

| Guide | # Reads | % Reads | % of INDELS | Type | INDEL Location | Size |
|---|---|---|---|---|---|---|
| GTCTGATTGCCTGTCGTTGCCCCTCCCAGATCAT GGAGGAGTTGGCAGA (SEQ ID NO: 373) | 92294 | 99.40 | | | | |
| GTCTGATTGCCTGTCGTTGCCCCTCCCA--------AGGAGTTGGCAGA (SEQ ID NO: 595) | 263 | 0.28 | 54.22 | Deletion | +19 | 8 |
| GTCTGATTGCCTGTCGTTGCCCctaagtgtatta agcattgtctcagagattttGGAGGAGTTGGCAG A (SEQ ID NO: 596) | 222 | 0.24 | 45.77 | Insertion | +13 | 20 |

TABLE 7.2

Specific insertions and deletions for Guide 831 using APG09106 T849R

| Guide | # Reads | % Reads | % of INDELS | Type | INDEL Location | Size |
|---|---|---|---|---|---|---|
| GTCTGATTGCCTGTCGTTGCCCCTCCCAGATCAT GGAGGAGTTGGCAGA (SEQ ID NO: 373) | 189881 | 97.64 | | | | |
| GTCTGATTGCCTGTCGTTGCCCC----------TGGAGGAGTTGGCAGA (SEQ ID NO: 597) | 602 | 0.309 | 13.129 | Deletion | +14 | 10 |
| GTCTGATTGCCTGTCGTTGCCCCTCCCAGATC-GGAGGAGTTGGCAGA (SEQ ID NO: 598) | 394 | 0.202 | 8.593 | Deletion | +23 | 2 |
| GTCTGATTGCCTGTCGTTGCCCCTCCCAGAT-----AGGAGTTGGCAGA (SEQ ID NO: 599) | 399 | 0.205 | 8.702 | Deletion | +22 | 5 |
| GTCTGATTGCCTGTCGTTGCCCaTC--------TG--GGAGTTGGCAGA (SEQ ID NO: 600) | 379 | 0.194 | 8.266 | Deletion & Mutation | +16 | 10 |
| GTCTGATTGCCTGTCGTTGCCCCTC--------TGGAGGAGTTGGCAGA (SEQ ID NO: 601) | 350 | 0.179 | 7.633 | Deletion | +16 | 8 |
| GTCTGAT----------------------TGGAGGAGTTGGCAGA (SEQ ID NO: 602) | 309 | 0.158 | 6.739 | Deletion | −1 | 26 |
| GTCTGATTGCCTGTCGTTGCCCCTC---------GGAGGAGTTGGCAGA (SEQ ID NO: 603) | 280 | 0.143 | 6.106 | Deletion | +16 | 9 |
| GTCTGATTGCCTGTCGTTGCCCCTCC-------aGGAGGAGTTGGCAGA (SEQ ID NO: 604) | 274 | 0.140 | 5.976 | Deletion & Mutation | +17 | 7 |

TABLE 7.2-continued

Specific insertions and deletions for Guide 831 using APG09106 T849R

| Guide | # Reads | % Reads | % of INDELS | Type | INDEL Location | Size |
|---|---|---|---|---|---|---|
| G<u>TCT</u>GATT<u>G</u>CCTGTCGTTGCCC------------<br>---GGAGTTGGCAGA (SEQ ID NO: 605) | 251 | 0.129 | 5.474 | Deletion | +13 | 15 |
| G<u>TCT</u>GATT<u>G</u>CCTGTCGTTGCCC-------<br>ATCATGGAGGAGTTGGCAGA (SEQ ID NO: 606) | 250 | 0.128 | 5.452 | Deletion | +13 | 7 |
| G<u>TCT</u>GATT<u>G</u>CCTGTCGTTGCCCCTC------<br>CATGGAGGAGTTGGCAGA (SEQ ID NO: 607) | 231 | 0.118 | 5.038 | Deletion | +16 | 6 |
| G<u>TCT</u>GATT<u>G</u>CCTGTCGTTGCCCCTCCCA------<br>------------------------<br>(SEQ ID NO: 608) | 218 | 0.112 | 4.754 | Deletion | +19 | 30 |
| G<u>TCT</u>GATT<u>G</u>CCTGTCGTTGCCCC-----<br>aATCtTGGAGGAGTTGGCAGA (SEQ ID NO: 609) | 206 | 0.105 | 4.492 | Deletion & Mutation | +14 | 5 |
| G<u>TCT</u>GATT<u>G</u>CCTGTCGTTGCCC--------<br>TgggATGGAGGAGTTGGCAGA (SEQ ID NO: 610) | 162 | 0.083 | 3.533 | Deletion & Mutation | +13 | 8 |
| G<u>TCT</u>GATT<u>G</u>CCTGTCGTTGCCCCTC---------<br>-----AGTTGGCAGA (SEQ ID NO: 611) | 158 | 0.081 | 3.446 | Deletion | +16 | 14 |
| G<u>TCT</u>GATT<u>G</u>CCTGTCGTTGCCCC-------<br>TCATGGAGGAGTTGGCAGA (SEQ ID NO: 612) | 122 | 0.062 | 2.660 | Deletion | +14 | 7 |

Example 6: Demonstration of Gene Editing Activity in Plant Cells

RNA-guided nuclease activity of an RGN of the invention is demonstrated in plant cells using protocols adapted from Li, et al., 2013 (*Nat. Biotech.* 31:688-691). Briefly, a plant codon optimized version of an RGN of the invention (SEQ ID NOs: 1, 16, 24, 35, 43 or 50) operably linked to a nucleic acid sequence encoding for an N-terminal SV40 nuclear localization signal are cloned behind the strong constitutive 35S promoter in a transient transformation vector. sgRNAs targeting one or more sites in the plant PDS gene that flank an appropriate PAM sequence are cloned behind a plant U6 promoter in a second transient expression vector. The expression vectors are introduced into *Nicotiana benthamiana* mesophyll protoplasts using PEG-mediated transformation. The transformed protoplasts are incubated in the dark for up to 36 hr. Genomic DNA is isolated from the protoplasts using a DNeasy Plant Mini Kit (Qiagen). The genomic region flanking the RGN target site is PCR amplified, and products are purified using QiaQuick Spin Column (Qiagen) following the manufacturer's protocol. 200-500 ng total of the purified PCR products are mixed with 1 µl 10×Taq DNA Polymerase PCR buffer (Enzymatics) and ultrapure water to a final volume of 10 µl, and subjected to a re-annealing process to enable heteroduplex formation: 95° C. for 10 min, 95° C. to 85° C. ramping at −2° C./s, 85° C. to 25° C. at −0.25° C./s, and 25° C. hold for 1 min.

After reannealing, products are treated with SURVEYOR nuclease and SURVEYOR enhancer S (Integrated DNA Technologies) following the manufacturer's recommended protocol and analyzed on 4-20% Novex TBE polyacrylamide gels (Life Technologies). Gels are stained with SYBR Gold DNA stain (Life Technologies) for 10 min and imaged with a Gel Doc gel imaging system (Bio-rad). Quantification is based on relative band intensities. Indel percentage is determined by the formula, $100 \times (1-(1-(b+c)/(a+b+c))^{1/2})$, where a is the integrated intensity of the undigested PCR product, and b and c are the integrated intensities of each cleavage product.

Example 7: Identification of Disease Targets

A database of clinical variants was obtained from NCBI ClinVar database, which is available through the world wide web at the NCBI ClinVar website. Pathogenic Single Nucleotide Polymorphisms (SNPs) were identified from this list. Using the genomic locus information, CRISPR targets in the region overlapping and surrounding each SNP were identified. A selection of SNPs that can be corrected using base editing in combination with the RGNs of the invention to target the causal mutation ("Cas1 Mut.") is listed in Table 8. In Table 8, only one alias of each disease is listed. The "RS #" corresponds to the RS accession number through the SNP database at the NCBI website. The AlleleID corresponds to a causal allele accession number, and the Chromosome Accession number also provides accession reference information found through the NCBI website. Table 8 also provides genomic target sequence information suitable for the RGN listed for each disease. The target sequence information also provides protospacer sequence for the production of the necessary sgRNA for the corresponding RGN of the invention.

TABLE 8

Disease Targets for RGNs of the invention

| Disease | RS# | RGN | Cas1 Mut. | Allele ID | Chromosome Accession | Gene Symbol | Target (SEQ ID NO.) |
|---|---|---|---|---|---|---|---|
| ABCA4-Related Disorder | 1800553 | APG00969 | C > T | 22927 | NC_000001.10, NC_000001.11 | ABCA4 | 91 |
| ABCA4-Related Disorder | 1800553 | APG03128 | C > T | 22927 | NC_000001.10, NC_000001.11 | ABCA4 | 92 |
| Stargardt disease 1 | 1800728 | APG00969 | A > G | 98777 | NC_000001.10, NC_000001.11 | ABCA4 | 93 |
| Stargardt disease 1 | 1800728 | APG09748, APG09106, APG02789 | A > G | 98777 | NC_000001.10, NC_000001.11 | ABCA4 | 94 |
| Glycogen storage disease type 1A | 1801175 | APG09748, APG09106, APG02789 | C > T | 27037 | NC_000017.10, NC_000017.11 | G6PC | 95 |
| Severe combined immunodeficiency disease | 3218716 | APG00969 | C > T | 52071 | NC_000014.8, NC_000014.9 | MYH7 | 96 |
| Severe combined immunodeficiency disease | 3218716 | APG09748, APG09106, APG02789 | C > T | 52071 | NC_000014.8, NC_000014.9 | MYH7 | 97 |
| Hereditary cancer-predisposing syndrome | 5030818 | APG03128 | C > T | 17256 | NC_000003.11, NC_000003.12 | VHL | 98 |
| Phenylketonuria | 5030851 | APG00969 | G > A | 15628 | NC_000012.11, NC_000012.12 | PAH | 99 |
| Phenylketonuria | 5030858 | APG00969 | G > A | 15616 | NC_000012.11, NC_000012.12 | PAH | 100 |
| Phenylketonuria | 5030858 | APG09748, APG09106, APG02789 | G > A | 15616 | NC_000012.11, NC_000012.12 | PAH | 101 |
| Hyperphenylalaninemia | 5030860 | APG00969 | T > C | 15632 | NC_000012.11, NC_000012.12 | PAH | 102 |
| Hyperphenylalaninemia | 5030860 | APG03128 | T > C | 15632 | NC_000012.11, NC_000012.12 | PAH | 103 |
| Hyperphenylalaninemia | 5030860 | APG09748, APG09106, APG02789 | T > C | 15632 | NC_000012.11, NC_000012.12 | PAH | 104 |
| CBS-deficiency | 5742905 | APG00969 | A > G | 15159 | NC_000021.8, NC_000021.9 | CBS | 105 |
| CBS-deficiency | 5742905 | APG03128 | A > G | 15159 | NC_000021.8, NC_000021.9 | CBS | 106 |
| Congenital microcephaly | 11555217 | APG00969 | C > T | 34125 | NC_000011.9, NC_000011.10 | DHCR7 | 107 |
| Alpha-1-antitrypsin deficiency | 28929474 | APG00969 | C > T | 33006 | NC_000014.8, NC_000014.9 | SERPINA1 | 108 |
| Alpha-1-antitrypsin deficiency | 28929474 | APG03128 | C > T | 33006 | NC_000014.8, NC_000014.9 | SERPINA1 | 109 |
| Alpha-1-antitrypsin deficiency | 28929474 | APG09748, APG09106, APG02789 | C > T | 33006 | NC_000014.8, NC_000014.9 | SERPINA1 | 110 |
| Limb-girdle muscular dystrophy, type 2D | 28933693 | APG00969 | C > T | 24476 | NC_000017.10, NC_000017.11 | SGCA | 111 |
| Limb-girdle muscular dystrophy, type 2D | 28933693 | APG03128 | C > T | 24476 | NC_000017.10, NC_000017.11 | SGCA | 112 |
| Focal cortical dysplasia type II | 28934872 | APG00969 | G > A | 27436 | NC_000016.9, NC_000016.10 | TSC2 | 113 |
| Hyperimmunoglobulin D with periodic fever | 28934897 | APG00969 | G > A | 26968 | NC_000012.11, NC_000012.12 | MVK | 114 |
| Hyperimmunoglobulin D with periodic fever | 28934897 | APG03128 | G > A | 26968 | NC_000012.11, NC_000012.12 | MVK | 115 |
| MECP2-Related Disorders | 28934906 | APG00969 | G > A | 26850 | NC_000023.10, NC_000023.11 | MECP2 | 116 |
| MECP2-Related Disorders | 28934906 | APG09748, APG09106, APG02789 | G > A | 26850 | NC_000023.10, NC_000023.11 | MECP2 | 117 |
| MECP2-Related Disorders | 28935468 | APG00969 | G > A | 26863 | NC_000023.10, NC_000023.11 | MECP2 | 118 |
| MECP2-Related Disorders | 28935468 | APG00771 | G > A | 26863 | NC_000023.10, NC_000023.11 | MECP2 | 119 |
| Inclusion body myopathy 2 | 28937594 | APG00969 | A > G | 21064 | NC_000009.11, NC_000009.12 | GNE | 120 |
| Inclusion body myopathy 2 | 28937594 | APG03128 | A > G | 21064 | NC_000009.11, NC_000009.12 | GNE | 121 |
| Inclusion body myopathy 2 | 28937594 | APG09748, APG09106, APG02789 | A > G | 21064 | NC_000009.11, NC_000009.12 | GNE | 122 |
| Inclusion body myopathy 2 | 28937594 | APG00771 | A > G | 21064 | NC_000009.11, NC_000009.12 | GNE | 123 |

TABLE 8-continued

Disease Targets for RGNs of the invention

| Disease | RS# | RGN | Cas1 Mut. | Allele ID | Chromosome Accession | Gene Symbol | Target (SEQ ID NO.) |
|---|---|---|---|---|---|---|---|
| Congenital disorder of glycosylation | 28939378 | APG00969 | C > T | 19763 | NC_000016.9, NC_000016.10 | ALG1 | 124 |
| Familial Mediterranean fever | 28940579 | APG00969 | A > G | 17579 | NC_000016.9, NC_000016.10 | MEFV | 125 |
| Familial hypercholesterolemia | 28942080 | APG00969 | G > A | 18735 | NC_000019.9, NC_000019.10 | LDLR | 126 |
| Familial hypercholesterolemia | 28942080 | APG03128 | G > A | 18735 | NC_000019.9, NC_000019.10 | LDLR | 127 |
| MUTYH-associated polyposis | 34612342 | APG00969 | T > C | 20332 | NC_000001.10, NC_000001.11 | MUTYH | 128 |
| MUTYH-associated polyposis | 36053993 | APG00969 | C > T | 20333 | NC_000001.10, NC_000001.11 | MUTYH | 129 |
| MUTYH-associated polyposis | 36053993 | APG03128 | C > T | 20333 | NC_000001.10, NC_000001.11 | MUTYH | 130 |
| Cardiomyopathy | 36211715 | APG00969 | C > T | 29159 | NC_000014.8, NC_000014.9 | MYH7 | 131 |
| Cardiomyopathy | 36211715 | APG03128 | C > T | 29159 | NC_000014.8, NC_000014.9 | MYH7 | 132 |
| Von Willebrand disease | 41276738 | APG00969 | C > T | 15335 | NC_000012.11, NC_000012.12 | VWF | 133 |
| Von Willebrand disease | 41276738 | APG03128 | C > T | 15335 | NC_000012.11, NC_000012.12 | VWF | 134 |
| Von Willebrand disease | 41276738 | APG09748, APG09106, APG02789 | C > T | 15335 | NC_000012.11, NC_000012.12 | VWF | 135 |
| Breast and/or ovarian cancer | 41293455 | APG00969 | G > A | 32714 | NC_000017.10, NC_000017.11 | BRCA1 | 136 |
| Breast and/or ovarian cancer | 41293455 | APG09748, APG09106, APG02789 | G > A | 32714 | NC_000017.10, NC_000017.11 | BRCA1 | 137 |
| Breast and/or ovarian cancer | 41293465 | APG00969 | G > A | 70268 | NC_000017.10, NC_000017.11 | BRCA1 | 138 |
| Breast and/or ovarian cancer | 41293465 | APG03128 | G > A | 70268 | NC_000017.10, NC_000017.11 | BRCA1 | 139 |
| Breast and/or ovarian cancer | 45580035 | APG00969 | C > T | 67431 | NC_000013.10, NC_000013.11 | BRCA2 | 140 |
| Breast and colorectal cancer | 55770810 | APG00969 | G > A | 70063 | NC_000017.10, NC_000017.11 | BRCA1 | 141 |
| MECP2-Related Disorders | 61749721 | APG00969 | G > A | 26868 | NC_000023.10, NC_000023.11 | MECP2 | 142 |
| MECP2-Related Disorders | 61749721 | APG03128 | G > A | 26868 | NC_000023.10, NC_000023.11 | MECP2 | 143 |
| MECP2-Related Disorders | 61750240 | APG00969 | G > A | 26854 | NC_000023.10, NC_000023.11 | MECP2 | 144 |
| MECP2-Related Disorders | 61750240 | APG03128 | G > A | 26854 | NC_000023.10, NC_000023.11 | MECP2 | 145 |
| MECP2-Related Disorders | 61750240 | APG09748, APG09106, APG02789 | G > A | 26854 | NC_000023.10, NC_000023.11 | MECP2 | 146 |
| Stargardt disease 1 | 61751374 | APG00969 | G > A | 22933 | NC_000001.10, NC_000001.11 | ABCA4 | 147 |
| Stargardt disease 1 | 61751374 | APG03128 | G > A | 22933 | NC_000001.10, NC_000001.11 | ABCA4 | 148 |
| Familial Mediterranean fever | 61752717 | APG00969 | T > C | 17577 | NC_000016.9, NC_000016.10 | MEFV | 149 |
| MEFV-Related Disorder | 61752717 | APG09748, APG09106, APG02789 | T > C | 17577 | NC_000016.9, NC_000016.10 | MEFV | 150 |
| MEFV-Related Disorder | 61752717 | APG00771 | T > C | 17577 | NC_000016.9, NC_000016.10 | MEFV | 151 |
| Phenylketonuria | 62508698 | APG03128 | C > T | 15619 | NC_000012.11, NC_000012.12 | PAH | 152 |
| Breast and/or ovarian cancer | 62625307 | APG00969 | G > A | 69596 | NC_000017.10, NC_000017.11 | BRCA1 | 153 |
| Breast and/or ovarian cancer | 62625307 | APG03128 | G > A | 69596 | NC_000017.10, NC_000017.11 | BRCA1 | 154 |
| Breast and/or ovarian cancer | 62625307 | APG09748, APG09106, APG02789 | G > A | 69596 | NC_000017.10, NC_000017.11 | BRCA1 | 155 |
| Breast and/or ovarian cancer | 62625308 | APG00969 | G > A | 32710 | NC_000017.10, NC_000017.11 | BRCA1 | 156 |
| Breast and/or ovarian cancer | 62625308 | APG03128 | G > A | 32710 | NC_000017.10, NC_000017.11 | BRCA1 | 157 |

TABLE 8-continued

Disease Targets for RGNs of the invention

| Disease | RS# | RGN | Cas1 Mut. | Allele ID | Chromosome Accession | Gene Symbol | Target (SEQ ID NO.) |
|---|---|---|---|---|---|---|---|
| Breast and/or ovarian cancer | 62625308 | APG09748, APG09106, APG02789 | G > A | 32710 | NC_000017.10, NC_000017.11 | BRCA1 | 158 |
| Hereditary cancer-predisposing syndrome | 63749795 | APG09748, APG09106, APG02789 | C > T | 95218 | NC_000003.11, NC_000003.12 | MLH1 | 159 |
| Hereditary cancer-predisposing syndrome | 63749843 | APG00969 | C > T | 94826 | NC_000002.11, NC_000002.12 | MSH6 | 160 |
| Hereditary cancer-predisposing syndrome | 63749843 | APG03128 | C > T | 94826 | NC_000002.11, NC_000002.12 | MSH6 | 161 |
| Hereditary cancer-predisposing syndrome | 63749849 | APG09748, APG09106, APG02789 | C > T | 96029 | NC_000002.11, NC_000002.12 | MSH2 | 162 |
| Hereditary cancer-predisposing syndrome | 63750636 | APG00969 | C > T | 96378 | NC_000002.11, NC_000002.12 | MSH2 | 163 |
| Hereditary cancer-predisposing syndrome | 63750636 | APG03128 | C > T | 96378 | NC_000002.11, NC_000002.12 | MSH2 | 164 |
| Hereditary cancer-predisposing syndrome | 63750636 | APG09748, APG09106, APG02789 | C > T | 96378 | NC_000002.11, NC_000002.12 | MSH2 | 165 |
| Carnitine palmitoyltransferase II deficiency | 74315294 | APG00969 | C > T | 23992 | NC_000001.10, NC_000001.11 | CPT2 | 166 |
| Carnitine palmitoyltransferase II deficiency | 74315294 | APG09748, APG09106, APG02789 | C > T | 23992 | NC_000001.10, NC_000001.11 | CPT2 | 167 |
| Carnitine palmitoyltransferase II deficiency | 74315294 | APG00771 | C > T | 23992 | NC_000001.10, NC_000001.11 | CPT2 | 168 |
| Cystic fibrosis | 74597325 | APG09748, APG09106, APG02789 | C > T | 22161 | NC_000007.13, NC_000007.14 | CFTR | 169 |
| RET-Related Disorders | 74799832 | APG00969 | T > C | 28958 | NC_000010.10, NC_000010.11 | RET | 170 |
| Deficiency of UDPglucose-hexose-1-phosphate uridylyltransferase | 75391579 | APG00969 | A > G | 18653 | NC_000009.11, NC_000009.12 | GALT | 171 |
| Deficiency of UDPglucose-hexose-1-phosphate uridylyltransferase | 75391579 | APG03128 | A > G | 18653 | NC_000009.11, NC_000009.12 | GALT | 172 |
| Deficiency of UDPglucose-hexose-1-phosphate uridylyltransferase | 75391579 | APG09748, APG09106, APG02789 | A > G | 18653 | NC_000009.11, NC_000009.12 | GALT | 173 |
| Cystic fibrosis | 75527207 | APG09748, APG09106, APG02789 | G > A | 22159 | NC_000007.13, NC_000007.14 | CFTR | 174 |
| Deafness, X-linked | 76434661 | APG00969 | C > T | 53916 | NC_000013.10, NC_000013.11 | GJB2 | 175 |
| Deafness, X-linked | 76434661 | APG03128 | C > T | 53916 | NC_000013.10, NC_000013.11 | GJB2 | 176 |
| Amyloidogenic transthyretin amyloidosis | 76992529 | APG00969 | G > A | 28465 | NC_000018.9, NC_000018.10 | TTR | 177 |
| Amyloidogenic transthyretin amyloidosis | 76992529 | APG03128 | G > A | 28465 | NC_000018.9, NC_000018.10 | TTR | 178 |
| Amyloidogenic transthyretin amyloidosis | 76992529 | APG09748, APG09106, APG02789 | G > A | 28465 | NC_000018.9, NC_000018.10 | TTR | 179 |
| Amyloidogenic transthyretin amyloidosis | 76992529 | APG00771 | G > A | 28465 | NC_000018.9, NC_000018.10 | TTR | 180 |
| Cystic fibrosis | 77010898 | APG00969 | G > A | 22168 | NC_000007.13, NC_000007.14 | CFTR | 181 |
| Cystic fibrosis | 77010898 | APG09748, APG09106, APG02789 | G > A | 22168 | NC_000007.13, NC_000007.14 | CFTR | 182 |
| Metachromatic leukodystrophy | 80338815 | APG00969 | C > T | 18090 | NC_000022.10, NC_000022.11 | ARSA | 183 |
| Metachromatic leukodystrophy | 80338815 | APG09748, APG09106, APG02789 | C > T | 18090 | NC_000022.10, NC_000022.11 | ARSA | 184 |
| Cowden syndrome 3 | 80338844 | APG00969 | C > T | 21935 | NC_000011.9, NC_000011.10 | SDHD | 185 |
| Cowden syndrome 3 | 80338844 | APG03128 | C > T | 21935 | NC_000011.9, NC_000011.10 | SDHD | 186 |
| Cowden syndrome 3 | 80338844 | APG09748, APG09106, APG02789 | C > T | 21935 | NC_000011.9, NC_000011.10 | SDHD | 187 |
| Cowden syndrome 3 | 80338844 | APG00771 | C > T | 21935 | NC_000011.9, NC_000011.10 | SDHD | 188 |

TABLE 8-continued

Disease Targets for RGNs of the invention

| Disease | RS# | RGN | Cas1 Mut. | Allele ID | Chromosome Accession | Gene Symbol | Target (SEQ ID NO.) |
|---|---|---|---|---|---|---|---|
| Smith-Lemli-Opitz syndrome | 80338853 | APG00969 | G > A | 21822 | NC_000011.9, NC_000011.10 | DHCR7 | 189 |
| Smith-Lemli-Opitz syndrome | 80338853 | APG03128 | G > A | 21822 | NC_000011.9, NC_000011.10 | DHCR7 | 190 |
| Smith-Lemli-Opitz syndrome | 80338853 | APG09748, APG09106, APG02789 | G > A | 21822 | NC_000011.9, NC_000011.10 | DHCR7 | 191 |
| Hypertyrosinemia | 80338901 | APG00969 | G > A | 26909 | NC_000015.9, NC_000015.10 | FAH | 192 |
| Hypertyrosinemia | 80338901 | APG03128 | G > A | 26909 | NC_000015.9, NC_000015.10 | FAH | 193 |
| Hypertyrosinemia | 80338901 | APG00771 | G > A | 26909 | NC_000015.9, NC_000015.10 | FAH | 194 |
| Deafness, X-linked | 80338940 | APG03128 | C > T | 32068 | NC_000013.10, NC_000013.11 | GJB2 | 195 |
| Deafness, X-linked | 80338945 | APG00969 | A > G | 32055 | NC_000013.10, NC_000013.11 | GJB2 | 196 |
| Breast and/or ovarian cancer | 80356962 | APG00969 | C > T | 70247 | NC_000017.10, NC_000017.11 | BRCA1 | 197 |
| Breast and/or ovarian cancer | 80356962 | APG03128 | C > T | 70247 | NC_000017.10, NC_000017.11 | BRCA1 | 198 |
| Breast and/or ovarian cancer | 80356962 | APG09748, APG09106, APG02789 | C > T | 70247 | NC_000017.10, NC_000017.11 | BRCA1 | 199 |
| Breast and/or ovarian cancer | 80356969 | APG03128 | G > A | 70213 | NC_000017.10, NC_000017.11 | BRCA1 | 200 |
| Breast and/or ovarian cancer | 80357123 | APG09748, APG09106, APG02789 | G > A | 70147 | NC_000017.10, NC_000017.11 | BRCA1 | 201 |
| Inborn genetic diseases | 80358259 | APG00969 | A > G | 18006 | NC_000018.9, NC_000018.10 | NPC1 | 202 |
| Inborn genetic diseases | 80358259 | APG09748, APG09106, APG02789 | A > G | 18006 | NC_000018.9, NC_000018.10 | NPC1 | 203 |
| Breast and/or ovarian cancer | 80359212 | APG00969 | C > T | 67494 | NC_000013.10, NC_000013.11 | BRCA2 | 204 |
| Breast and/or ovarian cancer | 80359212 | APG09748, APG09106, APG02789 | C > T | 67494 | NC_000013.10, NC_000013.11 | BRCA2 | 205 |
| Fanconi anemia | 104886457 | APG00969 | G > A | 27086 | NC_000009.11, NC_000009.12 | FANCC | 206 |
| Fanconi anemia | 104886457 | APG09748, APG09106, APG02789 | G > A | 27086 | NC_000009.11, NC_000009.12 | FANCC | 207 |
| SLC26A2-Related Disorders | 104893915 | APG00969 | C > T | 19128 | NC_000005.9, NC_000005.10 | SLC26A2 | 208 |
| SLC26A2-Related Disorders | 104893915 | APG03128 | C > T | 19128 | NC_000005.9, NC_000005.10 | SLC26A2 | 209 |
| SLC26A2-Related Disorders | 104893915 | APG09748, APG09106, APG02789 | C > T | 19128 | NC_000005.9, NC_000005.10 | SLC26A2 | 210 |
| Oculocutaneous albinism | 104894313 | APG00969 | C > T | 18816 | NC_000011.9, NC_000011.10 | TYR | 211 |
| Cardiomyopathy | 104894368 | APG09748, APG09106, APG02789 | C > T | 29104 | NC_000012.11, NC_000012.12 | MYL2 | 212 |
| Deafness, X-linked | 104894396 | APG09748, APG09106, APG02789 | C > T | 32041 | NC_000013.10, NC_000013.11 | GJB2 | 213 |
| Inborn genetic diseases | 104894635 | APG00969 | C > T | 20146 | NC_000017.10, NC_000017.11 | SGSH | 214 |
| Inborn genetic diseases | 104894635 | APG03128 | C > T | 20146 | NC_000017.10, NC_000017.11 | SGSH | 215 |
| Inborn genetic diseases | 104894635 | APG09748, APG09106, APG02789 | C > T | 20146 | NC_000017.10, NC_000017.11 | SGSH | 216 |
| Familial Mediterranean fever | 104895097 | APG00969 | C > T | 17588 | NC_000016.9, NC_000016.10 | MEFV | 217 |
| Familial Mediterranean fever | 104895097 | APG09748, APG09106, APG02789 | C > T | 17588 | NC_000016.9, NC_000016.10 | MEFV | 218 |
| Familial Mediterranean fever | 104895097 | APG00771 | C > T | 17588 | NC_000016.9, NC_000016.10 | MEFV | 219 |

TABLE 8-continued

Disease Targets for RGNs of the invention

| Disease | RS# | RGN | Cas1 Mut. | Allele ID | Chromosome Accession | Gene Symbol | Target (SEQ ID NO.) |
|---|---|---|---|---|---|---|---|
| Familial dysautonomia | 111033171 | APG09748, APG09106, APG02789 | A > G | 21124 | NC_000009.11, NC_000009.12 | ELP1 | 220 |
| Familial dysautonomia | 111033171 | APG00771 | A > G | 21124 | NC_000009.11, NC_000009.12 | ELP1 | 221 |
| Shwachman syndrome | 113993993 | APG00969 | A > G | 18235 | NC_000007.13, NC_000007.14 | SBDS | 222 |
| Shwachman syndrome | 113993993 | APG09748, APG09106, APG02789 | A > G | 18235 | NC_000007.13, NC_000007.14 | SBDS | 223 |
| POLG-related condition | 113994095 | APG00969 | C > T | 28535 | NC_000015.9, NC_000015.10 | POLG | 224 |
| POLG-related condition | 113994098 | APG00969 | C > T | 28541 | NC_000015.9, NC_000015.10 | POLG | 225 |
| POLG-related condition | 113994098 | APG03128 | C > T | 28541 | NC_000015.9, NC_000015.10 | POLG | 226 |
| Very long chain acyl-CoA dehydrogenase deficiency | 113994167 | APG00969 | T > C | 33877 | NC_000017.10, NC_000017.11 | ACADVL | 227 |
| Very long chain acyl-CoA dehydrogenase deficiency | 113994167 | APG03128 | T > C | 33877 | NC_000017.10, NC_000017.11 | ACADVL | 228 |
| Very long chain acyl-CoA dehydrogenase deficiency | 113994167 | APG00771 | T > C | 33877 | NC_000017.10, NC_000017.11 | ACADVL | 229 |
| Glycogen storage disease | 116987552 | APG00969 | G > A | 17337 | NC_000011.9, NC_000011.10 | PYGM | 230 |
| Glycogen storage disease | 116987552 | APG03128 | G > A | 17337 | NC_000011.9, NC_000011.10 | PYGM | 231 |
| Glycogen storage disease | 116987552 | APG00771 | G > A | 17337 | NC_000011.9, NC_000011.10 | PYGM | 232 |
| RYR1-Related Disorders | 118192172 | APG00969 | C > T | 28003 | NC_000019.9, NC_000019.10 | RYR1 | 233 |
| RYR1-Related Disorders | 118192172 | APG09748, APG09106, APG02789 | C > T | 28003 | NC_000019.9, NC_000019.10 | RYR1 | 234 |
| Ceroid lipofuscinosis neuronal 2 | 119455955 | APG09748, APG09106, APG02789 | G > A | 17682 | NC_000011.9, NC_000011.10 | TPP1 | 235 |
| Medium-chain acyl-coenzyme A dehydrogenase deficiency | 121434274 | APG09748, APG09106, APG02789 | G > A | 18627 | NC_000001.10, NC_000001.11 | ACADM | 236 |
| Familial hypercholesterolemia | 121908026 | APG00969 | C > T | 18725 | NC_000019.9, NC_000019.10 | LDLR | 237 |
| Familial hypercholesterolemia | 121908026 | APG03128 | C > T | 18725 | NC_000019.9, NC_000019.10 | LDLR | 238 |
| Primary hyperoxaluria | 121908529 | APG00969 | G > A | 38436 | NC_000002.11, NC_000002.12 | AGXT | 239 |
| Primary hyperoxaluria | 121908529 | APG03128 | G > A | 38436 | NC_000002.11, NC_000002.12 | AGXT | 240 |
| Primary hyperoxaluria | 121908529 | APG09748, APG09106, APG02789 | G > A | 38436 | NC_000002.11, NC_000002.12 | AGXT | 241 |
| Cardio-facio-cutaneous syndrome | 121908595 | APG00969 | A > G | 28390 | NC_000015.9, NC_000015.10 | MAP2K1 | 242 |
| Cardiomyopathy | 121908987 | APG00969 | C > T | 21885 | NC_000007.13, NC_000007.14 | PRKAG2 | 243 |
| Cardiomyopathy | 121908987 | APG09748, APG09106, APG02789 | C > T | 21885 | NC_000007.13, NC_000007.14 | PRKAG2 | 244 |
| Cowden syndrome | 121909219 | APG00969 | C > T | 22852 | NC_000010.10, NC_000010.11 | PTEN | 245 |
| Cowden syndrome | 121909219 | APG09748, APG09106, APG02789 | C > T | 22852 | NC_000010.10, NC_000010.11 | PTEN | 246 |
| FGFR3-Related Disorders | 121913482 | APG00969 | C > T | 31371 | NC_000004.11, NC_000004.12 | FGFR3 | 247 |
| FGFR3-Related Disorders | 121913482 | APG03128 | C > T | 31371 | NC_000004.11, NC_000004.12 | FGFR3 | 248 |
| Cardiomyopathy | 121913625 | APG00969 | G > A | 29128 | NC_000014.8, NC_000014.9 | MYH7 | 249 |
| Cardiomyopathy | 121913628 | APG09748, APG09106, APG02789 | C > T | 29131 | NC_000014.8, NC_000014.9 | MYH7 | 250 |
| Hypophosphatasia | 121918007 | APG00969 | G > A | 28709 | NC_000001.10, NC_000001.11 | ALPL | 251 |

TABLE 8-continued

Disease Targets for RGNs of the invention

| Disease | RS# | RGN | Cas1 Mut. | Allele ID | Chromosome Accession | Gene Symbol | Target (SEQ ID NO.) |
|---|---|---|---|---|---|---|---|
| Methylmalonic acidemia | 121918241 | APG00969 | C > T | 16462 | NC_000001.10, NC_000001.11 | MMACHC | 252 |
| Methylmalonic acidemia | 121918241 | APG03128 | C > T | 16462 | NC_000001.10, NC_000001.11 | MMACHC | 253 |
| Methylmalonic acidemia | 121918241 | APG00771 | C > T | 16462 | NC_000001.10, NC_000001.11 | MMACHC | 254 |
| Inborn genetic diseases | 121918243 | APG09748, APG09106, APG02789 | G > A | 16464 | NC_000001.10, NC_000001.11 | MMACHC | 255 |
| PTPN11-related disorder | 121918457 | APG00969 | C > T | 28370 | NC_000012.11, NC_000012.12 | PTPN11 | 256 |
| PTPN11-related disorder | 121918457 | APG09748, APG09106, APG02789 | C > T | 28370 | NC_000012.11, NC_000012.12 | PTPN11 | 257 |
| PTPN11-related disorder | 121918457 | APG00771 | C > T | 28370 | NC_000012.11, NC_000012.12 | PTPN11 | 258 |
| B lymphoblastic leukemia lymphoma, no ICD-O subtype | 121918459 | APG00969 | A > G | 28372 | NC_000012.11, NC_000012.12 | PTPN11 | 259 |
| Juvenile myelomonocytic leukemia | 121918462 | APG09748, APG09106, APG02789 | C > T | 28373 | NC_000012.11, NC_000012.12 | PTPN11 | 260 |
| Juvenile myelomonocytic leukemia | 121918466 | APG03128 | A > G | 28379 | NC_000012.11, NC_000012.12 | PTPN11 | 261 |
| Juvenile myelomonocytic leukemia | 121918466 | APG09748, APG09106, APG02789 | A > G | 28379 | NC_000012.11, NC_000012.12 | PTPN11 | 262 |
| Juvenile myelomonocytic leukemia | 121918466 | APG00771 | A > G | 28379 | NC_000012.11, NC_000012.12 | PTPN11 | 263 |
| Mucopolysaccharidosis type I | 121965019 | APG00969 | G > A | 26947 | NC_000004.11, NC_000004.12 | IDUA | 264 |
| Mucopolysaccharidosis type I | 121965019 | APG03128 | G > A | 26947 | NC_000004.11, NC_000004.12 | IDUA | 265 |
| Mucopolysaccharidosis type I | 121965020 | APG00969 | C > T | 26948 | NC_000004.11, NC_000004.12 | IDUA | 266 |
| Mucopolysaccharidosis type I | 121965020 | APG03128 | C > T | 26948 | NC_000004.11, NC_000004.12 | IDUA | 267 |
| Mucopolysaccharidosis type I | 121965020 | APG09748, APG09106, APG02789 | C > T | 26948 | NC_000004.11, NC_000004.12 | IDUA | 268 |
| Ceroid lipofuscinosis neuronal 1 | 137852700 | APG00969 | G > A | 23943 | NC_000001.10, NC_000001.11 | PPT1 | 269 |
| Ceroid lipofuscinosis neuronal 1 | 137852700 | APG09748, APG09106, APG02789 | G > A | 23943 | NC_000001.10, NC_000001.11 | PPT1 | 270 |
| Polycystic kidney dysplasia | 137852944 | APG00969 | G > A | 19147 | NC_000006.11, NC_000006.12 | PKHD1 | 271 |
| CHEK2-Related Cancer Susceptibility | 137853007 | APG09748, APG09106, APG02789 | G > A | 20631 | NC_000022.10, NC_000022.11 | CHEK2 | 272 |
| Colorectal cancer | 137854568 | APG00969 | C > T | 15837 | NC_000005.9, NC_000005.10 | APC | 273 |
| Colorectal cancer | 137854568 | APG03128 | C > T | 15837 | NC_000005.9, NC_000005.10 | APC | 274 |
| Colorectal cancer | 137854568 | APG09748, APG09106, APG02789 | C > T | 15837 | NC_000005.9, NC_000005.10 | APC | 275 |
| Brugada syndrome | 137854601 | APG00969 | C > T | 24416 | NC_000003.11, NC_000003.12 | SCN5A | 276 |
| Familial hypercholesterolemia | 137929307 | APG00969 | G > A | 171217 | NC_000019.9, NC_000019.10 | LDLR | 277 |
| Familial hypercholesterolemia | 137929307 | APG09748, APG09106, APG02789 | G > A | 171217 | NC_000019.9, NC_000019.10 | LDLR | 278 |
| Spastic Paraplegia | 141659620 | APG03128 | G > A | 21858 | NC_000016.9, NC_000016.10 | SPG7 | 279 |
| Cardio-facio-cutaneous syndrome | 180177035 | APG00969 | T > C | 29012 | NC_000007.13, NC_000007.14 | BRAF | 280 |
| Cardio-facio-cutaneous syndrome | 180177035 | APG09748, APG09106, APG02789 | T > C | 29012 | NC_000007.13, NC_000007.14 | BRAF | 281 |
| Cardio-facio-cutaneous syndrome | 180177035 | APG00771 | T > C | 29012 | NC_000007.13, NC_000007.14 | BRAF | 282 |
| Familial cancer of breast | 180177083 | APG00969 | G > A | 132139 | NC_000016.10, NC_000016.9 | PALB2 | 283 |

TABLE 8-continued

Disease Targets for RGNs of the invention

| Disease | RS# | RGN | Cas1 Mut. | Allele ID | Chromosome Accession | Gene Symbol | Target (SEQ ID NO.) |
|---|---|---|---|---|---|---|---|
| Familial cancer of breast | 180177083 | APG09748, APG09106, APG02789 | G > A | 132139 | NC_000016.10, NC_000016.9 | PALB2 | 284 |
| MYBPC3-Related Disorders | 200411226 | APG00969 | C > T | 174776 | NC_000011.9, NC_000011.10 | MYBPC3 | 285 |
| MYBPC3-Related Disorders | 200411226 | APG03128 | C > T | 174776 | NC_000011.9, NC_000011.10 | MYBPC3 | 286 |
| MYBPC3-Related Disorders | 200411226 | APG09748, APG09106, APG02789 | C > T | 174776 | NC_000011.9, NC_000011.10 | MYBPC3 | 287 |
| MYBPC3-Related Disorders | 200411226 | APG00771 | C > T | 174776 | NC_000011.9, NC_000011.10 | MYBPC3 | 288 |
| RYR1-Related Disorders | 200563280 | APG00969 | C > T | 169564 | NC_000019.9, NC_000019.10 | RYR1 | 289 |
| RYR1-Related Disorders | 200563280 | APG09748, APG09106, APG02789 | C > T | 169564 | NC_000019.9, NC_000019.10 | RYR1 | 290 |
| Cardiomyopathy | 371898076 | APG00969 | C > T | 52045 | NC_000014.8, NC_000014.9 | MYH7 | 291 |
| Breast-ovarian cancer, familial 4 | 387906843 | APG00969 | G > A | 39241 | NC_000017.10, NC_000017.11 | RAD51D | 292 |
| Breast-ovarian cancer, familial 4 | 387906843 | APG03128 | G > A | 39241 | NC_000017.10, NC_000017.11 | RAD51D | 293 |
| MYBPC3-Related Disorders | 387907267 | APG00969 | G > A | 45725 | NC_000011.9, NC_000011.10 | MYBPC3 | 294 |
| MYBPC3-Related Disorders | 387907267 | APG03128 | G > A | 45725 | NC_000011.9, NC_000011.10 | MYBPC3 | 295 |
| MYBPC3-Related Disorders | 387907267 | APG09748, APG09106, APG02789 | G > A | 45725 | NC_000011.9, NC_000011.10 | MYBPC3 | 296 |
| PTPN11-related disorder | 397507547 | APG00969 | A > G | 49032 | NC_000012.11, NC_000012.12 | PTPN11 | 297 |
| Desmoid disease, hereditary | 397515734 | APG09748, APG09106, APG02789 | C > T | 51418 | NC_000005.9, NC_000005.10 | APC | 298 |
| Marfan Syndrome/Loeys-Dietz Syndrome/Familial Thoracic Aortic Aneurysms and Dissections | 397515757 | APG00969 | C > T | 51454 | NC_000015.9, NC_000015.10 | FBN1 | 299 |
| Marfan Syndrome/Loeys-Dietz Syndrome/Familial Thoracic Aortic Aneurysms and Dissections | 397515757 | APG09748, APG09106, APG02789 | C > T | 51454 | NC_000015.9, NC_000015.10 | FBN1 | 300 |
| MYBPC3-Related Disorders | 397516074 | APG00969 | C > T | 51962 | NC_000011.9, NC_000011.10 | MYBPC3 | 301 |
| MYBPC3-Related Disorders | 397516074 | APG03128 | C > T | 51962 | NC_000011.9, NC_000011.10 | MYBPC3 | 302 |
| Immunodeficiency 14 | 397518423 | APG00969 | G > A | 94255 | NC_000001.10, NC_000001.11 | PIK3CD | 303 |
| Immunodeficiency 14 | 397518423 | APG09748, APG09106, APG02789 | G > A | 94255 | NC_000001.10, NC_000001.11 | PIK3CD | 304 |
| Inborn genetic diseases | 398123009 | APG09748, APG09106, APG02789 | C > T | 48180 | NC_000011.9, NC_000011.10 | PACS1 | 305 |
| B lymphoblastic leukemia lymphoma, no ICD-O subtype | 529008617 | APG03128 | G > A | 152318 | NC_000001.10, NC_000001.11 | MUTYH | 306 |
| B lymphoblastic leukemia lymphoma, no ICD-O subtype | 529008617 | APG09748, APG09106, APG02789 | G > A | 152318 | NC_000001.10, NC_000001.11 | MUTYH | 307 |
| Familial cancer of breast | 587780021 | APG03128 | G > A | 133177 | NC_000002.11, NC_000002.12 | BARD1 | 308 |
| Familial cancer of breast | 587780021 | APG09748, APG09106, APG02789 | G > A | 133177 | NC_000002.11, NC_000002.12 | BARD1 | 309 |
| Marfan Syndrome/Loeys-Dietz Syndrome/Familial Thoracic Aortic Aneurysms and Dissections | 727503054 | APG00969 | A > G | 175979 | NC_000015.9, NC_000015.10 | FBN1 | 310 |
| Marfan Syndrome/Loeys-Dietz Syndrome/Familial Thoracic Aortic Aneurysms and Dissections | 727503054 | APG03128 | A > G | 175979 | NC_000015.9, NC_000015.10 | FBN1 | 311 |
| Familial hypercholesterolemia | 746118995 | APG00969 | C > T | 228192 | NC_000019.9, NC_000019.10 | LDLR | 312 |
| Familial hypercholesterolemia | 746118995 | APG03128 | C > T | 228192 | NC_000019.9, NC_000019.10 | LDLR | 313 |

TABLE 8-continued

Disease Targets for RGNs of the invention

| Disease | RS# | RGN | Casl Mut. | Allele ID | Chromosome Accession | Gene Symbol | Target (SEQ ID NO.) |
|---|---|---|---|---|---|---|---|
| Familial hypercholesterolemia | 746118995 | APG09748, APG09106, APG02789 | C > T | 228192 | NC_000019.9, NC_000019.10 | LDLR | 314 |
| Familial hypercholesterolemia | 746118995 | APG00771 | C > T | 228192 | NC_000019.9, NC_000019.10 | LDLR | 315 |
| Familial hypercholesterolemia | 765696008 | APG00969 | G > A | 228162 | NC_000019.10, NC_000019.9 | LDLR | 316 |
| Familial hypercholesterolemia | 765696008 | APG03128 | G > A | 228162 | NC_000019.10, NC_000019.9 | LDLR | 317 |
| Familial hypercholesterolemia | 769370816 | APG00969 | G > A | 228176 | NC_000019.10, NC_000019.9 | LDLR | 318 |
| Familial hypercholesterolemia | 769370816 | APG03128 | G > A | 228176 | NC_000019.10, NC_000019.9 | LDLR | 319 |
| Familial hypercholesterolemia | 769370816 | APG09748, APG09106, APG02789 | G > A | 228176 | NC_000019.10, NC_000019.9 | LDLR | 320 |
| Familial hypercholesterolemia | 769370816 | APG00771 | G > A | 228176 | NC_000019.10, NC_000019.9 | LDLR | 321 |
| Hereditary cancer-predisposing syndrome | 786201042 | APG00969 | C > T | 181998 | NC_000002.12, NC_000002.11 | MSH6 | 322 |

Example 8: Targeting Mutations Responsible for Hurler Syndrome

The following describes a potential treatment for Hurler Syndrome, also referred to as MPS-1, using an RNA directed base editing system that corrects a mutation responsible for Hurler syndrome in a large proportion of patients with the disease. This approach utilizes a base editing fusion protein that is RNA guided and that can be packaged into a single AAV vector for delivery to a wide range of tissue types. Depending on the exact regulatory elements and base editor domain used, it may also be possible to engineer a single vector that encodes for both the base editing fusion protein and a single guide RNA to target the diseased locus.

Example 8.1: Identifying RGN with Ideal PAM

The genetic disease MPS-1 is a lysosomal storage disease characterized at the molecular level by the accumulation of dermatan sulfate and heparan sulfate in lysosomes. This disease is generally an inherited genetic disorder caused by mutations in the IDUA gene (NCBI Reference sequence NG_008103.1), which encodes α-L-iduronidase. The disease is a result of a deficiency of α-L-iduronidase. The most common IDUA mutations found in studies of individuals of Northern European background are W402X and Q70X, both nonsense mutations resulting in premature termination of translation (Bunge et al. (1994), Hum. Mol. Genet, 3(6): 861-866, herein incorporated by reference). Reversion of a single nucleotide would restore the wild-type coding sequence and result in protein expression controlled by the endogenous regulatory mechanisms of the genetic locus.

The W402X mutation of the human Idua gene accounts for a high proportion of MPS-1H cases. Base editors can target a narrow sequence window relative to the binding site of the protospacer component of the guide RNA and thus the presence of a PAM sequence a specific distance from the target locus is essential for the success of the strategy. Given the constraints that the target mutation must be on the exposed non-target strand (NTS) during the interaction of the base editing protein and that the footprint of the RGN domain will block access to the region near the PAM, an accessible locus is thought to be 10-30 bp from the PAM. To avoid editing and mutagenesis of other nearby adenosine bases in this window, different linkers are screened. The ideal window is 12-16 bp from the PAM.

RGN APG00969 possesses a compatible PAM sequence. APG00969 has a PAM sequence of 5'-nnARV-3' (SEQ ID NO: 7) and is compact in size—potentially allowing delivery via a single AAV vector. This delivery approach bestows multiple advantages relative to others, such as access to a wide range of tissues (liver, muscle, CNS) and well established safety profile and manufacturing techniques.

Cas9 from *S. pyogenes* (SpyCas9) requires a PAM sequence of NGG (SEQ ID NO: 323), which is present near the W402X locus, but the size of SpyCas9 prevents packaging into a single AAV vector, and thus forgoes the aforementioned advantages of this approach. While a dual delivery strategy may be employed (for example, Ryu et al, (2018), Nat. Biotechnol., 36(6): 536-539, herein incorporated by reference), it would add significant manufacturing complexity and cost. Additionally, dual viral vector delivery significantly decreases the efficiency of gene correction, since a successful edit in a given cell requires infection with both vectors and assembly of the fusion protein in the cell.

A commonly used Cas9 ortholog from *S. aureus* (SauCas9) is considerably smaller in size relative to SpyCas9, but has a more complex PAM requirement—NGRRT (SEQ ID NO: 324). This sequence, however, is not within a range expected to be useful for base editing of the causative locus.

Example 8.2: RGN Fusion Constructs and sgRNA Sequences

A DNA sequence encoding a fusion protein with the following domains is produced using standard molecular biology techniques: 1) an RGN domain with mutations that inactivate the DNA cleavage activity ("dead" or "nickase"); 2) an adenosine deaminase useful for base editing. The construct described in the table below (Table 9) comprises a fusion protein with the base editing active domain, in this example a mutated variant of APG02312 (SEQ ID NO: 325), operably fused to the N-terminal end of the dead RGN APG00969 (SEQ ID NO: 327). The base editing active domain could be any adenosine deaminase of the invention, such as for example SEQ ID NOs: 514 or 572-584. It is known in the art that a fusion protein could also be made with the base-editing enzyme at the C-terminal end of the RGN. Additionally, the RGN and the base editor of the fusion protein are typically separated by a linker amino sequence. It is known in the art that lengths of standard linkers range from 15-30 amino acids. Further, it is known in the art that certain fusion proteins between an RGN and a base-editing enzyme may also comprise at least one uracil glycosylase inhibitor (UGI) domain (SEQ ID NO: 570), which may increase base editing efficiency (U.S. Pat. No. 10,167,457, herein incorporated by reference). Therefore, a fusion protein may comprise RGN APG00969 or variant thereof, an adenosine deaminase, and optionally at least one UGI.

TABLE 9

Construct for RNA-targeted base editing

| Seq ID No. | Construct | RGN | Dead (D) or Nickase (N) | Base editor | Linker (SEQ ID NO.) |
|---|---|---|---|---|---|
| 326 | Nuc-ADAT-Linker-dAPG00969-Linker-SV40 | APG00969 | D | ADAT | 546 |

The accessible editing sites of an RGN are determined by the PAM sequence. When combining an RGN with a base editing domain, the target residue for editing must reside on the non-target strand (NTS), since the NTS is single stranded while the RGN is associated with the locus. Evaluating a number of nucleases and corresponding guide RNAs enables the selection of the most appropriate gene editing tool for this particular locus. Several potential PAM sequences that can be targeted by the constructs described above in the human Idua gene are in the proximity of the mutant nucleotide responsible for the W402X mutation. A sequence encoding a guide RNA transcript containing 1) a "spacer" that is complementary to the non-coding DNA strand at the disease locus; and 2) RNA sequence required for association of the guide RNA with the RGN is also produced. Such a sgRNA may be encoded by, for example, SEQ ID NO: 356. This sgRNA or similar sgRNAs that may be devised by one of skill in the art, can be evaluated for their efficiency in directing the base editors above or base editors with different RGN-deaminase fusions to the locus of interest.

Example 8.3: Assay for Activity in Cells from Hurler Disease Patients

To verify the genotype strategy and evaluate the constructs described above, fibroblasts from Hurler disease patients are used. A vector is designed containing appropriate promoters upstream of the fusion protein coding sequence and the sgRNA encoding sequence for expression of these in human cells, similar to those vectors described in Example 5. It is recognized that promoters and other DNA elements (for example enhancers, or terminators) which either are known for high levels of expression in human cells or may specifically express well in fibroblast cells may also be used. The vector is transfected into the fibroblasts using standard techniques, for example transfection similar to what is described in Example 5. Alternatively, electroporation may be used. The cells are cultured for 1-3 days. Genomic DNA (gDNA) is isolated using standard techniques. The editing efficiency is determined by performing a qPCR genotyping assay and/or next generation sequencing on the purified gDNA, as described further below.

Taqman™ qPCR analysis utilizes probes specific for the wild-type and mutant allele. These probes bear fluorophores which are resolved by their spectral excitation and/or emission properties using a qPCR instrument. A genotyping kit containing PCR primers and probes can be obtained commercially (i.e. Thermo Fisher Taqman™ SNP genotyping assayID C__27862753_10 for SNP ID rs121965019) or designed. An example of a designed primer and probe set is shown in Table 10.

TABLE 10

RT-PCR primers and probes

| Description | Sequence | SEQ ID NO. |
|---|---|---|
| Forward Amplification Primer | 5'-GACTCCTTCACCAAG-3' | 328 |
| Reverse Amplification Primer | 5'-GTAGATCAGCACCG-3' | 329 |
| Wild Type Probe | 5'-CTCTGGGCCGAAGT-3' | 330 |
| W402X Probe | 5'-CTCTAGGCCGAAGT-3' | 331 |

Following the editing experiment, the gDNA is subjected to qPCR analysis using standard methods and the primers and probes described above. Expected results are shown in Table 11. This in vitro system can be used to expediently evaluate constructs and choose one with high editing efficiency for further studies. The systems will be evaluated in comparison with cells with and without the W402X mutation, and preferably with some that are heterozygous for this mutation. The Ct values will be compared to either a reference gene or the total amplification of the locus using a dye such as Sybr green.

TABLE 11

Expected qPCR results

| Genotype | Transfected with base editor | Expected PCR result |
|---|---|---|
| Idua$^{WT/WT}$ | No | Homozygous WT |
| Idua$^{WT/W402X}$ | No | Heterozygous: 50% WT, 50% W402X |
| Idua$^{W402X/W402X}$ | No | Homozygous W402X |
| Idua$^{W402X/W402X}$ | Yes | Variable |

The tissues can also be analyzed by next generation sequencing. Primer binding sites such as the ones shown below (Table 12), or other suitable primer binding sites that can be identified by a person of skill in the art, can be used. Following PCR amplification, products containing Illumina Nextera XT overhang sequences undergo library preparation following the Illumina 16S Metagenomic Sequencing Library protocol. Deep sequencing is performed on an Illumina Mi-Seq platform. Typically, 200,000 of 250 bp paired-end reads (2×100,000 reads) are generated per amplicon. The reads are analyzed using CRISPResso (Pinello et al., 2016) to calculate the rates of editing. Output alignments are hand-curated to confirm insertion and deletion sites as well as identify microhomology sites at the recombination sites.

TABLE 12

NGS primer binding sites

| Direction | Sequence | SEQ ID NO. |
|---|---|---|
| Forward | 5'-ACTTCCTCCAGCC-3' | 332 |
| Reverse | 5'-GAACCCCGGCTTA-3' | 333 |

Western blotting of cell lysate of transfected cells and control cells using an anti-IDUA antibody is performed to verify expression of the full-length protein and an enzyme activity assay on the cell lysate using substrate 4-methylumbelliferyl α-L-iduronide verifies that the enzyme is catalytically active (Hopwood et al., Clin. Chim. Acta (1979), 92(2): 257-265, incorporated by reference herein). These experiments are performed in comparison with the original Idua$^{W402X/W402X}$ cell line (without transfection), the Idua$^{W402X/W402X}$ cell line transfected with the base editing construct and a random guide sequence, and a cell line expressing wild-type IDUA.

Example 8.4: Disease Treatment Validation in a Murine Model

To verify the efficacy of this therapeutic approach, a mouse model with a nonsense mutation in the analogous amino acid is used. The mouse strain bears a W392X mutation in its Idua gene (Gene ID: 15932) which corresponds to the homologous mutation in Hurler syndrome patients (Bunge et al., (1994), Hum. Mol. Genet. 3(6): 861-866, incorporated by reference herein). This locus comprises a distinct nucleotide sequence relative to that in humans, which lacks the PAM sequence necessary for correction with the base editors described in the previous examples, and thus necessitates design of a distinct fusion protein to perform the nucleotide correction. Amelioration of the disease in this animal can validate the therapeutic approach of correcting the mutation in tissues accessible by a gene delivery vector.

Mice homozygous for this mutation display a number of phenotypic characteristics similar to Hurler syndrome patients. A base editing-RGN fusion protein as described above (Table 9) along with an RNA guide sequence are incorporated into an expression vector that allows protein expression and RNA transcription in mice. A study design is shown below in Table 13. The study includes groups that are treated with a high dose of the expression vector comprising the base-editing fusion protein and RNA guide sequence, a low dose of same expression vector, control which is the model mouse treated with an expression vector that does not comprise the base editing fusion protein or the guide RNA, and a second control which is a wild type mouse treated with the same empty vector.

TABLE 13

Genome editing experiment in murine model

| Group | Mouse strain | N | Treatment |
|---|---|---|---|
| 1 | Idua-W392X[1] | ≥5 | Low dose of vector |
| 2 | Idua-W392X | ≥5 | High dose of vector |
| 3 | Idua-W392X | ≥5 | Vehicle |
| 4 | 129/Sv (WT) | 5 | Vehicle |

Endpoints to evaluate include body weight, urine GAG excretion, serum IDUA enzymatic activity, IDUA activity in tissues of interest, tissue pathology, genotyping of tissues of interest to verify correction of the SNP, and behavioral and neurological evaluation. Since some endpoints are terminal, additional groups may be added for evaluation of, for example, tissue pathology and tissue IDUA activities before the end of the study. Additional examples of endpoints can be found in published papers establishing Hurler syndrome animal models (Shull et al. (1994), Proc. Natl. Acad. Sci. U.S.A., 91(26): 12937-12941; Wang et al. (2010), Mol. Genet. Metab., 99(1): 62-71; Hartung et al. (2004), Mol. Ther., 9(6): 866-875; Liu et al. (2005), Mol. Ther., 11(1): 35-47; Clarke et al. (1997), Hum. Mol. Genet. 6(4): 503-511; all herein incorporated by reference).

One possible delivery vector utilizes the adeno associated virus (AAV). A vector is produced to include a base editor-dRGN fusion protein coding sequence (for example, Nuc-ADAT-Linker-dAPG19748-Linker-SV40, as described above) preceded by a CMV enhancer (SEQ ID NO: 335) and promoter (SEQ ID NO: 334), or other suitable enhancer and promoter combination, optionally a Kozak sequence, and operably fused at the 3' end to a terminator sequence and a poly adenylation sequence such as the minimal sequence described in Levitt, N.; Briggs, D.; Gil, A.; Proudfoot, N. J. Definition of an Efficient Synthetic Poly(A) Site. Genes Dev. 1989, 3 (7), 1019-1025. The vector may further comprise an expression cassette encoding for a single guide RNA operably linked at its 5' end to a human U6 promoter (SEQ ID NO: 336) or another promoter suitable for production of small non-coding RNAs, and further comprising inverted terminal repeat (ITR) sequences necessary and well-known in the art for packaging into the AAV capsid. Production and viral packaging is performed by standard methods, such as those described in U.S. Pat. No. 9,587,250, herein incorporated by reference.

Other possible viral vectors include adenovirus and lentivirus vectors, which are commonly used and would contain similar elements, with different packaging capabilities and requirements. Non-viral delivery methods can also be used, such as mRNA and sgRNA encapsulated by lipid nanoparticles (Cullis, P. R. and Allen, T. M. (2013), Adv. Drug Deliv. Rev. 65(1): 36-48; Finn et al. (2018), Cell Rep. 22(9): 2227-2235, both incorporated by reference), hydrodynamic injection of plasmid DNA (Suda T and Liu D, 2007, Mol. Ther. 15(12): 2063-2069, herein incorporated by reference), or ribonucleoprotein complexes of sgRNA and associated with gold nanoparticles (Lee, K.; Conboy, M.; Park, H. M.; Jiang, F.; Kim, H. J.; Dewitt, M. A.; Mackley, V. A.; Chang, K.; Rao, A.; Skinner, C.; et al., Nat. Biomed. Eng. 2017, 1 (11), 889-90).

Example 8.5: Disease Correction in a Murine Model with a Humanized Locus

To evaluate the efficacy of an identical base editor construct as would be used for human therapy, a mouse model in which the nucleotides near W392 are altered to match the sequence in humans around W402 is needed. This can be accomplished by a variety of techniques, including use of an RGN and an HDR template to cut and replace the locus in mouse embryos.

Due to the high degree of amino acid conservation, most nucleotides in the mouse locus can be altered to those of the human sequence with silent mutations as shown in Table 14. The only base changes resulting in altered coding sequence in the resulting engineered mouse genome occur after the introduced stop codon.

guide sequence. Many nucleases used for genome editing, such as the commonly used Cas9 nuclease from *S. pyogenes* (SpCas9), are too large to be packaged into adeno-associated viral (AAV) vectors, especially when considering the length of the SpCas9 gene and the guide RNA in addition to other genetic elements required for functional expression cassettes. This makes a viable approach using SpCas9 unlikely.

The compact RNA guided nucleases of the invention, particularly APG09748 and APG09106, are uniquely well suited for the excision of the FRDA instability region. Each RGN has a PAM requirement that is in the vicinity of the FRDA instability region. Additionally, each of these RGNs can be packaged into an AAV vector along with a guide RNA. Packing two guide RNAs would likely require a second vector, but this approach still compares favorably to

TABLE 14

Nucleotide mutations to generate a humanized mouse locus

| Feature | Human (W402X) Nucleotide (SEQ ID NO: 337) | Human (W402X) Encoded AA (SEQ ID NOS: 614 & 615) | Mouse (W392X) Nucleotide (SEQ ID NO: 338) | Mouse (W392X) Encoded AA (SEQ ID NOs: 616 & 617) | Humanized Mouse Nucleotide (SEQ ID NO: 339) | Humanized Mouse Encoded AA (SEQ ID NOS: 616 & 615) |
|---|---|---|---|---|---|---|
| Protospacer | G | E | A | G | G | G |
| | G | E | G | E | G | E |
| | A | | A | | A | |
| | G | | A | | G | |
| | C | Q | C | Q | C | Q |
| | A | | A | | A | |
| | G | | A | | G | |
| | C | L | C | L | C | L |
| | T | | T | | T | |
| | C | | C | | C | |
| | T | STOP | T | STOP | T | STOP |
| | A | | A | | A | |
| | G | | G | | G | |
| | G | A | G | A | G | A |
| | C | | C | | C | |
| | C | | A | | C | |
| | G | E | G | E | G | E |
| | A | | A | | A | |
| | A | | G | | A | |
| | G | V | G | V | G | V |
| | T | | T | | T | |
| | G | | C | | G | |
| | T | S | T | S | T | S |
| | C | | C | | C | |
| | G | | A | | G | |
| PAM, non-critical | C | Q | A | K | C | Q |
| | A | | A | | A | |
| | G | | G | | G | |
| | G | A | G | A | G | A |
| PAM, critical | C | | C | | C | |
| | C | | T | | C | |

Upon engineering of this mouse strain, similar experiments will be performed as described in Example 8.4.

Example 9: Targeting Mutations Responsible for Friedreich Ataxia

The expansion of the trinucleotide repeat sequence causing Friedreich's Ataxia (FRDA) occurs in a defined genetic locus within the FXN gene, referred to as the FRDA instability region. RNA guided nucleases (RGNs) may be used for excising the instability region in FRDA patient cells. This approach requires 1) an RGN and guide RNA sequence that can be programmed to target the allele in the human genome; and 2) a delivery approach for the RGN and what would be required of a larger nuclease such as SpCas9, which would require splitting the protein sequence between two vectors.

Table 15 shows the location of genomic target sequences suitable for targeting APG09748 or APG09106 to the 5' and 3' flanks of the FRDA instability region, as well as the sequence of the sgRNAs for the genomic targets. Once at the locus, the RGN would excise the FA instability region. Excision of the region can be verified with Illumina sequencing of the locus.

TABLE 15

Genomic target sequences for RGN systems

| Guide No. | Location relative to FRDA instability region | Genome target sequence (SEQ ID NO.) | sgRNA (SEQ ID NO.) |
|---|---|---|---|
| 1 | 5' | 340 | 344 |
| 2 | 5' | 341 | 345 |
| 3 | 3' | 342 | 346 |
| 4 | 3' | 343 | 347 |

Example 10: Targeting Mutations Responsible for Sickle Cell Diseases

Targeting sequences within the BCL11A enhancer region (SEQ ID NO: 348) may provide a mechanism for increasing fetal hemoglobulin (HbF) to either cure or alleviate the symptoms of sickle cell diseases. For example, genome wide association studies have identified a set of genetic variations at BCL11A that are associated with increased HbF levels. These variations are a collection of SNPs found in non-coding regions of BCL11A that function as a stage-specific, lineage-restricted enhancer region. Further investigation revealed that this BCL11A enhancer is required in erythroid cells for BCL11A expression (Bauer et al, (2013) *Science* 343:253-257, incorporated by reference herein). The enhancer region was found within intron 2 of the BCL11A gene, and three areas of DNaseI hypersensitivity (often indicative of a chromatin state that is associated with regulatory potential) in intron 2 were identified. These three areas were identified as "+62", "+58" and "+55" in accordance with the distance in kilobases from the transcription start site of BCL11A. These enhancer regions are roughly 350 (+55); 550 (+58); and 350 (+62) nucleotides in length (Bauer et al., 2013).

Example 10.1: Identifying Preferred RGN Systems

Here is described a potential treatment for beta-hemoglobinopathies using an RGN system that disrupts BCL11A binding to its binding site within the HBB locus, which is the gene responsible for making beta-globin in adult hemoglobin. This approach uses NHEJ which is more efficient in mammalian cells. In addition, this approach uses a nuclease of sufficiently small size that can be packaged into a single AAV vector for in vivo delivery.

The GATA1 enhancer motif in the human BCL11A enhancer region (SEQ ID NO: 348) is an ideal target for disruption using RNA guided nucleases (RGNs) to reduce BCL11A expression with concurrent re-expression of HbF in adult human erythrocytes (Wu et al. (2019) *Nat Med* 387:2554). Several PAM sequences compatible with APG09748 or APG09106 are readily apparent at the genetic locus surrounding this GATA1 site. These nucleases have a PAM sequence of 5'-DTTN-3' (SEQ ID NO: 30) and are compact in size, potentially allowing their delivery along with an appropriate guide RNA in a single AAV or adenoviral vector. This delivery approach bestows multiple advantages relative to others, such as access to hematopoietic stem cells and a well-established safety profile and manufacturing techniques.

The commonly used Cas9 nuclease from *S. pyogenes* (SpyCas9) requires a PAM sequence of 5'-NGG-3', (SEQ ID NO: 323) several of which are present near the GATA1 motif. However, the size of SpyCas9 prevents packaging into a single AAV or adenoviral vector and thus forgoes the aforementioned advantages of this approach. While a dual delivery strategy may be employed, it would add significant manufacturing complexity and cost. Additionally, dual viral vector delivery significantly decreases the efficiency of gene correction, since a successful edit in a given cell requires infection with both vectors.

An expression cassette encoding a human codon optimized APG09748 (SEQ ID NO: 349) or APG09106 (SEQ ID NO: 360) is produced, similar to those described in Example 5. Expression cassettes which express guide RNAs for RGNs APG09748 or APG09106 are also produced. These guide RNAs comprise: 1) a protospacer sequence that is complementary to either the non-coding or coding DNA strand within the BCL11A enhancer locus (the target sequence) and 2) an RNA sequence required for association of the guide RNA with the RGN. Because several potential PAM sequences for targeting by APG09748 or APG09106 surround the BCL11A GATA1 enhancer motif, several potential guide RNA constructs are produced to determine the best protospacer sequence that produces robust cleavage and NHEJ mediated disruption of the BCL11A GATA1 enhancer sequence. The target genomic sequences in Table 16 are evaluated to direct the RGN to this locus using the sgRNA provided in Table 16.

TABLE 16

Target Sequences for BCL11A GATA1 enhancer locus using APG09748

| Guide | Target genomic sequence (SEQ ID NO.) | sgRNA (SEQ ID NO.) |
|---|---|---|
| 1 | 350 | 353 |
| 2 | 351 | 354 |
| 3 | 352 | 355 |

To evaluate the efficiency with which APG09748 or APG09106 generates insertions or deletions that disrupt the BCL11A enhancer region, human cell lines such as human embryonic kidney cells (HEK cells) are used. A DNA vector comprising an RGN expression cassette (for example, as described in Example 5) is produced. A separate vector comprising an expression cassette comprising a coding sequence for a guide RNA sequence of Table 16 is also produced. Such an expression cassette may further comprise a human RNA polymerase III U6 promoter (SEQ ID NO: 336), as described in Example 5. Alternatively, a single vector comprising expression cassettes of both the RGN and guide RNA may be used. The vector is introduced into HEK cells using standard techniques such as those described in Example 5, and the cells are cultured for 1-3 days. Following this culture period, genomic DNA is isolated and the frequency of insertions or deletions is determined by using T7 Endonuclease I digestion and/or direct DNA sequencing, as described in Example 5.

A region of DNA encompassing the target BCL11A region is amplified by PCR with primers containing Illumina Nextera XT overhang sequences. These PCR amplicons are either examined for NHEJ formation using T7 Endonuclease I digestion, or undergo library preparation following the Illumina 16S Metagenomic Sequencing Library protocol or a similar Next Generation Sequencing (NGS) library preparation. Following deep sequencing, the reads generated are analyzed by CRISPResso to calculate rates of editing. Output alignments are hand-curated to confirm insertion and deletion sites. This analysis identifies the preferred RGN and the corresponding preferred guide RNA (sgRNA). The analysis may result in both APG09748 or APG09106 being equally preferred. Additionally, the analysis may determine there is more than one preferred guide RNA, or that all target genomic sequences in Table 16 are equally preferred.

Example 10.2: Assay for Expression of Fetal Hemoglobin

In this example, APG09748 or APG09106 generated insertions or deletions disrupting the BCL11A enhancer region are assayed for expression of fetal hemoglobin. Healthy human donor $CD34^+$ hematopoietic stem cells (HSCs) are used. These HSCs are cultured and vector(s) comprising expression cassettes comprising the coding regions of the preferred RGN and the preferred sgRNA are introduced using methods similar to those described in Example 8.3. Following electroporation, these cells are differentiated in vitro into erythrocytes using established protocols (for example, Giarratana et al. (2004) Nat Biotechnology 23:69-74, herein incorporated by reference). The expression of HbF is then measured using western blotting with an anti-human HbF antibody, or quantified via High Performance Liquid Chromatography (HPLC). It is expected that successful disruption of the BCL11A enhancer locus will lead to an increase in HbF production when compared to HSCs electroporated with only the RGN but no guide.

Example 10.3: Assay for Decreased Sickle Cell Formation

In this example, APG09748 or APG09106 generated insertions or deletions disrupting the BCL11A enhancer region are assayed for decreased sickle-cell formation. Donor $CD34^+$ hematopoietic stem cells (HSCs) from patients afflicted with sickle cell disease are used. These HSCs are cultured and vector(s) comprising expression cassettes comprising the coding regions of preferred RGN and the preferred sgRNA are introduced using methods similar to those described in Example 8.3. Following electroporation, these cells are differentiated in vitro into erythrocytes using established protocols (Giarratana et al. (2004) Nat Biotechnology 23:69-74). The expression of HbF is then measured using western blotting with an anti-human HbF antibody, or quantified via High Performance Liquid Chromatography (HPLC). It is expected that successful disruption of the BCL11A enhancer locus will lead to an increase in HbF production when compared to HSCs electroporated with only the RGN but no guide.

Sickle cell formation is induced in these differentiated erythrocytes by the addition of metabisulfite. The numbers of sickled vs normal erythrocytes are counted using a microscope. It is expected that the numbers of sickled cells are less in cells treated with APG09748 or APG09106 plus sgRNAs than with cells untreated, or treated with RGNs alone.

Example 10.4: Disease Treatment Validation in a Murine Model

To evaluate the efficacy of using APG09748 or APG09106 disruption of the BCL11A locus, suitable humanized mouse models of sickle cell anemia are used. Expression cassettes encoding for the preferred RGN and for the preferred sgRNA are packaged into AAV vectors or adenovirus vectors. In particular, adenovirus type Ad5/35 is effective at targeting HSCs. A suitable mouse model containing a humanized HBB locus with sickle cell alleles is chosen such as B6; FVB-Tg(LCR-HBA2,LCR-HBB*E26K)53Hhb/J or B6.Cg-Hbatm1Paz Hbbtm1Tow Tg(HBA-HBBs)41Paz/HhbJ. These mice are treated with granulocyte colony-stimulating factor alone or in combination with plerixafor to mobilize HSCs into circulation. AAVs or adenoviruses carrying the RGN and guide plasmid are then injected intravenously, and the mice are allowed to recover for a week. Blood obtained from these mice is tested in an in vitro sickling assay using metabisulfite, and the mice are followed longitudinally to monitor mortality rates and hematopoietic function. It is expected that treatment with AAVs or adenoviruses carrying an RGN and guide RNA will reduce sickling, mortality, and improve hematopoietic function when compared to mice treated with viruses lacking both expression cassettes, or with viruses carrying the RGN expression cassette alone.

Example 11: Identification of Deaminases

Microbial cultures were grown in liquid culture in standard laboratory media. Cultures were grown to saturation (16 to 24 hours) before DNA preparation. DNA was extracted from bacterial cells by detergent lysis, followed by binding to a silica matrix and washing with an ethanol buffer. Purified DNA was eluted from the silica matrix with a mildly alkaline aqueous buffer.

DNA for sequencing was tested for purity and concentration by spectrophotometry. Sequencing libraries were prepared using the Nextera XT library preparation kit according to the manufacturer's protocol. Sequence data was generated on a HiSeq 2000 according to the Illumina HiSeq 2000 System User Guide protocol.

Sequencing reads were assembled into draft genomes using the CLC Bio Assembly Cell software package. Following assembly, gene calls were made by several methods and resulting gene sequences were interrogated to identify novel homologs of deaminase genes. Novel genes were identified by BLAST and by domain composition. The catalytic domain D/H/C-[X]-E-[X15-45]-P-C-[X2]-C(SEQ ID NO: 613) was predicted in all enzymes. Additionally, sequences identified in the NCBI databases which are hypothetical deaminases from the genomes of sequenced eukaryotic organisms were also examined. The 268 APOBEC domain proteins identified were clustered at 65% homology, and 47 candidates were selected for deaminase activity assays. The 392 ADAT domain proteins identified were clustered at 65% homology, and further selected based on sequence length. 125 ADAT domain proteins, all of which are less than 220 amino acids in length, were selected for deaminase activity assays.

Table 17 indicates the 47 selected APOBEC domain proteins and the 125 ADAT domain proteins. The SEQ ID NO. and the APG ID, which provides the unique identification code for each polypeptide, are indicated. If available, the NCBI and Uniprot Accession Numbers are provided. "Domain Description" indicates if the deaminase possesses an ADAT or an APOBEC domain. The start and end of the ADAT or APOBEC domains within the identified polypeptide sequence are also indicated.

TABLE 17

| | | | Identified Deaminases | | | |
|---|---|---|---|---|---|---|
| SEQ ID NO. | APG ID | NCBI Accession No. | Uniprot Accession No. | Domain Description | Domain Start | Domain End |
| 374 | APG00868 | N/A | B2XR68_FELCA | APOBEC-domain | 69 | 103 |
| 375 | APG01021 | WP_003372040 | N/A | APOBEC-domain | 334 | 370 |
| 376 | APG01179 | N/A | N/A | APOBEC-domain | 137 | 170 |
| 377 | APG01180 | N/A | A0A2K6U5H6_SAIBB | APOBEC-domain | 56 | 90 |
| 378 | APG01527 | N/A | A0A2I0LXZ8_COLLI | APOBEC-domain | 63 | 95 |
| 379 | APG01650 | N/A | A0A3B3ZFB9_9GOBI | APOBEC-domain | 212 | 243 |
| 380 | APG01689 | N/A | A0A0A1X9Q9_ZEUCU | APOBEC-domain | 71 | 102 |
| 381 | APG02207 | N/A | N/A | APOBEC-domain | 321 | 357 |
| 382 | APG02282 | N/A | N/A | APOBEC-domain | 131 | 165 |
| 383 | APG02316 | WP_002598246 | N/A | APOBEC-domain | 311 | 347 |
| 384 | APG02472 | N/A | A0A1V4JAP2_PATFA | APOBEC-domain | 54 | 89 |
| 385 | APG02810 | N/A | N/A | APOBEC-domain | 131 | 164 |
| 386 | APG03038 | N/A | N/A | APOBEC-domain | 136 | 170 |
| 387 | APG03237 | N/A | A0A2I3GCB3_NOMLE | APOBEC-domain | 262 | 275 |
| 388 | APG03260 | N/A | N/A | APOBEC-domain | 138 | 172 |
| 389 | APG03331 | N/A | M3W3R0_FELCA | APOBEC-domain | 54 | 88 |
| 390 | APG03526 | N/A | GIRYY7_NOMLE | APOBEC-domain | 263 | 299 |
| 391 | APG03683 | N/A | A0A0K0MJ25_HUMAN | APOBEC-domain | 58 | 81 |
| 392 | APG03857 | N/A | U3JMS2_FICAL | APOBEC-domain | 94 | 117 |
| 393 | APG04050 | N/A | A0A340X469_LIPVE | APOBEC-domain | 267 | 301 |
| 394 | APG04117 | N/A | G1TLT9_RABIT | APOBEC-domain | 69 | 103 |
| 395 | APG04613 | N/A | A0A2R2X2H4_PTEAL | APOBEC-domain | 74 | 108 |
| 396 | APG05200 | N/A | A0A2R2X2I7_PTEVA | APOBEC-domain | 74 | 108 |
| 397 | APG05241 | N/A | ABEC1_MONDO | APOBEC-domain | 60 | 95 |
| 398 | APG05731 | WP_015392428 | N/A | APOBEC-domain | 316 | 352 |
| 399 | APG05840 | N/A | G8GPV9_SAGOE | APOBEC-domain | 74 | 108 |
| 400 | APG05874 | N/A | A0A2R2X2I2_PTEVA | APOBEC-domain | 84 | 124 |
| 401 | APG06119 | N/A | ABC3G_LAGLA | APOBEC-domain | 254 | 288 |
| 402 | APG06544 | N/A | A0A218ULD2_9PASE | APOBEC-domain | 57 | 89 |
| 403 | APG06662 | N/A | A0A2R2X2I3_PTEVA | APOBEC-domain | 84 | 124 |
| 404 | APG06719 | N/A | A0A2U3Y3M5_LEPWE | APOBEC-domain | 61 | 96 |
| 405 | APG07092 | N/A | N/A | APOBEC-domain | 143 | 176 |
| 406 | APG07277 | N/A | N/A | APOBEC-domain | 130 | 163 |
| 407 | APG07280 | N/A | A0A1S3FTE2_DIPOR | APOBEC-domain | 88 | 123 |
| 408 | APG07386 | N/A | F6M3K7_MACMU | APOBEC-domain | 271 | 305 |
| 409 | APG07674 | N/A | E2RL86_CANLF | APOBEC-domain | 53 | 87 |
| 410 | APG07774 | N/A | A0A151P6M4_ALLMI | APOBEC-domain | 62 | 97 |
| 411 | APG08360 | N/A | A0A287AD63_PIG | APOBEC-domain | 81 | 115 |
| 412 | APG08501 | N/A | N/A | APOBEC-domain | 315 | 351 |
| 413 | APG08616 | N/A | A0A340WXU3_LIPVE | APOBEC-domain | 156 | 190 |
| 414 | APG09260 | N/A | A0A1S3T3Q2_SALSA | APOBEC-domain | 88 | 106 |
| 415 | APG09664 | N/A | A0A2K6NPI0_RHIRO | APOBEC-domain | 73 | 107 |
| 416 | APG09688 | N/A | G1TVM9_RABIT | APOBEC-domain | 92 | 127 |
| 417 | APG09693 | N/A | A0A2K5XQK6_MANLE | APOBEC-domain | 257 | 290 |
| 418 | APG09710 | N/A | F7EWS7_RAT | APOBEC-domain | 85 | 122 |
| 419 | APG09739 | N/A | S4RNJ9_PETMA | APOBEC-domain | 72 | 117 |
| 420 | APG09980 | N/A | A0A2R2Z4D8_PTEAL | APOBEC-domain | 68 | 102 |
| 421 | APG00835 | WP_006418834 | N/A | ADAT-domain | 64 | 97 |
| 422 | APG00921 | WP_005583886 | N/A | ADAT-domain | 58 | 91 |
| 423 | APG00970 | WP_013486656 | N/A | ADAT-domain | 58 | 91 |
| 424 | APG00990 | WP_008706930 | N/A | ADAT-domain | 62 | 95 |
| 425 | APG01340 | WP_009534123 | N/A | ADAT-domain | 89 | 122 |
| 426 | APG01499 | N/A | A0A0VOJ9J5_SCHSO | ADAT-domain | 46 | 85 |
| 427 | APG01593 | N/A | N/A | ADAT-domain | 65 | 98 |
| 428 | APG01603 | WP_005610988 | N/A | ADAT-domain | 71 | 104 |
| 429 | APG01612 | N/A | N/A | ADAT-domain | 60 | 92 |
| 430 | APG01755 | N/A | H0V5A6_CAVPO | ADAT-domain | 71 | 110 |
| 431 | APG01974 | WP_011736131 | N/A | ADAT-domain | 64 | 97 |
| 432 | APG02173 | WP_003322111 | N/A | ADAT-domain | 55 | 88 |
| 433 | APG02281 | N/A | N/A | ADAT-domain | 29 | 68 |
| 434 | APG02312 | WP_016147568 | N/A | ADAT-domain | 53 | 86 |
| 435 | APG02334 | WP_011244898 | N/A | ADAT-domain | 55 | 88 |
| 436 | APG02339 | WP_005584387 | N/A | ADAT-domain | 51 | 84 |
| 437 | APG02410 | WP_009215532 | N/A | ADAT-domain | 76 | 109 |
| 438 | APG02412 | N/A | N/A | ADAT-domain | 64 | 101 |
| 439 | APG02420 | WP_015561774 | N/A | ADAT-domain | 59 | 92 |
| 440 | APG02442 | WP_017549959 | N/A | ADAT-domain | 63 | 96 |
| 441 | APG02591 | N/A | A0A2P8YEP2_BLAGE | ADAT-domain | 50 | 89 |
| 442 | APG02600 | WP_005358896 | N/A | ADAT-domain | 76 | 109 |
| 443 | APG02751 | N/A | N/A | ADAT-domain | 57 | 90 |
| 444 | APG02786 | WP_005997489 | N/A | ADAT-domain | 55 | 88 |
| 445 | APG02813 | WP_013282182 | N/A | ADAT-domain | 76 | 109 |
| 446 | APG03010 | WP_007203795 | N/A | ADAT-domain | 56 | 89 |
| 447 | APG03046 | N/A | N/A | ADAT-domain | 59 | 91 |
| 448 | APG03093 | WP_013270915 | N/A | ADAT-domain | 53 | 86 |

TABLE 17-continued

Identified Deaminases

| SEQ ID NO. | APG ID | NCBI Accession No. | Uniprot Accession No. | Domain Description | Domain Start | Domain End |
|---|---|---|---|---|---|---|
| 449 | APG03110 | WP_009677004 | N/A | ADAT-domain | 67 | 100 |
| 450 | APG03120 | WP_015923794 | N/A | ADAT-domain | 53 | 86 |
| 451 | APG03140 | WP_006701669 | N/A | ADAT-domain | 61 | 94 |
| 452 | APG03224 | WP_005353279 | N/A | ADAT-domain | 54 | 87 |
| 453 | APG03336 | N/A | N/A | ADAT-domain | 57 | 90 |
| 454 | APG03390 | N/A | ROMCR5_NOSB1 | ADAT-domain | 51 | 82 |
| 455 | APG03467 | N/A | N/A | ADAT-domain | 10 | 43 |
| 456 | APG03468 | WP_010285589 | N/A | ADAT-domain | 53 | 86 |
| 457 | APG03474 | WP_009643257 | N/A | ADAT-domain | 53 | 86 |
| 458 | APG03542 | WP_005838301 | N/A | ADAT-domain | 51 | 84 |
| 459 | APG03557 | WP_013497948 | N/A | ADAT-domain | 55 | 88 |
| 460 | APG03605 | N/A | A0A1D1XUG0_9ARAE | ADAT-domain | 61 | 103 |
| 461 | APG03691 | WP_012446504 | N/A | ADAT-domain | 57 | 90 |
| 462 | APG03856 | WP_019678962 | N/A | ADAT-domain | 52 | 85 |
| 463 | APG03876 | N/A | A0A179V3P5_BLAGS | ADAT-domain | 66 | 99 |
| 464 | APG03980 | WP_015537265 | N/A | ADAT-domain | 52 | 85 |
| 465 | APG04036 | WP_008982263 | N/A | ADAT-domain | 52 | 85 |
| 466 | APG04273 | N/A | MORA73_RAT | ADAT-domain | 71 | 107 |
| 467 | APG04283 | WP_005999210 | N/A | ADAT-domain | 46 | 79 |
| 468 | APG04338 | WP_007506011 | N/A | ADAT-domain | 56 | 89 |
| 469 | APG04430 | WP_009220054 | N/A | ADAT-domain | 53 | 86 |
| 470 | APG04436 | WP_006908309 | N/A | ADAT-domain | 67 | 100 |
| 471 | APG04514 | N/A | N/A | ADAT-domain | 57 | 91 |
| 472 | APG04571 | WP_004636848 | N/A | ADAT-domain | 55 | 88 |
| 473 | APG04758 | N/A | N/A | ADAT-domain | 56 | 98 |
| 474 | APG04788 | N/A | A0A1C7M4C9_GRIFR | ADAT-domain | 67 | 106 |
| 475 | APG04795 | WP_016424318 | N/A | ADAT-domain | 53 | 86 |
| 476 | APG04815 | N/A | N/A | ADAT-domain | 43 | 75 |
| 477 | APG04852 | N/A | N/A | ADAT-domain | 69 | 102 |
| 478 | APG04968 | WP_012157903 | N/A | ADAT-domain | 53 | 86 |
| 479 | APG05022 | WP_006785792 | N/A | ADAT-domain | 52 | 85 |
| 480 | APG05211 | WP_002441139 | N/A | ADAT-domain | 53 | 86 |
| 481 | APG05314 | WP_008301499 | N/A | ADAT-domain | 66 | 99 |
| 482 | APG05320 | WP_004832879 | N/A | ADAT-domain | 53 | 86 |
| 483 | APG05415 | WP_013171002 | N/A | ADAT-domain | 58 | 91 |
| 484 | APG05461 | WP_008909404 | N/A | ADAT-domain | 52 | 85 |
| 485 | APG05486 | WP_018131372 | N/A | ADAT-domain | 100 | 133 |
| 486 | APG05507 | WP_009061460 | N/A | ADAT-domain | 56 | 89 |
| 487 | APG05573 | N/A | N/A | ADAT-domain | 55 | 94 |
| 488 | APG05582 | N/A | A0A2U4CP64_TURTR | ADAT-domain | 71 | 110 |
| 489 | APG05694 | WP_008590218 | N/A | ADAT-domain | 53 | 86 |
| 490 | APG05703 | N/A | N/A | ADAT-domain | 43 | 75 |
| 491 | APG05759 | N/A | A0A1V4JLA3_PATFA | ADAT-domain | 57 | 96 |
| 492 | APG05844 | WP_013248301 | N/A | ADAT-domain | 57 | 90 |
| 493 | APG05922 | N/A | N/A | ADAT-domain | 44 | 98 |
| 494 | APG06120 | WP_005841945 | N/A | ADAT-domain | 54 | 87 |
| 495 | APG06219 | N/A | N/A | ADAT-domain | 4 | 53 |
| 496 | APG06225 | N/A | N/A | ADAT-domain | 46 | 79 |
| 497 | APG06334 | WP_014116671 | N/A | ADAT-domain | 52 | 85 |
| 498 | APG06393 | WP_005489257 | N/A | ADAT-domain | 53 | 86 |
| 499 | APG06572 | WP_011339999 | N/A | ADAT-domain | 46 | 79 |
| 500 | APG06638 | WP_006875450 | N/A | ADAT-domain | 52 | 85 |
| 501 | APG06645 | WP_013656057 | N/A | ADAT-domain | 53 | 86 |
| 502 | APG06703 | N/A | V8NRA1_OPHHA | ADAT-domain | 24 | 63 |
| 503 | APG06776 | WP_003147612 | N/A | ADAT-domain | 53 | 86 |
| 504 | APG06861 | WP_010624847 | N/A | ADAT-domain | 59 | 92 |
| 505 | APG06951 | WP_012809557 | N/A | ADAT-domain | 56 | 89 |
| 506 | APG06953 | N/A | A0A0A9YIX6_LYGHE | ADAT-domain | 54 | 88 |
| 507 | APG06973 | WP_010630866 | N/A | ADAT-domain | 86 | 119 |
| 508 | APG07045 | N/A | N/A | ADAT-domain | 67 | 100 |
| 509 | APG07128 | WP_005345192 | N/A | ADAT-domain | 61 | 94 |
| 510 | APG07164 | WP_006525269 | N/A | ADAT-domain | 53 | 86 |
| 511 | APG07264 | WP_013276874 | N/A | ADAT-domain | 55 | 88 |
| 512 | APG07331 | WP_012939070 | N/A | ADAT-domain | 63 | 96 |
| 513 | APG07449 | N/A | ADAT2_DANRE | ADAT-domain | 70 | 109 |
| 514 | APG07458 | WP_004035644 | N/A | ADAT-domain | 53 | 86 |
| 515 | APG07614 | WP_009015861 | N/A | ADAT-domain | 57 | 90 |
| 516 | APG07667 | N/A | N/A | ADAT-domain | 61 | 94 |
| 517 | APG07706 | N/A | Q16JL7_AEDAE | ADAT-domain | 60 | 99 |
| 518 | APG07733 | WP_011345539 | N/A | ADAT-domain | 52 | 85 |
| 519 | APG07861 | N/A | A0A1X0QE95_9MICR | ADAT-domain | 54 | 86 |
| 520 | APG07900 | WP_019468226 | N/A | ADAT-domain | 53 | 86 |
| 521 | APG07952 | WP_017471628 | N/A | ADAT-domain | 52 | 85 |
| 522 | APG07964 | N/A | N/A | ADAT-domain | 57 | 87 |
| 523 | APG07975 | N/A | N/A | ADAT-domain | 71 | 137 |

TABLE 17-continued

Identified Deaminases

| SEQ ID NO. | APG ID | NCBI Accession No. | Uniprot Accession No. | Domain Description | Domain Start | Domain End |
|---|---|---|---|---|---|---|
| 524 | APG08010 | WP_016475938 | N/A | ADAT-domain | 69 | 102 |
| 525 | APG08054 | WP_015357810 | N/A | ADAT-domain | 51 | 84 |
| 526 | APG08311 | WP_013485444 | N/A | ADAT-domain | 58 | 91 |
| 527 | APG08447 | WP_015912349 | N/A | ADAT-domain | 52 | 85 |
| 528 | APG08494 | WP_013779369 | N/A | ADAT-domain | 59 | 92 |
| 529 | APG08613 | N/A | A0A1S9RJZ5_9EURO | ADAT-domain | 69 | 102 |
| 530 | APG08766 | N/A | A0A034WM03_BACDO | ADAT-domain | 71 | 110 |
| 531 | APG08799 | WP_002835051 | N/A | ADAT-domain | 54 | 87 |
| 532 | APG08810 | N/A | N/A | ADAT-domain | 58 | 97 |
| 533 | APG08893 | WP_014394804 | N/A | ADAT-domain | 53 | 86 |
| 534 | APG08939 | WP_004098361 | N/A | ADAT-domain | 56 | 89 |
| 535 | APG08952 | WP_006789980 | N/A | ADAT-domain | 53 | 86 |
| 536 | APG08955 | WP_014969075 | N/A | ADAT-domain | 53 | 86 |
| 537 | APG09011 | WP_011937002 | N/A | ADAT-domain | 71 | 104 |
| 538 | APG09180 | WP_007222730 | N/A | ADAT-domain | 57 | 90 |
| 539 | APG09204 | WP_006588115 | N/A | ADAT-domain | 57 | 90 |
| 540 | APG09216 | WP_019878409 | N/A | ADAT-domain | 56 | 89 |
| 541 | APG09352 | WP_015558044 | N/A | ADAT-domain | 54 | 87 |
| 542 | APG09356 | WP_018923319 | N/A | ADAT-domain | 54 | 87 |
| 543 | APG09546 | WP_009796283 | N/A | ADAT-domain | 61 | 94 |
| 544 | APG09753 | N/A | N/A | ADAT-domain | 29 | 70 |
| 545 | APG09981 | N/A | N/A | ADAT-domain | 83 | 116 |

Example 12: Assay for Deaminase Activity

Example 12.1: Selection of Putative Deaminases

The coding sequences of the selected proteins shown in Table 17 were codon-optimized for expression in bacteria, synthesized, and introduced into standard bacterial expression vectors well-known in the art, operably linked at the 5' end to the T7 promoter.

Example 12.2: Deaminase Activity Assays

The deaminase activity assay is based on Garibyan et al. (*DNA Repair* 2: 593-608, 2003). Mutations in the rpoB gene of *Escherichia coli* result in resistance to the antibiotic rifampicin (Rif') by altering the β subunit of RNA polymerase.

A bacterial expression vector encoding for a putative deaminase, as described in Example 12.1, was introduced into T7 Express *E. coli* cells (NEBioLabs). The cells may also contain a separate expression plasmid encoding for Uracil DNA glycosylase inhibitor (UGI; SEQ ID NO: 570) and for a carbenicillin selectable marker. The cells were grown to saturation and then used as a source for inoculum of a self-inducing media (MagicMedia™, Thermo Fisher Scientific), and then grown for an additional 5 hours. Cells were dilution-plated on LB with kanamycin or LB with kanamycin and carbenicillin, depending on if they also contained the UGI expression plasmid. These dilution-plates were used to get a total cell count. The same cells were also plated on LB with rifampicin or LB with rifampicin and carbenicillin to identify putative deaminase expression vectors which were able to successfully introduce mutations into the rpoB gene.

Deaminase expression vectors were isolated from bacterial colonies which grew on the LB plates containing rifampicin, and the assay was repeated at least twice. Following confirmation, the bacterial cells were sequenced. Unexpectedly, of the 47 APOBEC domain containing proteins selected for evaluation, only nine showed deaminase activity. Of the 125 ADAT domain containing proteins selected for evaluation, none showed deaminase activity. This suggests that deaminase activity cannot be predicted based on the amino acid sequence of the polypeptide, but instead must be empirically determined. Results for the nine active deaminases identified by this assay are shown in Table 18. The rpoB gene from the rifampicin-resistant colonies was sequenced to identify the induced mutations. The mutation rate was calculated by taking the number of resistant colonies comprising each active deaminase compared to the total number of colonies.

TABLE 18

NGS analysis of mutation rate of active deaminases

| APG ID | SEQ ID NO. | Mutation Rate |
|---|---|---|
| APG05241 | 397 | 42% |
| APG07280 | 407 | 36.90% |
| APG09260 | 414 | 35.30% |
| APG08360 | 411 | 36.90% |
| APG09980 | 420 | 30.50% |
| APG07386 | 408 | 36.80% |
| APG09688 | 416 | 19.20% |
| APG05840 | 399 | 25.80% |
| APG02316 | 383 | 48.40% |

Example 13: Base Editing Activity in Bacterial Cells

APG00868 (SEQ ID NO: 374) was also identified as an active deaminase in a subsequent activity screen. Coding sequences of the ten identified active deaminases were introduced into an expression cassette which produces a fusion protein comprising an NLS at its N-terminal end (SEQ ID NO: 10) operably linked at its C-terminal end to an active deaminase of Table 18, operably linked at its C-terminal end to a linker sequence (SEQ ID NO: 546), operably linked at its C-terminal end to a RNA-guided, DNA binding protein, namely a nuclease-inactive RNA-guided nuclease (RGN) dAPG08290.1 variant (SEQ ID NO: 547), operably linked at its C-terminal end to a second NLS, operably linked at its C-terminal end to a TEV site (SEQ ID NO: 548), operably linked at its C-terminal end to a 10×His (SEQ ID NO 594) tag. Selected deaminases identified in Example 12 and APG00868 were assayed for targeted base editing activity in bacterial cells.

This activity assay was very similar to Example 12. However, for these experiments the deaminases were linked to an inactive RGN, to enable targeting to a particular region of the rpoB gene to introduce targeted C to T mutations. Additionally, vectors comprising expression cassettes capable of expressing guide RNAs for targeting of the RGN-deaminase fusion were produced. Four different guide RNAs were used in these experiments. The first guide, referred to in Table 19 as "untargeted" (SEQ ID NO: 549), guided the RGN-deaminase fusion to a region of genomic bacterial DNA that was not the rpoB gene. Target 1 (SEQ ID NO: 550) was to a region of the rpoB gene that would introduce an R529C mutation in the rpoB protein. Target 2 (SEQ ID NO: 551) was to a region of the rpoB gene that would introduce an A532V mutation in the rpoB protein, and Target 3 (SEQ ID NO: 552) was to a region of the rpoB gene that would introduce a Q513R mutation in the rpoB protein. The desired mutations of targets 1 and 2 would be a result of base editing from a GC pair to an AT pair. The desired mutation of target 3 would be a result of base editing from an AT pair to a GC pair. Other possible mutations also can be found in these targets.

The fusion protein expression vectors, along with vectors comprising expression cassettes capable of expressing guide RNAs that targeted to locations of interest on the rpoB gene, were introduced into T7 Express *E. coli* cells (NEBioLabs). The cells were grown to saturation and then used as a source for inoculum of a self-inducing media (MagicMedia™, Thermo Fisher Scientific), and then grown for an additional 5 hours. Cells were dilution-plated on LB with kanamycin; these dilution-plates were used to get a total cell count. The same cells were also plated on LB with rifampicin to identify colonies which carried mutations in the rpoB gene. Mutation rates for the "untargeted" and for the targeted deaminase-RGN fusion proteins ("targeted") were calculated and are shown in Table 19. The percent increase ("% increase") in the mutation rate of the targeted deaminase-RGN fusions compared to the deaminase-RGN fusions not targeted to the rpoB gene is also indicated in Table 19. A positive control mammalian APOBEC known to function as a deaminase was also included.

TABLE 19

Mutation rates of targeted and untargeted deaminases

| Deaminase APG ID | Type of Guide RNA | Target (SEQ ID NO.) | Mutation rate | % Increase |
|---|---|---|---|---|
| APG05241 | Untargeted | 549 | 1.71 * 10 − 8 | — |
| APG05241 | Targeted | 550 | 1.42 * 10 − 7 | 8.31 |
| APG05241 | Targeted | 551 | 5.95 * 10 − 9 | 0.35 |
| APG05241 | Targeted | 552 | 3.62 * 10 − 8 | 2.12 |
| APG08360 | Untargeted | 549 | 4.00 * 10 − 11 | — |
| APG08360 | Targeted | 550 | 4.74 * 10 − 10 | 11.84 |
| APG08360 | Targeted | 551 | 2.38 * 10 − 11 | 0.60 |
| APG08360 | Targeted | 552 | 4.70 * 10 − 8 | 2175.00 |
| APG00868 | Untargeted | 549 | 1.82 * 10 − 9 | — |
| APG00868 | Targeted | 550 | 1.43 * 10 − 7 | 78.68 |
| APG00868 | Targeted | 551 | 3.79 * 10 − 9 | 2.09 |
| APG00868 | Targeted | 552 | 1.18 * 10 − 6 | 650.00 |
| control | Untargeted | 549 | 1.53 * 10 − 8 | — |
| control | Targeted | 550 | 6.37 * 10 − 6 | 417.36 |
| control | Targeted | 551 | 2.59 * 10 − 7 | 16.98 |
| control | Targeted | 552 | 3.79 − 10 − 7 | 24.86 |

TABLE 19-continued

Example 14: Base Editing Activity in Mammalian Cells

Coding sequences of the identified active deaminases were codon-optimized for expression in mammalian cells and introduced into an expression cassette which produces a fusion protein comprising an NLS at its N-terminal end (SEQ ID NO: 10), operably linked at its C-terminal end to a 3×FLAG tag (SEQ ID NO: 11), operably linked at its C-terminal end to a deaminase of the invention, operably linked at its C-terminal end to an amino acid linker (SEQ ID NO: 546), operably linked at its C-terminal end to an RNA-guided, DNA-binding polypeptide, namely an RGN which has been mutated to function as a nickase (nAPG07433.1; SEQ ID NO: 553), operably linked at its C-terminal end to a second NLS. Additionally, N-terminal and C-terminal fragments of APG07386 (APG07386-NTD as SEQ ID NO: 554 and APG07386-CTD as-SEQ ID NO: 555, respectively) were individually introduced into an expression cassette to produce deaminase-RGN fusions of each fragment. These expression cassettes were each introduced into a vector capable of driving expression of the fusion protein in mammalian cells. Vectors were also produced that were capable of expressing guide RNAs to target the deaminase-RGN fusion protein to a determined genomic location. These guide RNAs are capable of guiding the deaminase-RGN fusion protein to a targeted genomic sequence for base editing. SEQ ID NOs: 556-561 encode the guide RNAs tested.

Example 14.1: Efficiencies and Sequence Specificity Amongst Deaminases

Vectors capable of expressing the deaminase-RGN fusion proteins and guide RNAs described above were transfected into HEK293T cells, using either lipofection or electroporation. For lipofection, cells were seeded at $1 \times 10^5$ cells/well in 24-well plates the day prior to transfection in growth medium (DMEM+10% Fetal Bovine Serum+1% Penicillin/streptomycin). 500 ng of the deaminase-RGN fusion expression vector and 1 µg of the guide RNA expression vector were transfected using Lipofectamine® 3000 reagent (Thermo Fisher Scientific) following manufacturer's instructions. For electroporation, cells were electroporated using the Neon® Transfection System (Thermo Fisher Scientific) following manufacturer's instructions.

24-48 hours after lipofection or electroporation, genomic DNA was harvested from the transfected or electroporated cells and the DNA was sequenced and analyzed for the presence of the targeted base-editing mutations.

Table 20 below shows the editing rates of cytidine bases for each deaminase, including for the C-terminal and N-terminal fragments of APG07386. The number line indicates the position of the cytidine base in the targeted genomic sequence relative to the PAM of the RGN. The rate of editing of C nucleotides at each position is shown as an average of multiple targets. The number of targets (n) is listed for each position underneath the column. The standard deviation is shown in parenthesis. In this assay, APG09980, APG07386-CTD, APG05840, APG05241, APG07280, APG09688 and APG00868 show at least some level of cytidine base editing activity of at least one cytidine.

TABLE 20

Editing rate of C nucleotides in mammalian cells

| APG ID | Position in Target | | | | | | | | | |
|---|---|---|---|---|---|---|---|---|---|---|
| | 1 | 2 | 3 | 4 | 5 | 6 | 7 | 8 | 9 | 10 |
| APG05241 | 0% | 0.1% | 0.25% | 1.367% | — | 0.4% | 6.55% | 6.4% | 4.7% | 5.9% |
| | (0) | (0.17) | (0.35) | (1.72) | | (0) | (12.04) | (8.63) | (0) | (3.54) |
| APG07280 | 0% | 0.08% | 0% | 0.067% | — | 0% | 1.675% | 6.45% | 0.5% | 1.15% |
| | (0) | (0.18) | (0) | (0.12) | | (0) | (2.56) | (9.12) | (0) | (1.2) |
| APG09260 | 0% | 0% | 0% | 0% | — | 0% | 0.075% | 0.05% | 0% | 0% |
| | (0) | (0) | (0) | (0) | | (0) | (0.05) | (0.07) | (0) | (0) |
| APG08360 | 0% | 0.02% | 0% | 0.167% | — | 0% | 0.025% | 0% | 1.4% | 0% |
| | (0) | (0.04) | (0) | (0.29) | | (0) | (0.05) | (0) | (0) | (0) |
| APG09980 | 0% | 0.1% | 0% | 1.267% | — | 16% | 12.875% | 8.55% | 6.9% | 5.7% |
| | (0) | (0.22) | (0) | (1.36) | | (0) | (10.43) | (8.41) | (0) | (5.8) |
| APG07386 | 0% | 0% | 0% | 1.033% | — | 0% | 0.025% | 0.4% | 6.6% | 0.25% |
| | (0) | (0) | (0) | (1.79) | | (0) | (0.05) | (0) | (0) | (0.35) |
| APG07386-CTD | 0% | 0.2% | 0.6% | 2.233% | — | 1.3% | 2.15% | 1.95% | 21.1% | 2.35% |
| | (0) | (0.45) | (0.85) | (3.44) | | (0) | (2.9) | (0.21) | (0) | (1.34) |
| APG07386-NTD | 0% | 0% | 0% | 0% | — | 0.1% | 0.175% | 0.45% | 0% | 0% |
| | (0) | (0) | (0) | (0) | | (0) | (0.29) | (0.64) | (0) | (0) |
| APG09688 | 0% | 0.02% | 0% | 0.267% | — | 0% | 1.1% | 9.5% | 0.6% | 0.2% |
| | (0) | (0.04) | (0) | (0.46) | | (0) | (1.87) | (13.44) | (0) | (0) |
| APG05840 | 0% | 0.1% | 0.15% | 0.167% | — | 15.3% | 10.475% | 13.25% | 7.1% | 16.7% |
| | (0) | (0.22) | (0.21) | (0.29) | | (0) | (10.9) | (11.1) | (0) | (6.93) |
| APG02316 | 0.1% | 0.02% | 0% | 0% | — | 0.1% | 0.075% | 0.1% | 0% | 0% |
| | (0) | (0.04) | (0) | (0) | | (0) | (0.05) | (0.14) | (0) | (0) |
| APG00868 | 0% | 0.2% | 0.15% | 0.967% | — | 29.4% | 22.85% | 8.4% | 7.4% | 4% |
| | (0) | (0.39) | (0.21) | (1.34) | | (0) | (7.35) | (2.12) | (0) | (2.69) |
| control 1 | 0.1% | 0.12% | 0% | 0.567% | — | 0.3% | 3.25% | 13.65% | 0% | 2.5% |
| | (0) | (0.22) | (0) | (0.9) | | (0) | (5.84) | (19.02) | (0) | (3.11) |
| control 2 | 0% | 0.52% | 0% | 0.7% | — | 37.2% | 12.75% | 10.1% | 1.8% | 7.45% |
| | (0) | (0.52) | (0) | (0.89) | | (0) | (5.71) | (9.9) | (0) | (8.84) |
| No. of targets | n = 1 | n = 5 | n = 2 | n = 3 | n = 0 | n = 1 | n = 4 | n = 2 | n = 1 | n = 2 |

| APG ID | Position in Target | | | | | | | | | |
|---|---|---|---|---|---|---|---|---|---|---|
| | 11 | 12 | 13 | 14 | 15 | 16 | 17 | 18 | 19 | 20 |
| APG05241 | 1.1% | 0% | 22.3% | 0% | 12.5% | 0% | 15% | 0.4% | 0.1% | 1.225% |
| | (1.56) | (0) | (0) | (0) | (16.4) | (0) | (0) | (0.57) | (0.14) | (1.8) |
| APG07280 | 0% | 0% | 13.9% | 0% | 12.95% | 0% | 7.5% | 0.25% | 0.1% | 1.575% |
| | (0) | (0) | (0) | (0) | (16.33) | (0) | (0) | (0.35) | (0.14) | (2.36) |
| APG09260 | 0% | 0% | 0% | 0% | 0% | 0% | 0% | 0% | 0.1% | 0% |
| | (0) | (0) | (0) | (0) | (0) | (0) | (0) | (0) | (0.14) | (0) |
| APG08360 | 0% | 0% | 0.7% | 0% | 4.65% | 0% | 6.3% | 0.7% | 0.05% | 1.75% |
| | (0) | (0) | (0) | (0) | (6.43) | (0) | (0) | (0.99) | (0.07) | (3.18) |
| APG09980 | 0% | 0% | 21.1% | 3.4% | 12.4% | 0% | 11.1% | 1.5% | 0% | 1.375% |
| | (0) | (0) | (0) | (0) | (17.11) | (0) | (0) | (2.12) | (0) | (2.55) |
| APG07386 | 0.65% | 0% | 6.3% | 0% | 11.25% | 3.2% | 4.1% | 1.7% | 0% | 2.925% |
| | (0.92) | (0) | (0) | (0) | (13.93) | (0) | (0) | (2.4) | (0) | (4.22) |
| APG07386-CTD | 5.4% | 0% | 21.8% | 0% | 23.3% | 2.1% | 8.8% | 3.25% | 0% | 1.125% |
| | (2.69) | (0) | (0) | (0) | (24.89) | (0) | (0) | (4.6) | (0) | (1.37) |
| APG07386-NTD | 0% | 0% | 0% | 0% | 0% | 0% | 0.9% | 0% | 0% | 0% |
| | (0) | (0) | (0) | (0) | (0) | (0) | (0) | (0) | (0) | (0) |
| APG09688 | 0% | 0% | 21.9% | 0% | 19.95% | 0% | 10.6% | 0.4% | 0% | 1.325% |
| | (0) | (0) | (0) | (0) | (28.07) | (0) | (0) | (0.57) | (0) | (2.32) |
| APG05840 | 1.8% | 4% | 19.1% | 12.5% | 18.9% | 4.2% | 29.2% | 3.5% | 0% | 2.825% |
| | (0.42) | (0) | (0) | (0) | (8.06) | (0) | (0) | (2.55) | (0) | (2.84) |
| APG02316 | 0% | 0% | 3.6% | 0% | 0% | 0% | 0% | 0% | 0% | 0.025% |
| | (0) | (0) | (0) | (0) | (0) | (0) | (0) | (0) | (0) | (0.05) |
| APG00868 | 7.8% | 14.6% | 4.6% | 6.2% | 9.3% | 2.7% | 12.8% | 1.85% | 5.3% | 2% |
| | (0.99) | (0) | (0) | (0) | (5.8) | (0) | (0) | (1.63) | (1.7) | (1.45) |
| control 1 | 3.15% | 0% | 35% | 9.1% | 18.45% | 0% | 28.6% | 1.55% | 1.4% | 2.375% |
| | (4.17) | (0) | (0) | (0) | (24.25) | (0) | (0) | (1.63) | (1.98) | (3.39) |
| control 2 | 0.95% | 40.6% | 2.8% | 14.5% | 3.6% | 0.7% | 4.6% | 1% | 0.65% | 1.425% |
| | (0.07) | (0) | (0) | (0) | (0.71) | (0) | (0) | (0.57) | (0.92) | (0.98) |
| No. of targets | n = 2 | n = 1 | n = 1 | n = 1 | n = 2 | n = 1 | n = 1 | n = 2 | n = 2 | n = 4 |

Example 14.2: Fluorescence Assay for Targeted Base Editing

A vector harboring Enhanced Green Fluorescent Protein (EGFP) containing a Y66H mutation which causes a fluorescence shift to blue fluorescent protein (BFP, SEQ ID NO: 562) was constructed such that the H66 codon can be reverted from histidine (CAT) to the wildtype tyrosine (TAT) residue using a cytosine deaminase to alter the first position C to T. Successful C to T conversion results in the expression of EGFP which can be quantified. A second vector capable of expressing a guide RNA which targets the deaminase-RGN fusion protein to the region around the Y66H mutation (SEQ ID NO: 563) was also produced.

This BFP to EGFP reporter vector, along with the vectors capable of expressing the deaminase-RGN fusion protein and the guide RNA, were transfected into HEK293T cells, using either lipofection or electroporation. For lipofection, cells were seeded at $1 \times 10^5$ cells/well in 24-well plates the day prior to transfection in growth medium (DMEM+10% Fetal Bovine Serum+1% Penicillin/streptomycin). 500 ng each of the BFP reporter vector, deaminase-RGN expression vector, and guide RNA expression vector were transfected using Lipofectamine® 3000 reagent (Thermo Fisher Scientific) following manufacturer's instructions. For electroporation, cells are electroporated using the Neon® Transfection System (Thermo Fisher Scientific) following manufacturer's instructions.

24-48 hours after lipofection or electroporation, the expression of GFP was determined by microscopically surveying the cells for the presence of GFP+ cells. Following visual inspection, the proportion of GFP+ cells versus GFP− cells may be determined. Fluorescence was observed for mammalian cells expressing deaminase-RGN fusion proteins reported in Table 21. A person of skill in the art will appreciate that the cells may also be lysed using RIPA buffer, and the resulting lysate may be analyzed on a fluorescence plate reader to determine the fluorescence intensity for BFP and GFP. Additionally, the cells may be analyzed by cell sorting to determine the exact proportions of BFP+, GFP+, and GFP− cells.

TABLE 21

Mammalian Cytosine Deaminase Fluorescence Reporter Results

| Deaminase ID | Relative GFP+ Cells |
|---|---|
| APG09260 | N.D. |
| APG09980 | + |
| APG07386-CTD | ++ |
| APG05840 | + |
| APG00868 | ++ |

N.D = None Detected;
+ = few GFP+ cells detected,
++ = many GFP+ cells detected

Example 15: Diversification of Deaminases for Creation of Adenosine and Cytosine Base Editors Adenosine base editors (ABEs), which are capable of changing an A or T residue in a DNA sequence to a G or a C, are not known to naturally occur. The following diversification strategies were used to generate deaminase variants for the goal of identifying an ABE which acts on a DNA template.

The first strategy was random mutagenesis by error prone PCR enzymes, similar to Gaudelli et al (*Nature*, 2017, doi:10.1038/nature24644, incorporated by reference herein). Primers were designed and nucleotide sequences to the 125 ADAT enzymes of Table 17 were produced. Error prone PCR was carried out following manufacturer's instructions using the GenMorph II Random Mutagenesis Kit (Agilent Technologies). Mutated ADAT PCR products were purified following manufacturer's instructions using the ZR-96 DNA Clean-up Kit™ (Zymo Research). From this approach, about 10 million ADAT variants were produced.

A second strategy pursued was gene shuffling, similar to Stemmer, W. P. C. (*Proc. Natl. Acad. Sci. USA*, 1994). Coding sequences for the 125 ADAT enzymes of Table 17 were PCR-amplified essentially following manufacturer's instructions using Phusion® High-Fidelity DNA Polymerase (NEBiolabs) and purified using the DNA Clean & Concentrator™-5 (Zymo Research) following manufacturer's instructions. The purified DNA of the different ADAT coding sequences was pooled and subjected to restriction digestion by the enzymes RsaI, AfeI, BsaAI, and BsaHI in Cutsmart® buffer at 37° C. for 60 minutes. Following digestion, the reactions were separated by gel electrophoresis and digested fragments were purified using the Zymoclean™ Gel DNA Recovery Kit. The purified fragments were then assembled using PCR amplification, and the assembled amplified products were purified. From this approach, about 2 million ADAT variants were produced.

The final strategy was to target residues homologous to structural residues that potentially interact with nucleic acids. For ADAT-like enzymes, careful examination of the crystal structure of *Staphylococcus aureus* tRNA Adenosine Deaminase, TadA, in complex with RNA (RCSB Protein Data Bank ID No: 2B3J; Losey et al., 2006, *Nat. Struct. Mol. Biol.* 13: 153-159) revealed potential interactions at residues homologous to *E. coli* TadA (UniProt P68398 and GenBank Acc. No. NP_417054) P48, L84, A106, D108, and K110. Saturation mutagenesis of these homologous residues was then undertaken for 125 ADAT-domain deaminases from Table 17. From this approach, about one million ADAT variants were produced.

A person of skill in the art will appreciate that these approaches are not exclusive and can be combined and applied to the output of each successive round of improvement. Saturation mutagenesis or iterative saturation mutagenesis (Reetz and Carballeira, 2007, *Nature Protocols*, 2 (4): 891-903) are known to be iterative, meaning that the best performing candidates from one round are selected for further rounds of mutation and screening until an optimal candidate is identified.

Example 16: Determination of Active Diversified Deaminases for the Creation of Adenosine Base Editors and Cytosine Base Editors

Example 16.1: Bacterial Activity Assays for Diversified Deaminases

The ADAT mutant variant products from the diversified rounds of Example 15 above were introduced into an expression cassette which produces a fusion protein comprising an NLS at its N-terminal end (SEQ ID NO: 10) operably linked at its C-terminal end to a mutated deaminase, operably linked at its C-terminal end to a linker sequence (SEQ ID NO: 546), operably linked at its C-terminal end to a RNA-guided, DNA binding protein, namely a nuclease-inactive RNA-guided nuclease (RGN) dAPG08290.1 variant (SEQ ID NO: 547), operably linked at its C-terminal end to a second NLS, operably linked at its C-terminal end to a TEV site (SEQ ID NO: 548), operably linked at its C-terminal end to a 10× His tag (SEQ ID NO: 594).

This activity assay was very similar to Example 13. However, for these experiments constructs were made that had a deactivated Chloramphenicol gene that had H193 mutated to either H193R (SEQ ID NO: 566) for Cytosine Base Editing Selection, or H193Y (SEQ ID NO: 567) for Adenosine Base Editing Selection. Each plasmid also contained a guide RNA to target the RGN-deaminase fusion to the appropriate region of the plasmid. Upon successful CG to TA conversion (for SEQ ID NO: 566) or AT to GC conversion (for SEQ ID NO: 567), the bacterial cells would be capable of surviving in a media containing chloramphenicol.

The fusion protein expression vectors, along with vectors comprising the deactivated Chloramphenicol gene and targeting sgRNA, were introduced into T7 Express *E. coli* cells (NEBioLabs). The cells were grown to saturation and then used as a source for inoculum of a self-inducing media (MagicMedia™, Thermo Fisher Scientific), and then grown for an additional 5 hours. Cells were dilution-plated on LB with kanamycin and carbenicillin; these dilution-plates were used to get a total cell count. The same cells were also plated on LB with kanamycin, carbenicillin, and chloramphenicol to identify colonies which carried active mutated deaminases. Representative clones were picked and sequenced and then tested individually. Additionally, the same cells were also plated on LB with kanamycin and rifampicin to measure "untargeted" mutation rates. Mutation rates ("Mutn Rate") for the targeted deaminase-RGN fusion proteins to the H193R plasmid ("CBE") were calculated and the mutation rates for the targeted deaminase-RGN fusion proteins to the H193Y plasmid ("ABE") and are shown in Table 22. The relative rates for adenine base editing ("ABE Rel Rate"), cytosine base editing ("CBE Rel Rate"), and off-targeting ("Off-T Rel Rate) compared to the background observed in cells containing only the dead RGN (dAPG08290.1; SEQ ID NO: 547) are also indicated. Positive control mammalian deaminases known to function as a cytosine deaminase were also included.

Example 16.2: Fluorescence Assay for Targeted Base Editing

A vector harboring Enhanced Green Fluorescent Protein (EGFP) containing a W58* mutation which causes a premature STOP codon (SEQ ID NO: 564) was constructed such that the W58 codon can be reverted from STOP (TGA) to the wildtype tryptophan (TGG) residue using an adenosine deaminase to alter the third position A to G. Successful A to G conversion results in the expression of EGFP which can be quantified. A second vector capable of expressing a guide RNA which targets the deaminase-RGN fusion protein to the region around the W58* mutation (SEQ ID NO: 565) was also produced.

This dead EGFP to EGFP reporter vector, along with the vectors capable of expressing the deaminase-RGN fusion protein and the guide RNA, were transfected into HEK293T cells, using either lipofection or electroporation. For lipofection, cells were seeded at $1 \times 10^5$ cells/well in 24-well plates the day prior to transfection in growth medium (DMEM+10% Fetal Bovine Serum+1% Penicillin/streptomycin). 500 ng each of the dead EGFP reporter vector, deaminase-RGN expression vector, and guide RNA expression vector were transfected using Lipofectamine® 3000 reagent (Thermo Fisher Scientific) following manufacturer's instructions. For electroporation, cells are electroporated using the Neon® Transfection System (Thermo Fisher Scientific) following manufacturer's instructions.

24-48 hours after lipofection or electroporation, the expression of GFP was determined by microscopically surveying the cells for the presence of GFP+ cells. Following visual inspection, the proportion of GFP+ cells versus GFP− cells may be determined. Fluorescence was observed for mammalian cells expressing deaminase-RGN fusion proteins reported in Table 23. A person of skill in the art will appreciate that the cells may also be lysed using RIPA buffer, and the resulting lysate may be analyzed on a fluorescence plate reader to determine the fluorescence intensity for GFP. Additionally, the cells may be analyzed by cell sorting to determine the exact proportions of GFP+, and GFP− cells.

TABLE 22

Mutation rates of selected mutated deaminases

| Deaminase ID | SEQ ID NO. | ABE Mutn Rate | CBE Mutn Rate | Off Target | ABE Rel Rate | CBE Rel Rate | Off-T Rel Rate |
|---|---|---|---|---|---|---|---|
| APG05241 | 397 | 4.44E−09 | 5.25E−05 | 3.64E−06 | 14 | 1110 | 170 |
| APG08360 | 411 | 0.00E+00 | 8.72E−07 | 1.40E−08 | 0 | 18 | 1 |
| APG09980 | 420 | 4.57E−09 | 6.35E−06 | 1.10E−05 | 14 | 134 | 514 |
| APG00868 | 374 | 6.57E−10 | 2.27E−04 | 5.02E−07 | 2 | 4796 | 23 |
| APOBEC3A (positive control) | 571 | 0.00E+00 | 6.06E−04 | 8.45E−06 | 0 | 12809 | 395 |
| APG07164_T102K_D104Y_K106T | 572 | 6.46E−08 | 5.76E−05 | 1.16E−08 | 204 | 1218 | 1 |
| NTerm_APG03542(1-88)&Cterm_APG02410(114-179) | 573 | 9.93E−08 | 3.56E−08 | 1.69E−08 | 313 | 1 | 1 |
| APG07458 | 514 | 5.13E−07 | 2.31E−08 | 2.60E−08 | 1621 | 0 | 1 |
| APG06334_A101E_D103S_A105K | 574 | 3.56E−08 | 8.13E−08 | ND | 112 | 2 | ND |
| APG03856_A101K_D103L_K105E | 575 | 1.62E−08 | 7.30E−09 | ND | 51 | 0 | ND |
| APG08799_D105A_K107R | 576 | 5.74E−07 | 3.16E−06 | 2.60E−08 | 1812 | 67 | 1 |
| APG02312_A102G_D104S_K106R | 577 | 1.10E−07 | 4.46E−07 | 2.56E−08 | 347 | 9 | 1 |
| APG09352_D105S_K107T | 578 | 1.36E−06 | 9.34E−08 | 4.34E−08 | 4293 | 2 | 2 |
| APG02312_A102S_D104Q_K106G | 579 | 1.36E−06 | 9.34E−08 | 4.34E−08 | 4293 | 2 | 2 |
| APG03140_D111G | 580 | 1.24E−06 | 4.48E−08 | 4.63E−08 | 3921 | 1 | 2 |
| APG03557_A104Q_D106G_K108R | 581 | 1.12E−06 | 6.90E−07 | 3.80E−08 | 3522 | 15 | 1 |
| APG07164_T102R D104W K106E | 582 | 3.83E−08 | 1.81E−07 | 2.24E−08 | 121 | 4 | 1 |
| APG02312_D104R_K106S | 583 | 2.11E−06 | 6.53E−08 | 1.64E−08 | 6663 | 1 | 1 |
| APG03140_A110F_D112S_K114T | 584 | 4.16E−07 | 3.50E−08 | 4.61E−08 | 1314 | 1 | 2 |
| dAPG08290.1 | 547 | 3.17E−10 | 4.73E−08 | 2.14E−08 | 1 | 1 | 1 |

TABLE 23

Mammalian Adenosine Deaminase Fluorescence Reporter Results

| Deaminase ID | SEQ ID NO. | Relative GFP+ Cells |
| --- | --- | --- |
| APG07164 T102K D104Y K106T | 572 | + |
| NTerm_APG03542(1-88)&Cterm_APG02410(114-179) | 573 | + |
| APG06334_A101E_D103S_A105K | 574 | ++ |
| APG03856_A101K_D103L_K105E | 575 | + |
| APG08799_D105A_K107R | 576 | ++ |
| APG09352_D105S_K107T | 578 | + |
| APG02312_A102S_D104Q_K106G | 579 | + |
| APG03140_D111G | 580 | + |

TABLE 23-continued

Mammalian Adenosine Deaminase Fluorescence Reporter Results

| Deaminase ID | SEQ ID NO. | Relative GFP+ Cells |
| --- | --- | --- |
| APG03557_A104Q_D106G_K108R | 581 | +++ |
| APG02312_D104R_K106S | 583 | + |
| APG03140_A110F_D112S_K114T | 584 | + |

+ = few GFP+ cells detected,
++ = many GFP+ cells detected,
+++ = highest number of GFP+ cells observed

---

SEQUENCE LISTING

```
Sequence total quantity: 617
SEQ ID NO: 1            moltype = AA   length = 1060
FEATURE                 Location/Qualifiers
REGION                  1..1060
                        note = source = /note="APG00969"
source                  1..1060
                        mol_type = protein
                        organism = Bacillus sp.
SEQUENCE: 1
MKQTSYSLGL DIGIASVGYG LIDNDENIVD AGVRLFPEAN SKNNDGRRKS RGSKRLIRRK   60
RHRIARVKHL LKESGIDVSY ENTVLTNPYE IRCKGLTLPL TNHELSIALL HLAKRRGVHN  120
VKSMDQEKVK GNELSTKEQL TINDNLLEEK FICELQLERL NKEGIVRSHS NRFKTADYIK  180
EIKNLLETQA KQNTLVTEEF IEKYIEIFSG RRKYYEGPGG ESKYGWKGDI EKWYEGLMGK  240
CTYFPKELRC VKHAYSAALF NLLNDLNNLS INREEDTKLS QYEKEQIIEK IFKVRKTPTL  300
TQIAKLLKVD PTNIKGFRTK ANGTPDFLSI KIYHDLKGII DDKQLLDDIA FLDNVAQILT  360
VWQDSQSIQE KLKTLNKNLD DKTIKEISEL KKYTQTHSLS LKLINVLLPE LWETTKNQMT  420
ILSELKLKPR KIDLHNCNEI PVNMINDLIV SPVVRRSLTQ SIEMINQIIK DYGHPREIVI  480
ELAREKNSEE KKNFIKSLNE KNKQINDEVI EKLNASNHRD NKGMFNKVKL WILQDGHCLY  540
SLKPIRLEDL LNNPNHYEID HIIPKSVSFD DSMSNKVLVY QIENSKKGNR TPYQYLTSAD  600
KTITYEKFKA NITQLAKSNH KISKKKLDYL LEERDINRFH IKKEFINRNL VDTRYATRSL  660
INLLKYYFSE KDINVKVKSI NGSFTDYLRK LWNFPKDREF YHKHHAEDAL IIAMANKIFT  720
TRKIFKEQNS VFSDEQILDG EVTNILSDDQ FQAEFTEKFY KVQAIKKYDK YKYSHRVDKK  780
PNRQLFDDTL YSTREFEGEE YYIGKIKDIY NLKDKRLKKI FTKSPEKILM YQHDSQTFKK  840
LKQIMRSYED EVNPLAKYHK ETGEYLRKEC KKGNGPIVKS LKYRVTKLGV HKDITHKYEN  900
SKNKVVILSL KPFRMDVFKE NGVYKFITIR YCDLKETVNS YTISEHLYKA KLKAKDIKSM  960
DSFKWSFYKN DLLEYNGELC TFKGVNDDKK NKIEVNWVEK NFAIYAEKKN LKSKQLVKSI 1020
TKSTVKSLLK YTTDILGNRY PVRNEKLKLM IRKQTFRGDL                      1060

SEQ ID NO: 2            moltype = RNA   length = 16
FEATURE                 Location/Qualifiers
misc_feature            1..16
                        note = source = /note="crRNA"
source                  1..16
                        mol_type = other RNA
                        organism = Bacillus sp.
SEQUENCE: 2
gttttagtac tctgtg                                                   16

SEQ ID NO: 3            moltype = RNA   length = 73
FEATURE                 Location/Qualifiers
misc_feature            1..73
                        note = source = /note="tracrRNA"
source                  1..73
                        mol_type = other RNA
                        organism = Bacillus sp.
SEQUENCE: 3
cacagaatct actaaaataa ggcataatgc cgtatttaat cccatcataa ttctgatggg   60
atttttata ttt                                                       73

SEQ ID NO: 4            moltype = RNA   length = 118
FEATURE                 Location/Qualifiers
misc_feature            1..118
                        note = source = /note="Description of Artificial Sequence:
                         Syntheticpolynucleotide"
source                  1..118
                        mol_type = other RNA
                        organism = synthetic construct
SEQUENCE: 4
nnnnnnnnnn nnnnnnnnnn nnnngttttt agtactctgt gaaagcacag aatctactaa   60
```

-continued

```
aataaggcat aatgccgtat ttaatcccat cataattctg atgggatttt ttatattt      118

SEQ ID NO: 5              moltype = RNA   length = 123
FEATURE                   Location/Qualifiers
misc_feature              1..123
                          note = source = /note="Description of Artificial Sequence:
                          Syntheticpolynucleotide"
source                    1..123
                          mol_type = other RNA
                          organism = synthetic construct
SEQUENCE: 5
gagcggacag cagcttccta tatctcgtac gttttagtac tctgtgaaag cacagaatct     60
actaaaataa ggcataatgc cgtatttaat cccatcataa ttctgatggg attttttata    120
ttt                                                                  123

SEQ ID NO: 6              moltype = RNA   length = 123
FEATURE                   Location/Qualifiers
misc_feature              1..123
                          note = source = /note="Description of Artificial Sequence:
                          Syntheticpolynucleotide"
source                    1..123
                          mol_type = other RNA
                          organism = synthetic construct
SEQUENCE: 6
ccatgatata gacgttgtgg ctgttgtagt gttttagtac tctgtgaaag cacagaatct    60
actaaaataa ggcataatgc cgtatttaat cccatcataa ttctgatggg attttttata   120
ttt                                                                 123

SEQ ID NO: 7              moltype =    length =
SEQUENCE: 7
000

SEQ ID NO: 8              moltype =    length =
SEQUENCE: 8
000

SEQ ID NO: 9              moltype = DNA   length = 13
FEATURE                   Location/Qualifiers
misc_feature              1..13
                          note = source = /note="Description of Artificial Sequence:
                          Syntheticoligonucleotide"
source                    1..13
                          mol_type = other DNA
                          organism = synthetic construct
SEQUENCE: 9
gccgccrcca tgg                                                       13

SEQ ID NO: 10             moltype = AA   length = 7
FEATURE                   Location/Qualifiers
REGION                    1..7
                          note = source = /note="Description of Artificial Sequence:
                          Syntheticpeptide"
source                    1..7
                          mol_type = protein
                          organism = synthetic construct
SEQUENCE: 10
PKKKRKV                                                              7

SEQ ID NO: 11             moltype = AA   length = 22
FEATURE                   Location/Qualifiers
REGION                    1..22
                          note = source = /note="Description of Artificial Sequence:
                          Syntheticpeptide"
source                    1..22
                          mol_type = protein
                          organism = synthetic construct
SEQUENCE: 11
DYKDHDGDYK DHDIDYKDDD DK                                             22

SEQ ID NO: 12             moltype = AA   length = 16
FEATURE                   Location/Qualifiers
REGION                    1..16
                          note = source = /note="Description of Artificial Sequence:
                          Syntheticpeptide"
source                    1..16
                          mol_type = protein
                          organism = synthetic construct
SEQUENCE: 12
KRPAATKKAG QAKKKK                                                    16
```

```
SEQ ID NO: 13          moltype =    length =
SEQUENCE: 13
000

SEQ ID NO: 14          moltype = DNA   length = 38
FEATURE                Location/Qualifiers
misc_feature           1..38
                       note = source = /note="Description of Artificial Sequence:
                         Syntheticoligonucleotide"
source                 1..38
                       mol_type = other DNA
                       organism = synthetic construct
SEQUENCE: 14
gagcggacag cagcttccta tatctcgtac nnnnnnnn                              38

SEQ ID NO: 15          moltype = DNA   length = 38
FEATURE                Location/Qualifiers
misc_feature           1..38
                       note = source = /note="Description of Artificial Sequence:
                         Syntheticoligonucleotide"
source                 1..38
                       mol_type = other DNA
                       organism = synthetic construct
SEQUENCE: 15
ccatgatata gacgttgtgg ctgttgtagt nnnnnnnn                              38

SEQ ID NO: 16          moltype = AA   length = 1090
FEATURE                Location/Qualifiers
REGION                 1..1090
                       note = source = /note="APG03128"
source                 1..1090
                       mol_type = protein
                       organism = Rhizobium sp.
SEQUENCE: 16
MNNLLYSFDI GTNSIGWCVF ALDEVGDPCR IVDLGARIYA DGRDPQTKTS LAVARREARA      60
MSRRRDRSLR RRKATLRTMI EYGLMPAHKV EQETLLRKTG DREGGDEGFN PYALRARALG     120
EKLPPFYIGR ALFHLGQRRG FKSNRKTDRK DNDKGKIALG IDELRAAMHR SGSPTLGAWL     180
AMRRADGHPV RLRAGSEVFD AEGYAFYPER SLLEDEFRQI WTAQAVHHPQ LLTSERRAHL     240
FRVMFYQRPL KKPLVGRCSF NPAEARLSRA HPLFQEFRLY KEVNDLEVVL PDQSHRKLTL     300
DERNALVAKL KSSRKASFSV LRRTLKLTPD LAFNKESEAR KDLLGDEINS ALADAKMFGV     360
RWGGFPRARQ WEIITHLKEE ENPARLSDWL KSEFGLDDER VVAIANIALP EGYGRLGETA     420
LASMLEEMKT AVIPESEAAK RCGYDHSNLA KEQDEGLDIL PEYQEILERH IPPGTGDPDD     480
IYDIRKGRIT NPTVHIGLNQ LRRVVNALIK RHGKPRHIVV ELARDLQLSE KQKADVNRRI     540
AKNTREAEGR SQKLIEMGQL DTGYNRLLLK LWEELNQDKP EDRVCIYSGK PIGIAMLFSG     600
EVDIDHILPW SKTLDDSQAN KLLCLKSANR QKRNRTPSDV PEWRDCYEEV LARAARLPKN     660
KRWRFAADAM QQFEAEGGFL ARQLTDTQYL SRMAFEYLSA LFPSEEADKW GELRQRKRVH     720
VVPGRLTELL RRNWGLNTLL PDHNLGEMAQ EKNRKDHRHH AIDAAVIGVT SRSLLQRMSG     780
AAARLDDVAF DDLVRTVVKD NPPWPGFREE LLGCINRVTV SHKPDHGTVS RAAYAQGKGQ     840
TAGKLHNDTA YGITGLQDMK GSPLVVRRKP FMALEVKDIA SIRDTELQSA LYDAIGSLTE     900
KKALQEALVR FRDRHPQFKG IRRVRVLEAL SVIPIVDNNG KAYKGYKGDA NYRYEVWETL     960
DGRWHTEVVS MFDAHQPGWQ SPFHRQHPAA RRVLKQQND MVAYEHPADG YTIARVVKFS     1020
NDKRIYFASH RESGSLKARD ADKGDPFTYF AKANNGLRDI KCRQVRIDAA GRVFDPGPQD    1080
REARQSKGRA                                                          1090

SEQ ID NO: 17          moltype = RNA   length = 31
FEATURE                Location/Qualifiers
misc_feature           1..31
                       note = source = /note="crRNA"
source                 1..31
                       mol_type = other RNA
                       organism = Rhizobium sp.
SEQUENCE: 17
ggttgcggct ggaccgcgtt ttctgatctg c                                    31

SEQ ID NO: 18          moltype = RNA   length = 79
FEATURE                Location/Qualifiers
misc_feature           1..79
                       note = source = /note="tracrRNA"
source                 1..79
                       mol_type = other RNA
                       organism = Rhizobium sp.
SEQUENCE: 18
gcaaatcaga aaacgcggtc tggccgttaa caagcctcga ccagcaccag ataaggcggt     60
ccctccgggg gcgtttttt                                                  79

SEQ ID NO: 19          moltype = RNA   length = 139
FEATURE                Location/Qualifiers
misc_feature           1..139
```

```
                        note = source = /note="Description of Artificial Sequence:
                            Syntheticpolynucleotide"
source                  1..139
                        mol_type = other RNA
                        organism = synthetic construct
SEQUENCE: 19
nnnnnnnnnn nnnnnnnnnn nnnnnggttg cggctggacc gcgttttctg atctgcaaag    60
gcaaatcaga aaacgcggtc tggccgttaa caagcctcga ccagcaccag ataaggcggt   120
ccctccgggg gccgttttt                                                139

SEQ ID NO: 20           moltype = RNA   length = 144
FEATURE                 Location/Qualifiers
misc_feature            1..144
                        note = source = /note="Description of Artificial Sequence:
                            Syntheticpolynucleotide"
source                  1..144
                        mol_type = other RNA
                        organism = synthetic construct
SEQUENCE: 20
gagcggacag cagcttccta tatctcgtac ggttgcggct ggaccgcgtt ttctgatctg    60
caaaggcaaa tcagaaaacg cggtctggcc gttaacaagc ctcgaccagc accagataag   120
gcggtccctc cggggccgt tttt                                           144

SEQ ID NO: 21           moltype = RNA   length = 144
FEATURE                 Location/Qualifiers
misc_feature            1..144
                        note = source = /note="Description of Artificial Sequence:
                            Syntheticpolynucleotide"
source                  1..144
                        mol_type = other RNA
                        organism = synthetic construct
SEQUENCE: 21
ccatgatata gacgttgtgg ctgttgtagt ggttgcggct ggaccgcgtt ttctgatctg    60
caaaggcaaa tcagaaaacg cggtctggcc gttaacaagc ctcgaccagc accagataag   120
gcggtccctc cggggccgt tttt                                           144

SEQ ID NO: 22           moltype =    length =
SEQUENCE: 22
000

SEQ ID NO: 23           moltype =    length =
SEQUENCE: 23
000

SEQ ID NO: 24           moltype = AA   length = 1108
FEATURE                 Location/Qualifiers
REGION                  1..1108
                        note = source = /note="APG09748"
source                  1..1108
                        mol_type = protein
                        organism = Brevibacillus sp.
SEQUENCE: 24
MAIRSIKLKL KTRTGPEAQN LRKGIWRTHR LLNEGVAYYM KMLLLFRQES TGGQTKKELQ    60
EELVRHIREQ QQKNRADKNT QALPLDKAFA ALRQLYELLV PSSIGQSGDA QIISRKFLSP   120
LVDPNSEGGK GTSKAGAKPT WQKKKEANDP TWEQDYEKWK KRREEDPTAS VITTLEEYGI   180
RPIFPLYTNT VADIAWLPLQ SNQFVRTWDR DMLQQAIERL LSWESWNKRV QEEYSKLQEK   240
MTQLNEQLEG GQEWISLLEQ YEEQREQELI ENMTAANDKY RITKRQMKGW NELYEQWSTV   300
LPNASHEQYR EALKRVQQRL RGRFGDAHFF QYLMKEEHHL IWKGNPQRIH YFVARNELKK   360
RLEEAKQNAT MTLPDARKHP LWVRFDARGG NLQDYYLTAE ADNPRSRRFV TFSQLIWPNE   420
SGWMEKQDVE VELALSKQFY QQVTLQKNDK GKQEIEFKDK GSGSTFSGHL GGAKLQLERG   480
DLEKEEKDFE GGEIGSVYLN IVIDFEPLQE VKNGRLQSPY GQVLQLVRRP NEFPKVTTYK   540
SEELVEWIKS STKDSAGVES LESGFRVMSI DLGLRTAAAT SIFSVEESND ANAAGFSYWI   600
EGTPLVAVHK RSYMLKLPGE QVEKQVREKR DERQDQQRRV RFQIRILSQV IRMAKKQNRE   660
RADELDHLSQ ALEKQKSLLD QTDRTFWNGI VCDLTDALRE KEGGWEQAVV QIHRKAEEHV   720
GKVVQAWRKR FDADERKGIA GLSMWSIEEL DSLRKLLISW SRRTRNPREI NCFEQGHTSH   780
QRLLTHIQNV KEDRLKQLSH AIVMTALGYV YDEKKLEWFA KYPACQVILF ENLSQYRSNM   840
DRSTKENSTL MKWAHRSIPK YVHMQAEPYG IQIGDVRAEY SSRFHAKTGT PGIRCKMVSG   900
HDLQGRRFEN LQKRLISEQF LTEEQVKQLR PGDIVPDDSG EGKEVVFLQA   960
DINAAQNLQK RFWQRYNELF KVSCRVLIRG EEEYLIPKTK SVQAKLGKGL FVKKTDTVMK  1020
DVYVWDSQAK LKGKTTFTEE SESPEQLEDF QEIIEEAEEA KGTYRTLFRD PSGVFFPEFV  1080
WSTQKDFWSE VKRRLYGKLR ERFLMKTR                                     1108

SEQ ID NO: 25           moltype = RNA   length = 22
FEATURE                 Location/Qualifiers
misc_feature            1..22
                        note = source = /note="crRNA"
source                  1..22
                        mol_type = other RNA
                        organism = Brevibacillus sp.
```

```
SEQUENCE: 25
tggaaagctt cgaggttagc ac                                                    22

SEQ ID NO: 26              moltype = RNA   length = 95
FEATURE                    Location/Qualifiers
misc_feature               1..95
                           note = source = /note="tracrRNA"
source                     1..95
                           mol_type = other RNA
                           organism = Brevibacillus sp.
SEQUENCE: 26
cgacggttag aggccgtatg tcgatttgct ttaatttcgt gcgtgtgcat tgtcgtcctc           60
cattacaggg cggctaccac gaatagccac gaagt                                      95

SEQ ID NO: 27              moltype = RNA   length = 151
FEATURE                    Location/Qualifiers
misc_feature               1..151
                           note = source = /note="Description of Artificial Sequence:
                             Syntheticpolynucleotide"
source                     1..151
                           mol_type = other RNA
                           organism = synthetic construct
SEQUENCE: 27
cgacggttag aggccgtatg tcgatttgct ttaatttcgt gcgtgtgcat tgtcgtcctc           60
cattacaggg cggctaccac gaatagtcac gaagttccac tgagtaaagt ggaaagcttc          120
gaggttagca cnnnnnnnnn nnnnnnnnnn n                                         151

SEQ ID NO: 28              moltype = RNA   length = 145
FEATURE                    Location/Qualifiers
misc_feature               1..145
                           note = source = /note="Description of Artificial Sequence:
                             Syntheticpolynucleotide"
source                     1..145
                           mol_type = other RNA
                           organism = synthetic construct
SEQUENCE: 28
cgacggttag aggccgtatg tcgatttgct ttaatttcgt gcgtgtgcat tgtcgtcctc           60
cattacaggg cggctaccac gaatagccac gaagtaaaag cttcgtggct agcacgtacg          120
agatatagga agctgctgtc cgctc                                                145

SEQ ID NO: 29              moltype = RNA   length = 145
FEATURE                    Location/Qualifiers
misc_feature               1..145
                           note = source = /note="Description of Artificial Sequence:
                             Syntheticpolynucleotide"
source                     1..145
                           mol_type = other RNA
                           organism = synthetic construct
SEQUENCE: 29
cgacggttag aggccgtatg tcgatttgct ttaatttcgt gcgtgtgcat tgtcgtcctc           60
cattacaggg cggctaccac gaatagccac gaagtaaaag cttcgtggct agcacactac          120
aacagccaca acgtctatat catgg                                                145

SEQ ID NO: 30              moltype =       length =
SEQUENCE: 30
000

SEQ ID NO: 31              moltype =       length =
SEQUENCE: 31
000

SEQ ID NO: 32              moltype = DNA   length = 38
FEATURE                    Location/Qualifiers
misc_feature               1..38
                           note = source = /note="Description of Artificial Sequence:
                             Syntheticoligonucleotide"
source                     1..38
                           mol_type = other DNA
                           organism = synthetic construct
SEQUENCE: 32
nnnnnnnngt acgagatata ggaagctgct gtccgctc                                   38

SEQ ID NO: 33              moltype = DNA   length = 37
FEATURE                    Location/Qualifiers
misc_feature               1..37
                           note = source = /note="Description of Artificial Sequence:
                             Syntheticoligonucleotide"
source                     1..37
                           mol_type = other DNA
```

```
                              organism = synthetic construct
SEQUENCE: 33
nnnnnnnnac tacaacagcc acaacgtcta tatcatg                              37

SEQ ID NO: 34            moltype =    length =
SEQUENCE: 34
000

SEQ ID NO: 35            moltype = AA   length = 1429
FEATURE                  Location/Qualifiers
REGION                   1..1429
                         note = source = /note="APG00771"
source                   1..1429
                         mol_type = protein
                         organism = Chryseobacterium sp.
SEQUENCE: 35
MTKNILGLDL GTNSIGWALI KQDFENKQGE ILGMGSRIIP MDAGDMGKFA EGATVSKTAD   60
RTKYRSVRRL RERFLLRRER LHRVLHLLNF LPQHYASQID FEKRFGKFKV ETEPKLAWKN  120
IEGKFSFLFQ NSFNEMLEDF KANEQDLKIP YDWTIYFLRK KALSQKIEKE ELAWILLNFN  180
QKRGYYQLRG EEEEENPNKL VEFYSLKVVD VLADEPQKGK SEIWYSLVLK NGWIYRRASK  240
IPLFEWKDKT RDFIVTTDLN DDGSIKKDKD GNEKRSFRAP GENDWTLVKK KTEQEIEQSH  300
KTVGTYIYET LLLNPKQKIK GKLVRTIERK FYKDELKQIL EKQKEFHQEL QNDDLYNDCI  360
RELYRNNEAH QLTLSKKDFV HLLMDDLIFY QRPLRSQKSS ISNCTLEFRK YKDENGIEHT  420
QYLKAIPKSN PYYQEFRLWQ WIYNLNIYRK DDEVNVTKDF LNTTKEFENL FEFLNSRKEV  480
DQKALLKYFK LNEKTHRWNF VEDKKYPCNE TKTMISSRLD KVENISDDFL TRNIEQKIWH  540
IIYSVNDKIE YEKALKSFAR KHHLDETSFF EAFRKFPPFK SEYGSFSEKA IKKLLPLMRL  600
GKYWNYADID KYSRERIQKI ITGEYDENIK DKIREKAIHL TKENDFQGLQ LWLAQYLVYG  660
RHSEASMIGK WNSADDLEVF LKDFKQHSLR NPIVEQVITE TLRVVKDIWL KYGNGTKDFF  720
NEIHIELGRE MKLPADDRKK LTSQISENEN TNLRIKALLA EMINDHSVEN VRPFSPMQQE  780
ILKIYEDGVL NSDIEIEDDI LKISKTAQPS PSDLKRYKLW LEQKPKSPYT GQIIPLNKLF  840
TPEYEIEHII PQSRYFDDSF SNKVICESAV NKLKDNYIGL EFIKKLGGTV VECGNGKSVT  900
VLKEDQYEDF VKKHYANNRG KRNKLLMEDI PEKMIERQLN DTRYISKYIS GVLSNIVRVE  960
DGSDEGINSK NIVPGNGKIT SQLKQDWGLN DVWNDLILPR FERMNQLTNS TDFTAWNENY 1020
QKFLPTVPIE YSKGFSKKRI DHRHHALDAL VIACATKDHV NLLNNQSAKS DTKRYDLKKK 1080
LMKFEKVVYH HTQTGEKIER EIPRQFLKPW ENFTVDAKHN LESIIVSFKQ NLRVINKATN 1140
YYEKYVEKDG TKNKERVEQT GTNWAIRKPM HKDTVSGKVD LPWVKVPKGK ILTATRKSLD 1200
TSFDLKSIGS ITDTGIQKIL KNYLAFKDGN PEMAFSPEGI DDLNKNIEKY NDGKPHQPIN 1260
KVRVFELGSK FQVGQTGNKK DKYVEAAKGT NLFFAVYEDE KGKRSYETIP LNEVIERQKQ 1320
GLSVVDLKDT NDFYLCPNDL VYIPSGDELE NVNNVDFKDI KKDKNERIYK VVSFSGSQIF 1380
FVRQDIATFI VNKAELSTLN KMERAIDGSM IKENCIKLNI DRLGNISKA              1429

SEQ ID NO: 36            moltype = RNA   length = 20
FEATURE                  Location/Qualifiers
misc_feature             1..20
                         note = source = /note="crRNA"
source                   1..20
                         mol_type = other RNA
                         organism = Chryseobacterium sp.
SEQUENCE: 36
gttgtgaatt gctttcaaaa                                                 20

SEQ ID NO: 37            moltype = RNA   length = 76
FEATURE                  Location/Qualifiers
misc_feature             1..76
                         note = source = /note="tracrRNA"
source                   1..76
                         mol_type = other RNA
                         organism = Chryseobacterium sp.
SEQUENCE: 37
ttttgaaagc aattcacaat aaggattatt ccgttgtgaa acattcaag gcggggcaac     60
tcgcctttttt tcgttt                                                   76

SEQ ID NO: 38            moltype = RNA   length = 125
FEATURE                  Location/Qualifiers
misc_feature             1..125
                         note = source = /note="Description of Artificial Sequence:
                           Syntheticpolynucleotide"
source                   1..125
                         mol_type = other RNA
                         organism = synthetic construct
SEQUENCE: 38
nnnnnnnnnn nnnnnnnnnn nnnnngttgt gaattgcttt caaaaaaagt tttgaaagca    60
attcacaata aggattattc cgttgtgaaa acattcaagg cggggcaact cgccttttttt  120
cgttt                                                                125

SEQ ID NO: 39            moltype = RNA   length = 130
FEATURE                  Location/Qualifiers
misc_feature             1..130
                         note = source = /note="Description of Artificial Sequence:
```

```
                        Syntheticpolynucleotide"
source                  1..130
                        mol_type = other RNA
                        organism = synthetic construct
SEQUENCE: 39
gagcggacag cagcttccta tatctcgtac gttgtgaatt gctttcaaaa aaagttttga     60
aagcaattca caataaggat tattccgttg tgaaaacatt caaggcgggg caactcgcct    120
tttttcgttt                                                           130

SEQ ID NO: 40           moltype = RNA   length = 130
FEATURE                 Location/Qualifiers
misc_feature            1..130
                        note = source = /note="Description of Artificial Sequence:
                        Syntheticpolynucleotide"
source                  1..130
                        mol_type = other RNA
                        organism = synthetic construct
SEQUENCE: 40
ccatgatata gacgttgtgg ctgttgtagt gttgtgaatt gctttcaaaa aaagttttga     60
aagcaattca caataaggat tattccgttg tgaaaacatt caaggcgggg caactcgcct    120
tttttcgttt                                                           130

SEQ ID NO: 41           moltype =   length =
SEQUENCE: 41
000

SEQ ID NO: 42           moltype =   length =
SEQUENCE: 42
000

SEQ ID NO: 43           moltype = AA   length = 1112
FEATURE                 Location/Qualifiers
REGION                  1..1112
                        note = source = /note="APG02789"
source                  1..1112
                        mol_type = protein
                        organism = Bacillus sp.
SEQUENCE: 43
MAIRSIKLKM KTNSGTDSIY LRKALWRTHQ LINEGIAYYM NLLTLYRQEA IGDKTKEAYQ     60
AELINIIRNQ QRNNGSSEEH GSDQEILALL RQLYELIIPS SIGESGDANQ LGNKFLYPLV    120
DPNSQSGKGT SNAGRKPRWK RLKEEGNPDW ELEKKKDEER KAKDPTVKIF DNLNKYGLLP    180
LFPLFTNIQK DIEWLPLGKR QSVRKWDKDM FIQAIERLLS WESWNRRVAD EYKQLKEKTE    240
SYYKEHLTGG EEWIEKIRKF EKERNMELEK NAFAPNDGYF ITSRQIRGWD RVYEKWSKLP    300
ESASPEELWK VVAEQQNKMS EGFGDPKVFS FLANRENRDI WRGHSERIYH IAAYNGLQKK    360
LSRTKEQATF TLPDAIEHPL WIRYESPGGT NLNLFKLEEK QKKNYVTLS KIIWPSEEKW    420
IEKENIEIPL APSIQFNRQI KLKQHVKGKQ EISFSDYSSR ISLDGVLGGS RIQFNRKYIK    480
NHKELLGEGD IGPVFFNLVV DVAPLQETRN GRLQSPIGKA LKVISSDFSK VIDYKPKELM    540
DWMNTGSASN SFGVASLLEG MRVMSIDMGQ RTSASVSIFE VVKELPKDQE QKLFYSINDT    600
ELFAIHKRSF LLNLPGEVVT KNNKQQRQER RKKRQFVRSQ IRMLANVLRL ETKKTPDERK    660
KAIHKLMEIV QSYDSWTASQ KEVWEKELNL LTNMAAFNDE IWKESLVELH HRIEPYVGQI    720
VSKWRKGLSE GRKNLAGISM WNIDELEDTR RLLISWSKRS RTPGEANRIE TDEPFGSSLL    780
QHIQNVKDDR LKQMANLIIM TALGFKYDKE EKDRYKRWKE TYPACQIILF ENLNRYLFNL    840
DRSRRENSRL MKWAHRSIPR TVSMQGEMFG LQVGDVRSEY SSRFHAKTGA PGIRCHALTE    900
EDLKAGSNTL KRLIEDGFIN ESELAYLKKG DIIPSQGGEL FVTLSKRYKK DSDNNELTVI    960
HADINAAQNL QKRFWQQNSE VYRVPCQLAR MGEDKLYIPK SQTETIKKYF GKGSFVKNNT   1020
EQEVYKWEKS EKMKIKTDTT FDLQDLDGFE DISKTIELAQ EQQKKYLTMF RDPSGYFFNN   1080
ETWRPQKEYW SIVNNIIKSC LKKKILSNKV EL                                 1112

SEQ ID NO: 44           moltype = RNA   length = 36
FEATURE                 Location/Qualifiers
misc_feature            1..36
                        note = source = /note="crRNA"
source                  1..36
                        mol_type = other RNA
                        organism = Bacillus sp.
SEQUENCE: 44
gcctgaatac ttagcagaaa taatgatgat tggcac                               36

SEQ ID NO: 45           moltype = RNA   length = 100
FEATURE                 Location/Qualifiers
misc_feature            1..100
                        note = source = /note="tracrRNA"
source                  1..100
                        mol_type = other RNA
                        organism = Bacillus sp.
SEQUENCE: 45
ataataaagg tgacctatag ggtcaatgaa tctgtgcgtg tgccataagt aattaaaaat     60
tacccaccac aggattatct tatttctgct aagtgtttag                          100
```

```
SEQ ID NO: 46              moltype = RNA   length = 160
FEATURE                    Location/Qualifiers
misc_feature               1..160
                           note = source = /note="Description of Artificial Sequence:
                           Syntheticpolynucleotide"
source                     1..160
                           mol_type = other RNA
                           organism = synthetic construct
SEQUENCE: 46
ataataaagg tgacctatag ggtcaatgaa tctgtgcgtg tgccataagt aattaaaaat    60
tacccaccac aggattatct tatttctgct aagtgtttag aaaggcctga atacttagca   120
gaaataatga tgattggcac nnnnnnnnnn nnnnnnnnnn                         160

SEQ ID NO: 47              moltype = RNA   length = 170
FEATURE                    Location/Qualifiers
misc_feature               1..170
                           note = source = /note="Description of Artificial Sequence:
                           Syntheticpolynucleotide"
source                     1..170
                           mol_type = other RNA
                           organism = synthetic construct
SEQUENCE: 47
ataataaagg tgacctatag ggtcaatgaa tctgtgcgtg tgccataagt aattaaaaat    60
tacccaccac aggattatct tatttctgct aagtgtttag aaaggcctga atacttagca   120
gaaataatga tgattggcac gtacgagata taggaagctg ctgtccgctc              170

SEQ ID NO: 48              moltype = RNA   length = 170
FEATURE                    Location/Qualifiers
misc_feature               1..170
                           note = source = /note="Description of Artificial Sequence:
                           Syntheticpolynucleotide"
source                     1..170
                           mol_type = other RNA
                           organism = synthetic construct
SEQUENCE: 48
ataataaagg tgacctatag ggtcaatgaa tctgtgcgtg tgccataagt aattaaaaat    60
tacccaccac aggattatct tatttctgct aagtgtttag aaaggcctga atacttagca   120
gaaataatga tgattggcac actacaacag ccacaacgtc tatatcatgg              170

SEQ ID NO: 49              moltype =    length =
SEQUENCE: 49
000

SEQ ID NO: 50              moltype = AA   length = 1108
FEATURE                    Location/Qualifiers
REGION                     1..1108
                           note = source = /note="APG09106"
source                     1..1108
                           mol_type = protein
                           organism = Brevibacillus sp.
SEQUENCE: 50
MAIRSIKLKL KTRTGPEAQN LRKGIWRTHR LLNEGVAYYM KMLLLFRQES TGGQTKKELQ    60
EELVRHIREQ QQKNRADKNT QALPLDKAFA ALRQLYELLV PSSIGQSDA  QIISRKFLSP   120
LVDPNSEGGK GTSKAGAKPT WQKKEANDP  TWEQDYEKWK KRREEDPTAS VITTLEEYGI   180
RPIFPLYTNT VADIAWLPLQ SNQFVRTWDR DMLQQAIERL LSWESWNKRV QEEYSKLQEK   240
MTQLNEQLEG GQEWISLLEQ YEEQREQELI ENMTAANDKY RITKRQMKGW NELYEQWSTV   300
LPNASHEQYR EALKRVQQRL RGRFGDAHPF QYLMKEEHHL IWKGNPQRIH YFVARNELKK   360
RLEEAKQNAT MTLPDARKHP LWVRFDARGG NLQDYYLTAE ADNPRSRRFV TFSQLIWPNE   420
SGWMEKQDVE VELALSKQFY QQVTLQKNDK GKQEIEFKDE GSGSTFSGHL GGAKLQLERG   480
DLEKEEKDFE GGEIGSVYLN IVIDFEPLQE VKNGRLQSPY GQVLQLVRRP NEFPKVTTYK   540
SEELVEWMKA SQNHSSGVES LESGFRVMSI DLGLRTAAAT SIFSVEESND ANAAGFSYWI   600
EGTPLVAVHK RSYMLKLPGE QVEKQVREKR DERQDQQRRV RFQIRILSQV IRMAKKQNRE   660
RADELDHLSQ ALEKQKSLLD QTDRTFWNGI VCDLTDALRE KEGGWEQAVV QIHRKAEEHV   720
GKVVQAWRKR FDADERKGIA GLSMWSIEEL DSLRKLLISW SRRTRNPQEI NRFEQGHTSH   780
QRLLTHIQNV KEDRLKQLSH AIVMTALGYV YDEKKLEWFA KYPACQVILF ENLSQYRSHM   840
DRSTKENSTL MKWAHRSIPK YVHMQAEPYG IQIGDVRAEY SSRFHAKTGT PGIRCKMVKG   900
QELQGKRFEN LQKRLVSEQF LTEEQVKQLR PGDIVPDDSG EWFMTLSDGS EGKEVVFLQA   960
DINAAQNLQK RFWQRYNELF KVSCRVLIRG EEEYLIPKAK SVQAKLGKGL FVKKTDTVMK  1020
DVYVWDSQAK LKGKTTFTEE SESPEQLEDF QEIIEEAEEA KGTYRTLFRD PSGVFFPEFV  1080
WNTQKDFWSE VKRRLYGKLR ERFLMKTR                                    1108

SEQ ID NO: 51              moltype = RNA   length = 22
FEATURE                    Location/Qualifiers
misc_feature               1..22
                           note = source = /note="crRNA"
source                     1..22
                           mol_type = other RNA
                           organism = Brevibacillus sp.
SEQUENCE: 51
```

```
tggaaagctt cgaggttagc ac                                            22

SEQ ID NO: 52           moltype = RNA   length = 105
FEATURE                 Location/Qualifiers
misc_feature            1..105
                        note = source = /note="tracrRNA"
source                  1..105
                        mol_type = other RNA
                        organism = Brevibacillus sp.
SEQUENCE: 52
cgacggttag aggccgtatg tcgatttgct ttaatttcgt gcgtgtgcat tgtcgtcctc   60
cattacaggg cggctaccac gaatagtcac gaagttccac tgagt                  105

SEQ ID NO: 53           moltype = RNA   length = 151
FEATURE                 Location/Qualifiers
misc_feature            1..151
                        note = source = /note="Description of Artificial Sequence:
                         Syntheticpolynucleotide"
source                  1..151
                        mol_type = other RNA
                        organism = synthetic construct
SEQUENCE: 53
cgacggttag aggccgtatg tcgatttgct ttaatttcgt gcgtgtgcat tgtcgtcctc   60
cattacaggg cggctaccac gaatagtcac gaagttccac tgagtaaagt ggaaagcttc   120
gaggttagca cnnnnnnnnn nnnnnnnnnn n                                 151

SEQ ID NO: 54           moltype = RNA   length = 161
FEATURE                 Location/Qualifiers
misc_feature            1..161
                        note = source = /note="Description of Artificial Sequence:
                         Syntheticpolynucleotide"
source                  1..161
                        mol_type = other RNA
                        organism = synthetic construct
SEQUENCE: 54
cgacggttag aggccgtatg tcgatttgct ttaatttcgt gcgtgtgcat tgtcgtcctc   60
cattacaggg cggctaccac gaatagtcac gaagttccac tgagtaaagt ggaaagcttc   120
gaggttagca cgtacgagat ataggaagct gctgtccgct c                      161

SEQ ID NO: 55           moltype = RNA   length = 161
FEATURE                 Location/Qualifiers
misc_feature            1..161
                        note = source = /note="Description of Artificial Sequence:
                         Syntheticpolynucleotide"
source                  1..161
                        mol_type = other RNA
                        organism = synthetic construct
SEQUENCE: 55
cgacggttag aggccgtatg tcgatttgct ttaatttcgt gcgtgtgcat tgtcgtcctc   60
cattacaggg cggctaccac gaatagtcac gaagttccac tgagtaaagt ggaaagcttc   120
gaggttagca cactacaaca gccacaacgt ctatatcatg g                      161

SEQ ID NO: 56           moltype = RNA   length = 135
FEATURE                 Location/Qualifiers
misc_feature            1..135
                        note = source = /note="Description of Artificial Sequence:
                         Syntheticpolynucleotide"
source                  1..135
                        mol_type = other RNA
                        organism = synthetic construct
SEQUENCE: 56
cgacggttag aggccgtatg tcgatttgct ttaatttcgt gcgtgtgcat tgtcgtcctc   60
cattacaggg cggctaccac gaatagccac gaagtaaaag cttcgtggct agcacccgt    120
ataaagcatg agacc                                                   135

SEQ ID NO: 57           moltype = RNA   length = 135
FEATURE                 Location/Qualifiers
misc_feature            1..135
                        note = source = /note="Description of Artificial Sequence:
                         Syntheticpolynucleotide"
source                  1..135
                        mol_type = other RNA
                        organism = synthetic construct
SEQUENCE: 57
cgacggttag aggccgtatg tcgatttgct ttaatttcgt gcgtgtgcat tgtcgtcctc   60
cattacaggg cggctaccac gaatagccac gaagtaaaag cttcgtggct agcacctcag   120
actgtttgcc cctta                                                   135

SEQ ID NO: 58           moltype = RNA   length = 156
```

```
FEATURE                 Location/Qualifiers
misc_feature            1..156
                        note = source = /note="Description of Artificial Sequence:
                        Syntheticpolynucleotide"
source                  1..156
                        mol_type = other RNA
                        organism = synthetic construct
SEQUENCE: 58
cgacggttag aggccgtatg tcgatttgct ttaatttcgt gcgtgtgcat tgtcgtcctc    60
cattacaggg cggctaccac gaatagtcac gaagttccac tgagtaaagt ggaaagcttc   120
gaggttagca ccccgtataa agcatgagac cgtgac                             156

SEQ ID NO: 59           moltype = RNA   length = 156
FEATURE                 Location/Qualifiers
misc_feature            1..156
                        note = source = /note="Description of Artificial Sequence:
                        Syntheticpolynucleotide"
source                  1..156
                        mol_type = other RNA
                        organism = synthetic construct
SEQUENCE: 59
cgacggttag aggccgtatg tcgatttgct ttaatttcgt gcgtgtgcat tgtcgtcctc    60
cattacaggg cggctaccac gaatagtcac gaagttccac tgagtaaagt ggaaagcttc   120
gaggttagca cctcagactg tttgcccctt actgct                             156

SEQ ID NO: 60           moltype = DNA   length = 25
FEATURE                 Location/Qualifiers
misc_feature            1..25
                        note = source = /note="Description of Artificial Sequence:
                        Syntheticoligonucleotide"
source                  1..25
                        mol_type = other DNA
                        organism = synthetic construct
SEQUENCE: 60
cccgtataaa gcatgagacc gtgac                                          25

SEQ ID NO: 61           moltype = DNA   length = 25
FEATURE                 Location/Qualifiers
misc_feature            1..25
                        note = source = /note="Description of Artificial Sequence:
                        Syntheticoligonucleotide"
source                  1..25
                        mol_type = other DNA
                        organism = synthetic construct
SEQUENCE: 61
ctcagactgt ttgcccctta ctgct                                          25

SEQ ID NO: 62           moltype = RNA   length = 95
FEATURE                 Location/Qualifiers
misc_feature            1..95
                        note = source = /note="Description of Artificial Sequence:
                        Syntheticoligonucleotide"
source                  1..95
                        mol_type = other RNA
                        organism = synthetic construct
SEQUENCE: 62
cgacggttag aggccgtatg tcgatttgct ttaatttcgt gcgtgtgcat tgtcgtcctc    60
cattacaggg cggctaccac gaatagccac gaagt                               95

SEQ ID NO: 63           moltype = RNA   length = 16
FEATURE                 Location/Qualifiers
misc_feature            1..16
                        note = source = /note="Description of Artificial Sequence:
                        Syntheticoligonucleotide"
source                  1..16
                        mol_type = other RNA
                        organism = synthetic construct
SEQUENCE: 63
gcttcgtggc tagcac                                                    16

SEQ ID NO: 64           moltype = RNA   length = 135
FEATURE                 Location/Qualifiers
misc_feature            1..135
                        note = source = /note="Description of Artificial Sequence:
                        Syntheticpolynucleotide"
source                  1..135
                        mol_type = other RNA
                        organism = synthetic construct
SEQUENCE: 64
```

```
cgacggttag aggccgtatg tcgatttgct ttaatttcgt gcgtgtgcat tgtcgtcctc    60
cattacaggg cggctaccac gaatagccac gaagtaaaag cttcgtggct agcacnnnnn   120
nnnnnnnnnn nnnnn                                                   135

SEQ ID NO: 65           moltype = RNA   length = 135
FEATURE                 Location/Qualifiers
misc_feature            1..135
                        note = source = /note="Description of Artificial Sequence:
                          Syntheticpolynucleotide"
source                  1..135
                        mol_type = other RNA
                        organism = synthetic construct
SEQUENCE: 65
cgacggttag aggccgtatg tcgatttgct ttaatttcgt gcgtgtgcat tgtcgtcctc    60
cattacaggg cggctaccac gaatagtcac gaagtaaaag cttcgaggtt agcacnnnnn   120
nnnnnnnnnn nnnnn                                                   135

SEQ ID NO: 66           moltype = RNA   length = 144
FEATURE                 Location/Qualifiers
misc_feature            1..144
                        note = source = /note="Description of Artificial Sequence:
                          Syntheticpolynucleotide"
source                  1..144
                        mol_type = other RNA
                        organism = synthetic construct
SEQUENCE: 66
cgacggttag aggccgtatg tcgatttgct ttaatttcgt gcgtgtgcat tgtcgtcctc    60
cattacaggg cggctaccac gaatagccac gaagttccaa aatggaaagc ttcgtggcta   120
gcacnnnnnn nnnnnnnnnn nnnn                                         144

SEQ ID NO: 67           moltype = DNA   length = 30
FEATURE                 Location/Qualifiers
misc_feature            1..30
                        note = source = /note="Description of Artificial Sequence:
                          Syntheticoligonucleotide"
source                  1..30
                        mol_type = other DNA
                        organism = synthetic construct
SEQUENCE: 67
gtacgagata taggaagctg ctgtccgctc                                    30

SEQ ID NO: 68           moltype = DNA   length = 29
FEATURE                 Location/Qualifiers
misc_feature            1..29
                        note = source = /note="Description of Artificial Sequence:
                          Syntheticoligonucleotide"
source                  1..29
                        mol_type = other DNA
                        organism = synthetic construct
SEQUENCE: 68
actacaacag ccacaacgtc tatatcatg                                     29

SEQ ID NO: 69           moltype = RNA   length = 149
FEATURE                 Location/Qualifiers
misc_feature            1..149
                        note = source = /note="Description of Artificial Sequence:
                          Syntheticpolynucleotide"
source                  1..149
                        mol_type = other RNA
                        organism = synthetic construct
SEQUENCE: 69
cgacggttag aggccgtatg tcgatttgct ttaatttcgt gcgtgtgcat tgtcgtcctc    60
cattacaggg cggctaccac gaatagtcac gaagttccac tgagtaaagt ggaaagcttc   120
gaggttagca cactacaaca gccacaacg                                    149

SEQ ID NO: 70           moltype = RNA   length = 151
FEATURE                 Location/Qualifiers
misc_feature            1..151
                        note = source = /note="Description of Artificial Sequence:
                          Syntheticpolynucleotide"
source                  1..151
                        mol_type = other RNA
                        organism = synthetic construct
SEQUENCE: 70
cgacggttag aggccgtatg tcgatttgct ttaatttcgt gcgtgtgcat tgtcgtcctc    60
cattacaggg cggctaccac gaatagtcac gaagttccac tgagtaaagt ggaaagcttc   120
gaggttagca cgtacgagat ataggaagct g                                 151

SEQ ID NO: 71           moltype = RNA   length = 151
```

```
FEATURE                   Location/Qualifiers
misc_feature              1..151
                          note = source = /note="Description of Artificial Sequence:
                              Syntheticpolynucleotide"
source                    1..151
                          mol_type = other RNA
                          organism = synthetic construct
SEQUENCE: 71
cgacggttag aggccgtatg tcgatttgct ttaatttcgt gcgtgtgcat tgtcgtcctc    60
cattacaggg cggctaccac gaatagtcac gaagttccac tgagtaaagt ggaaagcttc   120
gaggttagca cactacaaca gccacaacgt c                                  151

SEQ ID NO: 72             moltype = RNA   length = 156
FEATURE                   Location/Qualifiers
misc_feature              1..156
                          note = source = /note="Description of Artificial Sequence:
                              Syntheticpolynucleotide"
source                    1..156
                          mol_type = other RNA
                          organism = synthetic construct
SEQUENCE: 72
cgacggttag aggccgtatg tcgatttgct ttaatttcgt gcgtgtgcat tgtcgtcctc    60
cattacaggg cggctaccac gaatagtcac gaagttccac tgagtaaagt ggaaagcttc   120
gaggttagca cgtacgagat ataggaagct gctgtc                             156

SEQ ID NO: 73             moltype = RNA   length = 156
FEATURE                   Location/Qualifiers
misc_feature              1..156
                          note = source = /note="Description of Artificial Sequence:
                              Syntheticpolynucleotide"
source                    1..156
                          mol_type = other RNA
                          organism = synthetic construct
SEQUENCE: 73
cgacggttag aggccgtatg tcgatttgct ttaatttcgt gcgtgtgcat tgtcgtcctc    60
cattacaggg cggctaccac gaatagtcac gaagttccac tgagtaaagt ggaaagcttc   120
gaggttagca cactacaaca gccacaacgt ctatat                             156

SEQ ID NO: 74             moltype = RNA   length = 140
FEATURE                   Location/Qualifiers
misc_feature              1..140
                          note = source = /note="Description of Artificial Sequence:
                              Syntheticpolynucleotide"
source                    1..140
                          mol_type = other RNA
                          organism = synthetic construct
SEQUENCE: 74
cgacggttag aggccgtatg tcgatttgct ttaatttcgt gcgtgtgcat tgtcgtcctc    60
cattacaggg cggctaccac gaatagtcac gaagtaaaag cttcgaggtt agcacactac   120
aacagccaca acgtctatat                                               140

SEQ ID NO: 75             moltype = RNA   length = 149
FEATURE                   Location/Qualifiers
misc_feature              1..149
                          note = source = /note="Description of Artificial Sequence:
                              Syntheticpolynucleotide"
source                    1..149
                          mol_type = other RNA
                          organism = synthetic construct
SEQUENCE: 75
cgacggttag aggccgtatg tcgatttgct ttaatttcgt gcgtgtgcat tgtcgtcctc    60
cattacaggg cggctaccac gaatagccac gaagttccaa aatggaaagc ttcgtggcta   120
gcacactaca acagccacaa cgtctatat                                     149

SEQ ID NO: 76             moltype = RNA   length = 140
FEATURE                   Location/Qualifiers
misc_feature              1..140
                          note = source = /note="Description of Artificial Sequence:
                              Syntheticpolynucleotide"
source                    1..140
                          mol_type = other RNA
                          organism = synthetic construct
SEQUENCE: 76
cgacggttag aggccgtatg tcgatttgct ttaatttcgt gcgtgtgcat tgtcgtcctc    60
cattacaggg cggctaccac gaatagccac gaagtaaaag cttcgtggct agcacactac   120
aacagccaca acgtctatat                                               140

SEQ ID NO: 77             moltype = RNA   length = 135
FEATURE                   Location/Qualifiers
```

```
misc_feature         1..135
                     note = source = /note="Description of Artificial Sequence:
                         Syntheticpolynucleotide"
source               1..135
                     mol_type = other RNA
                     organism = synthetic construct
SEQUENCE: 77
cgacggttag aggccgtatg tcgatttgct ttaatttcgt gcgtgtgcat tgtcgtcctc    60
cattacaggg cggctaccac gaatagccac gaagtaaaag cttcgtggct agcacactac   120
aacagccaca acgtc                                                   135

SEQ ID NO: 78        moltype = RNA   length = 140
FEATURE              Location/Qualifiers
misc_feature         1..140
                     note = source = /note="Description of Artificial Sequence:
                         Syntheticpolynucleotide"
source               1..140
                     mol_type = other RNA
                     organism = synthetic construct
SEQUENCE: 78
cgacggttag aggccgtatg tcgatttgct ttaatttcgt gcgtgtgcat tgtcgtcctc    60
cattacaggg cggctaccac gaatagccac gaagtaaaag cttcgtggct agcacgtacg   120
agatatagga agctgctgtc                                               140

SEQ ID NO: 79        moltype = RNA   length = 111
FEATURE              Location/Qualifiers
misc_feature         1..111
                     note = source = /note="Description of Artificial Sequence:
                         Syntheticpolynucleotide"
source               1..111
                     mol_type = other RNA
                     organism = synthetic construct
SEQUENCE: 79
gacctatagg gtcaatgaat ctgtgcgtgt gccataagta attaaaaatt acccaccaca    60
ggagcacctg aaaacaggtg cttggcacgg ctcagcaggc acctgcctca g            111

SEQ ID NO: 80        moltype = RNA   length = 111
FEATURE              Location/Qualifiers
misc_feature         1..111
                     note = source = /note="Description of Artificial Sequence:
                         Syntheticpolynucleotide"
source               1..111
                     mol_type = other RNA
                     organism = synthetic construct
SEQUENCE: 80
gacctatagg gtcaatgaat ctgtgcgtgt gccataagta attaaaaatt acccaccaca    60
ggagcacctg aaaacaggtg cttggcactt ctccctggg aagcatccct g             111

SEQ ID NO: 81        moltype = RNA   length = 111
FEATURE              Location/Qualifiers
misc_feature         1..111
                     note = source = /note="Description of Artificial Sequence:
                         Syntheticpolynucleotide"
source               1..111
                     mol_type = other RNA
                     organism = synthetic construct
SEQUENCE: 81
gacctatagg gtcaatgaat ctgtgcgtgt gccataagta attaaaaatt acccaccaca    60
ggagcacctg aaaacaggtg cttggcactt catggagaaa atattcagaa t             111

SEQ ID NO: 82        moltype = RNA   length = 113
FEATURE              Location/Qualifiers
misc_feature         1..113
                     note = source = /note="Description of Artificial Sequence:
                         Syntheticpolynucleotide"
source               1..113
                     mol_type = other RNA
                     organism = synthetic construct
SEQUENCE: 82
gacctatagg gtcaatgaat ctgtgcgtgt gccataagta attaaaaatt acccaccaca    60
ggagcacctg aaaacaggtg cttggcactg tttggagtta cttagggcca tgc          113

SEQ ID NO: 83        moltype = RNA   length = 113
FEATURE              Location/Qualifiers
misc_feature         1..113
                     note = source = /note="Description of Artificial Sequence:
                         Syntheticpolynucleotide"
source               1..113
                     mol_type = other RNA
```

```
                        organism = synthetic construct
SEQUENCE: 83
gacctatagg gtcaatgaat ctgtgcgtgt gccataagta attaaaaatt acccaccaca    60
ggagcacctg aaaacaggtg cttggcacga gatgtcccca gtgaactcca aat          113

SEQ ID NO: 84           moltype = RNA   length = 113
FEATURE                 Location/Qualifiers
misc_feature            1..113
                        note = source = /note="Description of Artificial Sequence:
                        Syntheticpolynucleotide"
source                  1..113
                        mol_type = other RNA
                        organism = synthetic construct
SEQUENCE: 84
gacctatagg gtcaatgaat ctgtgcgtgt gccataagta attaaaaatt acccaccaca    60
ggagcacctg aaaacaggtg cttggcaccc tgtcgttgcc cctcccagat cat          113

SEQ ID NO: 85           moltype = RNA   length = 113
FEATURE                 Location/Qualifiers
misc_feature            1..113
                        note = source = /note="Description of Artificial Sequence:
                        Syntheticpolynucleotide"
source                  1..113
                        mol_type = other RNA
                        organism = synthetic construct
SEQUENCE: 85
gacctatagg gtcaatgaat ctgtgcgtgt gccataagta attaaaaatt acccaccaca    60
ggagcacctg aaaacaggtg cttggcacgg aggctgagac aggagagttg ctt          113

SEQ ID NO: 86           moltype = RNA   length = 113
FEATURE                 Location/Qualifiers
misc_feature            1..113
                        note = source = /note="Description of Artificial Sequence:
                        Syntheticpolynucleotide"
source                  1..113
                        mol_type = other RNA
                        organism = synthetic construct
SEQUENCE: 86
gacctatagg gtcaatgaat ctgtgcgtgt gccataagta attaaaaatt acccaccaca    60
ggagcacctg aaaacaggtg cttggcacat agccccccctt gagcacacag agg          113

SEQ ID NO: 87           moltype = RNA   length = 113
FEATURE                 Location/Qualifiers
misc_feature            1..113
                        note = source = /note="Description of Artificial Sequence:
                        Syntheticpolynucleotide"
source                  1..113
                        mol_type = other RNA
                        organism = synthetic construct
SEQUENCE: 87
gacctatagg gtcaatgaat ctgtgcgtgt gccataagta attaaaaatt acccaccaca    60
ggagcacctg aaaacaggtg cttggcacgt tcacacgtgt aatcccagca ctt          113

SEQ ID NO: 88           moltype = RNA   length = 113
FEATURE                 Location/Qualifiers
misc_feature            1..113
                        note = source = /note="Description of Artificial Sequence:
                        Syntheticpolynucleotide"
source                  1..113
                        mol_type = other RNA
                        organism = synthetic construct
SEQUENCE: 88
gacctatagg gtcaatgaat ctgtgcgtgt gccataagta attaaaaatt acccaccaca    60
ggagcacctg aaaacaggtg cttggcactt gttggtctgg atgcgctgac tga          113

SEQ ID NO: 89           moltype = RNA   length = 113
FEATURE                 Location/Qualifiers
misc_feature            1..113
                        note = source = /note="Description of Artificial Sequence:
                        Syntheticpolynucleotide"
source                  1..113
                        mol_type = other RNA
                        organism = synthetic construct
SEQUENCE: 89
gacctatagg gtcaatgaat ctgtgcgtgt gccataagta attaaaaatt acccaccaca    60
ggagcacctg aaaacaggtg cttggcacga tgtctgggcc tctgtacttt gga          113

SEQ ID NO: 90           moltype = RNA   length = 113
FEATURE                 Location/Qualifiers
```

```
misc_feature         1..113
                     note = source = /note="Description of Artificial Sequence:
                     Syntheticpolynucleotide"
source               1..113
                     mol_type = other RNA
                     organism = synthetic construct
SEQUENCE: 90
gacctatagg gtcaatgaat ctgtgcgtgt gccataagta attaaaaatt acccaccaca    60
ggagcacctg aaaacaggtg cttggcacgg tgtgtgctga ccctgatctc cct          113

SEQ ID NO: 91        moltype = DNA   length = 25
FEATURE              Location/Qualifiers
source               1..25
                     mol_type = genomic DNA
                     organism = Homo sapiens
SEQUENCE: 91
acctctccag ggcgaactct gacac                                          25

SEQ ID NO: 92        moltype = DNA   length = 25
FEATURE              Location/Qualifiers
source               1..25
                     mol_type = genomic DNA
                     organism = Homo sapiens
SEQUENCE: 92
tgtgtcagag ttcgccctgg agagg                                          25

SEQ ID NO: 93        moltype = DNA   length = 25
FEATURE              Location/Qualifiers
source               1..25
                     mol_type = genomic DNA
                     organism = Homo sapiens
SEQUENCE: 93
gggaagtagg actgttggaa acggg                                          25

SEQ ID NO: 94        moltype = DNA   length = 25
FEATURE              Location/Qualifiers
source               1..25
                     mol_type = genomic DNA
                     organism = Homo sapiens
SEQUENCE: 94
ccaacagtcc tacttccctg tttca                                          25

SEQ ID NO: 95        moltype = DNA   length = 25
FEATURE              Location/Qualifiers
source               1..25
                     mol_type = genomic DNA
                     organism = Homo sapiens
SEQUENCE: 95
tctttggaca gtgtccatac tggtg                                          25

SEQ ID NO: 96        moltype = DNA   length = 25
FEATURE              Location/Qualifiers
source               1..25
                     mol_type = genomic DNA
                     organism = Homo sapiens
SEQUENCE: 96
cgaggtgtgc tcaccagaat ggagt                                          25

SEQ ID NO: 97        moltype = DNA   length = 25
FEATURE              Location/Qualifiers
source               1..25
                     mol_type = genomic DNA
                     organism = Homo sapiens
SEQUENCE: 97
tggtgagcac acctcgggac tgggc                                          25

SEQ ID NO: 98        moltype = DNA   length = 25
FEATURE              Location/Qualifiers
source               1..25
                     mol_type = genomic DNA
                     organism = Homo sapiens
SEQUENCE: 98
tgaaagagtg atgcctccag gttgt                                          25

SEQ ID NO: 99        moltype = DNA   length = 25
FEATURE              Location/Qualifiers
source               1..25
                     mol_type = genomic DNA
                     organism = Homo sapiens
```

```
SEQUENCE: 99
acccccgaat cgtgagtact gtcct                                              25

SEQ ID NO: 100          moltype = DNA   length = 25
FEATURE                 Location/Qualifiers
source                  1..25
                        mol_type = genomic DNA
                        organism = Homo sapiens
SEQUENCE: 100
tgagaagggc caaggtattg tggca                                              25

SEQ ID NO: 101          moltype = DNA   length = 25
FEATURE                 Location/Qualifiers
source                  1..25
                        mol_type = genomic DNA
                        organism = Homo sapiens
SEQUENCE: 101
ctgccacaat accttggccc ttctc                                              25

SEQ ID NO: 102          moltype = DNA   length = 25
FEATURE                 Location/Qualifiers
source                  1..25
                        mol_type = genomic DNA
                        organism = Homo sapiens
SEQUENCE: 102
tctcagttcg ctgcgaccca tacac                                              25

SEQ ID NO: 103          moltype = DNA   length = 25
FEATURE                 Location/Qualifiers
source                  1..25
                        mol_type = genomic DNA
                        organism = Homo sapiens
SEQUENCE: 103
ggtgtatggg tcgcagcgaa ctgag                                              25

SEQ ID NO: 104          moltype = DNA   length = 25
FEATURE                 Location/Qualifiers
source                  1..25
                        mol_type = genomic DNA
                        organism = Homo sapiens
SEQUENCE: 104
gctgcgaccc atacacccaa aggat                                              25

SEQ ID NO: 105          moltype = DNA   length = 25
FEATURE                 Location/Qualifiers
source                  1..25
                        mol_type = genomic DNA
                        organism = Homo sapiens
SEQUENCE: 105
ctctgcagat cactggggtg gatcc                                              25

SEQ ID NO: 106          moltype = DNA   length = 25
FEATURE                 Location/Qualifiers
source                  1..25
                        mol_type = genomic DNA
                        organism = Homo sapiens
SEQUENCE: 106
gccgcgccct ctgcagatca ctggg                                              25

SEQ ID NO: 107          moltype = DNA   length = 25
FEATURE                 Location/Qualifiers
source                  1..25
                        mol_type = genomic DNA
                        organism = Homo sapiens
SEQUENCE: 107
gctcctcacg cacctgctct ggttt                                              25

SEQ ID NO: 108          moltype = DNA   length = 25
FEATURE                 Location/Qualifiers
source                  1..25
                        mol_type = genomic DNA
                        organism = Homo sapiens
SEQUENCE: 108
ataaggctgt gctgaccatc gacaa                                              25

SEQ ID NO: 109          moltype = DNA   length = 25
FEATURE                 Location/Qualifiers
source                  1..25
                        mol_type = genomic DNA
```

```
                                organism = Homo sapiens
SEQUENCE: 109
aaggctgtgc tgaccatcga caaga                                              25

SEQ ID NO: 110          moltype = DNA  length = 25
FEATURE                 Location/Qualifiers
source                  1..25
                        mol_type = genomic DNA
                        organism = Homo sapiens
SEQUENCE: 110
ttgtcgatgg tcagcacagc cttat                                              25

SEQ ID NO: 111          moltype = DNA  length = 25
FEATURE                 Location/Qualifiers
source                  1..25
                        mol_type = genomic DNA
                        organism = Homo sapiens
SEQUENCE: 111
acctgccccg gtggctctgc tacac                                              25

SEQ ID NO: 112          moltype = DNA  length = 25
FEATURE                 Location/Qualifiers
source                  1..25
                        mol_type = genomic DNA
                        organism = Homo sapiens
SEQUENCE: 112
ggctgcgctg ggtgtagcag agcca                                              25

SEQ ID NO: 113          moltype = DNA  length = 25
FEATURE                 Location/Qualifiers
source                  1..25
                        mol_type = genomic DNA
                        organism = Homo sapiens
SEQUENCE: 113
tgccaatcgc gagcagcatc cagct                                              25

SEQ ID NO: 114          moltype = DNA  length = 25
FEATURE                 Location/Qualifiers
source                  1..25
                        mol_type = genomic DNA
                        organism = Homo sapiens
SEQUENCE: 114
atgccggggg caccgatgct ggttt                                              25

SEQ ID NO: 115          moltype = DNA  length = 25
FEATURE                 Location/Qualifiers
source                  1..25
                        mol_type = genomic DNA
                        organism = Homo sapiens
SEQUENCE: 115
ggtggctgag tggatggaga tgccg                                              25

SEQ ID NO: 116          moltype = DNA  length = 25
FEATURE                 Location/Qualifiers
source                  1..25
                        mol_type = genomic DNA
                        organism = Homo sapiens
SEQUENCE: 116
ctccctctcc cagttaccat gaagt                                              25

SEQ ID NO: 117          moltype = DNA  length = 25
FEATURE                 Location/Qualifiers
source                  1..25
                        mol_type = genomic DNA
                        organism = Homo sapiens
SEQUENCE: 117
tgacttcatg gtaactggga gaggg                                              25

SEQ ID NO: 118          moltype = DNA  length = 25
FEATURE                 Location/Qualifiers
source                  1..25
                        mol_type = genomic DNA
                        organism = Homo sapiens
SEQUENCE: 118
aagaagtgca agacccggga gacgg                                              25

SEQ ID NO: 119          moltype = DNA  length = 25
FEATURE                 Location/Qualifiers
source                  1..25
```

```
                            mol_type = genomic DNA
                            organism = Homo sapiens
SEQUENCE: 119
ctcccgggtc ttgcacttct tgatg                                         25

SEQ ID NO: 120              moltype = DNA  length = 25
FEATURE                     Location/Qualifiers
source                      1..25
                            mol_type = genomic DNA
                            organism = Homo sapiens
SEQUENCE: 120
tgctgccagc acggttctgg actac                                         25

SEQ ID NO: 121              moltype = DNA  length = 25
FEATURE                     Location/Qualifiers
source                      1..25
                            mol_type = genomic DNA
                            organism = Homo sapiens
SEQUENCE: 121
gcacggttct ggactacaca acacg                                         25

SEQ ID NO: 122              moltype = DNA  length = 25
FEATURE                     Location/Qualifiers
source                      1..25
                            mol_type = genomic DNA
                            organism = Homo sapiens
SEQUENCE: 122
tgtagtccag aaccgtgctg gcagc                                         25

SEQ ID NO: 123              moltype = DNA  length = 25
FEATURE                     Location/Qualifiers
source                      1..25
                            mol_type = genomic DNA
                            organism = Homo sapiens
SEQUENCE: 123
acggttctgg actacacaac acgca                                         25

SEQ ID NO: 124              moltype = DNA  length = 25
FEATURE                     Location/Qualifiers
source                      1..25
                            mol_type = genomic DNA
                            organism = Homo sapiens
SEQUENCE: 124
cagtcacgga gcggttggcc ttcac                                         25

SEQ ID NO: 125              moltype = DNA  length = 25
FEATURE                     Location/Qualifiers
source                      1..25
                            mol_type = genomic DNA
                            organism = Homo sapiens
SEQUENCE: 125
gggcatcttc gtggactaca gagct                                         25

SEQ ID NO: 126              moltype = DNA  length = 25
FEATURE                     Location/Qualifiers
source                      1..25
                            mol_type = genomic DNA
                            organism = Homo sapiens
SEQUENCE: 126
gatccaccat gatggccctt ggctt                                         25

SEQ ID NO: 127              moltype = DNA  length = 25
FEATURE                     Location/Qualifiers
source                      1..25
                            mol_type = genomic DNA
                            organism = Homo sapiens
SEQUENCE: 127
aggatccacc atgatggccc ttggc                                         25

SEQ ID NO: 128              moltype = DNA  length = 25
FEATURE                     Location/Qualifiers
source                      1..25
                            mol_type = genomic DNA
                            organism = Homo sapiens
SEQUENCE: 128
ccggccacga gaatagcagc ccagg                                         25

SEQ ID NO: 129              moltype = DNA  length = 25
FEATURE                     Location/Qualifiers
```

```
source                   1..25
                         mol_type = genomic DNA
                         organism = Homo sapiens
SEQUENCE: 129
cctgccagca gatctgagag ggagg                                              25

SEQ ID NO: 130           moltype = DNA  length = 25
FEATURE                  Location/Qualifiers
source                   1..25
                         mol_type = genomic DNA
                         organism = Homo sapiens
SEQUENCE: 130
gatctgagag ggagggcagc caggc                                              25

SEQ ID NO: 131           moltype = DNA  length = 25
FEATURE                  Location/Qualifiers
source                   1..25
                         mol_type = genomic DNA
                         organism = Homo sapiens
SEQUENCE: 131
gaggctcgcc acaaggagct ggagg                                              25

SEQ ID NO: 132           moltype = DNA  length = 25
FEATURE                  Location/Qualifiers
source                   1..25
                         mol_type = genomic DNA
                         organism = Homo sapiens
SEQUENCE: 132
gctagagaag tccgaggctc gccac                                              25

SEQ ID NO: 133           moltype = DNA  length = 25
FEATURE                  Location/Qualifiers
source                   1..25
                         mol_type = genomic DNA
                         organism = Homo sapiens
SEQUENCE: 133
actgctccta gtgtctgtca ggacc                                              25

SEQ ID NO: 134           moltype = DNA  length = 25
FEATURE                  Location/Qualifiers
source                   1..25
                         mol_type = genomic DNA
                         organism = Homo sapiens
SEQUENCE: 134
ctcctagtgt ctgtcaggac ctgaa                                              25

SEQ ID NO: 135           moltype = DNA  length = 25
FEATURE                  Location/Qualifiers
source                   1..25
                         mol_type = genomic DNA
                         organism = Homo sapiens
SEQUENCE: 135
cacttcaggt cctgacagac actag                                              25

SEQ ID NO: 136           moltype = DNA  length = 25
FEATURE                  Location/Qualifiers
source                   1..25
                         mol_type = genomic DNA
                         organism = Homo sapiens
SEQUENCE: 136
cccttgagga cctgtgaaat ccaga                                              25

SEQ ID NO: 137           moltype = DNA  length = 25
FEATURE                  Location/Qualifiers
source                   1..25
                         mol_type = genomic DNA
                         organism = Homo sapiens
SEQUENCE: 137
cacaggtcct caagggcaga agagt                                              25

SEQ ID NO: 138           moltype = DNA  length = 25
FEATURE                  Location/Qualifiers
source                   1..25
                         mol_type = genomic DNA
                         organism = Homo sapiens
SEQUENCE: 138
gacctgagag tgggtgttgg acagt                                              25

SEQ ID NO: 139           moltype = DNA  length = 25
```

```
FEATURE                 Location/Qualifiers
source                  1..25
                        mol_type = genomic DNA
                        organism = Homo sapiens
SEQUENCE: 139
tccaacaccc actctcaggt cacca                                              25

SEQ ID NO: 140          moltype = DNA   length = 25
FEATURE                 Location/Qualifiers
source                  1..25
                        mol_type = genomic DNA
                        organism = Homo sapiens
SEQUENCE: 140
cagccatggg agcccttca cttca                                               25

SEQ ID NO: 141          moltype = DNA   length = 25
FEATURE                 Location/Qualifiers
source                  1..25
                        mol_type = genomic DNA
                        organism = Homo sapiens
SEQUENCE: 141
gctgagtttg tgtgtgaatg gacac                                              25

SEQ ID NO: 142          moltype = DNA   length = 25
FEATURE                 Location/Qualifiers
source                  1..25
                        mol_type = genomic DNA
                        organism = Homo sapiens
SEQUENCE: 142
tgatcaaacg ccccggcagg aagtg                                              25

SEQ ID NO: 143          moltype = DNA   length = 25
FEATURE                 Location/Qualifiers
source                  1..25
                        mol_type = genomic DNA
                        organism = Homo sapiens
SEQUENCE: 143
gtcggcctca gcttttcact tcctg                                              25

SEQ ID NO: 144          moltype = DNA   length = 25
FEATURE                 Location/Qualifiers
source                  1..25
                        mol_type = genomic DNA
                        organism = Homo sapiens
SEQUENCE: 144
aggccattcc caagaaacgg ggctg                                              25

SEQ ID NO: 145          moltype = DNA   length = 25
FEATURE                 Location/Qualifiers
source                  1..25
                        mol_type = genomic DNA
                        organism = Homo sapiens
SEQUENCE: 145
cagccccgtt tcttgggaat ggcct                                              25

SEQ ID NO: 146          moltype = DNA   length = 25
FEATURE                 Location/Qualifiers
source                  1..25
                        mol_type = genomic DNA
                        organism = Homo sapiens
SEQUENCE: 146
ccaagaaacg gggctgaaag ccggg                                              25

SEQ ID NO: 147          moltype = DNA   length = 25
FEATURE                 Location/Qualifiers
source                  1..25
                        mol_type = genomic DNA
                        organism = Homo sapiens
SEQUENCE: 147
cccaggagga ggtccagctg gagat                                              25

SEQ ID NO: 148          moltype = DNA   length = 25
FEATURE                 Location/Qualifiers
source                  1..25
                        mol_type = genomic DNA
                        organism = Homo sapiens
SEQUENCE: 148
cttccatctc cagctggacc tcctc                                              25
```

```
SEQ ID NO: 149         moltype = DNA   length = 25
FEATURE                Location/Qualifiers
source                 1..25
                       mol_type = genomic DNA
                       organism = Homo sapiens
SEQUENCE: 149
gctactgggt ggtgataatg gtgaa                                              25

SEQ ID NO: 150         moltype = DNA   length = 25
FEATURE                Location/Qualifiers
source                 1..25
                       mol_type = genomic DNA
                       organism = Homo sapiens
SEQUENCE: 150
tccttcacca ttatcaccac ccagt                                              25

SEQ ID NO: 151         moltype = DNA   length = 25
FEATURE                Location/Qualifiers
source                 1..25
                       mol_type = genomic DNA
                       organism = Homo sapiens
SEQUENCE: 151
ggctactggg tggtgataat ggtga                                              25

SEQ ID NO: 152         moltype = DNA   length = 25
FEATURE                Location/Qualifiers
source                 1..25
                       mol_type = genomic DNA
                       organism = Homo sapiens
SEQUENCE: 152
tcacggtttg ggggtataca tgggc                                              25

SEQ ID NO: 153         moltype = DNA   length = 25
FEATURE                Location/Qualifiers
source                 1..25
                       mol_type = genomic DNA
                       organism = Homo sapiens
SEQUENCE: 153
gcttagggtt accgaagagg ggcca                                              25

SEQ ID NO: 154         moltype = DNA   length = 25
FEATURE                Location/Qualifiers
source                 1..25
                       mol_type = genomic DNA
                       organism = Homo sapiens
SEQUENCE: 154
cacatttggc ttagggttac cgaag                                              25

SEQ ID NO: 155         moltype = DNA   length = 25
FEATURE                Location/Qualifiers
source                 1..25
                       mol_type = genomic DNA
                       organism = Homo sapiens
SEQUENCE: 155
ggcttagggt taccgaagag gggcc                                              25

SEQ ID NO: 156         moltype = DNA   length = 25
FEATURE                Location/Qualifiers
source                 1..25
                       mol_type = genomic DNA
                       organism = Homo sapiens
SEQUENCE: 156
gctcagggtt actgaagagg ggcca                                              25

SEQ ID NO: 157         moltype = DNA   length = 25
FEATURE                Location/Qualifiers
source                 1..25
                       mol_type = genomic DNA
                       organism = Homo sapiens
SEQUENCE: 157
cacatttggc tcagggttac tgaag                                              25

SEQ ID NO: 158         moltype = DNA   length = 25
FEATURE                Location/Qualifiers
source                 1..25
                       mol_type = genomic DNA
                       organism = Homo sapiens
SEQUENCE: 158
ggctcagggt tactgaagag gggcc                                              25
```

```
SEQ ID NO: 159              moltype = DNA   length = 20
FEATURE                     Location/Qualifiers
source                      1..20
                            mol_type = genomic DNA
                            organism = Homo sapiens
SEQUENCE: 159
cctaaaggaa atgactgcag                                                     20

SEQ ID NO: 160              moltype = DNA   length = 25
FEATURE                     Location/Qualifiers
source                      1..25
                            mol_type = genomic DNA
                            organism = Homo sapiens
SEQUENCE: 160
aggaccatca cccctagac tatag                                                25

SEQ ID NO: 161              moltype = DNA   length = 25
FEATURE                     Location/Qualifiers
source                      1..25
                            mol_type = genomic DNA
                            organism = Homo sapiens
SEQUENCE: 161
catcaccccc tagactatag ttagc                                               25

SEQ ID NO: 162              moltype = DNA   length = 20
FEATURE                     Location/Qualifiers
source                      1..20
                            mol_type = genomic DNA
                            organism = Homo sapiens
SEQUENCE: 162
acttcgtcta ttcccagatc                                                     20

SEQ ID NO: 163              moltype = DNA   length = 25
FEATURE                     Location/Qualifiers
source                      1..25
                            mol_type = genomic DNA
                            organism = Homo sapiens
SEQUENCE: 163
ctagtagggg ctggtgacag tcaat                                               25

SEQ ID NO: 164              moltype = DNA   length = 25
FEATURE                     Location/Qualifiers
source                      1..25
                            mol_type = genomic DNA
                            organism = Homo sapiens
SEQUENCE: 164
attgtggact gcatcttagc cctag                                               25

SEQ ID NO: 165              moltype = DNA   length = 20
FEATURE                     Location/Qualifiers
source                      1..20
                            mol_type = genomic DNA
                            organism = Homo sapiens
SEQUENCE: 165
tggactgcat cttagcccta                                                     20

SEQ ID NO: 166              moltype = DNA   length = 25
FEATURE                     Location/Qualifiers
source                      1..25
                            mol_type = genomic DNA
                            organism = Homo sapiens
SEQUENCE: 166
acagcccagc ctacctaccc aaaat                                               25

SEQ ID NO: 167              moltype = DNA   length = 25
FEATURE                     Location/Qualifiers
source                      1..25
                            mol_type = genomic DNA
                            organism = Homo sapiens
SEQUENCE: 167
tgggtaggta ggctgggctg tgggt                                               25

SEQ ID NO: 168              moltype = DNA   length = 25
FEATURE                     Location/Qualifiers
source                      1..25
                            mol_type = genomic DNA
                            organism = Homo sapiens
SEQUENCE: 168
```

```
attttgggta ggtaggctgg gctgt                                              25

SEQ ID NO: 169         moltype = DNA   length = 25
FEATURE                Location/Qualifiers
source                 1..25
                       mol_type = genomic DNA
                       organism = Homo sapiens
SEQUENCE: 169
ttgctcattg acctccactc agtgt                                              25

SEQ ID NO: 170         moltype = DNA   length = 25
FEATURE                Location/Qualifiers
source                 1..25
                       mol_type = genomic DNA
                       organism = Homo sapiens
SEQUENCE: 170
ccgtccattt aactggaatc cgacc                                              25

SEQ ID NO: 171         moltype = DNA   length = 25
FEATURE                Location/Qualifiers
source                 1..25
                       mol_type = genomic DNA
                       organism = Homo sapiens
SEQUENCE: 171
ttctaacccc cacccccact gccgg                                              25

SEQ ID NO: 172         moltype = DNA   length = 25
FEATURE                Location/Qualifiers
source                 1..25
                       mol_type = genomic DNA
                       organism = Homo sapiens
SEQUENCE: 172
cccccactgc cgggtaaggg tgtca                                              25

SEQ ID NO: 173         moltype = DNA   length = 25
FEATURE                Location/Qualifiers
source                 1..25
                       mol_type = genomic DNA
                       organism = Homo sapiens
SEQUENCE: 173
taaccccccac ccccactgcc gggta                                             25

SEQ ID NO: 174         moltype = DNA   length = 25
FEATURE                Location/Qualifiers
source                 1..25
                       mol_type = genomic DNA
                       organism = Homo sapiens
SEQUENCE: 174
ttgctcgttg atctccactc agtgt                                              25

SEQ ID NO: 175         moltype = DNA   length = 25
FEATURE                Location/Qualifiers
source                 1..25
                       mol_type = genomic DNA
                       organism = Homo sapiens
SEQUENCE: 175
gcagcatctt cttccgggtc atctt                                              25

SEQ ID NO: 176         moltype = DNA   length = 25
FEATURE                Location/Qualifiers
source                 1..25
                       mol_type = genomic DNA
                       organism = Homo sapiens
SEQUENCE: 176
ggacctacac aagcagcatc ttctt                                              25

SEQ ID NO: 177         moltype = DNA   length = 25
FEATURE                Location/Qualifiers
source                 1..25
                       mol_type = genomic DNA
                       organism = Homo sapiens
SEQUENCE: 177
tccaccacgg ctgtcgacac caatc                                              25

SEQ ID NO: 178         moltype = DNA   length = 25
FEATURE                Location/Qualifiers
source                 1..25
                       mol_type = genomic DNA
                       organism = Homo sapiens
```

```
SEQUENCE: 178
gctgtcgaca ccaatcccaa ggaat                                            25

SEQ ID NO: 179          moltype = DNA   length = 20
FEATURE                 Location/Qualifiers
source                  1..20
                        mol_type = genomic DNA
                        organism = Homo sapiens
SEQUENCE: 179
caccacggct gtcgacacca                                                  20

SEQ ID NO: 180          moltype = DNA   length = 25
FEATURE                 Location/Qualifiers
source                  1..25
                        mol_type = genomic DNA
                        organism = Homo sapiens
SEQUENCE: 180
accacggctg tcgacaccaa tccca                                            25

SEQ ID NO: 181          moltype = DNA   length = 25
FEATURE                 Location/Qualifiers
source                  1..25
                        mol_type = genomic DNA
                        organism = Homo sapiens
SEQUENCE: 181
actccaaagg ctttcctcca ctgtt                                            25

SEQ ID NO: 182          moltype = DNA   length = 20
FEATURE                 Location/Qualifiers
source                  1..20
                        mol_type = genomic DNA
                        organism = Homo sapiens
SEQUENCE: 182
caacagtgga ggaaagcctt                                                  20

SEQ ID NO: 183          moltype = DNA   length = 25
FEATURE                 Location/Qualifiers
source                  1..25
                        mol_type = genomic DNA
                        organism = Homo sapiens
SEQUENCE: 183
catcccgtac tcccacgacc agata                                            25

SEQ ID NO: 184          moltype = DNA   length = 25
FEATURE                 Location/Qualifiers
source                  1..25
                        mol_type = genomic DNA
                        organism = Homo sapiens
SEQUENCE: 184
ctatctggtc gtgggagtac gggat                                            25

SEQ ID NO: 185          moltype = DNA   length = 25
FEATURE                 Location/Qualifiers
source                  1..25
                        mol_type = genomic DNA
                        organism = Homo sapiens
SEQUENCE: 185
aagcagcagg aagcagaccc aggag                                            25

SEQ ID NO: 186          moltype = DNA   length = 25
FEATURE                 Location/Qualifiers
source                  1..25
                        mol_type = genomic DNA
                        organism = Homo sapiens
SEQUENCE: 186
tcaaataagc agcaggaagc agacc                                            25

SEQ ID NO: 187          moltype = DNA   length = 20
FEATURE                 Location/Qualifiers
source                  1..20
                        mol_type = genomic DNA
                        organism = Homo sapiens
SEQUENCE: 187
aaataagcag caggaagcag                                                  20

SEQ ID NO: 188          moltype = DNA   length = 25
FEATURE                 Location/Qualifiers
source                  1..25
                        mol_type = genomic DNA
```

```
                          organism = Homo sapiens
SEQUENCE: 188
cctgggtctg cttcctgctg cttat                                              25

SEQ ID NO: 189          moltype = DNA  length = 25
FEATURE                 Location/Qualifiers
source                  1..25
                        mol_type = genomic DNA
                        organism = Homo sapiens
SEQUENCE: 189
tgggccaaga ctccacctat atcga                                              25

SEQ ID NO: 190          moltype = DNA  length = 25
FEATURE                 Location/Qualifiers
source                  1..25
                        mol_type = genomic DNA
                        organism = Homo sapiens
SEQUENCE: 190
ggctttcctc gatataggtg gagtc                                              25

SEQ ID NO: 191          moltype = DNA  length = 20
FEATURE                 Location/Qualifiers
source                  1..20
                        mol_type = genomic DNA
                        organism = Homo sapiens
SEQUENCE: 191
ctcgatatag gtggagtctt                                                    20

SEQ ID NO: 192          moltype = DNA  length = 25
FEATURE                 Location/Qualifiers
source                  1..25
                        mol_type = genomic DNA
                        organism = Homo sapiens
SEQUENCE: 192
tattcaccgg cccgctgatg gtccc                                              25

SEQ ID NO: 193          moltype = DNA  length = 25
FEATURE                 Location/Qualifiers
source                  1..25
                        mol_type = genomic DNA
                        organism = Homo sapiens
SEQUENCE: 193
agccctcagt gcagccagat attca                                              25

SEQ ID NO: 194          moltype = DNA  length = 25
FEATURE                 Location/Qualifiers
source                  1..25
                        mol_type = genomic DNA
                        organism = Homo sapiens
SEQUENCE: 194
gatattcacc ggcccgctga tggtc                                              25

SEQ ID NO: 195          moltype = DNA  length = 25
FEATURE                 Location/Qualifiers
source                  1..25
                        mol_type = genomic DNA
                        organism = Homo sapiens
SEQUENCE: 195
cttcctcccg acgcagatga gcccg                                              25

SEQ ID NO: 196          moltype = DNA  length = 25
FEATURE                 Location/Qualifiers
source                  1..25
                        mol_type = genomic DNA
                        organism = Homo sapiens
SEQUENCE: 196
gccactggga gcgctggcgt ggaca                                              25

SEQ ID NO: 197          moltype = DNA  length = 25
FEATURE                 Location/Qualifiers
source                  1..25
                        mol_type = genomic DNA
                        organism = Homo sapiens
SEQUENCE: 197
tagacagagg acaatggctt ccatg                                              25

SEQ ID NO: 198          moltype = DNA  length = 25
FEATURE                 Location/Qualifiers
source                  1..25
```

```
                        mol_type = genomic DNA
                        organism = Homo sapiens
SEQUENCE: 198
gacagaggac aatggcttcc atggt                                              25

SEQ ID NO: 199          moltype = DNA   length = 25
FEATURE                 Location/Qualifiers
source                  1..25
                        mol_type = genomic DNA
                        organism = Homo sapiens
SEQUENCE: 199
tggttgtgca gccagatgcc tagac                                              25

SEQ ID NO: 200          moltype = DNA   length = 25
FEATURE                 Location/Qualifiers
source                  1..25
                        mol_type = genomic DNA
                        organism = Homo sapiens
SEQUENCE: 200
atagctgtgt ggtgcttctg tggtg                                              25

SEQ ID NO: 201          moltype = DNA   length = 25
FEATURE                 Location/Qualifiers
source                  1..25
                        mol_type = genomic DNA
                        organism = Homo sapiens
SEQUENCE: 201
tcttgctcac tttggacctt ggtgg                                              25

SEQ ID NO: 202          moltype = DNA   length = 25
FEATURE                 Location/Qualifiers
source                  1..25
                        mol_type = genomic DNA
                        organism = Homo sapiens
SEQUENCE: 202
cccgacttac agccagtaat gtcac                                              25

SEQ ID NO: 203          moltype = DNA   length = 25
FEATURE                 Location/Qualifiers
source                  1..25
                        mol_type = genomic DNA
                        organism = Homo sapiens
SEQUENCE: 203
ctggctgtaa gtcgggcttt cttca                                              25

SEQ ID NO: 204          moltype = DNA   length = 25
FEATURE                 Location/Qualifiers
source                  1..25
                        mol_type = genomic DNA
                        organism = Homo sapiens
SEQUENCE: 204
agcaacctcc agtggtgacc agaat                                              25

SEQ ID NO: 205          moltype = DNA   length = 25
FEATURE                 Location/Qualifiers
source                  1..25
                        mol_type = genomic DNA
                        organism = Homo sapiens
SEQUENCE: 205
ctgcaagcaa cctccagtgg tgacc                                              25

SEQ ID NO: 206          moltype = DNA   length = 25
FEATURE                 Location/Qualifiers
source                  1..25
                        mol_type = genomic DNA
                        organism = Homo sapiens
SEQUENCE: 206
tcagaaaaac tggctcgaga gctcc                                              25

SEQ ID NO: 207          moltype = DNA   length = 20
FEATURE                 Location/Qualifiers
source                  1..20
                        mol_type = genomic DNA
                        organism = Homo sapiens
SEQUENCE: 207
aggagctctc gagccagttt                                                    20

SEQ ID NO: 208          moltype = DNA   length = 25
FEATURE                 Location/Qualifiers
```

```
source                 1..25
                       mol_type = genomic DNA
                       organism = Homo sapiens
SEQUENCE: 208
attagtcaga ggaaggttga gccca                                  25

SEQ ID NO: 209         moltype = DNA   length = 25
FEATURE                Location/Qualifiers
source                 1..25
                       mol_type = genomic DNA
                       organism = Homo sapiens
SEQUENCE: 209
ctcaaccttc ctctgactaa tggtg                                  25

SEQ ID NO: 210         moltype = DNA   length = 20
FEATURE                Location/Qualifiers
source                 1..20
                       mol_type = genomic DNA
                       organism = Homo sapiens
SEQUENCE: 210
gtcagaggaa ggttgagccc                                        20

SEQ ID NO: 211         moltype = DNA   length = 25
FEATURE                Location/Qualifiers
source                 1..25
                       mol_type = genomic DNA
                       organism = Homo sapiens
SEQUENCE: 211
agtggctccg aaggcaccgt cttct                                  25

SEQ ID NO: 212         moltype = DNA   length = 25
FEATURE                Location/Qualifiers
source                 1..25
                       mol_type = genomic DNA
                       organism = Homo sapiens
SEQUENCE: 212
gggtctgttt gaacatggag aacac                                  25

SEQ ID NO: 213         moltype = DNA   length = 25
FEATURE                Location/Qualifiers
source                 1..25
                       mol_type = genomic DNA
                       organism = Homo sapiens
SEQUENCE: 213
gaaagatcta gctcaccgtc tctt                                   25

SEQ ID NO: 214         moltype = DNA   length = 25
FEATURE                Location/Qualifiers
source                 1..25
                       mol_type = genomic DNA
                       organism = Homo sapiens
SEQUENCE: 214
agtacaccac cgtcggccac atgga                                  25

SEQ ID NO: 215         moltype = DNA   length = 25
FEATURE                Location/Qualifiers
source                 1..25
                       mol_type = genomic DNA
                       organism = Homo sapiens
SEQUENCE: 215
cgctcagtac accaccgtcg gccac                                  25

SEQ ID NO: 216         moltype = DNA   length = 25
FEATURE                Location/Qualifiers
source                 1..25
                       mol_type = genomic DNA
                       organism = Homo sapiens
SEQUENCE: 216
tgcaagccca ccttggtcca tgtgg                                  25

SEQ ID NO: 217         moltype = DNA   length = 25
FEATURE                Location/Qualifiers
source                 1..25
                       mol_type = genomic DNA
                       organism = Homo sapiens
SEQUENCE: 217
ttcagccctg ggacacatga tggag                                  25

SEQ ID NO: 218         moltype = DNA   length = 25
```

| | | |
|---|---|---|
| FEATURE | Location/Qualifiers | |
| source | 1..25<br>mol_type = genomic DNA<br>organism = Homo sapiens | |
| SEQUENCE: 218<br>ttccctccat catgtgtccc agggc | | 25 |
| SEQ ID NO: 219<br>FEATURE<br>source | moltype = DNA   length = 25<br>Location/Qualifiers<br>1..25<br>mol_type = genomic DNA<br>organism = Homo sapiens | |
| SEQUENCE: 219<br>ttcagccctg ggacacatga tggag | | 25 |
| SEQ ID NO: 220<br>FEATURE<br>source | moltype = DNA   length = 25<br>Location/Qualifiers<br>1..25<br>mol_type = genomic DNA<br>organism = Homo sapiens | |
| SEQUENCE: 220<br>ggaagtggtt ggacaagtaa gcgcc | | 25 |
| SEQ ID NO: 221<br>FEATURE<br>source | moltype = DNA   length = 25<br>Location/Qualifiers<br>1..25<br>mol_type = genomic DNA<br>organism = Homo sapiens | |
| SEQUENCE: 221<br>ggcgcttact tgtccaacca cttcc | | 25 |
| SEQ ID NO: 222<br>FEATURE<br>source | moltype = DNA   length = 25<br>Location/Qualifiers<br>1..25<br>mol_type = genomic DNA<br>organism = Homo sapiens | |
| SEQUENCE: 222<br>caaactgaaa tctgtaagca ggcgg | | 25 |
| SEQ ID NO: 223<br>FEATURE<br>source | moltype = DNA   length = 25<br>Location/Qualifiers<br>1..25<br>mol_type = genomic DNA<br>organism = Homo sapiens | |
| SEQUENCE: 223<br>cccgcctgct tacagatttc agttt | | 25 |
| SEQ ID NO: 224<br>FEATURE<br>source | moltype = DNA   length = 25<br>Location/Qualifiers<br>1..25<br>mol_type = genomic DNA<br>organism = Homo sapiens | |
| SEQUENCE: 224<br>tggcaggcat cattggtcag atcca | | 25 |
| SEQ ID NO: 225<br>FEATURE<br>source | moltype = DNA   length = 25<br>Location/Qualifiers<br>1..25<br>mol_type = genomic DNA<br>organism = Homo sapiens | |
| SEQUENCE: 225<br>ccagcaccat cactcgccgg gctgt | | 25 |
| SEQ ID NO: 226<br>FEATURE<br>source | moltype = DNA   length = 25<br>Location/Qualifiers<br>1..25<br>mol_type = genomic DNA<br>organism = Homo sapiens | |
| SEQUENCE: 226<br>tgccagcacc atcactcgcc gggct | | 25 |
| SEQ ID NO: 227<br>FEATURE<br>source | moltype = DNA   length = 25<br>Location/Qualifiers<br>1..25<br>mol_type = genomic DNA<br>organism = Homo sapiens | |
| SEQUENCE: 227<br>atgccccga agccctctc caccg | | 25 |

```
SEQ ID NO: 228            moltype = DNA  length = 25
FEATURE                   Location/Qualifiers
source                    1..25
                          mol_type = genomic DNA
                          organism = Homo sapiens
SEQUENCE: 228
cgcaaaagct gtgatcttct ccttc                                          25

SEQ ID NO: 229            moltype = DNA  length = 25
FEATURE                   Location/Qualifiers
source                    1..25
                          mol_type = genomic DNA
                          organism = Homo sapiens
SEQUENCE: 229
aagcccctct ccaccgcaaa agctg                                          25

SEQ ID NO: 230            moltype = DNA  length = 25
FEATURE                   Location/Qualifiers
source                    1..25
                          mol_type = genomic DNA
                          organism = Homo sapiens
SEQUENCE: 230
aaaggaccgc aatgtggcca cccca                                          25

SEQ ID NO: 231            moltype = DNA  length = 25
FEATURE                   Location/Qualifiers
source                    1..25
                          mol_type = genomic DNA
                          organism = Homo sapiens
SEQUENCE: 231
caccccaaga gactactact ttgct                                          25

SEQ ID NO: 232            moltype = DNA  length = 25
FEATURE                   Location/Qualifiers
source                    1..25
                          mol_type = genomic DNA
                          organism = Homo sapiens
SEQUENCE: 232
tggggtggcc acattgcggt ccttt                                          25

SEQ ID NO: 233            moltype = DNA  length = 25
FEATURE                   Location/Qualifiers
source                    1..25
                          mol_type = genomic DNA
                          organism = Homo sapiens
SEQUENCE: 233
gtaatggtgt ggctgtactc tccaa                                          25

SEQ ID NO: 234            moltype = DNA  length = 20
FEATURE                   Location/Qualifiers
source                    1..20
                          mol_type = genomic DNA
                          organism = Homo sapiens
SEQUENCE: 234
gagagtacag ccacaccatt                                                20

SEQ ID NO: 235            moltype = DNA  length = 25
FEATURE                   Location/Qualifiers
source                    1..25
                          mol_type = genomic DNA
                          organism = Homo sapiens
SEQUENCE: 235
tatcacttac ggatcacaga ggggg                                          25

SEQ ID NO: 236            moltype = DNA  length = 25
FEATURE                   Location/Qualifiers
source                    1..25
                          mol_type = genomic DNA
                          organism = Homo sapiens
SEQUENCE: 236
gtgacagagc tggtttcaaa gttgc                                          25

SEQ ID NO: 237            moltype = DNA  length = 25
FEATURE                   Location/Qualifiers
source                    1..25
                          mol_type = genomic DNA
                          organism = Homo sapiens
SEQUENCE: 237
gcgaagatgg cttggatgag tggcc                                          25
```

```
SEQ ID NO: 238           moltype = DNA  length = 25
FEATURE                  Location/Qualifiers
source                   1..25
                         mol_type = genomic DNA
                         organism = Homo sapiens
SEQUENCE: 238
cttggatgag tggccgcagc gctgt                                               25

SEQ ID NO: 239           moltype = DNA  length = 25
FEATURE                  Location/Qualifiers
source                   1..25
                         mol_type = genomic DNA
                         organism = Homo sapiens
SEQUENCE: 239
cctgtggcag agttccctga agcca                                               25

SEQ ID NO: 240           moltype = DNA  length = 25
FEATURE                  Location/Qualifiers
source                   1..25
                         mol_type = genomic DNA
                         organism = Homo sapiens
SEQUENCE: 240
tcagggaact ctgccacagg tgagc                                               25

SEQ ID NO: 241           moltype = DNA  length = 25
FEATURE                  Location/Qualifiers
source                   1..25
                         mol_type = genomic DNA
                         organism = Homo sapiens
SEQUENCE: 241
cctgaagcca tcaaggggct gcagc                                               25

SEQ ID NO: 242           moltype = DNA  length = 25
FEATURE                  Location/Qualifiers
source                   1..25
                         mol_type = genomic DNA
                         organism = Homo sapiens
SEQUENCE: 242
tcgccatcgc tgtagaacgc accac                                               25

SEQ ID NO: 243           moltype = DNA  length = 25
FEATURE                  Location/Qualifiers
source                   1..25
                         mol_type = genomic DNA
                         organism = Homo sapiens
SEQUENCE: 243
gtccaagcag cgccactgtg ggaga                                               25

SEQ ID NO: 244           moltype = DNA  length = 25
FEATURE                  Location/Qualifiers
source                   1..25
                         mol_type = genomic DNA
                         organism = Homo sapiens
SEQUENCE: 244
tttactctcc cacagtggcg ctgct                                               25

SEQ ID NO: 245           moltype = DNA  length = 25
FEATURE                  Location/Qualifiers
source                   1..25
                         mol_type = genomic DNA
                         organism = Homo sapiens
SEQUENCE: 245
cctccaattc aggacccaca tgacg                                               25

SEQ ID NO: 246           moltype = DNA  length = 25
FEATURE                  Location/Qualifiers
source                   1..25
                         mol_type = genomic DNA
                         organism = Homo sapiens
SEQUENCE: 246
ctccaattca ggacccacat gacgg                                               25

SEQ ID NO: 247           moltype = DNA  length = 25
FEATURE                  Location/Qualifiers
source                   1..25
                         mol_type = genomic DNA
                         organism = Homo sapiens
SEQUENCE: 247
```

```
agtgctcccc gcaccggccc atcct                                               25

SEQ ID NO: 248          moltype = DNA   length = 25
FEATURE                 Location/Qualifiers
source                  1..25
                        mol_type = genomic DNA
                        organism = Homo sapiens
SEQUENCE: 248
ctgccccac agagtgctcc ccgca                                                25

SEQ ID NO: 249          moltype = DNA   length = 25
FEATURE                 Location/Qualifiers
source                  1..25
                        mol_type = genomic DNA
                        organism = Homo sapiens
SEQUENCE: 249
gaccaagcag ccatgccagt acttc                                               25

SEQ ID NO: 250          moltype = DNA   length = 25
FEATURE                 Location/Qualifiers
source                  1..25
                        mol_type = genomic DNA
                        organism = Homo sapiens
SEQUENCE: 250
atctcctcct catcctccag cctct                                               25

SEQ ID NO: 251          moltype = DNA   length = 25
FEATURE                 Location/Qualifiers
source                  1..25
                        mol_type = genomic DNA
                        organism = Homo sapiens
SEQUENCE: 251
gacaacaaga tgcccctga ggcct                                                25

SEQ ID NO: 252          moltype = DNA   length = 25
FEATURE                 Location/Qualifiers
source                  1..25
                        mol_type = genomic DNA
                        organism = Homo sapiens
SEQUENCE: 252
ctggggctgc ttactactac caatg                                               25

SEQ ID NO: 253          moltype = DNA   length = 25
FEATURE                 Location/Qualifiers
source                  1..25
                        mol_type = genomic DNA
                        organism = Homo sapiens
SEQUENCE: 253
gacaagatgt ggaggctgac ccatg                                               25

SEQ ID NO: 254          moltype = DNA   length = 25
FEATURE                 Location/Qualifiers
source                  1..25
                        mol_type = genomic DNA
                        organism = Homo sapiens
SEQUENCE: 254
ctggggctgc ttactactac caatg                                               25

SEQ ID NO: 255          moltype = DNA   length = 25
FEATURE                 Location/Qualifiers
source                  1..25
                        mol_type = genomic DNA
                        organism = Homo sapiens
SEQUENCE: 255
gggggctggt ttgccatcca agggg                                               25

SEQ ID NO: 256          moltype = DNA   length = 25
FEATURE                 Location/Qualifiers
source                  1..25
                        mol_type = genomic DNA
                        organism = Homo sapiens
SEQUENCE: 256
aatgaacatc cctgtccggc caatt                                               25

SEQ ID NO: 257          moltype = DNA   length = 25
FEATURE                 Location/Qualifiers
source                  1..25
                        mol_type = genomic DNA
                        organism = Homo sapiens
```

-continued

```
SEQUENCE: 257
gccggacagg gatgttcatt gtgat                                              25

SEQ ID NO: 258          moltype = DNA   length = 25
FEATURE                 Location/Qualifiers
source                  1..25
                        mol_type = genomic DNA
                        organism = Homo sapiens
SEQUENCE: 258
aatcacaatg aacatccctg tccgg                                              25

SEQ ID NO: 259          moltype = DNA   length = 25
FEATURE                 Location/Qualifiers
source                  1..25
                        mol_type = genomic DNA
                        organism = Homo sapiens
SEQUENCE: 259
gattactgtg acctgtatgg agggg                                              25

SEQ ID NO: 260          moltype = DNA   length = 25
FEATURE                 Location/Qualifiers
source                  1..25
                        mol_type = genomic DNA
                        organism = Homo sapiens
SEQUENCE: 260
gccattttgg ctgagttggt ccagt                                              25

SEQ ID NO: 261          moltype = DNA   length = 25
FEATURE                 Location/Qualifiers
source                  1..25
                        mol_type = genomic DNA
                        organism = Homo sapiens
SEQUENCE: 261
tttggctgag ttggtccggt attac                                              25

SEQ ID NO: 262          moltype = DNA   length = 25
FEATURE                 Location/Qualifiers
source                  1..25
                        mol_type = genomic DNA
                        organism = Homo sapiens
SEQUENCE: 262
gccactttgg ctgagttggt ccggt                                              25

SEQ ID NO: 263          moltype = DNA   length = 25
FEATURE                 Location/Qualifiers
source                  1..25
                        mol_type = genomic DNA
                        organism = Homo sapiens
SEQUENCE: 263
ttggctgagt tggtccggta ttaca                                              25

SEQ ID NO: 264          moltype = DNA   length = 25
FEATURE                 Location/Qualifiers
source                  1..25
                        mol_type = genomic DNA
                        organism = Homo sapiens
SEQUENCE: 264
ccgcagatga ggagcagctc taggc                                              25

SEQ ID NO: 265          moltype = DNA   length = 25
FEATURE                 Location/Qualifiers
source                  1..25
                        mol_type = genomic DNA
                        organism = Homo sapiens
SEQUENCE: 265
agctctaggc cgaagtgtcg caggc                                              25

SEQ ID NO: 266          moltype = DNA   length = 25
FEATURE                 Location/Qualifiers
source                  1..25
                        mol_type = genomic DNA
                        organism = Homo sapiens
SEQUENCE: 266
tacgtcctca gctgggacta gcagc                                              25

SEQ ID NO: 267          moltype = DNA   length = 25
FEATURE                 Location/Qualifiers
source                  1..25
                        mol_type = genomic DNA
```

```
                                organism = Homo sapiens
SEQUENCE: 267
gactagcagc tcaacctcgc ctatg                                                25

SEQ ID NO: 268          moltype = DNA   length = 25
FEATURE                 Location/Qualifiers
source                  1..25
                        mol_type = genomic DNA
                        organism = Homo sapiens
SEQUENCE: 268
agctgctagt cccagctgag gacgt                                                25

SEQ ID NO: 269          moltype = DNA   length = 25
FEATURE                 Location/Qualifiers
source                  1..25
                        mol_type = genomic DNA
                        organism = Homo sapiens
SEQUENCE: 269
tctctcctgg gcatcaaggg agtcc                                                25

SEQ ID NO: 270          moltype = DNA   length = 25
FEATURE                 Location/Qualifiers
source                  1..25
                        mol_type = genomic DNA
                        organism = Homo sapiens
SEQUENCE: 270
ttggactccc ttgatgccca ggaga                                                25

SEQ ID NO: 271          moltype = DNA   length = 25
FEATURE                 Location/Qualifiers
source                  1..25
                        mol_type = genomic DNA
                        organism = Homo sapiens
SEQUENCE: 271
aatgactgtg atccacattc cccct                                                25

SEQ ID NO: 272          moltype = DNA   length = 20
FEATURE                 Location/Qualifiers
source                  1..20
                        mol_type = genomic DNA
                        organism = Homo sapiens
SEQUENCE: 272
cctaccctga aaatccgaaa                                                      20

SEQ ID NO: 273          moltype = DNA   length = 25
FEATURE                 Location/Qualifiers
source                  1..25
                        mol_type = genomic DNA
                        organism = Homo sapiens
SEQUENCE: 273
cacacactct gcaccttgaa ggctg                                                25

SEQ ID NO: 274          moltype = DNA   length = 25
FEATURE                 Location/Qualifiers
source                  1..25
                        mol_type = genomic DNA
                        organism = Homo sapiens
SEQUENCE: 274
gcaccttgaa ggctgacaag tcatc                                                25

SEQ ID NO: 275          moltype = DNA   length = 25
FEATURE                 Location/Qualifiers
source                  1..25
                        mol_type = genomic DNA
                        organism = Homo sapiens
SEQUENCE: 275
tagtagcaca cactctgcac cttga                                                25

SEQ ID NO: 276          moltype = DNA   length = 25
FEATURE                 Location/Qualifiers
source                  1..25
                        mol_type = genomic DNA
                        organism = Homo sapiens
SEQUENCE: 276
ttggtgctct cctccgtggc cacgc                                                25

SEQ ID NO: 277          moltype = DNA   length = 25
FEATURE                 Location/Qualifiers
source                  1..25
```

```
SEQUENCE: 277
agcatcgatg tcaacgaggg caacc                                      25

SEQ ID NO: 278         moltype = DNA  length = 25
FEATURE                Location/Qualifiers
source                 1..25
                       mol_type = genomic DNA
                       organism = Homo sapiens
SEQUENCE: 278
ccctcgttga catcgatgct tgaga                                      25

SEQ ID NO: 279         moltype = DNA  length = 25
FEATURE                Location/Qualifiers
source                 1..25
                       mol_type = genomic DNA
                       organism = Homo sapiens
SEQUENCE: 279
gggggctgag cagcagtgcg ccctt                                      25

SEQ ID NO: 280         moltype = DNA  length = 25
FEATURE                Location/Qualifiers
source                 1..25
                       mol_type = genomic DNA
                       organism = Homo sapiens
SEQUENCE: 280
agctgctttt ccggggtttc cgctg                                      25

SEQ ID NO: 281         moltype = DNA  length = 25
FEATURE                Location/Qualifiers
source                 1..25
                       mol_type = genomic DNA
                       organism = Homo sapiens
SEQUENCE: 281
gacagcggaa accccggaaa agcag                                      25

SEQ ID NO: 282         moltype = DNA  length = 25
FEATURE                Location/Qualifiers
source                 1..25
                       mol_type = genomic DNA
                       organism = Homo sapiens
SEQUENCE: 282
gtggaacttc tgtactacaa cgctg                                      25

SEQ ID NO: 283         moltype = DNA  length = 25
FEATURE                Location/Qualifiers
source                 1..25
                       mol_type = genomic DNA
                       organism = Homo sapiens
SEQUENCE: 283
gtctcagcag gatctctcac cgtag                                      25

SEQ ID NO: 284         moltype = DNA  length = 25
FEATURE                Location/Qualifiers
source                 1..25
                       mol_type = genomic DNA
                       organism = Homo sapiens
SEQUENCE: 284
acctgagtgt tttagctacg gtgag                                      25

SEQ ID NO: 285         moltype = DNA  length = 25
FEATURE                Location/Qualifiers
source                 1..25
                       mol_type = genomic DNA
                       organism = Homo sapiens
SEQUENCE: 285
gtggagctga ccagggagga gacct                                      25

SEQ ID NO: 286         moltype = DNA  length = 25
FEATURE                Location/Qualifiers
source                 1..25
                       mol_type = genomic DNA
                       organism = Homo sapiens
SEQUENCE: 286
tgaccaggga ggagaccttc aaata                                      25

SEQ ID NO: 287         moltype = DNA  length = 20
FEATURE                Location/Qualifiers
```

```
source                     1..20
                           mol_type = genomic DNA
                           organism = Homo sapiens
SEQUENCE: 287
gaaggtctcc tccctggtca                                                      20

SEQ ID NO: 288             moltype = DNA   length = 25
FEATURE                    Location/Qualifiers
source                     1..25
                           mol_type = genomic DNA
                           organism = Homo sapiens
SEQUENCE: 288
gtggagctga ccagggagga gacct                                                25

SEQ ID NO: 289             moltype = DNA   length = 25
FEATURE                    Location/Qualifiers
source                     1..25
                           mol_type = genomic DNA
                           organism = Homo sapiens
SEQUENCE: 289
cgctggttct gccggctgat tcagc                                                25

SEQ ID NO: 290             moltype = DNA   length = 25
FEATURE                    Location/Qualifiers
source                     1..25
                           mol_type = genomic DNA
                           organism = Homo sapiens
SEQUENCE: 290
ctgctgaatc agccggcaga accag                                                25

SEQ ID NO: 291             moltype = DNA   length = 25
FEATURE                    Location/Qualifiers
source                     1..25
                           mol_type = genomic DNA
                           organism = Homo sapiens
SEQUENCE: 291
ggatgggtgg agagcaagtt ggtca                                                25

SEQ ID NO: 292             moltype = DNA   length = 25
FEATURE                    Location/Qualifiers
source                     1..25
                           mol_type = genomic DNA
                           organism = Homo sapiens
SEQUENCE: 292
tgcaggagct tcgaggcact gtggc                                                25

SEQ ID NO: 293             moltype = DNA   length = 25
FEATURE                    Location/Qualifiers
source                     1..25
                           mol_type = genomic DNA
                           organism = Homo sapiens
SEQUENCE: 293
atgctggatg tgctgcagga gcttc                                                25

SEQ ID NO: 294             moltype = DNA   length = 25
FEATURE                    Location/Qualifiers
source                     1..25
                           mol_type = genomic DNA
                           organism = Homo sapiens
SEQUENCE: 294
ctgccatatt gtgtgcccgc actcg                                                25

SEQ ID NO: 295             moltype = DNA   length = 25
FEATURE                    Location/Qualifiers
source                     1..25
                           mol_type = genomic DNA
                           organism = Homo sapiens
SEQUENCE: 295
gggggcccgg ctgcttttc gagtg                                                 25

SEQ ID NO: 296             moltype = DNA   length = 20
FEATURE                    Location/Qualifiers
source                     1..20
                           mol_type = genomic DNA
                           organism = Homo sapiens
SEQUENCE: 296
tgtgcccgca ctcgaaaaag                                                      20

SEQ ID NO: 297             moltype = DNA   length = 25
```

```
FEATURE             Location/Qualifiers
source              1..25
                    mol_type = genomic DNA
                    organism = Homo sapiens
SEQUENCE: 297
ctcagaggtc agggagggtc cagac                                       25

SEQ ID NO: 298      moltype = DNA   length = 20
FEATURE             Location/Qualifiers
source              1..20
                    mol_type = genomic DNA
                    organism = Homo sapiens
SEQUENCE: 298
cttgggactg taaaagctgt                                             20

SEQ ID NO: 299      moltype = DNA   length = 25
FEATURE             Location/Qualifiers
source              1..25
                    mol_type = genomic DNA
                    organism = Homo sapiens
SEQUENCE: 299
gtaagtgatc catcctaggt tggca                                       25

SEQ ID NO: 300      moltype = DNA   length = 20
FEATURE             Location/Qualifiers
source              1..20
                    mol_type = genomic DNA
                    organism = Homo sapiens
SEQUENCE: 300
gtaagtgatc catcctaggt                                             20

SEQ ID NO: 301      moltype = DNA   length = 25
FEATURE             Location/Qualifiers
source              1..25
                    mol_type = genomic DNA
                    organism = Homo sapiens
SEQUENCE: 301
gccccctcac cttggacagt gagat                                       25

SEQ ID NO: 302      moltype = DNA   length = 25
FEATURE             Location/Qualifiers
source              1..25
                    mol_type = genomic DNA
                    organism = Homo sapiens
SEQUENCE: 302
cttcaatctc actgtccaag gtgag                                       25

SEQ ID NO: 303      moltype = DNA   length = 25
FEATURE             Location/Qualifiers
source              1..25
                    mol_type = genomic DNA
                    organism = Homo sapiens
SEQUENCE: 303
tttaacgaag ccctccgtga gagct                                       25

SEQ ID NO: 304      moltype = DNA   length = 20
FEATURE             Location/Qualifiers
source              1..20
                    mol_type = genomic DNA
                    organism = Homo sapiens
SEQUENCE: 304
aacgaagccc tccgtgagag                                             20

SEQ ID NO: 305      moltype = DNA   length = 20
FEATURE             Location/Qualifiers
source              1..20
                    mol_type = genomic DNA
                    organism = Homo sapiens
SEQUENCE: 305
caagaatctg accatcttgg                                             20

SEQ ID NO: 306      moltype = DNA   length = 25
FEATURE             Location/Qualifiers
source              1..25
                    mol_type = genomic DNA
                    organism = Homo sapiens
SEQUENCE: 306
actgtgggag ttctcgtccg tgacc                                       25
```

```
SEQ ID NO: 307            moltype = DNA   length = 20
FEATURE                   Location/Qualifiers
source                    1..20
                          mol_type = genomic DNA
                          organism = Homo sapiens
SEQUENCE: 307
tcgtccgtga cctgggagcc                                                   20

SEQ ID NO: 308            moltype = DNA   length = 25
FEATURE                   Location/Qualifiers
source                    1..25
                          mol_type = genomic DNA
                          organism = Homo sapiens
SEQUENCE: 308
cagatgaaca ctggtcagcg taggg                                             25

SEQ ID NO: 309            moltype = DNA   length = 20
FEATURE                   Location/Qualifiers
source                    1..20
                          mol_type = genomic DNA
                          organism = Homo sapiens
SEQUENCE: 309
acagatgaac actggtcagc                                                   20

SEQ ID NO: 310            moltype = DNA   length = 25
FEATURE                   Location/Qualifiers
source                    1..25
                          mol_type = genomic DNA
                          organism = Homo sapiens
SEQUENCE: 310
cagaacatcc ttgggggcta caggt                                             25

SEQ ID NO: 311            moltype = DNA   length = 25
FEATURE                   Location/Qualifiers
source                    1..25
                          mol_type = genomic DNA
                          organism = Homo sapiens
SEQUENCE: 311
gccagcatgg ctgccagaac atcct                                             25

SEQ ID NO: 312            moltype = DNA   length = 25
FEATURE                   Location/Qualifiers
source                    1..25
                          mol_type = genomic DNA
                          organism = Homo sapiens
SEQUENCE: 312
cggaacctgt gaggaggttg gcact                                             25

SEQ ID NO: 313            moltype = DNA   length = 25
FEATURE                   Location/Qualifiers
source                    1..25
                          mol_type = genomic DNA
                          organism = Homo sapiens
SEQUENCE: 313
gttgacatcg gaacctgtga ggagg                                             25

SEQ ID NO: 314            moltype = DNA   length = 20
FEATURE                   Location/Qualifiers
source                    1..20
                          mol_type = genomic DNA
                          organism = Homo sapiens
SEQUENCE: 314
tcagtgccaa cctcctcaca                                                   20

SEQ ID NO: 315            moltype = DNA   length = 25
FEATURE                   Location/Qualifiers
source                    1..25
                          mol_type = genomic DNA
                          organism = Homo sapiens
SEQUENCE: 315
cggaacctgt gaggaggttg gcact                                             25

SEQ ID NO: 316            moltype = DNA   length = 25
FEATURE                   Location/Qualifiers
source                    1..25
                          mol_type = genomic DNA
                          organism = Homo sapiens
SEQUENCE: 316
taggcgatgg agcctggggg ttcgg                                             25
```

```
SEQ ID NO: 317           moltype = DNA  length = 25
FEATURE                  Location/Qualifiers
source                   1..25
                         mol_type = genomic DNA
                         organism = Homo sapiens
SEQUENCE: 317
ggtaggcgat ggagcctggg ggttc                                               25

SEQ ID NO: 318           moltype = DNA  length = 25
FEATURE                  Location/Qualifiers
source                   1..25
                         mol_type = genomic DNA
                         organism = Homo sapiens
SEQUENCE: 318
gactggggaa ctcccgacaa gatca                                               25

SEQ ID NO: 319           moltype = DNA  length = 25
FEATURE                  Location/Qualifiers
source                   1..25
                         mol_type = genomic DNA
                         organism = Homo sapiens
SEQUENCE: 319
gggaactccc gacaagatca agaaa                                               25

SEQ ID NO: 320           moltype = DNA  length = 20
FEATURE                  Location/Qualifiers
source                   1..20
                         mol_type = genomic DNA
                         organism = Homo sapiens
SEQUENCE: 320
ttgatcttgt cgggagttcc                                                     20

SEQ ID NO: 321           moltype = DNA  length = 25
FEATURE                  Location/Qualifiers
source                   1..25
                         mol_type = genomic DNA
                         organism = Homo sapiens
SEQUENCE: 321
tcccgacaag atcaagaaag ggggc                                               25

SEQ ID NO: 322           moltype = DNA  length = 25
FEATURE                  Location/Qualifiers
source                   1..25
                         mol_type = genomic DNA
                         organism = Homo sapiens
SEQUENCE: 322
ctgagcaccc tgtacagctt cttcc                                               25

SEQ ID NO: 323           moltype =      length =
SEQUENCE: 323
000

SEQ ID NO: 324           moltype =      length =
SEQUENCE: 324
000

SEQ ID NO: 325           moltype = AA   length = 169
FEATURE                  Location/Qualifiers
REGION                   1..169
                         note = source = /note="Description of Artificial Sequence:
                         Syntheticpolypeptide"
source                   1..169
                         mol_type = protein
                         organism = synthetic construct
SEQUENCE: 325
MTEHEKFMNA ALKLARKAAA EGEVPVGCVV VRDGVIVGRG RNRRETKKDA LGHAEIEAIH   60
KACKKLGGWR LHQCDLYVTL EPCPMCTGAI INARIKTVYY GAPRLSAGSC GSVVNLFDLP  120
YNHKPELVSG LMEQECTEEL QKFFRQLRER KKLEKQLRKQ AQMNDLNEI              169

SEQ ID NO: 326           moltype = AA   length = 1254
FEATURE                  Location/Qualifiers
REGION                   1..1254
                         note = source = /note="Description of Artificial Sequence:
                         Syntheticpolypeptide"
source                   1..1254
                         mol_type = protein
                         organism = synthetic construct
SEQUENCE: 326
```

```
MTEHEKFMNA ALKLARKAAA EGEVPVGCVV VRDGVIVGRG RNRRETKKDA LGHAEIEAIH    60
KACKCKLGGWR LHQCDLYVTL EPCPMCTGAI INARIKTVYY GAPRLSAGSC GSVVNLFDLP  120
YNHKPELVSG LMEQECTEEL QKFFRQLRER KKLEKQLRKQ AQMNDLNEIS GSETPGTSES  180
ATPESSGGSS GGSSMKQTSY SLGLAIGIAS VGYGLIDNDE NIVDAGVRLF PEANSKNNDG  240
RRKSRGSKRL IRRKRHRIAR VKHLLKESGI DVSYENTVLT NPYEIRCKGL TLPLTNHELS  300
IALLHLAKRR GVHNVKSMDQ EKVKGNELST KEQLTINDNL LEEKFICELQ LERLNKEGIV  360
RSHSNRFKTA DYIKEIKNLL ETQAKQNTLV TEEFIEKYIE IFSGRRKYYE GPGGESKYGW  420
KGDIEKWYEG LMGKCTYFPK ELRCVKHAYS AALFNLLNDL NNLSINREED TKLSQYEKEQ  480
IIEKIFKVRK TPTLTQIAKL LKVDPTNIKG FRTKANGTPD FLSIKIYHDL KGIIDDKQLL  540
DDIAFLDNVA QILTVWQDSQ SIQEKLKTLN KNLDDKTIKE ISELKKYTQT HSLSLKLINV  600
LLPELWETTK NQMTILSELK LKPRKIDLHN CNEIPVNMIN DLIVSPVVRR SLTQSIEMIN  660
QIIKDYGHPR EIVIELAREK NSEEKKNFIK SLNEKNKQIN DEVIEKLNAS NHRDNKGMFN  720
KVKLWILQDG HCLYSLKPIR LEDLLNNPNH YEIDAIIPKS VSFDDSMSNK VLVYQIENSK  780
KGNRTPYQYL TSADKTITYE KFKANITQLA KSNHKISKKK LDYLLEERDI NRFHIKKEFI  840
NRNLVDTRYA TRSLINLLKY YFSEKDINVK VKSINGSFTD YLRKLWNFPK DREFYHKHHA  900
EDALIIAMAN KIFTTRKIFK EQNSVFSDEQ ILDGEVTNIL SDDQFQAEFT EKFYKVQAIK  960
KYDKYKYSHR VDKKPNRQLF DDTLYSTREF EGEEYYIGKI KDIYNLKDKR LKKIFTKSPE 1020
KILMYQHDSQ TFKKLKQIMR SYEDEVNPLA KYHKETGEYL RKECKKGNGP IVKSLKYRVT 1080
KLGVHKDITH KYENSKNKVV ILSLKPFRMD VFKENGVYKF ITIRYCDLKE TVNSYTISEH 1140
LYKAKLKAKD IKSMDSFKWS FYKNDLLEYN GELCTFKGVN DDKKNKIEVN WVEKNFAIYA 1200
EKKNLKSKQL VKSITKSTVK SLLKYTTDIL GNRYPVRNEK LKLMIRKQTF RGDL        1254

SEQ ID NO: 327          moltype = AA  length = 1060
FEATURE                 Location/Qualifiers
REGION                  1..1060
                        note = source = /note="Description of Artificial Sequence:
                        Syntheticpolypeptide"
source                  1..1060
                        mol_type = protein
                        organism = synthetic construct
SEQUENCE: 327
MKQTSYSLGL AIGIASVGYG LIDNDENIVD AGVRLFPEAN SKNNDGRRKS RGSKRLIRRK   60
RHRIARVKHL LKESGIDVSY ENTVLTNPYE IRCKGLTLPL TNHELSIALL HLAKRRGVHN  120
VKSMDQEKVK GNELSTKEQL TINDNLLEEK FICELQLERL NKEGIVRSHS NRFKTADYIK  180
EIKNLLETQA KQNTLVTEEF IEKYIEIFSG RRKYYEGPGG ESKYGWKGDI EKWYEGLMGK  240
CTYFPKELRC VKHAYSAALF NLLNDLNNLS INREEDTKLS QYEKEQIIEK IFKVRKTPTL  300
TQIAKLLKVD PTNIKGFRTK ANGTPDFLSI KIYHDLKGII DDKQLLDDIA FLDNVAQILT  360
VWQDSQSIQE KLKTLNKNLD DKTIKEISEL KKYTQTHSLS LKLINVLLPE LWETTKNQMT  420
ILSELKLKPR KIDLHNCNEI PVNMINDLIV SPVVRRSLTQ SIEMINQIIK DYGHPREIVI  480
ELAREKNSEE KKNFIKSLNE KNKQINDEVI EKLNASNHRD NKGMFNKVKL WILQDGHCLY  540
SLKPIRLEDL LNNPNHYEID AIIPKSVSFD DSMSNKVLVY QIENSKKGNR TPYQYLTSAD  600
KTITYEKFKA NITQLAKSNH KSKKKLDYL LEERDINRFH IKKEFINRNL VDTRYATRSL  660
INLLKYYFSE KDINVKVKSI NGSFTDYLRK LWNFPKDREF YHKHHAEDAL IIAMANKIFT  720
TRKIFKEQNS VFSDEQILDG EVTNILSDDQ FQAEFTEKFY KVQAIKKYDK YKYSHRVDKK  780
PNRQLFDDTL YSTREFEGEE YYIGKIKDIY NLKDKRLKKI FTKSPEKILM YQHDSQTFKK  840
LKQIMRSYED EVNPLAKYHK ETGEYLRKEC KKGNGPIVKS LKYRVTKLGV HKDITHKYEN  900
SKNKVVILSL KPFRMDVFKE NGVYKFITIR YCDLKETVNS YTISEHLYKA KLKAKDIKSM  960
DSFKWSFYKN DLLEYNGELC TFKGVNDDKK NKIEVNWVEK NFAIYAEKKN LKSKQLVKSI 1020
TKSTVKSLLK YTTDILGNRY PVRNEKLKLM IRKQTFRGDL                       1060

SEQ ID NO: 328          moltype = DNA  length = 15
FEATURE                 Location/Qualifiers
misc_feature            1..15
                        note = source = /note="Description of Artificial Sequence:
                        Syntheticoligonucleotide"
source                  1..15
                        mol_type = other DNA
                        organism = synthetic construct
SEQUENCE: 328
gactccttca ccaag                                                    15

SEQ ID NO: 329          moltype = DNA  length = 14
FEATURE                 Location/Qualifiers
misc_feature            1..14
                        note = source = /note="Description of Artificial Sequence:
                        Syntheticoligonucleotide"
source                  1..14
                        mol_type = other DNA
                        organism = synthetic construct
SEQUENCE: 329
gtagatcagc accg                                                     14

SEQ ID NO: 330          moltype = DNA  length = 14
FEATURE                 Location/Qualifiers
misc_feature            1..14
                        note = source = /note="Description of Artificial Sequence:
                        Syntheticoligonucleotide"
source                  1..14
                        mol_type = other DNA
```

|                  | -continued |
|---|---|

```
                           organism = synthetic construct
SEQUENCE: 330
ctctgggccg aagt                                                           14

SEQ ID NO: 331             moltype = DNA   length = 14
FEATURE                    Location/Qualifiers
misc_feature               1..14
                           note = source = /note="Description of Artificial Sequence:
                             Syntheticoligonucleotide"
source                     1..14
                           mol_type = other DNA
                           organism = synthetic construct
SEQUENCE: 331
ctctaggccg aagt                                                           14

SEQ ID NO: 332             moltype = DNA   length = 13
FEATURE                    Location/Qualifiers
misc_feature               1..13
                           note = source = /note="Description of Artificial Sequence:
                             Syntheticoligonucleotide"
source                     1..13
                           mol_type = other DNA
                           organism = synthetic construct
SEQUENCE: 332
acttcctcca gcc                                                            13

SEQ ID NO: 333             moltype = DNA   length = 13
FEATURE                    Location/Qualifiers
misc_feature               1..13
                           note = source = /note="Description of Artificial Sequence:
                             Syntheticoligonucleotide"
source                     1..13
                           mol_type = other DNA
                           organism = synthetic construct
SEQUENCE: 333
gaaccccggc tta                                                            13

SEQ ID NO: 334             moltype = DNA   length = 203
FEATURE                    Location/Qualifiers
misc_feature               1..203
                           note = source = /note="Description of Artificial Sequence:
                             Syntheticpolynucleotide"
source                     1..203
                           mol_type = other DNA
                           organism = synthetic construct
SEQUENCE: 334
tgatgcggtt ttggcagtac atcaatgggc gtggatagcg gtttgactca cggggatttc          60
caagtctcca ccccattgac gtcaatggga gtttgttttg gcaccaaaat caacgggact         120
ttccaaaatg tcgtaacaac tccgccccat tgacgcaaat gggcggtagg cgtgtacggt         180
gggaggtcta tataagcaga gct                                                203

SEQ ID NO: 335             moltype = DNA   length = 304
FEATURE                    Location/Qualifiers
misc_feature               1..304
                           note = source = /note="Description of Artificial Sequence:
                             Syntheticpolynucleotide"
source                     1..304
                           mol_type = other DNA
                           organism = synthetic construct
SEQUENCE: 335
cgttacataa cttacggtaa atggcccgcc tggctgaccg cccaacgacc cccgcccatt          60
gacgtcaata atgacgtatg ttcccatagt aacgccaata gggactttcc attgacgtca        120
atgggtggag tatttacggt aaactgccca cttggcagta catcaagtgt atcatatgcc        180
aagtacgccc cctattgacg tcaatgacgg taaatggccc gcctggcatt atgcccagta        240
catgacctta tgggactttc ctacttggca gtacatctac gtattagtca tcgctattac        300
catg                                                                     304

SEQ ID NO: 336             moltype = DNA   length = 318
FEATURE                    Location/Qualifiers
misc_feature               1..318
                           note = source = /note="Description of Artificial Sequence:
                             Syntheticpolynucleotide"
source                     1..318
                           mol_type = other DNA
                           organism = synthetic construct
SEQUENCE: 336
tgtacaaaaa agcaggcttt aaaggaacca attcagtcga ctggatccgg taccaaggtc          60
gggcaggaag agggcctatt tcccatgatt ccttcatatt tgcatatacg atacaaggct        120
gttagagaga taattagaat taatttgact gtaaacacaa agatattagt acaaaatacg        180
```

```
tgacgtagaa agtaataatt tcttgggtag tttgcagttt taaaattatg ttttaaaatg    240
gactatcata tgcttaccgt aacttgaaag tatttcgatt tcttggcttt atatatcttg    300
tggaaaggac gaaacacc                                                  318
```

SEQ ID NO: 337    moltype = DNA length = 31
FEATURE    Location/Qualifiers
misc_feature    1..31
    note = source = /note="Description of Artificial Sequence:
    Syntheticoligonucleotide"
source    1..31
    mol_type = other DNA
    organism = synthetic construct
SEQUENCE: 337
```
ggagcagctc taggccgaag tgtcgcaggc c                                   31
```

SEQ ID NO: 338    moltype = DNA length = 31
FEATURE    Location/Qualifiers
misc_feature    1..31
    note = source = /note="Description of Artificial Sequence:
    Syntheticoligonucleotide"
source    1..31
    mol_type = other DNA
    organism = synthetic construct
SEQUENCE: 338
```
agaacaactc taggcagagg tctcaaaggc t                                   31
```

SEQ ID NO: 339    moltype = DNA length = 31
FEATURE    Location/Qualifiers
misc_feature    1..31
    note = source = /note="Description of Artificial Sequence:
    Syntheticoligonucleotide"
source    1..31
    mol_type = other DNA
    organism = synthetic construct
SEQUENCE: 339
```
ggagcagctc taggccgaag tgtcgcaggc c                                   31
```

SEQ ID NO: 340    moltype = DNA length = 20
FEATURE    Location/Qualifiers
source    1..20
    mol_type = genomic DNA
    organism = Homo sapiens
SEQUENCE: 340
```
aagactaacc tggccaacat                                                20
```

SEQ ID NO: 341    moltype = DNA length = 20
FEATURE    Location/Qualifiers
source    1..20
    mol_type = genomic DNA
    organism = Homo sapiens
SEQUENCE: 341
```
gtcttgaact ccggacctca                                                20
```

SEQ ID NO: 342    moltype = DNA length = 20
FEATURE    Location/Qualifiers
source    1..20
    mol_type = genomic DNA
    organism = Homo sapiens
SEQUENCE: 342
```
gccgggcgtg gtgtcgcgcg                                                20
```

SEQ ID NO: 343    moltype = DNA length = 20
FEATURE    Location/Qualifiers
source    1..20
    mol_type = genomic DNA
    organism = Homo sapiens
SEQUENCE: 343
```
tcctgccgca gcctctggag                                                20
```

SEQ ID NO: 344    moltype = DNA length = 135
FEATURE    Location/Qualifiers
misc_feature    1..135
    note = source = /note="Description of Artificial Sequence:
    Syntheticpolynucleotide"
source    1..135
    mol_type = other DNA
    organism = synthetic construct
SEQUENCE: 344
```
cgacggttag aggccgtatg tcgatttgct ttaatttcgt gcgtgtgcat tgtcgtcctc    60
```

```
cattacaggg cggctaccac gaatagccac gaagtaaaag cttcgtggct agcacaagac    120
taacctggcc aacat                                                    135

SEQ ID NO: 345          moltype = DNA   length = 135
FEATURE                 Location/Qualifiers
misc_feature            1..135
                        note = source = /note="Description of Artificial Sequence:
                        Syntheticpolynucleotide"
source                  1..135
                        mol_type = other DNA
                        organism = synthetic construct
SEQUENCE: 345
cgacggttag aggccgtatg tcgatttgct ttaatttcgt gcgtgtgcat tgtcgtcctc    60
cattacaggg cggctaccac gaatagccac gaagtaaaag cttcgtggct agcacgtctt    120
gaactccgga cctca                                                    135

SEQ ID NO: 346          moltype = DNA   length = 135
FEATURE                 Location/Qualifiers
misc_feature            1..135
                        note = source = /note="Description of Artificial Sequence:
                        Syntheticpolynucleotide"
source                  1..135
                        mol_type = other DNA
                        organism = synthetic construct
SEQUENCE: 346
cgacggttag aggccgtatg tcgatttgct ttaatttcgt gcgtgtgcat tgtcgtcctc    60
cattacaggg cggctaccac gaatagccac gaagtaaaag cttcgtggct agcacgccgg    120
gcgtggtgtc gcgcg                                                    135

SEQ ID NO: 347          moltype = DNA   length = 135
FEATURE                 Location/Qualifiers
misc_feature            1..135
                        note = source = /note="Description of Artificial Sequence:
                        Syntheticpolynucleotide"
source                  1..135
                        mol_type = other DNA
                        organism = synthetic construct
SEQUENCE: 347
cgacggttag aggccgtatg tcgatttgct ttaatttcgt gcgtgtgcat tgtcgtcctc    60
cattacaggg cggctaccac gaatagccac gaagtaaaag cttcgtggct agcactcctg    120
ccgcagcctc tggag                                                    135

SEQ ID NO: 348          moltype = DNA   length = 500
FEATURE                 Location/Qualifiers
misc_feature            1..500
                        note = source = /note="Description of Artificial Sequence:
                        Syntheticpolynucleotide"
source                  1..500
                        mol_type = other DNA
                        organism = synthetic construct
SEQUENCE: 348
aaaaatggac aattatgagg aggggagagt gcagacaggg gaagcttcac ctcctttaca    60
attttgggag tccacacggc atggcataca aattatttca ttcccattga gaaataaaat    120
ccaattctcc atcaccaaga gagccttccg aaagaggccc cctgggcaa acggccaccg     180
atggagaggt ctgccagtcc tcttctaccc cacccaccta cccaccctaa tcagaggcca    240
aacccttcct ggagcctgtg ataaaagcaa ctgttagctt gcactagact agcttcaaag    300
ttgtattgac cctggtgtgt tatgtctaag agtagatgcc atatctcttt tctggcctat    360
gttattacct gtatggactt tgcactggaa tcagctatct gctcttactt atgcacacct    420
ggggcataga gccagccctg tatcgctttt cagccatctc actacagata actcccaagt    480
cctgtctagc tgccttcctt                                               500

SEQ ID NO: 349          moltype = DNA   length = 3324
FEATURE                 Location/Qualifiers
misc_feature            1..3324
                        note = source = /note="Description of Artificial Sequence:
                        Syntheticpolynucleotide"
source                  1..3324
                        mol_type = other DNA
                        organism = synthetic construct
SEQUENCE: 349
atggccattc ggagcatcaa gctcaagctg aagaccagaa ccgtcctga ggctcagaac      60
ctgcggaagg gcatctggag aacccaccgg ctgctgaacg agggcgtggc ctactacatg    120
aagatgctgc tgctcttccg gcaggaatcc actggcggcc agacaaagaa ggaactgcag    180
gaggaactgg tgcggcacat ccgggagcag cagcagaaaa acagagccga caagaatacc    240
caggcccctgc ctctggataa ggccttcgcc gctctgagac aactgtacga gctgctcgtg    300
ccatctagca tcgccagag cggcgatgcc cagatcatct ctagaaaatt cctgtctcct    360
ttggtggacc ctaacagcga gggcggcaag ggcactagca aggccggagc caagcccaca    420
tggcagaaaa agaaggaggc caatgaccct acatgggagc aagattacga gaagtggaaa    480
aagcgtagag aggaagatcc taccgccagt gtgataacaa ccctgaagga atatggaatt    540
```

```
agacctatct ttccactgta caccaacacc gtggccgata tcgcctggct gcctctgcag    600
tctaaccagt ttgtccggac atgggatcgg gacatgctgc agcaggccat cgagaggcta    660
ctctcttggg agtcttggaa caagcgggtg caagaggaat acagcaagct gcaggagaag    720
atgacgcaac tgaacgagca actggagggc ggacaggagt ggatcagcct gctggaacaa    780
tacgaggaac agagagagca ggagctgatc gaaaacatga ccgccgcaaa cgataaatac    840
cgcatcacca agcggcagat gaagggctgg aatgagctgt atgagcagtg gtctaccgtg    900
ctgcccaatg ccagccacga gcagtacaga gaggcactga aaagagtgca acagcggctg    960
agggcagat tcggcgacgc tcatttcttc cagtatctga tgaaagaaga acaccacctg    1020
atctggaagg ggaaccctca gagaatccac tacttcgtgg ccagaaacga gctgaagaaa    1080
agactcaggaag aagccaagca gaacgccacc atgacccgtgc ctgatgccag aaagcaccct    1140
ctgtgggtca gatttgacgc cagaggcgga aacctgcaag actactacct gacgccgaa    1200
gccgacaacc ccagaagcag aaggttcgtg accttcagcc aactgatctg gcctaacgag    1260
agcggctgga tggaaaaaca ggacgtgaa gttgaactgg ccctgagcaa gcagttctac    1320
cagcaagtga cactgcagaa aaacgacaag gggaagcagg aaatcgagtt caaagacaag    1380
ggcagtggca gcaccttcag cggccacctg ggcggggcca agctgcaact ggagagagga    1440
gatctggaga aggaagaaaa agactttgaa ggcggcgaaa tcggcagcgt gtacctgaac    1500
atcgtgatcg acttcgagcc actgcaggag gtgaagaacg gccgactgca atctccttac    1560
ggccaggtgc tgcaactggt cagaaggcct aatgagttcc ccaaggtgac cacctacaag    1620
tctgaggaac tggtcgagtg gatcaagagc agcaccaagg acagcgccgg cgtggagtcc    1680
ttagagagcg gttttagagt gatgagcatc gacctgggac tgcggaccgc cgccgcaaca    1740
agcatcttct ctgtagagga atccaacgac gccaacgccg cgggttttcag ctactggatc    1800
gagggaactc ctctggttgc cgttcataag cggtcatata tctgtgaaact gccccggagag    1860
caagtcgaaa agcaggtgcg agagaagcgg gacgagcggc aggatcagca gagaagagtg    1920
aggttccaaa tcagaatcct gagccaggtg atccggatgg ccaagaagca gaaccggag    1980
cgggctgatg agctggacca cctgtcccag gccctggaga agcaaaaatc tctgctggac    2040
cagaccgatc ggacctttg gaacggcatc gtgtgcgaac tgacagacgc tctgagagag    2100
aaagagggcg gatgggaaca ggccgtggtc cagatccaca ggaaggccga ggagcacgtg    2160
ggcaaggtgg tgcaagcctg gcggaaacgg ttcgacgccg atgaacgcaa gggcatcgcc    2220
ggcctgtcta tgtggtctat cgaggagctg gacagcctgc ggaagctgct gatctcttgg    2280
agcagaagaa caagaaaccc cagagaaatc aactgcttcg acagggcca cagcagccac    2340
cagcggctgc tgacacacat ccagaacgtg aaggaggacc ggctgaagca actgagccac    2400
gccattgtga tgcagccttt gggctacgtg tacgacgaga gaaattgga atggtttgcc    2460
aagtaccctg cttgtcaggt gatcctgttc gagaacctgt cccagtaccg gtccaacatg    2520
gacagaagca ccaaagagaa tagcaccctg atgaaatggg cccacaggag catccctaag    2580
tacgtgcaca tgcaggccga gccttacggc atccagatcg gcgatgtgcg ggccgagtac    2640
tccagcagat tccacgccaa gacaggcaca cctggcatcc ggtgcaagat ggtgtccgga    2700
cacgacctgc aaggcaggcg cttcgagaac ctgcagaagc ggttaatctc tgaacagttc    2760
ctgacagagg agcaagtgaa gcagctcaga cccggcgaca tcgtgcccga cgactccggc    2820
gagtggttca tgaccctgag cgacggcagc gaaggcaagc aggttgtgtt cctccaagcc    2880
gacatcaacg ccgccaaaaa tctgcaaaag agattctggc agcggtacaa cgagctgttt    2940
aaggtctcct gcagagtgct gatccgagga aagaggaat acctgatccc caagacaaag    3000
tccgtgcaag ccaagctggg caaaggcctg ttcgtgaaaa aaccgacac cgtgatgaag    3060
gacgtgtacg tgtgggacag ccaggctaag aaacaccatt caccgaggag    3120
tccgaaagcc ctgagcaact ggaggatttt caggagatca tcgaagaagc cgaagaagct    3180
aagggcacat acagaacact gtttagagac cccagcggac tgttcttccc tgagttcgtg    3240
tggtccaccc agaaagattt ctggtccgag gtgaagagac ggctgtacgg caagctgaga    3300
gagcggttcc tgatgaagac cagg                                            3324

SEQ ID NO: 350          moltype = DNA   length = 20
FEATURE                 Location/Qualifiers
source                  1..20
                        mol_type = genomic DNA
                        organism = Homo sapiens
SEQUENCE: 350
tattgaccct ggtgtgttat                                                  20

SEQ ID NO: 351          moltype = DNA   length = 20
FEATURE                 Location/Qualifiers
source                  1..20
                        mol_type = genomic DNA
                        organism = Homo sapiens
SEQUENCE: 351
gcttgcacta gactagcttc                                                  20

SEQ ID NO: 352          moltype = DNA   length = 20
FEATURE                 Location/Qualifiers
source                  1..20
                        mol_type = genomic DNA
                        organism = Homo sapiens
SEQUENCE: 352
cttttatcac aggctccagg                                                  20

SEQ ID NO: 353          moltype = DNA   length = 135
FEATURE                 Location/Qualifiers
misc_feature            1..135
                        note = source = /note="Description of Artificial Sequence:
                        Syntheticpolynucleotide"
source                  1..135
                        mol_type = other DNA
```

```
                          organism = synthetic construct
SEQUENCE: 353
cgacggttag aggccgtatg tcgatttgct ttaatttcgt gcgtgtgcat tgtcgtcctc    60
cattacaggg cggctaccac gaatagccac gaagtaaaag cttcgtggct agcactattg   120
accctggtgt gttat                                                    135

SEQ ID NO: 354          moltype = DNA   length = 135
FEATURE                 Location/Qualifiers
misc_feature            1..135
                          note = source = /note="Description of Artificial Sequence:
                          Syntheticpolynucleotide"
source                  1..135
                          mol_type = other DNA
                          organism = synthetic construct
SEQUENCE: 354
cgacggttag aggccgtatg tcgatttgct ttaatttcgt gcgtgtgcat tgtcgtcctc    60
cattacaggg cggctaccac gaatagccac gaagtaaaag cttcgtggct agcacgcttg   120
cactagacta gcttc                                                    135

SEQ ID NO: 355          moltype = DNA   length = 135
FEATURE                 Location/Qualifiers
misc_feature            1..135
                          note = source = /note="Description of Artificial Sequence:
                          Syntheticpolynucleotide"
source                  1..135
                          mol_type = other DNA
                          organism = synthetic construct
SEQUENCE: 355
cgacggttag aggccgtatg tcgatttgct ttaatttcgt gcgtgtgcat tgtcgtcctc    60
cattacaggg cggctaccac gaatagccac gaagtaaaag cttcgtggct agcacctttt   120
atcacaggct ccagg                                                    135

SEQ ID NO: 356          moltype = RNA   length = 118
FEATURE                 Location/Qualifiers
misc_feature            1..118
                          note = source = /note="Description of Artificial Sequence:
                          Syntheticpolynucleotide"
source                  1..118
                          mol_type = other RNA
                          organism = synthetic construct
SEQUENCE: 356
aggagcagct ctaggccgaa gtgtcgtttt agtactctgt gaaagcacag aatctactaa    60
aataaggcat aatgccgtat ttaatcccat cataattctg atgggatttt ttatattt    118

SEQ ID NO: 357          moltype = DNA   length = 3180
FEATURE                 Location/Qualifiers
misc_feature            1..3180
                          note = source = /note="Description of Artificial Sequence:
                          Syntheticpolynucleotide"
source                  1..3180
                          mol_type = other DNA
                          organism = synthetic construct
SEQUENCE: 357
atgaagcaga catcttattc tctgggcctg gatatcggca tcgcctctgt gggctacggc    60
ctgattgata acgacgaaaa catcgtggac gccggcgtca gactgtttcc tgaggccaat   120
agcaagaaca acgacggaag acggaagagc agaggctcca gcggctgat ccggcggaag    180
cgccacagaa tcgccagagt gaagcacctg ctgaaggaaa gcggcatcga cgtgtcctac   240
gaaaataccg tgctgaccaa cccttacgag atccggtgca agggcctgac cttaccactg   300
acgaaccacg agctttccat cgccctgctt catctggcta agagacgagg cgtgcacaac   360
gtgaagagca tggaccagga gaaagtcaag ggcaacgagc tgtctacaaa agagcaactg   420
accatcaatg ataatctgct ggaagaaaag ttcatctgcg agctgcaact ggagagactg   480
aacaaggaag gcatcgtgcg gagccactcc aacagattca agaccgccga ctacatcaaa   540
gagatcaaga acctgctgga aacacaggcc aagcagaaca cacttgttac cgaggagttc   600
atcgaaaagt acatcgagat tttcagcggc agaagaaagt actatgaagg ccccgggcga   660
gagagcaagt acgatgaag gggagatatt gaaagtggt acgaaggcct gatgggcaag   720
tgcacctact tccccaagga actgagatgt gtgaaacatg cctactctgc cgccctgttc   780
aacctgctga tgatctgaa caacctgagc atcaacagag aggaagatac caagctctcc   840
caatacgaaa aagagcagat aattgagaag atctttaagg tgcggaagac ccctacccfg   900
acacagatcg ccaagctgct gaaggtggac cctacaaaca tcaagggctt ccggacaaag   960
gccaacggta cacctgactt cctgagcatc aagatctacc acgacctgaa aggaatcatc  1020
gacgacaagc aacttctcga cgacatcgca ttcctggaca acgtgccca gattctgaca  1080
gtgtggcagg acagccagag catccaggag aagctgaaga ctctgaacaa gaacctggac  1140
gataagacca tcaaggagat cagcgaactg aagaagtaca cccagaccca cagcctgagc  1200
ctgaagctga acaacgtgct gctgcctgag ctgtgggaa ccacaaaaaa ccagatgcgg  1260
atcctgagcg agctgaagct gaagcccaga aaaatcgacc tgcacaattg caacgagatc  1320
cccgtgaaca tgataaacga cctgatcgtg tccctgtgg tgcggagatc cttgaccaa  1380
agcatcgaga tgatcaacca gattatcaag gactacggcc atcctagaga gatcgttatc  1440
gagctggcca gagaaaaaaa cagcgaggag aagaaaatt tcatcaagag cctgaacgag  1500
aagaacaaac agatcaatga cgaggtgatc gagaactga atgccagcaa ccacagggac  1560
```

```
aacaagggca tgttcaacaa ggtgaagctg tggattctgc aagacggcca ctgcctgtac 1620
agtctgaagc ctatcaggct ggaagacctg cttaacaacc ccaatcacta cgagatcgac 1680
cacatcatcc ctaagagcgt ttctttcgac gatagcatga gcaacaaggt gctggtgtac 1740
cagatcgaga actctaagaa aggcaataga acaccttacc agtacctgac cagcgctgat 1800
aagacaatca catacgagaa gttcaaggct aacatcgcca aactggccaa gtccaaccac 1860
aagattagca agaagaagtt ggattacctg ttagaggaaa gagatatcaa ccggtttcac 1920
atcaagaagg aatttatcaa tcgcaacctg gtggacaccc ggtacgccac cagaagcctg 1980
atcaacctgc tgaaatacta cttcagcgag aagatatta atgtgaaggt caaatccatc 2040
aatggcagct tcacagatta cctgcgtaaa ttgtggaact tcccaaagga tagagaattc 2100
taccacaaac accacgccga ggacgccctc atcatcgcta tggccaacaa gatcttcaca 2160
accaggaaaa tcttcaagga acaaaactcc gtgttctcag atgaacagat tctggatggc 2220
gaggtgacaa atatcctctc tgatgatcag ttccaggctg aattcaccga agagttttac 2280
aaagtgcaag ccatcaagaa atacgacaaa tataaatact cccaccgggt ggacaagaaa 2340
cctaaccggc agcttttga cgacaccctg tacagcacgc tggaattcga gggagaagag 2400
tactacatcg gcaaaattaa ggacatctat aacctgaagg acaaaagact gaaaagatc 2460
ttcaccaaga gccccgagaa gatcctgatg taccaacacg cagccagac cttcaagaag 2520
ctgaagcaga tcatgagaag ctacgaggac gaggtgaacc cctggccaa gtaccacaag 2580
gagacaggcg aatacctgag aaaggagtgc aagaaaggca acggccctat agtgaaatcc 2640
ctgaaatata gagtgactaa gctgggcgtg cacaaggaca tcacccacaa gtacgagaac 2700
agcaagaaca aggtcgtgat ccttagcctg aagcccttca gaatgacgt gttcaaggag 2760
aatggagtct acaagtttat caccatcaga tactgtgacc tgaaggaaac cgtgaactct 2820
tacaccatca gcgagcacct gtacaaggcc aagctaaagg ccaaggacat caagagcatg 2880
gacagcttca gtggtcctt ttacaagaac gacctgttgg aatacaacgg cgagctgtgt 2940
accttcaaag gcgttaacga tgacaagaag aacaagattg aagtgaactg ggtggaaaag 3000
aacttcgcca tatacgccga agaaaaaat ctgaagtcta acaactggt gaagtctatc 3060
accaagagca ccgtgaagtc cctgttaaag tacaccaccg acatcctggg aaacagatac 3120
cccgtgcgga acgagaagct gaagctgatg atccggaagc agaccttag aggcgacctg 3180

SEQ ID NO: 358        moltype = DNA  length = 3270
FEATURE               Location/Qualifiers
misc_feature          1..3270
                      note = source = /note="Description of Artificial Sequence:
                      Syntheticpolynucleotide"
source                1..3270
                      mol_type = other DNA
                      organism = synthetic construct
SEQUENCE: 358
atgaacaatc tgctctacag cttcgacatc ggcactaaca gcatcggctg gtgcgtgttc 60
gccctggatg aggttggcga cccttgtaga atcgttgacc tgggcgcccg gatctacgcc 120
gatggcagag atcctcaaac caagacaagc ctggccgtgg ccagaagaga agcacgggcg 180
atgagccggc gacgggaccg aagcctgcgg aggcgcaagg ccacactgcg gaccatgatc 240
gagtacggcc tgatgcctgc ccacaaggtg aacaggaga cactgctgcg caaaaccggg 300
gacagagaag gaggagcga agggttcaac ccctacgtcc tgaagctag agcccctggc 360
gagaagctgc ctccttttta catcggcaga gccctcttcc acctgggcca gcggagaggc 420
ttcaagagca accggaaaac cgacagaaaa gacaacgaca aaggaaaaat cgcacttgga 480
atcgacgagc tgagagccgc tatgcacaga tctggctccc ctaccctggg cgcctggctg 540
gccatgagaa gagcagacgg ccaccctgtg agactgagga ccggcagcga ggtgttcgat 600
gcagagggat acgcttttta ccccgagaga agcctgctgg aggacgaatt cagacaaatc 660
tggaccgccc aggccgtgca tcaccacaa ctgctgacca gcgagcggcg ggcccatctg 720
ttcagagtga tgttctacca gagacctctg aagaagcccc tggtgggcag atgtagcttc 780
aacccgccg aggctagact gtctagagcc cacccgctgt ttcaggagtt cagactctac 840
aaagaagtga atgacctgga ggtggtgctg cccgaccaga gccacagaaa gctcaccctc 900
gatgaaagaa acgcccctgt agcaaagctg aagagttcta gaaaggcctc tttcagcgtg 960
ctgagacgaa ccctcaagct gacccctgac ctggccttca caaggaaag cgaggcccgg 1020
aaggacctgc tgggcgacga gattaacagc gccctgctg atgccaagat gtttggcgtg 1080
cggtggggcg gctttcctag agcccggcag tgggaaatca tcacacacct gaaggaagaa 1140
gaaacccccg cccggttgag cgactggctg aaaagcgagt tcggcctgga cgacgagcgg 1200
gtggtggcta tcgccaatat cgccctccca gagggatacg gccgtctcgg cgaaacagcc 1260
ctggcatcta tgctggaaga aatgaagacc gccgtcatcc ccgagagcga agctgctaag 1320
cggtgcggct atgatcattc taatctggcc aaggagcagg acgaggggct cgacatcctg 1380
cctgaatatc aggagatcct ggaacggcat attcctcctg gcaccggcga tcccgatgac 1440
atctacgaca tccggaaggg cagaattaca acccctacag tccacatcgg actgaaccaa 1500
ctgagaagag tggtcaacgc cctgatcaag agacacggca gcccaggca tatcgtggtg 1560
gaactggcca gagatctgca actgacgag aaacagaag ccgacgtgaa cagcgactac 1620
gccaaaaaca caagagaggc cgagggcaga tcccagaaac tgatcgagat gggccaactg 1680
gacaccggct acaacggct gctgctgaag ctgtgggagg aactgaatca ggacaagcct 1740
gaggacagag tgtgcatcta ttctgggaag cccatcggaa tcgccatgct gttcagcgga 1800
gaggtggaca ttgatcacat cctgcgcttg tccaagaaccc tggacgatag ccaggccaac 1860
aagctgctgt gcctgaagtc tgctaaccgg caaaagccga acagacccct tagcgacgtg 1920
cctgagtgga gagattgcta cgaggaggtc ctggctagag ccgctaggct gcccaagaac 1980
aagcggtggc ggttcgccgc cgacgccatg cagcagttcg aggcagaagg cggcttcctg 2040
gccagacaac tgaccgacac ccagtacctg tcaagaatgg ccttcgagta cctgagcgct 2100
ctgttcccat ctgaagaggc cgataaatgg gggagctaa cacagcggaa gagagtccac 2160
gtggtgccg gcagctgac cgagctgctg agaagaaact gggactgaa caccctgctg 2220
cctgaccaca acctgggcga gatgcccag gagaagaacc ggaaagatca cagacaccac 2280
gccatcgacg ccgccgtgat cggagtgacc tccagatcgc tgctgcagcg gatgtctgga 2340
gccgccgcaa gacttgacga cgtggccttc gacgacctgg tgcggaccgt ggtgaaggac 2400
aatcctcctt ggcctggctt ccgggaagaa ctgcttggtt gtatcaacag agtcaccgtc 2460
agccacaagc cagaccacgg caccgtgagc agagccgcct acgcacaggg caagggccaa 2520
```

```
acagccggca aactgcacaa cgacacagct tatggaatca ccggactgca ggacatgaag    2580
ggcagcccac tggtggtgcg gagaaagcct tcatggccc tggaagtgaa ggacatcgct    2640
tctatcagag atactgagct gcaatctgcc ctgtacgacg ccatcggatc tctgacagag    2700
aagaaggccc tgcaagaagc cctggtgaga ttcagggaca gacacccgca gtttaagggc    2760
atcagaagag tgcgggtgct ggaagctcta agcgtgatcc ctatcgtgga caacaacgac    2820
aaggcctaca agggctacaa gggcgatgct aattacagat acgaggtttg ggagacactg    2880
gatggcagat ggcacaccga agtggtgtcc atgttcgacg cccaccagcc tggctggcag    2940
agccccttcc accggcaaca ccctgccgcc agaagagtgc tgaaactgca gcagaacgac    3000
atggtggcct acgaacaccc ggccgatggc tacaccatcg ctcgggtggt taagttctcc    3060
aacgacaaga gaatctactt cgcctcccac agagagagcg gaagcctgaa ggccagagac    3120
gccgacaagg gggacccctt cacctacttt gccaaggcca caacggcct gagagacatc    3180
aagtgccggc aagtgaggat cgacgccgcc ggacgggtgt tcgaccctgg acctcaggat    3240
cgagaggcca gacagtctaa gggaagagcc                                     3270

SEQ ID NO: 359         moltype = DNA   length = 3324
FEATURE                Location/Qualifiers
misc_feature           1..3324
                       note = source = /note="Description of Artificial Sequence:
                       Syntheticpolynucleotide"
source                 1..3324
                       mol_type = other DNA
                       organism = synthetic construct
SEQUENCE: 359
atggccattc ggagcatcaa gctcaagctg aagaccagaa ccggtcctga ggctcagaac     60
ctgcggaagg gcatctggag aacccaccgg ctgctgaacg agggcgtggc ctactacatg    120
aagatgctgc tgctcttccg gcaggaatcc actggcgtgc agacaaagaa ggaactgcag    180
gaggaactgg tgcggcacat ccgggagcag cagcagaaaa acagagccga caagaatacc    240
caggccctgc ctctggataa ggccttcgcc gctctgagac aactgtacga gctgctcgtg    300
ccatctgcca tcgccagag cggcgatgcc cagatcatct ctagaaaatt cctgtctcct    360
ttggtggacc ctaacagcga gggcggcaag ggcactagca ggccggagcc caagcccaca    420
tggcagaaaa agaaggaggc caatgaccct acatgggagc aagattacga gaagtggaaa    480
aagcgtagag aggaagatcc taccgccagt gtgataacaa ccctgggaaga atatggaatt    540
agacctatct ttccactgta caccaacacc gtggccgata tcgcctggct gcctctgcag    600
tctaaccagt ttgtccggac atgggatcgg gacatgctgc agcagcccat cgagaggcta    660
ctctcttggg agtcttggaa caagcgggtg caagaggaat acagcaagct gcaggagaag    720
atgacgcaac tgaacgagca actggagggc gacaggagt ggatcagcct gctgaacaa      780
tacgaggaac agagagagca ggagctgatc gaaaacatga ccgccgcaaa cgataaaatac    840
cgcatcacca agcggcagat gaagggctgg aatgagctgt atgagcagtg gtctaccgtg    900
ctgccaatgc ccagccacga gcagtacaga gaggcactga aaagtgca acagcggctg      960
aggggcagat tcggcgacgc tcatttcttc cagtatctga tgaaagaaga caccaacctg   1020
atctggaagg gaaccctca gagaatccac tacttcgtgg ccagaaacga gctgaagaaa    1080
agactggaag aagccaagca gaacgccacc atgaccctgc tgatgccag aaagcaccct   1140
ctgtgggtca gatttgacgc cagaggcggc aacctgcaag actactacct gacggccgaa    1200
gccgacaacc ccagaagcag aaggttcgtg accttcagcc aactgatctg gcctaacgag    1260
agcggctgga tggaaaaaca ggacgtggaa gttgaactgg ccctgagcaa gcagttctac    1320
cagcaagtga cactgcagaa aaacgacaag gggaagcagg aaatcgagtt caaagacaag    1380
ggcagtggca gcaccttcag cggccacctg gcggggagca agtgcaact gggagaagga    1440
gatctggaga aggaagaaaa agactttgaa ggcggcgaaa tcggcagcgt gtacctgaac    1500
atcgtgatcg acttcgagcc actgcaggag gtgaagaacg gccgactgca atctccttac    1560
ggccaggtgc tgcaactggt cagaaggcct aatgagttcc ccaaggtgac cacctacaag    1620
tctggagaac tggtcgagtg gatcaagagc agcaccaagc acagccgcgg cgtgagtcc    1680
ttagagagcg gttttagagt gatgagcatc gacctgggac tgcggaccgc cgccgcaaca    1740
agcatcttct ctgtagagga atccaacgac gccaacgccg cggtttcag ctactggatc    1800
gagggaactc ctctggttgc cgttcataag cggtcatata tgctgaaact gcccggagag    1860
caagtcgaaa agcaggtgcg agagaagcgg gacgagcggg aggatcagca gaagaagagtg    1920
aggttccaaa tcagaatcct gagccaggtg atccggatgg tcaagaagca gaaccgggag    1980
cgggctgatg agctggacca cctgtcccag gccctggaga gcaaaaatc tctgctggac    2040
cagaccgatc ggacctttg gaacggcatc gtgtgcgacc tgacagacgc tctgagagag    2100
aaagagggcg gatgggaaca ggccgtggtc cagatccgag ggaaggccga ggagcacgtg    2160
ggcaaggtgg tgcaagcctg gcggaaacgg ttcgacgccg atgaacgcaa gggcatcgtc    2220
ggcctgtcta tgtggtctat cgaggagctg gacagcctgc ggaagctgct gatctcttgg    2280
agcagaagaa caagaaaccc cagagaaatc aactgcttcg agcagggcca caccagccac    2340
cagcggctgc tgacacacat ccagaacgtg aaggaggacc ggctgaagca actgagccac    2400
gccattgtga tgcagccttt gggctacgtg tacgacgaga gaaattgaa atggtttgcc    2460
aagtaccctg cttgtcaggt gatcctgttc gagaacctgt cccagtaccg gtccaacatg    2520
gacagaagca ccaaagagaa tagcacccta atgaaatggg cccacaggag catccctaag    2580
tacgtgcaca tgcaggccga gccttacggc atccagatcg gcgatgtgcg ggccgagtac    2640
tccagcagat tccacgccaa gacaggacaca cctggcaaga gctgcaagat ggtgtccgga    2700
cacgacctgc aaggcaggcg cttcgagaac ctgcagaagc ggttaatctc tgaacagttc    2760
ctgacagagg agcaagtgaa gcagctcaga cccggcgaca tcgtgcccga cgactccggc    2820
gagtggttca tgaccctgag cgacggcagc gaaggcaaag aggttgtgtt cctcaagcc    2880
gacatcaacc ccgccaaaaa tctgcaaaag agattctggc agcggtacaa cgagctgttt    2940
aaggtctcct gcagagtgct gatccgagga aagaggaat acctgatccc caagacaaag    3000
tccgtgctgg caaaggcctg ttcgtgaaaa aaaccgacac cgtgatgaag                3060
gacgtgtacg tgtgggacag ccaggctaag ctgaagggca aaaaccacat caccgaggag    3120
tccgaaagcc ctgagcaact ggaggatttt caggagatca tcgaagaagc gaagaagct     3180
aagggcacat acagaacact gtttagagac cccagcggga tgttcttccc tgagttcgtg    3240
tggtccaccc agaaagattt ctggtccgag gtgaagagac ggctgtacgg caagctgaga    3300
gagcggttcc tgatgaagac cagg                                           3324
```

| SEQ ID NO: 360 | moltype = DNA length = 3324 |
|---|---|
| FEATURE | Location/Qualifiers |
| misc_feature | 1..3324 |
| | note = source = /note="Description of Artificial Sequence: Syntheticpolynucleotide" |
| source | 1..3324 |
| | mol_type = other DNA |
| | organism = synthetic construct |

SEQUENCE: 360

```
atggccatca gatctatcaa gctgaagctc aagaccagaa caggtcctga ggcccagaac    60
ctgcggaagg gcatttggcg gacacaccgc ctcctcaacg agggcgtcgc ctattatatg   120
aaaatgctgc tgctgttcag acaggagagc acaggcggcc agacaagaa agagctgcag   180
gaagaactgg tccggcacat cagagagcag cagcagaaga atcgggccga agaacacc    240
caggccctgc ctctggacaa ggcttttgcc gctctgcggc agctctacga gctgctggtg   300
ccttcttcta tcggccagag cggagacgcg cagatcatca gcagaaagtt cctgtccct    360
ctcgtggacc ccaacagcga gggcggcaag ggcacatcta agctggcgc aagcctaca    420
tggcagaaaa agaaggaggc caacgacccc acctgggaac aggattacga gaaatggaag   480
aagcggagag aggaggaccc taccgccagc gtgattacca ccctggaaga atacggcatc   540
agaccaatct tcccactgta caccaacacc gtggccgaca tcgcctggct gcctctgcag   600
tccaaccagt tcgtgcggac atgggacaga gacatgctgc agcaggctat cgagagactg   660
ctgagctggg aaagctggaa caagagagtg caagaggaat acatgaggct gcaagagaag   720
atgacacagc tcaacgagca actggagggc ggccaggagt ggatcagcct gctgaacag    780
tacgaggagc aacgggagca ggagctgatc gagaacatga ccgccgctaa cgacaaaatat   840
agaataacaa agcggcagat gaaggcggtg aacgagctgt acgagcagtg gagcaccgtg   900
ctgcccaatg cctctcacga gcagtaccgg gaagcccctta agcgggtcca gcaaagactg   960
cggggcagat tcggcgacgc tcatttcttc cagtatctga tgaaggaaga gcaccacctg  1020
atttggaagg gcaaccccca gagaatccac tactttgtgg ccagaaacga gctgaagaaa  1080
agactggaag aggccaagca gaacgccact atgaccctgc cagacgccag aaagcacccc  1140
ctgtgggtgc ggttcgacgc cagaggcgga aatctgcagt actactacct gaccgccgaa  1200
gccgataacc ccagatctag aagattcgtt acctttagcc agttgatctg gcctaacgaa  1260
tccggctgga tggaaaagca ggacgtggaa gtggaactcg ccctgagcaa gcagttctac  1320
cagcaagtga ccctgcagaa gaacgataag gggaaacagg agatcgagtt taaggacaag  1380
ggctccggat ctacgttcag tggccatctg ggcggggcta agctgcaact ggagcgaggc  1440
gacctggaga agaagagaaa ggactttgag ggcggagaa tcggaagcgt gtacctgaac  1500
atcgtgatcg acttcgagcc cttgcaggag gtgaaaaacg gcagactgca gagcccatac  1560
ggccaggtgc tgcagctcgt tcggagacct aatgagttcc ctaaggtgac cacatacaag  1620
tctgaagaac ttgttgagtg gatgaaggcc agccagaatc acagcagcgg cgtggagtct  1680
ctggagtcgg gcttcagagt gatgagcatc gatctgggac tgaggacagc cgctgccacc  1740
agcattttct ctgtgaaga aagcaacgat gccaacgccg ctggcttcag ctactggatc  1800
gagggcaccc ctctggtcgc cgtgcacaag agaagctaca tgctgaagct gccaggcgaa  1860
caagtggaaa acaggtgcg ggaaaagaga gatgagagac aagaccagca gaggcgcgtc  1920
agatttcaga tcagaatcct gagccaggtg atcaggatgg acagaaaaca aaacagagaa  1980
agagctgacg aactggacca cctgagccag gcactggaga agcagaagtc cctgctcgat  2040
cagaccgata gaacctttctg gaacggcatc gtttgtgacc tgaccgatgc gctgcgcgaa  2100
aaggaggag gctgggagca agccgtggtc caaatccaca gaaaggccga ggaacacgtg  2160
ggcaagtgg tgcaagcctg gcggaaaaga tttgacgcg atgagccgga gggcatcgcc  2220
ggcctgagca tgtggtccat agaagagctg gacagcctcc ggaagctgct cattagctgg  2280
agcagaagga caagaacccc tcaggagatc aacagattcg agcagggcca cactctcac  2340
cagcggctgc tgacacatat ccagaacgtg aggaagata gactgaagca actgagccac  2400
gccatcgtga tgaccgccct gggctacgtg tacgacgaga agaagctgga gtggttcgcc  2460
aaataccccg cctgccaggt gatcctgttc gagaatctgt ctcagtacag aagccacatg  2520
gacagatcca cgaaggaaaa tagcaccctg atgaatgggg cccacagaag catccctaag  2580
tacgtccaca tgcaggccga gccttacgga atccagatcg gagatgtgag agccgaatat  2640
agcaggaggt tccacgccaa gacagggaca cctggcatcc gttgcaagat ggtgaagga    2700
caagaactgc aaggcaagcg attcgagaac ctgcaaaaga gactggtgtc cgaacagttt  2760
ctgaccgagg aacaggtgaa gcagcttcgg cctggagata tcgtgccaga tgacagcgga  2820
gagtggttca tgaccctgag tgatggcagc gaaggcaagg aagtggtgtt cctgcaagcc  2880
gacatcaacg ccgcccagaa ccttcagaaa cgattctggc agagatacaa cgaactgttc  2940
aaggtgtcat gcagagtgct gatcagaggc gaggaagagt acctgatccc caaggccaag  3000
agcgtgcaag ccaaactcgg caagggactg ttcgtgaaga aaccgacac cgtgatgaag  3060
gacgtgtacg tgtgggatag ccaggccaaa ctgaagggca aaacaacctt caccgaggaa  3120
agcgagagcc ctgagcaact ggaggacttc caggagatca tcgaagaagc gaggaagcc  3180
aagggcacct acagaacact gtttagagat cctagcggcg ttttcttccc cgagttcgtg  3240
tggaataccc agaaagactt ctggtccgag gtgaagagaa ggctgtacgg caagctgcgc  3300
gagagattcc tgatgaagac ccgg                                         3324
```

| SEQ ID NO: 361 | moltype = DNA length = 3336 |
|---|---|
| FEATURE | Location/Qualifiers |
| misc_feature | 1..3336 |
| | note = source = /note="Description of Artificial Sequence: Syntheticpolynucleotide" |
| source | 1..3336 |
| | mol_type = other DNA |
| | organism = synthetic construct |

SEQUENCE: 361

```
atggccatta gatccatcaa gctgaaaatg aagaccaact ccggcaccga cagcatctac    60
ctgcggaagg ccctgtggag aacacaccaa ctgatcaacg agggcatcgc ctactacatg   120
aacctgctga cactgtacag acaggaggct attggcgata gaccaagga ggcctaccag   180
```

```
gctgaactga tcaacattat cagaaaccaa cagagaaaca acggcagctc tgaagagcac   240
ggctctgacc aggagatcct ggccctgctc agacaactct acgagctgat cattcccagc   300
agcatcggcg agagcggcga tgccaaccaa ctgggcaaca aattcctgta tcctttagtt   360
gaccccaaca gccagagcgg caagggcaca agcaacgccg gcagaaaacc tagatggaag   420
cggctgaagg aggaaggcaa ccctgactgg gagctgagga agaaaaagga cgaggaacgg   480
aaggctaaag acccaaccgt gaagatcttc gacaacctga caagtacgg cctgctgcct    540
ctgttccccc tgtttaccaa catccagaag gacatcgagt ggctgcctct gggcaaacgc   600
cagagcgtga ggaagtggga caaggatatg ttcatccagg ccatcgagcg gctgctgagc   660
tgggaatctt ggaatcggcg ggtggccgga gagtacaagc aactgaagga aaagaccgag   720
agctactaca aggaacacct gaccggcgga gaggagtgga tcgaaaaaat ccggaagttc   780
gagaaggaga gaaacatgga attagaaaag aacgccttcg cccctaacga cggatacttc   840
atcaccagca gacagatcag gggctgggat agagtttacg agaagtggtc caagctgccc   900
gagagcgcca gcccagaaga actgtggaag gtagtggccg agcagcaaaa caagatgagc   960
gagggattcg gcgaccctaa ggtgttcagc ttcctggcaa ccgagaaaa cagagatatc   1020
tggagaggcc actctgaacg gatctaccac atcgccgcct acaacggcct gcagaagaaa   1080
ctgtccagaa caaaggaaca agccacattc accctgcccg acgccataga acatcctctg   1140
tggatcagat atgagtctcc aggaggcacc aatctcaact gttcaagct ggaggaaaag    1200
cagaaaaaga actactacgt gacctgagc aagatcatct ggcctagcga gggaaatgg    1260
atcgaaaagg aaaatatcga gatcccctg gccctagcca tccagtttaa tagacagatc    1320
aagctgaaac agcacgtgaa aggtaagcaa gagatctcat ttagcgacta cagcagccgg   1380
atcagcctga tggagtgct gggaggctct agaatccagt tcaaccggaa atacatcaag    1440
aaccacaagg aactgttagg agaaggcgat attggtcctg tgttcttcaa cctggtggtg   1500
gacgtggctc ctctgcagga aaccagaaat ggcagactgc agtctcctat cggcaaggcc   1560
ctgaaggtga tctccagcga cttcagcaag gtgatcgact acaagcctaa ggaactgatg   1620
gactggatga ataccggcag cgcctctaat agtttcggcg tggccagcct gctggaaggc   1680
atgcggtaca tgtctatcga catgggacag agaacctcac ctagcgtgtc tattttcgag   1740
gtcgtcaagg agctgcccaa ggaccaggag cagaaactct tctacagcat caacgacacc   1800
gaactgtttg ccatccacaa aagatccttt ctgctgaacc tgcccgggga ggtggtgaca   1860
aagaacaaca agcagcagcg gcaagaaaga gaaagaaga cagttcgt gcggagccag      1920
atccggatgc tggccaatgt gctgagactg gaaacaaaga agacacctga cgagagaaag   1980
aaagccatcc acaagctgat ggaaatcgtg caaagctacg atagctggac agccagccag   2040
aaagaggtgt gggaaaagga gctgaacctg ctgaccaaca tggctgcctt caatgacgag   2100
atctggaagg aaagtctggt cgaactgcac acacagaatcg agcttacgt gggccagatc   2160
gtcagcaagt ggcggaaggg cctgagcgag ggcagaaaga acctggctgg catcagcatg   2220
tggaacattg atgaacttga agatacaaga agactgctta tctcttggaa caagagatct   2280
cggacacctg gcgaggccaa tagaatcgag acagatgaac ccttcggcag cagcctgctc   2340
caacacatcc agaacgtgaa ggacgataga ctgaagcaaa tggccaacct gatcatcatg   2400
accgccctgg gctttaagta cgataaggaa gaaaaggacc ggtacaagcg gtggaaagag   2460
acatacccg cctgtcagat catcctgttc gagaacctga acagtacct gtttaacctg     2520
gacagaagca gacgggagaa cagccggctg atgaaatggg cccaccggtc cattccaaga   2580
accgtgtcca tgcagggcga gatgttcgga ctgcaagtgg gcgatgtgcg gagcgagtat   2640
agctccagat tccacgccaa gaccggagcc ccaggcatca gatgccacgc tctgacagag   2700
gaagatctga aggccggcag caacaccctg aagcggttga tcgaggatgg cttcatcaac   2760
gaaagcgaat ggcctatct gaagaagggc gacattatcc cttctcaagg cggagaactg   2820
ttcgtgaccc tgtctaagag atacaagaaa gacagcgaca caacgagct gactgtgatt   2880
cacgccgaca tcaacgccgc ccagaacctg cagaagcggg tctggcagca aacagcgag    2940
gtgtatagag tgccttgcca actggccaga atgggcaaga taagctcta catccctaag   3000
tctcagaccg agacgatcaa gaagtacttt ggcaaaggca gcttcgtgaa gaacaatacc   3060
gagcaggaag tgtacaagtg ggagaagagc gaaaagatga gattaagac agacaccacc    3120
tttgacctgc aagatctgga cggcttcgag gacattagca gaccatcga gctagctcag    3180
gagcaacaga agaagtacct gactatgttc agagacctt ctggctactt cttcaacaac    3240
gagacatggc gcccccagaa ggagtactgg agctatgtga caacatcat caagtcctgc   3300
ctgaagaaga agattctgag caacaaggtg gaactc                              3336
```

SEQ ID NO: 362            moltype = DNA   length = 3324
FEATURE                  Location/Qualifiers
misc_feature        1..3324
                         note = source = /note="Description of Artificial Sequence:
                         Syntheticpolynucleotide"
source                   1..3324
                         mol_type = other DNA
                         organism = synthetic construct
SEQUENCE: 362

```
atggccatca gatctatcaa gctgaagctc aagaccagaa caggtcctga ggcccagaac    60
ctgcggaagg gcatttggcg gacacaccgc ctcctcaacg agggcgtcgc ctattatatg   120
aaaatgctgc tgctgttcag acaggagagc acaggcggcc agaccaagaa agagctgcag   180
gaagaactgt tccggcacat cagagagcag cagcagaaga tcgggccga caagaacacc    240
caggcccctgc ctctggacaa ggcttttgcc gctctgcggc agtctactga gctgctggtg   300
ccttcttcta tcggccagag caggacgcg cagatcatca gcagaaagtt cctgtcccct    360
ctcgtggacc ccaacagcga gggcggcaag ggcacatctc aagctggcgc caagcctaca   420
tggcagaaaa agaaggaggc caacgacccc acctgggaac aggattacga gaaatgaag    480
aagcggagag aggaggaccc taccgccagc gtgattacca cctgaaga atacggcatc    540
agaccaatct tcccactgta caccaacacc gtggccgaca tcgcctggct gcctctgcag   600
tccaaccagt tcgtgcggaa atgggaaga gactggtgc agcggctgca gagagactg      660
ctgagctggg aaagctggaa caagagagtg caagaggaat acagcaagct gcaagagaag   720
atgcacagc tcaacgagca actggaggc gccaggagt ggatcagct gctgaacag         780
tacgaggagc aacgggagca ggagctgatc gagaacatga ccgccgctaa cgacaaatat   840
agaataacaa agcggcagat gaagggctgg aacgagtgt acgagcagtg agcaccgtg     900
ctgcccaatg cctctcacga gcagtaccgg gaagcccta agcgggtcca gcaaagactg   960
```

```
cggggcagat tcggcgacgc tcatttcttc cagtatctga tgaaggaaga gcaccacctg   1020
atttggaagg gcaaccccca gagaatccac tactttgtgg ccagaaacga gctgaagaaa   1080
agactggaag aggccaagca gaacgccact atgaccctgc agacgccag aaagcacccc    1140
ctgtgggtgc ggttcgacgc cagaggcgga aatctgcagg actactacct gaccgccgag   1200
gccgataacc ccagatctag aagattcgtt acctttagcc agttgatctg gcctaacgag   1260
tccggctgga tggaaaagca ggacgtggaa gtggaactcg ccctgagcaa gcagttctac   1320
cagcaagtga ccctgcagaa gaacgataag gggaaacagg agatcgagtt taaggacaag   1380
ggctccggat ctacgttcag tggccatctg gcgggggcta agctgcaact ggagcgaggc   1440
gacctggaga aagaagaaa ggactttgag ggcggagaaa tcggaagcgt gtacctgaac    1500
atcgtgatcg acttcgagcc cttgcaggag gtgaaaaacg gcagactgca gagcccatac   1560
ggccaggtgc tgcagctcgt tcggagacct aatgagttcc ctaaggtgac cacatacaag   1620
tctgaagaac ttgttgagtg gatgaaggcc agccagaatc acagcagcgg cgtggagtct   1680
ctggagtcgg gcttcagagt gatgagcatc gatctggacc tgaggacagc cgctgccacc   1740
agcatttttct ctgtggaaga aagcaacgat gccaacgccg ctggcttcag ctactggatc   1800
gagggcaccc ctctggtcgc cgtgcacaag agaagctaca tgctgaagct gccaggcgaa   1860
caagtggaaa acaggtgcgg ggaaaagaga gatgagagac aagaccagca gaggcgcgtc   1920
agatttcaga tcagaatcct gagccaggtg atcaggatgg ccagaaaca aaacagagaa    1980
agagctgacg aactggacca cctgaccag gcactgacaga gcagaagtc cctgctcgat    2040
cagaccgata gaacccttctg gaacggcatc gtttgtgacc tgaccgatgc gctgcgcgaa   2100
aaggagggag gctgggagca agccgtggtc caaatccaca gaaaggccga ggaacacgtg   2160
ggcaaggtgg tgcaagcctg gcggaaaaga tttgacgccg atgagcggaa gggcatcgcc   2220
ggcctgaagca tgtggtccat agaagagctg gacagccttc ggaagctgct cattagctgg   2280
agcagaagga caagaaaccc tcaggagatc aacagattcg agcagggcca cctctcac    2340
cagcggctgc tgcacacatat ccagaacgtg aaggaagata gactgaagca actgagccac   2400
gccatcgtga tgaccgccct gggctacgtg tacgacgaga agaagctgga gtggttcgcc   2460
aaataccccg cctgccaggt gatcctgttc gagaatctgt ctcagtacag aagccacatg   2520
gacagatcca cgaaggaaaa tagccgcctg atgaaatggg cccacagaag catccctaag   2580
tacgtccaca tgcaggccga gccttacgga atccagatcg gagatgtgag agccgaatat   2640
agcagcaggt tccacgccaa gacagggaca cctggcatcc gttgcaagat ggtgaaggga   2700
caagaactgc aaggcaagcg attcgagaac ctgcaaaaga gactggtgtc gaacagttt    2760
ctgaccgagg aacaggtgaa gcagcttcgg cctggagata tcgtgccaga tgacagcgga   2820
gagtggttca tgaccctgag tgatggcagc gaaggcaagg aagtggtgtt cctgcaagcc   2880
gacatcaacc ccgccagaa ccttcagaaa cgattctggc agagatacaa cgaactgttc    2940
aaggtgtcat gcagagtgct gatcagaggc gaggaagagt acctgatccc caaggccaag   3000
agcgtgcaag ccaaactcgg caagggactg ttcgtgaaga aaaccgacac ctgtgatgaag   3060
gacgtgtacg tgtgggatag ccaggccaaa ctgaagggca aaacaacctt caccgaggaa   3120
agcgagagcc ctgagcaact ggaggacttc aggagatca tcgaagaagc cgaggaagcc    3180
aagggcacct acagaaacact gtttagagat cctagcggcc ttttcttccc cgagttcgtg   3240
tggaataccc agaaagactt ctggtccgag gtgaagagaa ggctgtacgg caagctgcgc   3300
gagagattcc tgatgaagac ccgg                                          3324

SEQ ID NO: 363          moltype = DNA   length = 21
FEATURE                 Location/Qualifiers
misc_feature            1..21
                        note = source = /note="Description of Artificial Sequence:
                        Syntheticoligonucleotide"
source                  1..21
                        mol_type = other DNA
                        organism = synthetic construct
SEQUENCE: 363
cccagcccta ggttgtttat t                                              21

SEQ ID NO: 364          moltype = DNA   length = 23
FEATURE                 Location/Qualifiers
misc_feature            1..23
                        note = source = /note="Description of Artificial Sequence:
                        Syntheticoligonucleotide"
source                  1..23
                        mol_type = other DNA
                        organism = synthetic construct
SEQUENCE: 364
ctggctacat cttccttgac tac                                            23

SEQ ID NO: 365          moltype = DNA   length = 20
FEATURE                 Location/Qualifiers
misc_feature            1..20
                        note = source = /note="Description of Artificial Sequence:
                        Syntheticoligonucleotide"
source                  1..20
                        mol_type = other DNA
                        organism = synthetic construct
SEQUENCE: 365
gagctgcaca tttgacgagc                                                20

SEQ ID NO: 366          moltype = DNA   length = 20
FEATURE                 Location/Qualifiers
misc_feature            1..20
                        note = source = /note="Description of Artificial Sequence:
                        Syntheticoligonucleotide"
```

```
source                  1..20
                        mol_type = other DNA
                        organism = synthetic construct
SEQUENCE: 366
attacaggtg tgagccacgg                                                       20

SEQ ID NO: 367          moltype = DNA  length = 20
FEATURE                 Location/Qualifiers
misc_feature            1..20
                        note = source = /note="Description of Artificial Sequence:
                        Syntheticoligonucleotide"
source                  1..20
                        mol_type = other DNA
                        organism = synthetic construct
SEQUENCE: 367
accagaacat gcctgatggg                                                       20

SEQ ID NO: 368          moltype = DNA  length = 20
FEATURE                 Location/Qualifiers
misc_feature            1..20
                        note = source = /note="Description of Artificial Sequence:
                        Syntheticoligonucleotide"
source                  1..20
                        mol_type = other DNA
                        organism = synthetic construct
SEQUENCE: 368
gcccctcaat catctctggg                                                       20

SEQ ID NO: 369          moltype = DNA  length = 20
FEATURE                 Location/Qualifiers
misc_feature            1..20
                        note = source = /note="Description of Artificial Sequence:
                        Syntheticoligonucleotide"
source                  1..20
                        mol_type = other DNA
                        organism = synthetic construct
SEQUENCE: 369
cccacccttt gagagtgcat                                                       20

SEQ ID NO: 370          moltype = DNA  length = 20
FEATURE                 Location/Qualifiers
misc_feature            1..20
                        note = source = /note="Description of Artificial Sequence:
                        Syntheticoligonucleotide"
source                  1..20
                        mol_type = other DNA
                        organism = synthetic construct
SEQUENCE: 370
gattgaaggg cagagggagg                                                       20

SEQ ID NO: 371          moltype = DNA  length = 25
FEATURE                 Location/Qualifiers
misc_feature            1..25
                        note = source = /note="Description of Artificial Sequence:
                        Syntheticoligonucleotide"
source                  1..25
                        mol_type = other DNA
                        organism = synthetic construct
SEQUENCE: 371
gagatgtccc cagtgaactc caaat                                                 25

SEQ ID NO: 372          moltype = DNA  length = 25
FEATURE                 Location/Qualifiers
misc_feature            1..25
                        note = source = /note="Description of Artificial Sequence:
                        Syntheticoligonucleotide"
source                  1..25
                        mol_type = other DNA
                        organism = synthetic construct
SEQUENCE: 372
cctgtcgttg cccctcccag atcat                                                 25

SEQ ID NO: 373          moltype = DNA  length = 49
FEATURE                 Location/Qualifiers
misc_feature            1..49
                        note = source = /note="Description of Artificial Sequence:
                        Syntheticoligonucleotide"
source                  1..49
                        mol_type = other DNA
```

```
                        organism = synthetic construct
SEQUENCE: 373
gtctgattgc ctgtcgttgc ccctcccaga tcatggagga gttggcaga           49

SEQ ID NO: 374          moltype = AA   length = 192
FEATURE                 Location/Qualifiers
REGION                  1..192
                        note = source = /note="Description of Artificial Sequence:
                         Syntheticpolypeptide"
source                  1..192
                        mol_type = protein
                        organism = synthetic construct
SEQUENCE: 374
MEPWRPSPRN PMDRIDPNTF RFHFPNLLYA SGRKLCYLCF QVETGDYFSC DDSDRGVFRN   60
KVHPWARCHA EQCFLSWFRD QYPCRDEYYN VTWFLSWSPC PTCAEEVVEF LEEYRNLTLS  120
IFTSRLYYFY HPNYQQGLRK LWDAGVQLDI MSCDDFEHCW DNFVDHKGMR FQRRNLLKDY  180
DFLAAELQEI LR                                                     192

SEQ ID NO: 375          moltype = AA   length = 398
FEATURE                 Location/Qualifiers
REGION                  1..398
                        note = source = /note="Description of Artificial Sequence:
                         Syntheticpolypeptide"
source                  1..398
                        mol_type = protein
                        organism = synthetic construct
SEQUENCE: 375
MQEKEVLNSL RCNTQSIEEE IQINTLLNKT KRNRIKINNL DEFKDVLKKE GYEINEFDEE   60
KPFKEDLVKIF QVDNGVIENL HTYINNPEIS YKVYDTSDLI DYIKKMILFE NEYNRLCKKI  120
SSVKKLDIDR VEYEREFSLQ DNVEDIIKAI EEIKDDISGI ISKEGKTRLE NLEREINKEY  180
LYAKDIELLK KMVIIENENV KEKYNIESKI KTISIKIPKK INYEHIVAKK GSVEYHDYLS  240
SNIPRMQRLI KNIHKYMKVD EKEKSTFKIN QSKALQDSIN IAVATYDNKE PKAISGSNDI  300
KNYCRRTPLE NATFKSSKVN KLGNLGIGYN RVNDSEKKIF EEIHRQIEKN TLKDEGNLIL  360
YTKLEPCPSC YYVISQFCKK HPNIKVQIKY SEKYGEWR                          398

SEQ ID NO: 376          moltype = AA   length = 201
FEATURE                 Location/Qualifiers
REGION                  1..201
                        note = source = /note="Description of Artificial Sequence:
                         Syntheticpolypeptide"
source                  1..201
                        mol_type = protein
                        organism = synthetic construct
SEQUENCE: 376
MEEKKLALVS KIHYELEDKG IELRNLALIH KDRTELLARI KAKSRKRPIY FYRYLEDLPE   60
FLGGNDAVLE YIPNGDNTNK KIYFANSFVN YTDSPFSDIY IEFTDSVYVL IPEDKKFDAI  120
ITNRDREIGN GHLRENDTEY KLMVEISDKI DTTVPGHINI YTYYEPCLSC DNVFIQFSKK  180
FPNVSVNVYF SDEYKSKKWV V                                            201

SEQ ID NO: 377          moltype = AA   length = 237
FEATURE                 Location/Qualifiers
REGION                  1..237
                        note = source = /note="Description of Artificial Sequence:
                         Syntheticpolypeptide"
source                  1..237
                        mol_type = protein
                        organism = synthetic construct
SEQUENCE: 377
MSLLTAETFS LQFNNRRQRR KKGTYYPKRT YLCYQLTPRN GSTPTRGYFK NKKNCHVEIC   60
FIDKIASMEL DKTQCYDVTC YLTWSPCPSC AQKLAAFAKA QDHLNLRIFA SRLYYHWRRS  120
YQKGLQLLWE SQIPVEVMGL PEFTDCWENF VDHGKPPPFN PSEKLQKLGE ASQSIKRRLE  180
RIKVRRCPAA AHCLLTARLG PTPDHASAHC SSPYFFFLLY LFYSIHPIIK YHRLGDS     237

SEQ ID NO: 378          moltype = AA   length = 197
FEATURE                 Location/Qualifiers
REGION                  1..197
                        note = source = /note="Description of Artificial Sequence:
                         Syntheticpolypeptide"
source                  1..197
                        mol_type = protein
                        organism = synthetic construct
SEQUENCE: 378
MAAVTNRDSA CRENNQRWKI QPNDFRRNYL PDKQPRVVYL LYEIRWRRGT IWRNWCSNNP   60
NQHAEVNFLK NYFNAMPSVS CSITWVLSTT PCGKCSIKIM EFLKLHPNVT LEIYAAKLFK  120
HLDIRNREGL RNLAKNGVII HIMNLADYSY WWKIFVTRQH GEEDYLPWSF ALHIFLNCIE  180
FQQILLGLPP LLPNFKY                                                 197

SEQ ID NO: 379          moltype = AA   length = 333
FEATURE                 Location/Qualifiers
```

| | | |
|---|---|---|
| REGION | 1..333 | |
| | note = source = /note="Description of Artificial Sequence: Syntheticpolypeptide" | |
| source | 1..333 | |
| | mol_type = protein | |
| | organism = synthetic construct | |

SEQUENCE: 379
```
MPCVLGLCKH LSETSAVHCP ALLIALRQAV ERLLAPLLQD PLYITATTLD PQFKLSWSNN    60
TDCLQTVMAD RSRIGAKKKE KSDEKALDKD KTKEKNAKKP DKVVKKSEKL PEKTLEKTSE   120
QSKADEESRT TEAEGATGST NEENGEFQPI ELPPFEIVKG EQMSPFYFKF QFRNVEYSSG   180
RNKTLLCYRV DTAGGSTEPL KGYMEDEHTT AHAEEAFFQQ VLPDSSQHHD VTWYVSSSPC   240
ADCAAKLASI LCQRKNLKLC VFCSRLFEWE EPEIVEGLRA LVTAGCKLRM MKPSDFMHVW   300
ETYVDKEEQN FSPWEDCQDN YNYYVEKLAE ILK                                333
```

| | | |
|---|---|---|
| SEQ ID NO: 380 | moltype = AA length = 207 | |
| FEATURE | Location/Qualifiers | |
| REGION | 1..207 | |
| | note = source = /note="Description of Artificial Sequence: Syntheticpolypeptide" | |
| source | 1..207 | |
| | mol_type = protein | |
| | organism = synthetic construct | |

SEQUENCE: 380
```
MAFGNFSNWI NEGVDEIQFT KELYEKLLKH SEQEAISYLF KLSSLEHFNQ WKFYLILLQT    60
LTSKCSDENG AFIRKYLKTR LTQIAALPKR EYMLHLLLSV RAATATTMDI DKNITAYADW   120
YKRNVADMKF VLKVEEFKAI IDLLEQCIPY ESLEDYLEIH ATFSISPPIH CGKLVQSYKS   180
KCKMQLAKIK SKVKQGNEHE ESIVIDD                                       207
```

| | | |
|---|---|---|
| SEQ ID NO: 381 | moltype = AA length = 383 | |
| FEATURE | Location/Qualifiers | |
| REGION | 1..383 | |
| | note = source = /note="Description of Artificial Sequence: Syntheticpolypeptide" | |
| source | 1..383 | |
| | mol_type = protein | |
| | organism = synthetic construct | |

SEQUENCE: 381
```
MTQTEIKIGR KKLRINIKTI DELEKAMKNE GYNVASFENL NVEEFKSEIC NLVNIKPNVA    60
EHIYFNMSQC EREISYRSNN VQDFLDYMEK ITEIKEYEKI LWKKIRKVDK IHIDRIEYDR   120
KPSIQEDVEH MINAIKNVKN TMCGKIDEYE KLRLYELETG IDENYIYAKD IELLKKMIIK   180
DKGKVKNTYD EFTCNKRIYI DIPENMNSSY IKPLEGSIEY HEHISRNIPR IKRLIKNLDK   240
YMKITSDEEG NKVCEINQSK ALQDSINIAV AVYNQKEFKA VSGSDEVDDY CMAMEKEETV   300
FESCRVNRLG KIGIGYNRFY DSEKKILEEI HKQIEEKKLD DRGNLVMYSR WEPCPSCYYV   360
ISQFCSAHPQ IEVSVKFDKS YGE                                           383
```

| | | |
|---|---|---|
| SEQ ID NO: 382 | moltype = AA length = 197 | |
| FEATURE | Location/Qualifiers | |
| REGION | 1..197 | |
| | note = source = /note="Description of Artificial Sequence: Syntheticpolypeptide" | |
| source | 1..197 | |
| | mol_type = protein | |
| | organism = synthetic construct | |

SEQUENCE: 382
```
MVTRVRKFHY SEDTNGQVLR RISKQYKKRI NLTARRKEKN DQDYSFEYRM SYPRFEGGND    60
AVLEYVRPGR TTKVERFLYY ANSAVNDRYS PFAMLGGRRG QYTLIPAEPK FSHFRTTRKR   120
EVNMGTLREN DTEYKLLERV TQDILSQDER GLIRMYTYYE PCLSCDYVMI QFINMYPNIK   180
IDVYYEEDYK PEEKGLI                                                  197
```

| | | |
|---|---|---|
| SEQ ID NO: 383 | moltype = AA length = 373 | |
| FEATURE | Location/Qualifiers | |
| REGION | 1..373 | |
| | note = source = /note="Description of Artificial Sequence: Syntheticpolypeptide" | |
| source | 1..373 | |
| | mol_type = protein | |
| | organism = synthetic construct | |

SEQUENCE: 383
```
MIENPALKIS KRDRIKISNL KDLKNALKNE NYNIKANDKE KFKDEVKKVF NINDDIFERL    60
DKCLNRDITY KVDNVEDFID YIKKIMIFED KHEIICEKLK RIKKLYINRE EYEREKSTRD   120
NVEHIIEVIE KTKENVSRKI SLEELERLEI LEEELEDKYL FAKDIEFLKK MILGNCKNVI   180
ESYNEKTKIK TLKMKIPKEI NYSYIKAKEG SVEYHQYLNN NINRMNRLIK SIDKYIEHYK   240
DDIFNINQSL ALQDSINIAL ATFDNKEFKA ISGKNDIEDY CKVIPIEKSR FKSRKVNKLG   300
ELGIGYNRIN DSEKKILEEI HEKIKQKILK DRGNLTLYTK WEPCPSCYFV ISQFCEKYPN   360
IKVEVKYNKK YGE                                                      373
```

| | | |
|---|---|---|
| SEQ ID NO: 384 | moltype = AA length = 330 | |
| FEATURE | Location/Qualifiers | |
| REGION | 1..330 | |

```
                        note = source = /note="Description of Artificial Sequence:
                            Syntheticpolypeptide"
source                  1..330
                        mol_type = protein
                        organism = synthetic construct
SEQUENCE: 384
MRRKKPSGMY ISKRALKDNF DPHKFPHDTY LLCKLQWGDT GRSWIHWIRK DRYHAEVYFL    60
EKIFKMRRSK NYVNCSITWY LSWSPCVRCC CEILNFLEKH SYVNIDIYVA RLYKIQNSEV   120
REGLKKLVSS KKVTIAVMEI KDYTYCWKNF IQGDADDDSW TVDFQSAITK NRLKLKDVFE   180
FLKSHPNVTL EIYAAKLFKH LDIRNREGLR NLAKNGVIIH IMNLADYSYW WKIFVTRQHG   240
EDDYLPWSFA LHIFLNCIEF QQILLVSRHL KESLRVKSNE KAQEKEVWRI PAMVLAEMIV   300
GKMNRDLMLH EQRANRARNC KGLWCYIVPL                                   330

SEQ ID NO: 385          moltype = AA   length = 195
FEATURE                 Location/Qualifiers
REGION                  1..195
                        note = source = /note="Description of Artificial Sequence:
                            Syntheticpolypeptide"
source                  1..195
                        mol_type = protein
                        organism = synthetic construct
SEQUENCE: 385
MSNVRKYHYS VNSVGEELKK LVEYHKRRTE MYARIKAKNN PSAYRNYLNE LPGFEGGNDA    60
ILIFQVNGNH KSRIRRCANS FVNDSTSSFA NIPVNFTGKY VLIPHPPAQK FSYICTNKHR   120
EIGVGHYRNN DTEYKLLEDI SRRITPTLVG HINLFTFYEP CLSCDYVIIQ FANKYPLITI   180
DVYFEEEYRP ENGVI                                                   195

SEQ ID NO: 386          moltype = AA   length = 202
FEATURE                 Location/Qualifiers
REGION                  1..202
                        note = source = /note="Description of Artificial Sequence:
                            Syntheticpolypeptide"
source                  1..202
                        mol_type = protein
                        organism = synthetic construct
SEQUENCE: 386
MVAIVRKMHY EDNKEGIRLQ RRSRQYKHAM LQMADRKATM DSVYQKVMNL SVLRFTGGND    60
AVLEYSICID PDRNKKLKKP VSRYHANSAV NDMNSPFAKI MGNRIRYTLI PQKSTFIHFH   120
TNRNREINNG TPRENDTEYK LLEKVKEDIH DRYQEGLIRM YTYYEPCLSC DYVIIQFTER   180
YPNIDIEIYY EEEYKPQEKG LI                                           202

SEQ ID NO: 387          moltype = AA   length = 365
FEATURE                 Location/Qualifiers
REGION                  1..365
                        note = source = /note="Description of Artificial Sequence:
                            Syntheticpolypeptide"
source                  1..365
                        mol_type = protein
                        organism = synthetic construct
SEQUENCE: 387
MNPQIRNPME RMYRRTFYYN FENKPILCGR SYTWLCYEVK IRKDPSKLPW DKGVFRGQVL    60
PKFQSNHRQE VYFQLENHAE MCFLSWFCGN QLPANRRFQI TWFVSWNPCL PCVAKVTEFL   120
AEHPNVTLTI SAARLYYYRG RDWRRALRRL HKAGARVKIM DYEDFAYCWE NFVCNEGQPF   180
KPWYKFNDNY AFLHHRLNEI LRNPMEVTYP HIFYFHFENL RKAYGRNETW LCFTMKVIKW   240
PSRVSWKSGV FRNQVAPKPH CHAEMCFLSC PCPECAGEVA EFLARHSNVN LTIFTARLYY   300
FWNTDYQEGL RSLSEEGASV EIMEYKHFKY CWENFVYNDD EPFKPWKGLK TNFRFLERKL   360
WEIIK                                                              365

SEQ ID NO: 388          moltype = AA   length = 204
FEATURE                 Location/Qualifiers
REGION                  1..204
                        note = source = /note="Description of Artificial Sequence:
                            Syntheticpolypeptide"
source                  1..204
                        mol_type = protein
                        organism = synthetic construct
SEQUENCE: 388
MVAKKTKVTK PHYKSNEHGI ELHKMCKAQN EWVLKMAKGR SERNLMYNVK YHLAFPRFKG    60
GNNAVLVHLE YVGKDKNKTR PRAVFPHASSA VDDSDSPFAR VGGGSRRKYA LIPSKPMFKP   120
IRTNRNRDIN HGHFRENDTE YKLLEKVSQY IDDKDEHSLI RMYTDLEPCL SCDYVIIQFT   180
KRYPNINIEV YYKDEYKPKG EGLI                                         204

SEQ ID NO: 389          moltype = AA   length = 242
FEATURE                 Location/Qualifiers
REGION                  1..242
                        note = source = /note="Description of Artificial Sequence:
                            Syntheticpolypeptide"
source                  1..242
                        mol_type = protein
```

```
                        organism = synthetic construct
SEQUENCE: 389
MNPLQEVIFC RQFGNQHRVP KPYYRRKTYL CYQLKLPEGT LIHKDCLRNK KKRHAEMCFI    60
DKIKALTRDT SQRFEIICYI TWSPCPFCAE ELVAFVKDNP HLSLRIFASR LYVHWRWKYQ   120
QGLRHLHASG IPVAVMSLPE FEDCWRNFVD HQDRSFQPWP NLDQYSKSIK RRLGKILTVR   180
SCPCCRHLAS LPLGLPFPAH RPLLSVLALC PQCPSTPFSF LETPVPPVGA PRLPLPSLAP   240
FS                                                                  242

SEQ ID NO: 390          moltype = AA  length = 486
FEATURE                 Location/Qualifiers
REGION                  1..486
                        note = source = /note="Description of Artificial Sequence:
                          Syntheticpolypeptide"
source                  1..486
                        mol_type = protein
                        organism = synthetic construct
SEQUENCE: 390
MNPQIRNPME RMYRPTFYYN FENEPILCRR SYTWLCYEVK IRKDPSKLPW DTGVFRGQMY    60
FQPEYHAEMC FLSWFCGNQL PAYKRFQITW FVSWTPCPDC VAKVAVFLAE HPNVTLTISA   120
ARLYYYWEKD WQRALCRLSQ AGARVKIMDY EEFEYCWENF VYNEGEPFMP WYKFDDNYAF   180
PHRFDANYAF LHHTLKEILR HLMDPDTFTF NFNNDPLVFG RHQTYLCYEV ERLDNGTWVK   240
MDQHRGFLHN QAKDPLYGFD GRHTELCFLG LIPYWQLDLA QTYRVTWFIS WSPCFSWGCA   300
EQVRAFLQEN THMRLRIFAA RIYDYDPLYK EALQMLRGAG AQVSIMTYDE FEHCWDTFVD   360
HQGRPFQPWD GLEEHSQALS GRLQAILLVR ASSLCPVPHR PPPPPLPSGP CLPLCSEPPL   420
GSLLPTGCPA PSLPFLLTAS LSPASRLLPV PSFHSLTSCS IQPSCSSIIR ETEGWASVSK   480
EGRDLV                                                              486

SEQ ID NO: 391          moltype = AA  length = 174
FEATURE                 Location/Qualifiers
REGION                  1..174
                        note = source = /note="Description of Artificial Sequence:
                          Syntheticpolypeptide"
source                  1..174
                        mol_type = protein
                        organism = synthetic construct
SEQUENCE: 391
MEASPASGPR HLMDPHIFTS NFNNGIGRHK TYLCYEVERL DNGTSVKMDQ HRGFLHNQLD    60
PAQIYRVTWF ISWSPCFSWG CAGEVRAFLQ ENTHVRLRIF AARIYDYDPL YKEALQMLRD   120
AGAQVSIMTY DEFKHCWDTF VDHQGCPFQP WDGLDEHSQA LSGRLRAILQ NQGN         174

SEQ ID NO: 392          moltype = AA  length = 189
FEATURE                 Location/Qualifiers
REGION                  1..189
                        note = source = /note="Description of Artificial Sequence:
                          Syntheticpolypeptide"
source                  1..189
                        mol_type = protein
                        organism = synthetic construct
SEQUENCE: 392
MAEKQEEPSN AQNGEPDNAE EGEGKKKKVK REDLPPFEIV TGERLPAIFF KFQFRNVEYS    60
SGRNKTFLCY VVETQGKEAA TSRGYLEDEH AAAHAEMAFF NSILPKCQAG ARHDVTWLFM   120
WEEPEMQAAL RGMKEAGCKL RIMKPQDFEY VWKNFVEPEE GEEAKSFVPW EDIQENFQYY   180
EEKLAEILH                                                           189

SEQ ID NO: 393          moltype = AA  length = 420
FEATURE                 Location/Qualifiers
REGION                  1..420
                        note = source = /note="Description of Artificial Sequence:
                          Syntheticpolypeptide"
source                  1..420
                        mol_type = protein
                        organism = synthetic construct
SEQUENCE: 393
MEPQHPRQRA GMGLASKGGC SQRPRIRNPV EWLDHQTFSF HFRNLRFASG RNCTYLCYQV    60
ERLKHFSPDS SDWGVFQNRV YPETPCHAEL CFLSWFRTKK LSPYEQYRIT WFLSWSPCLP   120
CAEQVAAFLK ENRNVRLSIF AARLYYFWKP DCQQGLRALH QQRAWVRIMS FRDFKYCWKN   180
FVYNQGMPFK PWKKLRKNYQ FLVAKLHEIL GNTMNLLKKH IFRQQFGNQH RVPQPYYRRK   240
TYLCYQLKQL DGFTLDKGCF QNKKQRHAEI RFIDKITSLN LDPNQSYKII CYVTWSPCPT   300
CAKELVDFIN GQDHLSLQIF ASRLYFHWVK VFQRGLQQLQ AAQVSVAVMT RSEFEDCWEE   360
FVDNQGMPFE SWDKLEQYSE SISRRLQKIL SPSNWNNLED SFRDLRLGSP SPSSLRSDSR   420

SEQ ID NO: 394          moltype = AA  length = 252
FEATURE                 Location/Qualifiers
REGION                  1..252
                        note = source = /note="Description of Artificial Sequence:
                          Syntheticpolypeptide"
source                  1..252
                        mol_type = protein
                        organism = synthetic construct
```

```
SEQUENCE: 394
MEDNAAPEPR PLLDQGTFMD HFANEDGGRG LNETYLCYEV QLLDGSSQHQ GFLRNKNFCI    60
DFDPSLRRHA ELCFLDLVPA WRLDPAQHYR VTWFISWSPC FLCAQAVAEF LRRNAHVSLR   120
IFAARIYTWR TDYKAGLQDL QRAGAQIAIM TPAEIQFCWN TFVDNQSNPF HSHLGLGHAK   180
PAPAEGAAEH PPGSLNRAGA LPGASRKKFC IRERRPRTPR TPRTPRRQPS PAVRRRPRRD   240
WSDALRVGMR RF                                                      252

SEQ ID NO: 395           moltype = AA  length = 413
FEATURE                  Location/Qualifiers
REGION                   1..413
                         note = source = /note="Description of Artificial Sequence:
                            Syntheticpolypeptide"
source                   1..413
                         mol_type = protein
                         organism = synthetic construct
SEQUENCE: 395
MAGLGQACEG CCGQMPEISY PMGRLDPKTF SFEFKNLLYA YRRKSSYLCF QVEREQHSSP    60
VPSDWGVFEN QFYHAELRFL NWFRAEKLSP YEHYDVTWFL SWSPCSTCAK KIAIFLSNHK   120
NVRLSIFVSR IYYFWKPAFR QGLQELDHLG VQLDAMSFHD FKYCWENFVD NQGMPFRCWK   180
KVHRNYKFVL RKLNEILRNM NLLSEKTFNY HFGNQLRVKK PQGRRRTYLC YKLKLPNETF   240
DKGYFINKKK NHAEIRFINK IRSLNLDQTQ SYKITCYITW SPCSYCAGKL VALVKSCPHL   300
SLQIFTSRLY YHWLKNQAG LRYLWKINIP VLVMKEPDFA DCWDNFVNHQ SRRFKPWEKL   360
TQYSNSTERR LLRILRINRT DLFLAQSSEQ DPGLNDLVDA IKRLFLDAHR PRD          413

SEQ ID NO: 396           moltype = AA  length = 120
FEATURE                  Location/Qualifiers
REGION                   1..120
                         note = source = /note="Description of Artificial Sequence:
                            Syntheticpolypeptide"
source                   1..120
                         mol_type = protein
                         organism = synthetic construct
SEQUENCE: 396
MAGLGHACEG CCGQMPEISY PMEGLDPETF FFEFQNLLYA YGRKSSYLCF QVEREQHSSP    60
VPSDCGVFKN QVWAPLLSKA GAKPVEDAEK NITCKMPSAS SHNNVQCPGP LMSLPDPPAS   120

SEQ ID NO: 397           moltype = AA  length = 235
FEATURE                  Location/Qualifiers
REGION                   1..235
                         note = source = /note="Description of Artificial Sequence:
                            Syntheticpolypeptide"
source                   1..235
                         mol_type = protein
                         organism = synthetic construct
SEQUENCE: 397
MNSKTGPSVG DATLRRRIKP WEFVAFFNPQ ELRKETCLLY EIKWGNQNIW RHSNQNTSQH    60
AEINFMEKFT AERHFNSSVR CSITWFLSWS PCWECSKAIR KFLDHYPNVT LAIFISRLYW   120
HMDQQHRQGL KELVHSGVTI QIMSYSEYHY CWRNFVDYPQ GEEDYWPKYP YLWIMLYVLE   180
LHCIILGLPP CLKISGSHSN QLALFSLDLQ DCHYQKIPYN VLVATGLVQP FVTWR         235

SEQ ID NO: 398           moltype = AA  length = 378
FEATURE                  Location/Qualifiers
REGION                   1..378
                         note = source = /note="Description of Artificial Sequence:
                            Syntheticpolypeptide"
source                   1..378
                         mol_type = protein
                         organism = synthetic construct
SEQUENCE: 398
MTQENTQLKK KIKKERIRIN NLSDFRAALK KEGYNINGLE EEKFIDKIID ILKLDRSVAK    60
KIFASFKDTA VTYRANDIMD FIDYMKKISL FENEHNKLCE KIRKIEKLSI ARVEYERELK   120
VKDDVEHIIT RIEEIKSDIS EIANHEEKEK LYSLEKEIEK EYLYAKDIEL LKKMLITRKE   180
CSREKYNEET KIKVVSIEIP KDIDYRYIPA QIGTIEYHQH LSNNIPRMQR LTKNINKYMR   240
VHENEKTTFK INQSKALQDS INIALATYDN KEFKAISGSN NIVDYCVAPK EEEAVFKSNK   300
VNKLGELGIG YNRVNDSEKK ILEEIHKQIE EKTLKDEGDL ILLSKWEPCP SCYFVISQFC   360
KMHPQIKVQV KYSKKYGE                                                378

SEQ ID NO: 399           moltype = AA  length = 201
FEATURE                  Location/Qualifiers
REGION                   1..201
                         note = source = /note="Description of Artificial Sequence:
                            Syntheticpolypeptide"
source                   1..201
                         mol_type = protein
                         organism = synthetic construct
SEQUENCE: 399
MEASPASRPR PLMDPHMFTG NFTNNPRVFG LHQTYLCYEV KRQGPDGTRD LMNEQRDFLC    60
NQAKNHFSGS EDHHAERCFL DRIPSWQLDP AQTYRVTCFI SWSPCFSCAQ EVAEFLHENP   120
HVNLRIFAAR IYDYLPRYEE GLQMLQNAGA QVSIMTSEEF GHCWDTFVDR QGHPFQPWEG   180
```

```
LDEHSQALSG RLQAILQNQG N                                                    201

SEQ ID NO: 400            moltype = AA   length = 137
FEATURE                   Location/Qualifiers
REGION                    1..137
                          note = source = /note="Description of Artificial Sequence:
                            Syntheticpolypeptide"
source                    1..137
                          mol_type = protein
                          organism = synthetic construct
SEQUENCE: 400
MHLQVWRKVT EAWREGYTLK PWSRNPMERL YHDYFYHFY  NLPTPKHRNG CYICYQVEGT          60
KNHSRMPLLR GVFENQGLRK LHDAGVHVAI MSYYEFKHCL NDFVFHQGRS FCPWNDLNKN          120
SKNLSNTLED ILQDQED                                                         137

SEQ ID NO: 401            moltype = AA   length = 381
FEATURE                   Location/Qualifiers
REGION                    1..381
                          note = source = /note="Description of Artificial Sequence:
                            Syntheticpolypeptide"
source                    1..381
                          mol_type = protein
                          organism = synthetic construct
SEQUENCE: 401
MKPQTRNTVV RMDPDTFFYN FYNRPILSHR NTVWLCYEVK MKTNDPSRPP LVANIFQGQV          60
SFNPEHHAEM YFLSWFRGNL LPACKRSQIT WFVSWNPCLY CVAKVAEFLA EHPKVTLTVS          120
TARLYCYRKK DWRRALRKLS QTGARVKIMD YEEFQHCWDN FVDNQREPFE PWNALPKHYT          180
LLRITLGEVL RHRMDPVTFT YNFTNDPSVL GQHQSYLCYK VEHLRNGTWV PLHQHRGFIL          240
NEASNSVSFP EGRHAELCLL DLISFWKLKQ AQRYRVTCFI SWSPCFSCAE KVAEFLQENP          300
HVNLHISAAR IYDYQRGYKK GLRRLDRAGT PISMMKYSEF KHCWDTFVDH QGHPFQPWEE          360
LNEHSQALSG RLQAILQNQG N                                                    381

SEQ ID NO: 402            moltype = AA   length = 184
FEATURE                   Location/Qualifiers
REGION                    1..184
                          note = source = /note="Description of Artificial Sequence:
                            Syntheticpolypeptide"
source                    1..184
                          mol_type = protein
                          organism = synthetic construct
SEQUENCE: 402
MYRRKMRGMY ISKRALRKHF DPRNYPRETY LLCELQWRGS HKSWQHWLRN DDSKDCHAEK          60
YFLEEIFEPR SYNICDMTWY LSWSPCGECC DIIQDFLEEQ PNVNINIRIA RLYYADRASN          120
RRGLMELANS PGVSIEIMDA DDYNDCWETF IQPGVYYRFS PENFESAIRR NCSQLEDILQ          180
GLHL                                                                       184

SEQ ID NO: 403            moltype = AA   length = 218
FEATURE                   Location/Qualifiers
REGION                    1..218
                          note = source = /note="Description of Artificial Sequence:
                            Syntheticpolypeptide"
source                    1..218
                          mol_type = protein
                          organism = synthetic construct
SEQUENCE: 403
MHLQVWRKVT EAWREGYTLK PWSRNPMERL YHDYFYHFY  NLPTPKHRNG CYICYQVEGT          60
KNHSRMPLLR GVFENQFFSK KRRHTELCFL SWFRTEKASL DMLLSSGEKY RVTWYISWSP          120
CFACVDEVVK FLREHKNVEL IIFAARLYHS DILQYRQGLR KLHDAGVHVA IMSYYEFKHC          180
LNDFVFHQGR SFCPWNDLNK NSKNLSNTLE DILQDQED                                  218

SEQ ID NO: 404            moltype = AA   length = 338
FEATURE                   Location/Qualifiers
REGION                    1..338
                          note = source = /note="Description of Artificial Sequence:
                            Syntheticpolypeptide"
source                    1..338
                          mol_type = protein
                          organism = synthetic construct
SEQUENCE: 404
MASDKGPSAG DATLRRRIKP WEFEVFFDPR ELRKETCLLY EIQWGTSHKI WRNSGKNTAN          60
HVEINFIEKF TSERQYCPSI RCSITWFLSW SPCWECSKAI RGFLSQHPSV TLVIYVARLF          120
WHMDPQNRQG LRDLINSGVT IQIMRVPEYD HCWRNFVNYL PGKEDHWPRY PVLWMKLYAL          180
ELHCIILPIE MPGKIRDAPN NMEIFSLFVG RYIPKTKPHV TCLLSDVRND DSHLDKTAPK          240
WIRFDSLQPV ASDPSAEHWK MKLPGRDDKT AVVVGTVTED VACAQGAKLY LCALRVHGHA          300
QRHFLKGRDE ILALDQLALD SPQGLWRQPD LRSHPLKG                                  338

SEQ ID NO: 405            moltype = AA   length = 207
FEATURE                   Location/Qualifiers
REGION                    1..207
```

```
                       note = source = /note="Description of Artificial Sequence:
                           Syntheticpolypeptide"
source                 1..207
                       mol_type = protein
                       organism = synthetic construct
SEQUENCE: 405
MQKFTDFLGG IQLGLVRKYH YSVDGVGVAL RDLIYIHKER LEKKARRRAK SSNKMFFEYI    60
TDFLEFEGGN DAILEYIPNG NNKAKRIFCA NSFVNDKTSP FANIRMPYTG QYALIPPKHA   120
QKFNYIITNR ERELGKGHRR ANDTEYKLLE LIASRISPVD VGHINLYTYY EPCLSCDYVI   180
VQFVKKYPNI SINVYFEEEY RPEKGVI                                      207

SEQ ID NO: 406         moltype = AA   length = 194
FEATURE                Location/Qualifiers
REGION                 1..194
                       note = source = /note="Description of Artificial Sequence:
                           Syntheticpolypeptide"
source                 1..194
                       mol_type = protein
                       organism = synthetic construct
SEQUENCE: 406
MKKVKGVSKM HYEQSIDGIN LRVKSDKMKE RVRKNTWIRV KKGIISKREF QEALPFFNSG    60
NDAVLQYTPL GEKIEKKKLF YANSSVSDFK NPFAYLRKYA LMPLEKDQNF NWIHTNRKRE   120
IHTGTPRNVD TEFKLLEKLA KYIDSGDVGT IDLYTYYEPC LSCDYVIIQF TKKYPNIKVN   180
VYFSEEYKPK KGMI                                                    194

SEQ ID NO: 407         moltype = AA   length = 262
FEATURE                Location/Qualifiers
REGION                 1..262
                       note = source = /note="Description of Artificial Sequence:
                           Syntheticpolypeptide"
source                 1..262
                       mol_type = protein
                       organism = synthetic construct
SEQUENCE: 407
MHHSARLPPN CIVSRYANAP WTVLPLPLPP TEAPATGDDT LRRRIEPWEF EAFFNPQELR    60
REACLLYQIT WSSHKVWRET AKNTVDSHVE VNFIQNLTAG RYCRPSTRCS ILWFLSWSPC   120
SSCSKAIRLF LSQHPGVSLV IYVARLFQHM DPQNRQGLRE LIHSGVTIQV MRPQEYDYCW   180
KNFVNYPPGQ EEHWPRYPVQ CMTLYNLELY CIIHNLPPCV RISKQRQSQL AFFSLGLENV   240
HYQRIPPPLL LLTGLVFVFP WK                                           262

SEQ ID NO: 408         moltype = AA   length = 395
FEATURE                Location/Qualifiers
REGION                 1..395
                       note = source = /note="Description of Artificial Sequence:
                           Syntheticpolypeptide"
source                 1..395
                       mol_type = protein
                       organism = synthetic construct
SEQUENCE: 408
MNPQIRNPME GMDRHAFNYN FENEPILYGR SYTWLCYEVK IRKDPSKLPW DTGVFRGQVR    60
PKLQSNRRYE LSNWECRKHV YFQPQYHAEM CFLSWFCGNQ LPAHKRFQIT WFVSWTPCPD   120
CVAKVTEFLA EHPNVTLTIS VARLYYYRGK DWRRALCRLH QAGARVKIMD YEEFAYCWEN   180
FVYNEGQSFM PWDKFDDNYA FLHHKLKEIL RNPMEATYPH IFYFHFPKNLR KAYGRNETWL   240
CFTMEIIKQH STVFWETGVF RNQVYPESLC HAERCFLSWF CEDILSPNTD YRVTWYTSWS   300
PCLDCAGEVA EFLARHSNVK LAIFAARLYY FWDPHYQQGL RSLSEKGASV EIMGYKDFKY   360
CWENFVYNGD EPFKPWKGLK YNFLFLDSKL QEILQ                             395

SEQ ID NO: 409         moltype = AA   length = 191
FEATURE                Location/Qualifiers
REGION                 1..191
                       note = source = /note="Description of Artificial Sequence:
                           Syntheticpolypeptide"
source                 1..191
                       mol_type = protein
                       organism = synthetic construct
SEQUENCE: 409
MNPLQEETFY QQFSNQRVPK PTYQRRTYLC YQLKPHEGSV IAKVCLQNQE KRHAEICFID    60
DIKSRQLDPS QKFEITCYVT WSPCPTCAKK LIAFVNDHPH ISLRLFASRL YPHWRQKYKR   120
ELRHLQKSGI PLAVMSYLEF KDCWEKFVDH KGRPFQPWNK LKQYSESIGR RLQRILQPLN   180
NLENDFRNLR L                                                       191

SEQ ID NO: 410         moltype = AA   length = 198
FEATURE                Location/Qualifiers
REGION                 1..198
                       note = source = /note="Description of Artificial Sequence:
                           Syntheticpolypeptide"
source                 1..198
                       mol_type = protein
                       organism = synthetic construct
```

```
SEQUENCE: 410
MAVEEEKGLL GTSQGWKIEL KDFQENYMPS TWPKVTHLLY EIRWGKGSKV WRNWCSNTLT    60
QHAEVNCLEN AFGKLQFNPP VPCHITWFLS WSPCCQCCRR ILQFLRAHSH ITLVIKAAQL   120
FKHMDERNRQ GLRDLVQSGV HVQVMDLPDY RYCWRTFVSH PHEGEGDFWP WFFPLWITFY   180
TLELQHILLQ QHALSYNL                                                 198

SEQ ID NO: 411           moltype = AA  length = 234
FEATURE                  Location/Qualifiers
REGION                   1..234
                         note = source = /note="Description of Artificial Sequence:
                            Syntheticpolypeptide"
source                   1..234
                         mol_type = protein
                         organism = synthetic construct
SEQUENCE: 411
MDPQRLRQWP GPGPASRGGY GQRPRIRNPE EWFHELSPRT FSFHFRNLRF ASGRNRSYIC    60
CQVEGKNCFF QGIFQNQKKR HAEIRFIDKI NSLNLDQNQC YRIICYVTWS PCHNCAKELV   120
DFISNRHHLS LQLFASRLYF HWVRCYQRGL QRLQANRVSV AVMKGPEFKD CWEKFVDHQG   180
ESFPSWEKLE QYSESISRRL SRILRFANQN NLEDSFRDLR LGSPSPSSSR SDSR         234

SEQ ID NO: 412           moltype = AA  length = 377
FEATURE                  Location/Qualifiers
REGION                   1..377
                         note = source = /note="Description of Artificial Sequence:
                            Syntheticpolypeptide"
source                   1..377
                         mol_type = protein
                         organism = synthetic construct
SEQUENCE: 412
MTKINIISNK RKKERIKINN LNDFKDALKK EGYKINYFDE EKFKIEVAKA FKVENSLIEE    60
LYKCIGEEQA TYRADDVSDL INYMKKIILF EYEHDRLWKK INSIKILNIN RIEYERDTVS   120
RDDVKDMLID IKEVKKRVSR IVSEKEKEKL EILEKELDND YLYSKDIELL KKMLLIKKER   180
VKESYNINTK VKTISIEIPK QIDYHYITPQ KGTVEYHQHL SNNIPRMQRL IKNINKYMKA   240
DEEERSIFKI NQSKTLQDSI NIAVAIYDNK EFKAISGSNN IKDYCHAPTK DESFFKSNKV   300
NKLGEFGIGY DRINDSEKKI IEEIHKQIEA KVLKDEGNLT LYSKWEPCPS CCFVISQFCK   360
KHPNIEVQVK YHKKYGE                                                  377

SEQ ID NO: 413           moltype = AA  length = 356
FEATURE                  Location/Qualifiers
REGION                   1..356
                         note = source = /note="Description of Artificial Sequence:
                            Syntheticpolypeptide"
source                   1..356
                         mol_type = protein
                         organism = synthetic construct
SEQUENCE: 413
MGPVRVCESA VIWAAGTSKA GEPLSWPSTP PGGAGYQRPS LAACTGTRLL TYILREETQH    60
GVPSFSARRA PGSLRQATAV LAAAGDSAMG RHGACPPGCL LDENTFAENY MNQISTRKTY   120
LCYKVEILGG DARVPPDESK GFVQNKGANE PGWPRHAELY FLDRIRSWNL DPGLRYRLTC   180
FISWTPCHTC AQELATFLGE NSHLSLHIFA SRIYSLPGYE AGLRTLQAAG AQIAIMTSQE   240
FEHCWKNFVD HQGRTFEPWD ELEVVSQHLC KKLQEILQAL CVLQEGAHGR LADNEAAFSG   300
AAKLRLSRGG LEPGAWQGAN WRGSPRLWYL SLAGPAGPGT AASALPVAPG AASHYR       356

SEQ ID NO: 414           moltype = AA  length = 211
FEATURE                  Location/Qualifiers
REGION                   1..211
                         note = source = /note="Description of Artificial Sequence:
                            Syntheticpolypeptide"
source                   1..211
                         mol_type = protein
                         organism = synthetic construct
SEQUENCE: 414
MEDFHCVCVY CPLQVSVMSD YQAASSSPDC PQCPQHILTG AEAAVSYSQF CETFGFHMGP    60
SGARALLLFY ELWGPSGTLV QRGQASNLLE VCEEVLYSNY MPCQECSQTL ISFLLRYPWV   120
RLDLLFSQLY HTAPSQTHSL DNQTGLRSLA VLTLSPNSGA AWGHLLRCFV RDVPPSALQL   180
PLLPERVEAD RVNAIHISAT TGIGPAFWTS H                                  211

SEQ ID NO: 415           moltype = AA  length = 230
FEATURE                  Location/Qualifiers
REGION                   1..230
                         note = source = /note="Description of Artificial Sequence:
                            Syntheticpolypeptide"
source                   1..230
                         mol_type = protein
                         organism = synthetic construct
SEQUENCE: 415
MTGAIWNFVH SALMNFLNAM ALLTAETFSL QFNNKRCVSK PYYPRKALLC YQLTRQNGST    60
PTRGYLKNKK KHHAEIRFIK KIESMGLDKT QCYQVTCYLT WSPCPSCAGE LVDFIQAHHH   120
LTLRIFASRL YYHWLGHYQE GLLLLCGSQV PVEVMGLREF TDCWENFVDH EEPPSFNPSE   180
```

```
KLEELDKNSR AIKRRLERIK QSRSVDVLEN GLRSLQLGPV TPSSSRCNSR              230

SEQ ID NO: 416           moltype = AA   length = 267
FEATURE                  Location/Qualifiers
REGION                   1..267
                         note = source = /note="Description of Artificial Sequence:
                             Syntheticpolypeptide"
source                   1..267
                         mol_type = protein
                         organism = synthetic construct
SEQUENCE: 416
MGTPKDTKSR HLAGRCHELH NSRGRSPESD TMASEKGPSN KDYTLRRRIE PWEFEVFFDP   60
QELRKEACLL YEIKWGASSK TWRSSGKNTT NHVEVNFLEK LTSEGRLGPS TCCSITWFLS  120
WSPCWECSTA IREFLSQHPG VTLVIFVARL FQHMDRRNRQ GLKDLVTSGV TVQVMSVSEY  180
CYCWENFVNY PPGKAAQWPR YPPRWMLMYA LELYCIILGL PPCLKISRRH QKQLTFFSLT  240
PQYCHYKMIP PYILLATGLL QPSVPWR                                     267

SEQ ID NO: 417           moltype = AA   length = 399
FEATURE                  Location/Qualifiers
REGION                   1..399
                         note = source = /note="Description of Artificial Sequence:
                             Syntheticpolypeptide"
source                   1..399
                         mol_type = protein
                         organism = synthetic construct
SEQUENCE: 417
MTNPQIRNMV KRMKPGIFVS NFNNKPILSG RNTVWLCCEV KTKDPSGPPL DAKIFRDKVY   60
SKAKYHPEMR FLRWFRKWRQ LHRDQEYEVT WYVSWSPCTG CANSVATFLA EDPKVTLTIF  120
VARLYYFWKP DYQEALRVLC QKRGSPHATM KIMNYNEFQH CWNKFVRGRR EPFEPWENLP  180
KHYTLLHATL GELLRHLMDP GTFTSNFNNK LWVSGQHETY LCYKVERPHN DTWVLLNQHR  240
GFLQNQAPDI HGFPKGRHAE LCFLDLIPFW KLDDQQYRVT CFTSWSPCFN CAQEMAKFIS  300
DNKHVSLRIF AARIYDDQGR CQEGLRTLHR DGAKIAMMNY SEFEYCWDTF VDRQGRPFQP  360
WDGLDEHSQD LSGRLRAILQ VTASSLFQGN KIMIPVSSW                         399

SEQ ID NO: 418           moltype = AA   length = 396
FEATURE                  Location/Qualifiers
REGION                   1..396
                         note = source = /note="Description of Artificial Sequence:
                             Syntheticpolypeptide"
source                   1..396
                         mol_type = protein
                         organism = synthetic construct
SEQUENCE: 418
MQPQGLGPNA GMGPVCLGCS HRRPYSPIRN PLKKLYQQTF YFHFKNVRYA WGRKNNFLCY   60
EVNGMDCALP VPLRQGVFRK QGHIHAELCF IYWFHDKVLR VLSPMEEFKV TWYMSWSPCS  120
KCAEQVARFL AAHRNLSLAI FSSRLYYYLR NPNYQQKLCR LIQEGVHVAA MDLPEFKKCW  180
NKFVDNDGQP FRPWMRLRIN FSFYDCKLQE IFSRMNLLRG DVFYLQFNNS HRVKPVQNRY  240
YRRKSYLCYQ LERANGQEPL KGYLLYKKGE QHVEILFLEK MRSMELSQVR ITCYLTWSPC  300
PNCARQLAAF KKDHPDLILR IYTSRLYFYW RKKFQKGLCT LWRSGIHVDV MDLPQFADCW  360
TNFVNPQRPF RPWNELEKNS WRIQRRLRRI KESWGL                           396

SEQ ID NO: 419           moltype = AA   length = 367
FEATURE                  Location/Qualifiers
REGION                   1..367
                         note = source = /note="Description of Artificial Sequence:
                             Syntheticpolypeptide"
source                   1..367
                         mol_type = protein
                         organism = synthetic construct
SEQUENCE: 419
MCPRCPRHVR VGSDSRVPYR EFCRSFGYPV ALARSAPWPG DDGALLGFYE LRGTGGPLVQ   60
RGHATGCAAR GHHPETLLFD AEGHLDSVLL TLGLGHGAAT RVALFSSHAP CGHEALGCVS  120
RILGFLEAHP GVRLEMYFAQ FESGFAEAGR GYHRPPYGHR DGTDEGGSLR DLVSLRPRVT  180
VAPISGGMWG KILRDFVSNV PPLALMNPVN HLRAREDSEN AARLAGITGV WPPYVDLAPV  240
PSKKSFSSSS PSSSSFPSSS SFPSSSSSTT SPLLGLFPTL DTFVVTVLTP AQTYAWPQAW  300
TPNWRQPQPQ VVRHMTLPDL PPPPKQKEKT IQEMLPPNGI IKDFTITQEK PVKQSADTTG  360
KSDRGKK                                                           367

SEQ ID NO: 420           moltype = AA   length = 230
FEATURE                  Location/Qualifiers
REGION                   1..230
                         note = source = /note="Description of Artificial Sequence:
                             Syntheticpolypeptide"
source                   1..230
                         mol_type = protein
                         organism = synthetic construct
SEQUENCE: 420
MAAGPAPEAR SLMDEQTFLD NFNNLKYPRK TYLCYEVELL VGENHIPLDD YKGFVHNEGF   60
DMGLERCHAE LIFLERMASW NLDTELRYRI TVFISWSPCP ECADELVKFL RENRHVNLRI  120
```

```
FAARIYDWYQ GYEAGLRALK AAGAEVAMMT LHEFEYCWNN FVDHQQDEDT PFPPWDNLVA   180
RSEELSQRLE GILQPSVLVF CWPSQVSVTA AHSDIMSQAS RAWEKRRDPP              230

SEQ ID NO: 421          moltype = AA  length = 175
FEATURE                 Location/Qualifiers
REGION                  1..175
                        note = source = /note="Description of Artificial Sequence:
                         Syntheticpolypeptide"
source                  1..175
                        mol_type = protein
                        organism = synthetic construct
SEQUENCE: 421
MIHVDQLLEA DRIHHETWMQ EALKEADKAL VLDEVPIGAV LVYQGQIVGR GHNVRESQER   60
ALGHAELMAI ETANQQLGHW RLEEASLYVT LEPCPMCAGA LMNCRIKEVI YGASDLKAGC   120
AGTLMNLLEE DRFNHRAQVI QGVLEQECSH KLSQFFKDLR QRKKMSKARQ TEHKE        175

SEQ ID NO: 422          moltype = AA  length = 156
FEATURE                 Location/Qualifiers
REGION                  1..156
                        note = source = /note="Description of Artificial Sequence:
                         Syntheticpolypeptide"
source                  1..156
                        mol_type = protein
                        organism = synthetic construct
SEQUENCE: 422
MKLNQEEMDR YWMREALLLA EEAGKLGEVP IGAVIVRNGE KIGQGYNRRE VDKNPLAHAE   60
ILAIQEASRT LKGWRLNGTT LYVTLEPCPM CGGAILQSRI PRLVFGARDP KAGAAGSILD   120
LMHEPRFNHQ VEVVEGVLAE EAGALLTQFF RRLRQR                             156

SEQ ID NO: 423          moltype = AA  length = 161
FEATURE                 Location/Qualifiers
REGION                  1..161
                        note = source = /note="Description of Artificial Sequence:
                         Syntheticpolypeptide"
source                  1..161
                        mol_type = protein
                        organism = synthetic construct
SEQUENCE: 423
MSLKQSKEDI FFMEQALVEA EKAMEIGEVP IGAIIVRDNV IIARGHNLRE QQQMVTNHAE   60
LIAIQKACEE VGSWRLEDCT LYVTLEPCPM CAGAIVQSRM KRVVYGAADP KAGCCGSLMN   120
LLDEPRLNHQ VYVTSGLYEE ESSRLLKDFF KKLRQKKKGT D                       161

SEQ ID NO: 424          moltype = AA  length = 181
FEATURE                 Location/Qualifiers
REGION                  1..181
                        note = source = /note="Description of Artificial Sequence:
                         Syntheticpolypeptide"
source                  1..181
                        mol_type = protein
                        organism = synthetic construct
SEQUENCE: 424
MQQQKGKEKL TDQERFMKEA IRQAKKAEAL EEVPIGCVIV HEGKIIARGY NRRNTDKNTL   60
SHAELNAIRK ASKKLGDWRL EGCTMYVTLE PCQMCSGALV QSRIDEVVIG CMNAKAGCAG   120
SVMNLLQVDG FNHQVKIIQG VLEEECSSML SEFFRKLREK KKQEKAALKA AQENPEGEPE   180
Q                                                                   181

SEQ ID NO: 425          moltype = AA  length = 189
FEATURE                 Location/Qualifiers
REGION                  1..189
                        note = source = /note="Description of Artificial Sequence:
                         Syntheticpolypeptide"
source                  1..189
                        mol_type = protein
                        organism = synthetic construct
SEQUENCE: 425
MNKITLNRGS MEENINFTDA ERTAMNLALE LAGKARERGD VPIGAVILYD GLKPDSPMGR   60
LCREKGIFPG EILGTGFNQR NFHGNALCHA EILAIEEACK KIGDWRLEDC TLYVNLEPCP   120
MCAGAILQAR IPRLQMSVRN PKAGFCGSVM NILQMKELNH RVEITEGLQA EEARKLLQDF   180
FAKLRLKEE                                                           189

SEQ ID NO: 426          moltype = AA  length = 164
FEATURE                 Location/Qualifiers
REGION                  1..164
                        note = source = /note="Description of Artificial Sequence:
                         Syntheticpolypeptide"
source                  1..164
                        mol_type = protein
                        organism = synthetic construct
SEQUENCE: 426
```

```
METAFDLAKE ALAANEVPIG CSFVYNGKVV ASGRNHVNEY RNASLHAEIL AIMELEQWCA    60
IQNLDFAEVL SQSILYVTAE PCIMCAAALR FSLPGQPLKI VYSAKNERFG GCGSVLSIHS   120
DPSPYPILVC EVDNRSDESI DLLKQFYKLE NANAPESKRI KKRQ                    164

SEQ ID NO: 427           moltype = AA  length = 184
FEATURE                  Location/Qualifiers
REGION                   1..184
                         note = source = /note="Description of Artificial Sequence:
                           Syntheticpolypeptide"
source                   1..184
                         mol_type = protein
                         organism = synthetic construct
SEQUENCE: 427
MREGNDEREV TERHEWFMRI ALDQAEKALR DKEVPVGCVF VHADSGTVLA TGANETNISL    60
NGTRHAEFVG VDAILKQHPA SILQETVLYV TVEPCVMCAA ALRQLQIKHV YFGCGNDRFG   120
GCGSVFSVHS DPVGRSVETP GYPVTSGIFS KEAIMLLRRF YLLQNDTAPN PALKAMRVLK   180
EVED                                                                184

SEQ ID NO: 428           moltype = AA  length = 180
FEATURE                  Location/Qualifiers
REGION                   1..180
                         note = source = /note="Description of Artificial Sequence:
                           Syntheticpolypeptide"
source                   1..180
                         mol_type = protein
                         organism = synthetic construct
SEQUENCE: 428
MEQLKNESET ELQNQSEAEM RDEKYMKEAL KQAKKAYALE ETPIGCVIVH EGKIIARGYN    60
RRNTDKSPLA HAEISAIKKA SKKLGDWRLE ECTLYVTLEP CQMCAGAIIQ SRIPRVVVGC   120
MNPKAGCAGS VLNLLDVQAF NHQAEVKTKV LEEECSLMMK QFFRELRAKQ KMKKKSLLSE   180

SEQ ID NO: 429           moltype = AA  length = 176
FEATURE                  Location/Qualifiers
REGION                   1..176
                         note = source = /note="Description of Artificial Sequence:
                           Syntheticpolypeptide"
source                   1..176
                         mol_type = protein
                         organism = synthetic construct
SEQUENCE: 429
MVGGRSSRGR RSPCRLCVCQ RWPSDRSSKE SDQRMAQCKG SSHPLDIMRG RPVNEQATLH    60
AELEAIDHLL PTNPAPLSSI TLYVTVEPCV MCASALRQIG IGRVIYGCGN DRFGGCGSVI   120
NVNSSCVSPL DVLLCPNPPR EMLDTHPPFV AEGGFYREEA IMLLRRFYMS ENQNGQ       176

SEQ ID NO: 430           moltype = AA  length = 209
FEATURE                  Location/Qualifiers
REGION                   1..209
                         note = source = /note="Description of Artificial Sequence:
                           Syntheticpolypeptide"
source                   1..209
                         mol_type = protein
                         organism = synthetic construct
SEQUENCE: 430
MEGTAAASAA GDGSHAVSAE ETAKWMEEAM RMAKEALKNT EVPVGCLMVY NNEVVGKGRN    60
EVNQTKNATR HAEMVAIDQV LDWCRENDLR PSAVFEHTVL YVTVEPCIMC AAALRLMSIL   120
WPCKFKPCSF PNERFGGCDI ASADLPNTGD NFRVLHTFSW AWFILLFSFH QCIPGYRAEE   180
AVELLKTFYK QENPNAPKSK VRKKECQKP                                     209

SEQ ID NO: 431           moltype = AA  length = 181
FEATURE                  Location/Qualifiers
REGION                   1..181
                         note = source = /note="Description of Artificial Sequence:
                           Syntheticpolypeptide"
source                   1..181
                         mol_type = protein
                         organism = synthetic construct
SEQUENCE: 431
MPVMIVEKKS IARSHEYWMQ RAIAEAGKAR SRDEVPIGCV IVRDNRIIAR GHNLRESSQD    60
PSAHAEMIAI RKAARKLSSW RLLDTTLYVT LEPCTMCMGA IILSRIPRVV FGCLDPKGGA   120
AGSLYDLSND PRLNHRVELL PGVLERDCSS LLSGFFAELR RRRREARLSS AGELPGTPQG   180
C                                                                   181

SEQ ID NO: 432           moltype = AA  length = 160
FEATURE                  Location/Qualifiers
REGION                   1..160
                         note = source = /note="Description of Artificial Sequence:
                           Syntheticpolypeptide"
source                   1..160
                         mol_type = protein
```

```
                                   -continued
                    organism = synthetic construct
SEQUENCE: 432
MLSSEDNKWM KLALDEADKA EKIGEVPIGA VIVKGEEIIA TAYNRREVDA QATAHAELIA   60
IQKACQHLDA WRLSGCTLYV TLEPCPMCAG AIIQSRIDRV VFGAYDPKAG CAGSLMNLLQ  120
DERFNHQTEV DCGCLADECG GKLSTFFRAL RQKKKGLKQK                        160

SEQ ID NO: 433          moltype = AA  length = 153
FEATURE                 Location/Qualifiers
REGION                  1..153
                        note = source = /note="Description of Artificial Sequence:
                           Syntheticpolypeptide"
source                  1..153
                        mol_type = protein
                        organism = synthetic construct
SEQUENCE: 433
MVGCVFAIES DIIAESRNSV NATHNPTRHA EINCIDYVIE YCKANNIDYR LYFKNVTVYV   60
TVEPCIMCAA ALSNLGVKEV VYGCANDRFG GKTVLDISNF YEHNYNLIGN LMANEAMALL  120
KQFYKGANPN APESKVKKKQ KKRQKAASAT LRS                               153

SEQ ID NO: 434          moltype = AA  length = 169
FEATURE                 Location/Qualifiers
REGION                  1..169
                        note = source = /note="Description of Artificial Sequence:
                           Syntheticpolypeptide"
source                  1..169
                        mol_type = protein
                        organism = synthetic construct
SEQUENCE: 434
MTEHEKFMNA ALKLARKAAA EGEVPVGCVV VRDGVIVGRG RNRRETKKDA LGHAEIEAIH   60
KACKKLGGWR LHQCDLYVTL EPCPMCTGAI INARIKTVYY GAPDLKAGSC GSVVNLFDLP  120
YNHKPELVSG LMEQECTEEL QKFFRQLRER KKLEKQLRKQ AQMNDLNEI             169

SEQ ID NO: 435          moltype = AA  length = 165
FEATURE                 Location/Qualifiers
REGION                  1..165
                        note = source = /note="Description of Artificial Sequence:
                           Syntheticpolypeptide"
source                  1..165
                        mol_type = protein
                        organism = synthetic construct
SEQUENCE: 435
MDQGTHEKWM NVALEEAAKA EEIGEVPIGA VIIKEGKLIA SAYNLREANH SALAHAELLA   60
IEQANKKLGA WRLEGCTLYV TLEPCPMCAG AIVQSRIPTV VYGAQDQKAG CAGTLMNLLQ  120
EQRFNHRCEV ISGVLEEGCG EKLSAFFRKL RADQKRKKQD LQEGR                  165

SEQ ID NO: 436          moltype = AA  length = 149
FEATURE                 Location/Qualifiers
REGION                  1..149
                        note = source = /note="Description of Artificial Sequence:
                           Syntheticpolypeptide"
source                  1..149
                        mol_type = protein
                        organism = synthetic construct
SEQUENCE: 436
MDEMYMSLAL EEAYKAFSTY EVPVGAVIVH DSKVISRGYN KRETLKDPTA HAEIIAIKEA   60
SKYLGGWRLI GCTMYVTLEP CSMCAGAIIN SRIERLVIGA KDPKRGCCGS VINLLDNPNF  120
NHKVEVEFGI LKDKCSNILT EFFKQIRCK                                    149

SEQ ID NO: 437          moltype = AA  length = 179
FEATURE                 Location/Qualifiers
REGION                  1..179
                        note = source = /note="Description of Artificial Sequence:
                           Syntheticpolypeptide"
source                  1..179
                        mol_type = protein
                        organism = synthetic construct
SEQUENCE: 437
MRELPYSPEE LMRLAIREAK KAERNGDVPI GCLIVYDGRL PGSRADQRAE EQSIRPGEII   60
GRGYNRRNRD KSALKHAEIS AISKACRRLG DWRLEDCTMI VTLEPCPMCA GAILQARIPR  120
LLFGAENPKA GFCGSVLDIL QLSALNHRVE LLPPVLREDC KRLMTDFFGR LRAHSDSEE   179

SEQ ID NO: 438          moltype = AA  length = 194
FEATURE                 Location/Qualifiers
REGION                  1..194
                        note = source = /note="Description of Artificial Sequence:
                           Syntheticpolypeptide"
source                  1..194
                        mol_type = protein
                        organism = synthetic construct
```

```
SEQUENCE: 438
MVSHLSYKAE EALIAREIPV GCVFVRNNEI IARGRNRTNE TRNVRPSSLS FLSLSNTHES   60
QASIHAELAA LSHILPNGSS RRQFEPLTDV TLYVTVEPCL MCASALRQVG IRKVIYGCAN  120
DRFGGCGGVL EIHNKYALFT SFHRAISMTR VPAPSCYIRN HWKLLEVTSA KRRSCFSGGS  180
TSLRTRRVSM TWHL                                                   194

SEQ ID NO: 439          moltype = AA  length = 159
FEATURE                 Location/Qualifiers
REGION                  1..159
                        note = source = /note="Description of Artificial Sequence:
                          Syntheticpolypeptide"
source                  1..159
                        mol_type = protein
                        organism = synthetic construct
SEQUENCE: 439
MERLQIKNDI EGMKEALIEA KKAFAIGEIP IGAIICDDKG NIISRGHNLR EKTFDATAHA   60
EIVAIRKACT KLQNWRLSDL TLYVTVEPCP MCAGAIFSSR LKRLVYGATD WRAGGCESVF  120
NIVNNHWLNH QTQIRAGVLE DECSLLVKKF FQTRRQNHN                         159

SEQ ID NO: 440          moltype = AA  length = 168
FEATURE                 Location/Qualifiers
REGION                  1..168
                        note = source = /note="Description of Artificial Sequence:
                          Syntheticpolypeptide"
source                  1..168
                        mol_type = protein
                        organism = synthetic construct
SEQUENCE: 440
MVNSSWERTA DKMHEEFMRA AIEEAKKAEA IGEVPIGAVI VHDGGIIARA HNRRETSQNP   60
LTHAEIIAID AASEKIGSWR LEDCTLYVTL EPCVMCSGAI VMSRIPHVVY GAKDPKGGTV  120
ESLMHLLDEP RFNHRAYITA GVLGEECSSM LTLFFRKLRG RRKRRAED               168

SEQ ID NO: 441          moltype = AA  length = 182
FEATURE                 Location/Qualifiers
REGION                  1..182
                        note = source = /note="Description of Artificial Sequence:
                          Syntheticpolypeptide"
source                  1..182
                        mol_type = protein
                        organism = synthetic construct
SEQUENCE: 441
MDSWMEEAFV QANEALQVGE VPVGCVFVFN DQVIARSRNT VNETHNATRH AEMNCVDQTV   60
TWCKETSHDF DEVMSAVKVW VTVEPCIMCA AALHSLRVAE VVVYGCNNDRF GGCTSVFDTS  120
LLYSPATPMK GGMQSDRAMQ LLKDFYKGTN PNAPQPKVKK DKKVASISDV SEIQHNKEAS  180
DS                                                                182

SEQ ID NO: 442          moltype = AA  length = 178
FEATURE                 Location/Qualifiers
REGION                  1..178
                        note = source = /note="Description of Artificial Sequence:
                          Syntheticpolypeptide"
source                  1..178
                        mol_type = protein
                        organism = synthetic construct
SEQUENCE: 442
MSGKVNDLNK DISNNVDLEE SYDSKKANKY MKEAIKQAKK AASIGEVPIG CVIVYQDKII   60
GRGYNRRMVD KNTLSHAELN AIKKASKKLD DWRLDDCELY VTTEPCQMCA GAIVQARIKK  120
VYIGCMNPKA GCAGSIMNLL QVDKFNHQVE MEKGILEEEC SNLLKDFFRN LRKKQKDE    178

SEQ ID NO: 443          moltype = AA  length = 169
FEATURE                 Location/Qualifiers
REGION                  1..169
                        note = source = /note="Description of Artificial Sequence:
                          Syntheticpolypeptide"
source                  1..169
                        mol_type = protein
                        organism = synthetic construct
SEQUENCE: 443
MDYTIEEKAM FMREALKEAE IALANDEIPI GCVLVKDGQI IGRGHNAREE LQRAVMHAEI   60
MAIEEANQRE NSWRLLDTTL FVTIEPCVMC SGAIGLARIP QVIYGATNQK FGGAGSLYDI  120
LADERLNHRV EVETGILEAE CAAIMQTFFR QGRERKKQAK LAAKAETQE              169

SEQ ID NO: 444          moltype = AA  length = 165
FEATURE                 Location/Qualifiers
REGION                  1..165
                        note = source = /note="Description of Artificial Sequence:
                          Syntheticpolypeptide"
source                  1..165
                        mol_type = protein
```

```
                          organism = synthetic construct
SEQUENCE: 444
MNQSDEHYM RRALDLARQA EQLGEVPVGA VVVLNGKVIA AAGNRRETWQ DPTAHAELIA    60
LREAAKRIDS WRLEEATLYV TLEPCIMCMG GIILSRIPRL VFGARDPRVG AVGSVFDLAD   120
DERFNHRVEV SEGVLAEECS EILSNFFRQL RQKKKAARMR SAKDE                  165

SEQ ID NO: 445           moltype = AA  length = 190
FEATURE                  Location/Qualifiers
REGION                   1..190
                         note = source = /note="Description of Artificial Sequence:
                           Syntheticpolypeptide"
source                   1..190
                         mol_type = protein
                         organism = synthetic construct
SEQUENCE: 445
MNLNMQMKPK ALGRISTKGL TQEEIQDIKF MKAAITQARK AYVLGEVPIG CVIVYEGKII    60
GRGYNRRNTD KTTLAHAEIT AIKRAGKVIG DWRLEGCKLY VTLEPCQMCA GAIVQARIPE   120
VIMAAENPKA GCAGSVLDIL NNPGFNHQVQ VKRGVLKDEC AKMLKEFFVE LRARNKAEKE   180
LKSSQGLDEN                                                         190

SEQ ID NO: 446           moltype = AA  length = 168
FEATURE                  Location/Qualifiers
REGION                   1..168
                         note = source = /note="Description of Artificial Sequence:
                           Syntheticpolypeptide"
source                   1..168
                         mol_type = protein
                         organism = synthetic construct
SEQUENCE: 446
MSSHPKDEYY MSLAIAEARK AEAIGEVPIG AVLVIDDEVV AAAYNLRESE HRAIAHAELL    60
AIDQACKKTG AWRLSGSTLY VTLEPCAMCA GAIVLSRVDR VVFGAHDPKA GCAGSLMNLL   120
EEEERFNHVCD VTTGVRKEEC SAMLSTFFRT LRQRNKEKRK QRLGDKQP               168

SEQ ID NO: 447           moltype = AA  length = 127
FEATURE                  Location/Qualifiers
REGION                   1..127
                         note = source = /note="Description of Artificial Sequence:
                           Syntheticpolypeptide"
source                   1..127
                         mol_type = protein
                         organism = synthetic construct
SEQUENCE: 447
MSYDLSRHFK YMAISLFVGY KALLNNETPV SCIVVNSKTD EIISIGYNYT NHSLNGTQHA    60
EFIALQRFES DESINYSDLI LYVTVEPCIM CASYLRQLGI GKVIFGCGND RFGGNGSIAS   120
TQRSKFT                                                            127

SEQ ID NO: 448           moltype = AA  length = 164
FEATURE                  Location/Qualifiers
REGION                   1..164
                         note = source = /note="Description of Artificial Sequence:
                           Syntheticpolypeptide"
source                   1..164
                         mol_type = protein
                         organism = synthetic construct
SEQUENCE: 448
MTIDEKYMRA AIRQAEKAGA MGEVPIGCVI VYEDKIIARG YNRRTIDKNV LSHAEINAIR    60
KACRKVGDWR LEGCTMYVTL EPCPMCAGAI VQARIPKVIM GCMNAKAGCA GSVLDLFHQD   120
GLNHQVETES GVLGDECSRL MKDFFKALRE KSKKKPEGIS FITP                   164

SEQ ID NO: 449           moltype = AA  length = 177
FEATURE                  Location/Qualifiers
REGION                   1..177
                         note = source = /note="Description of Artificial Sequence:
                           Syntheticpolypeptide"
source                   1..177
                         mol_type = protein
                         organism = synthetic construct
SEQUENCE: 449
METVQFDHDS HNPIQAEHEK WMREAMLEAD KAKALMEVPI GAVIVRGGEI IGRGHNLRET    60
SLDPTAHAEI IAIREASEKL GAWRLLDCRL YVTLEPCPMC AGAIVQSRVP QVIYGTPDPK   120
AGCAGTLMNL LQEERFNHCV DVISGVLQPE CASQLTDFFR ELRRRAKEAK KALPAEE      177

SEQ ID NO: 450           moltype = AA  length = 159
FEATURE                  Location/Qualifiers
REGION                   1..159
                         note = source = /note="Description of Artificial Sequence:
                           Syntheticpolypeptide"
source                   1..159
                         mol_type = protein
```

```
                        organism = synthetic construct
SEQUENCE: 450
MKTDEDFMEL ALEEARKALA LEEVPIGAVV VCNGEIVGSG HNLKETENDP TAHAEIVAIR     60
DAARKLSSWR LNECQLYVTI EPCPMCAGAI MQARLQRVVY GAVDPKAGVA GSLYNLLQDN    120
RFNHTVELKS GVLAAECRQI IKDFFSELRQ TRGRVGESG                           159

SEQ ID NO: 451          moltype = AA  length = 168
FEATURE                 Location/Qualifiers
REGION                  1..168
                        note = source = /note="Description of Artificial Sequence:
                          Syntheticpolypeptide"
source                  1..168
                        mol_type = protein
                        organism = synthetic construct
SEQUENCE: 451
MEKEEASLQG IHERWMRQAL EEADKAEQLN EVPIGAIIVK DQQIIGRGYN VRETQHQATG     60
HAEIQAIEDA NRHQQAWRLE GATMYVTLEP CPMCAGALIN SRIQTVVYGA SDLKAGCAGT   120
LMNLLQDDRF NHQVEVISGV LAEECGDKLS YFFRKLRQRK GKNIDRAE                168

SEQ ID NO: 452          moltype = AA  length = 150
FEATURE                 Location/Qualifiers
REGION                  1..150
                        note = source = /note="Description of Artificial Sequence:
                          Syntheticpolypeptide"
source                  1..150
                        mol_type = protein
                        organism = synthetic construct
SEQUENCE: 452
MTADEEYMTL CIELAKKAAE KGECPVGAIV VDKDGRIIGE GYNMREAEQM PTAHAEIIAI     60
EQAAKAMNSW RLTECTLYVT LEPCPMCAGA IINSRIKRLV YGAFDEKGGA CASLMEIFDY   120
PFNHRPMVRS RVLQDECAKL LTEFFKDLRT                                    150

SEQ ID NO: 453          moltype = AA  length = 182
FEATURE                 Location/Qualifiers
REGION                  1..182
                        note = source = /note="Description of Artificial Sequence:
                          Syntheticpolypeptide"
source                  1..182
                        mol_type = protein
                        organism = synthetic construct
SEQUENCE: 453
MTDTFTATPA HMQLALVQAQ HAWDLGEVPV GAVVVKDGEV IATGYNQPIG KHDPTAHAEI     60
MALRAAAEIL GNYRLPGCEL YVTLEPCVMC AGAMMHARLA RVVYGAADPK TGACGSVVNL   120
FAQEELNHHT ELVGGVMAEA CGQMLKSFFS ERREQLKQER LQRQAIAHAH ANAHSIDDEA   180
ND                                                                  182

SEQ ID NO: 454          moltype = AA  length = 154
FEATURE                 Location/Qualifiers
REGION                  1..154
                        note = source = /note="Description of Artificial Sequence:
                          Syntheticpolypeptide"
source                  1..154
                        mol_type = protein
                        organism = synthetic construct
SEQUENCE: 454
MHKIFLEEAY KEAIKALQEQ EVPVGCVIVQ NKQILSRSHN LTNKLHDPLA HAEINGLREL     60
LQQSITDDL TFYITCEPCI MCLGILNRIK ARIYYGCKNI IFGGITILET PSDSHFIEDK    120
RCYEILQKFY SNENEFAPEE KRKKKNNRNN GVPL                               154

SEQ ID NO: 455          moltype = AA  length = 159
FEATURE                 Location/Qualifiers
REGION                  1..159
                        note = source = /note="Description of Artificial Sequence:
                          Syntheticpolypeptide"
source                  1..159
                        mol_type = protein
                        organism = synthetic construct
SEQUENCE: 455
MLTSLKATRH AEFLGIDEIL SKYDKDVFKE TDLYVTVEPC VMCASALRQL EIRKVYFGAA     60
NDRFGGCGSV LSLHNHAKLP EPAYNVYPGF YRDEAIVMLR KFYVQENTKA PVPRGKKTRE   120
LKLEVEDNFD YSKFVGSEEE FINVYGKERL SEYRKLSSK                          159

SEQ ID NO: 456          moltype = AA  length = 169
FEATURE                 Location/Qualifiers
REGION                  1..169
                        note = source = /note="Description of Artificial Sequence:
                          Syntheticpolypeptide"
source                  1..169
                        mol_type = protein
```

```
                        organism = synthetic construct
SEQUENCE: 456
MKSDEFYMKL AIEEAKRAAE INEVPIGAVL VSNDEVIATA HNLRETEQRS IAHAELLVID    60
EACRRTGSWR LENATLYVTL EPCAMCSGAI VLSRVNRVVY GASDPKGGCA GTLMNLLQEK   120
RFNHQAEVLS GVCEEECGQL LSSFFRGIRE RKKKEKVNYI QQKSATSNE               169

SEQ ID NO: 457          moltype = AA  length = 171
FEATURE                 Location/Qualifiers
REGION                  1..171
                        note = source = /note="Description of Artificial Sequence:
                          Syntheticpolypeptide"
source                  1..171
                        mol_type = protein
                        organism = synthetic construct
SEQUENCE: 457
MRDNNLYMRE ALKEAYIAAE LGEVPVGAVI VKAGEIIAKA HNMVEAYASS SAHAEMLAMD    60
AAEARLGSKW LSGCELYVTL EPCSMCAGAM VLARLEKLCI GTMDPKNGAS GSIFDITGSD   120
SLNHRIDVER GILADECAEA LTSFFRELRI TKAQLRKSNI VKDKVDIPEE K            171

SEQ ID NO: 458          moltype = AA  length = 151
FEATURE                 Location/Qualifiers
REGION                  1..151
                        note = source = /note="Description of Artificial Sequence:
                          Syntheticpolypeptide"
source                  1..151
                        mol_type = protein
                        organism = synthetic construct
SEQUENCE: 458
MLEDFMRVAL EEAKKAYKQG EVPVGAVIVK NGKVISKAHN ETRQKKNAVA HAEILAIDKA    60
CKKLENERLV DTEMYVTLEP CAMCAGAIVQ ARIPEVMIGT RDLKSGAANT ILNVLENEKL   120
NHRAELRFGI FEEECSEILK TFFKELRDER K                                  151

SEQ ID NO: 459          moltype = AA  length = 158
FEATURE                 Location/Qualifiers
REGION                  1..158
                        note = source = /note="Description of Artificial Sequence:
                          Syntheticpolypeptide"
source                  1..158
                        mol_type = protein
                        organism = synthetic construct
SEQUENCE: 459
MTRDEMYMRK ALELAALAAD EDEVPVGAVV VKKSTGEIVG RGFNRREYGR SPLTHAEIVA    60
IDEASRKLGG WRLIDCELFV TLEPCPMCAG AVINSRVERV VFGAYDKKAG SCGSVVDLFG   120
LPYNHKPECI GGVLEEECAA VLTEFFKGLR KRKVKVNE                           158

SEQ ID NO: 460          moltype = AA  length = 191
FEATURE                 Location/Qualifiers
REGION                  1..191
                        note = source = /note="Description of Artificial Sequence:
                          Syntheticpolypeptide"
source                  1..191
                        mol_type = protein
                        organism = synthetic construct
SEQUENCE: 460
MVTVTREFSP SDLAFMELAL KQAKFAMSNL EVPVGCVVVV DGKIVASGCN RTNETRNATR    60
HAEMEAIDLL LEQWQKAGLS QVEVAEKFSR CVLYVTCEPC IMCATALSIL GIRDVYYGCA   120
NDKFGGCGSI LSLHESGCEQ LFRSSHENGF RCSGGLMASE AIALLRSFYE QGNPNAPKPH   180
RPVRMTQEDS T                                                        191

SEQ ID NO: 461          moltype = AA  length = 158
FEATURE                 Location/Qualifiers
REGION                  1..158
                        note = source = /note="Description of Artificial Sequence:
                          Syntheticpolypeptide"
source                  1..158
                        mol_type = protein
                        organism = synthetic construct
SEQUENCE: 461
MPSHNNTDKY WMQQAIDQAK LAYNKGEVPI GAVIVKDEQL IATGFNKRET SQDATSHAEI    60
IAIQSACNYL GGWRLLDCTL YVTIEPCPMC AGAILQSRIT KLVFGTEDPK AWGELSISQL   120
LQNPQLNHQV DIVEGICKEE SKDIIKQFFH ELRKRKKN                           158

SEQ ID NO: 462          moltype = AA  length = 152
FEATURE                 Location/Qualifiers
REGION                  1..152
                        note = source = /note="Description of Artificial Sequence:
                          Syntheticpolypeptide"
source                  1..152
                        mol_type = protein
```

```
                        organism = synthetic construct
SEQUENCE: 462
MDRYMTRALE LARLAFDEGE VPVGAVVVKK TTGEIIGEGR NMREGAKNAL AHAEIIAIDQ     60
ACRTLGGWRL PECAIYVTLE PCPMCCGAII NARIDNVIFG AYDLKSGSAA SVQKMFELPY    120
NYRPEVTGGI MEQECADILS EFFRQLRIRK KT                                 152

SEQ ID NO: 463          moltype = AA   length = 197
FEATURE                 Location/Qualifiers
REGION                  1..197
                        note = source = /note="Description of Artificial Sequence:
                          Syntheticpolypeptide"
source                  1..197
                        mol_type = protein
                        organism = synthetic construct
SEQUENCE: 463
MEQNSPGIRF ANDAQKHAFF MKKALDMGEE ALASGETPVG CVLVHNDEVI GSGMNDTNKS     60
MNGTRHAEFL AIEEVLRSHP RSIFRETDLY VTVEPCIMCA SALRQYQIRH VYFGCANERF    120
GGTGGVLKLH SDPGIDPPYG LTGGLFRKEA IMLLRRFYIQ ENERAPNPKP KKDRELKDDD    180
FGDVGAGMEF AGMLPRP                                                  197

SEQ ID NO: 464          moltype = AA   length = 166
FEATURE                 Location/Qualifiers
REGION                  1..166
                        note = source = /note="Description of Artificial Sequence:
                          Syntheticpolypeptide"
source                  1..166
                        mol_type = protein
                        organism = synthetic construct
SEQUENCE: 464
MTDFELMGLA LEEAAKAAAL GEVPVGAVVA RHGEVIATAH NTRETEKNAL HHAELLAIDA     60
ACKALGGWRL WECELFVTLE PCPMCAGGII NSRLRRVVYG AADTKAGCCG SVTDLFALPF    120
NHHPVVEKGL REAEAQQLLQ AFFVSLREKR AGRPRWKPPV PENRGK                  166

SEQ ID NO: 465          moltype = AA   length = 152
FEATURE                 Location/Qualifiers
REGION                  1..152
                        note = source = /note="Description of Artificial Sequence:
                          Syntheticpolypeptide"
source                  1..152
                        mol_type = protein
                        organism = synthetic construct
SEQUENCE: 465
MDHKDYMARA LELAAQAAEH GDVPVGCVIV KDGKIVGEGR NRREEHGDAT AHAELEAIRD     60
ACARLGSWRL HGCTLYVTLE PCPMCAGGII NSRIETVRYG ARDEKAGCCS SVLNLFEERF    120
NHHPRIYRGP LEPQCQKILQ DFFLDLREDG EN                                 152

SEQ ID NO: 466          moltype = AA   length = 188
FEATURE                 Location/Qualifiers
REGION                  1..188
                        note = source = /note="Description of Artificial Sequence:
                          Syntheticpolypeptide"
source                  1..188
                        mol_type = protein
                        organism = synthetic construct
SEQUENCE: 466
MEEKVESTTV PDGSCVVSVQ ETEKWMEEAM RMAKEALENI EVPVGCLMVY NNEVVGKGRN     60
EVNQTKNATR HAEMVPFDQV DWCHHTGQPS AVFEHTVLYV TVPCIMCAAV LALMSIPLAA    120
SGQRTDRRTT RRSALNIGFC FLFNAGRPFQ CIPGYRAEEA VELLKTFYKQ ENPNAPKSKV    180
RKKDCQKS                                                            188

SEQ ID NO: 467          moltype = AA   length = 151
FEATURE                 Location/Qualifiers
REGION                  1..151
                        note = source = /note="Description of Artificial Sequence:
                          Syntheticpolypeptide"
source                  1..151
                        mol_type = protein
                        organism = synthetic construct
SEQUENCE: 467
MKEALKEARK AAEMGEIPVG AVIVKDGEII SRGHNLTETT KDPTAHAEMI AIREAAKLLR     60
GWRLTGCDMY VTMEPCSMCA GALVWSRIEH LYIGADDPKT GACGSVFNIV QDDRLNHQIA    120
VDRGIMAEES SQLVREFFRN LRNKTKKPEE E                                  151

SEQ ID NO: 468          moltype = AA   length = 163
FEATURE                 Location/Qualifiers
REGION                  1..163
                        note = source = /note="Description of Artificial Sequence:
                          Syntheticpolypeptide"
source                  1..163
```

```
                              mol_type = protein
                              organism = synthetic construct
SEQUENCE: 468
MSAQSEHEKW  MARAIQLAKQ  AETLGEVPIG  AVIVKEGEVL  GEGYNRREID  RNPLAHAELM    60
AIQQACERLG  GWRLAGCDLY  VTLEPCPMCA  GAIVQARLRR  VIYGTEDPKA  GYAGSLHNTL   120
QDERLNHQTD  VIAGIRREEC  QHLLKDFFRR  LREQKKAAKG  MST                     163

SEQ ID NO: 469                moltype = AA   length = 155
FEATURE                       Location/Qualifiers
REGION                        1..155
                              note = source = /note="Description of Artificial Sequence:
                              Syntheticpolypeptide"
source                        1..155
                              mol_type = protein
                              organism = synthetic construct
SEQUENCE: 469
MDRDNYFLKE  AVKQAKKGAE  IGDVPIGCVI  VFEDKIIARG  YNRRNKDKST  LSHAEIIAIK    60
KACKKIGDWR  LEDCTMYITL  EPCPMCAGAI  IQSRIKRVVL  GAMNPKAGCA  GSIINILQTE   120
GFNHKTEISL  IDEPLHSECV  SLLTSFFKAL  RENKK                               155

SEQ ID NO: 470                moltype = AA   length = 181
FEATURE                       Location/Qualifiers
REGION                        1..181
                              note = source = /note="Description of Artificial Sequence:
                              Syntheticpolypeptide"
source                        1..181
                              mol_type = protein
                              organism = synthetic construct
SEQUENCE: 470
MPELIHVMNL  SNEEREDHEY  WMKEAMKEAL  KAQEKDEVPI  GAVIVYQGRI  IGRGHNIRET    60
QNLATGHAEI  QAIEAANHYL  GAWRLEGARL  YVTLEPCPMC  AGAAVLARIE  TIIYACRDPK   120
GGCTGSLMNL  AQEDRFNHQT  QVIEGVLDAA  CSQMMKDFFK  KLRKRKKLEK  LSTKTVDNAD   180
L                                                                       181

SEQ ID NO: 471                moltype = AA   length = 99
FEATURE                       Location/Qualifiers
REGION                        1..99
                              note = source = /note="Description of Artificial Sequence:
                              Syntheticpolypeptide"
source                        1..99
                              mol_type = protein
                              organism = synthetic construct
SEQUENCE: 471
MDLTQHFQRM  GLSLFVAFKA  LSINETPVAC  ILVSKKSSQV  ISIGYNDTNR  SLNGTRHAEF    60
IAIDYVLDNV  VDTLPVDDLI  LYVTVEPCIM  CASALKQVG                            99

SEQ ID NO: 472                moltype = AA   length = 162
FEATURE                       Location/Qualifiers
REGION                        1..162
                              note = source = /note="Description of Artificial Sequence:
                              Syntheticpolypeptide"
source                        1..162
                              mol_type = protein
                              organism = synthetic construct
SEQUENCE: 472
MEGIQHELFM  REALKEAEKA  RELDEVPIGA  VVVRDGEIIG  RGHNLRESTR  NATMHAEMVA    60
IQEANEQLAN  WRLEECDLYV  TVEPCVMCGG  AIIWSRMRTV  YFPGAHDPKGG  AAGSLLNVLE  120
DDRFNHTATV  YSGLLAEESQ  RLLKDFFREL  RKRKKQKNGE  HA                      162

SEQ ID NO: 473                moltype = AA   length = 98
FEATURE                       Location/Qualifiers
REGION                        1..98
                              note = source = /note="Description of Artificial Sequence:
                              Syntheticpolypeptide"
source                        1..98
                              mol_type = protein
                              organism = synthetic construct
SEQUENCE: 473
MVELEKHYEF  MRYALRLANN  ALHTNEVPVA  CVFVYDGQII  SYGSNNTNDS  LSGITHAEFR    60
GINIILDKVK  SSPDFQQVYQ  NPQDIFKDID  LYVTVEPC                             98

SEQ ID NO: 474                moltype = AA   length = 202
FEATURE                       Location/Qualifiers
REGION                        1..202
                              note = source = /note="Description of Artificial Sequence:
                              Syntheticpolypeptide"
source                        1..202
                              mol_type = protein
                              organism = synthetic construct
```

```
SEQUENCE: 474
MNDSTEQTDS DLQLEQEHIQ WMRVAMEMAE EALVAKEVPV GCIFVRDGRI IARARNRTNE    60
LRNATRHAEL EAIDGILSDK DLTPVLTDYP LSETTLYVTV EPCIMCASAL RQMGIKKVFY   120
GCANDRFGGC GSVLGVNRSL THPRHPAYQA VGGYLREDAI MILRRFYVTE NTNAPAPKSK   180
ANRVTTKCIT SAIYVYYRSS RI                                           202

SEQ ID NO: 475          moltype = AA  length = 159
FEATURE                 Location/Qualifiers
REGION                  1..159
                        note = source = /note="Description of Artificial Sequence:
                            Syntheticpolypeptide"
source                  1..159
                        mol_type = protein
                        organism = synthetic construct
SEQUENCE: 475
MTSHQYYMSL ALEEAREAAK KGEVPIGAII VKNEKVIARA HNLRETNQNP TAHAEHLAIE    60
QAAETLGTWR LEGCTLYVTL EPCVMCAGTI VMSRVDTVVF GAYDPKGGCT GSLMNLVQDQ   120
RMNHRAKVIE GVLAYSCGEI LRQFFRTLRQ RKAAKAMSN                          159

SEQ ID NO: 476          moltype = AA  length = 120
FEATURE                 Location/Qualifiers
REGION                  1..120
                        note = source = /note="Description of Artificial Sequence:
                            Syntheticpolypeptide"
source                  1..120
                        mol_type = protein
                        organism = synthetic construct
SEQUENCE: 476
MVSSSKTVKL SLEPEIGPTS GEMCVILSLP YRSSSDLPQA TLHAELEAID HLLPNNPAPL    60
SSITLYVTVE PCVMCASALR QIGIGKVIYG CGNDRFGGCG SVINVNSSFV LLGRVGEAGC   120

SEQ ID NO: 477          moltype = AA  length = 165
FEATURE                 Location/Qualifiers
REGION                  1..165
                        note = source = /note="Description of Artificial Sequence:
                            Syntheticpolypeptide"
source                  1..165
                        mol_type = protein
                        organism = synthetic construct
SEQUENCE: 477
MSPGYRGYAD LVSLPVPAAD DAAMTRALEL AADAPAHDDV PVGAVVTRGG QVVGEGRNLR    60
ERDGDPLAHA EIVALRAAAS ALGSWNLEDC TLVVTLEPCV MCAGAILQTR VGRVVFGAWD   120
EKAGAAGSVH DLLRDRRMPH RAEVLGGVRA AESAALLRDF FGQKR                   165

SEQ ID NO: 478          moltype = AA  length = 154
FEATURE                 Location/Qualifiers
REGION                  1..154
                        note = source = /note="Description of Artificial Sequence:
                            Syntheticpolypeptide"
source                  1..154
                        mol_type = protein
                        organism = synthetic construct
SEQUENCE: 478
MVLEENFMLE AIEEAKKAFN KKEVPIGAVV VKDNEIIGRG HNLRETTKNS ISHAEIMAIQ    60
EACKFLGGWR LTDCTLYVTI EPCPMCAGAI LQSRIQKVVI GAMDPKAGAC GSLVNLLNDS   120
RFNHQTEIEQ GVLEEECSLL MKEFFKALRE KRFG                               154

SEQ ID NO: 479          moltype = AA  length = 162
FEATURE                 Location/Qualifiers
REGION                  1..162
                        note = source = /note="Description of Artificial Sequence:
                            Syntheticpolypeptide"
source                  1..162
                        mol_type = protein
                        organism = synthetic construct
SEQUENCE: 479
MKHITYMQAA IEEAKKAQNL GEVPIGAVIV KDGEIIARGY NLRETSQLSN AHAEMIAIAK    60
ANEMVGSWRL EDCTLYVTLE PCPMCAGAIV QSRIPTVVFG AHDPKGGCCG TIYNLLDESK   120
FNHRCELVSG VLEEECGQLL SDFFRNLRQK KKQQRVDNET SN                      162

SEQ ID NO: 480          moltype = AA  length = 168
FEATURE                 Location/Qualifiers
REGION                  1..168
                        note = source = /note="Description of Artificial Sequence:
                            Syntheticpolypeptide"
source                  1..168
                        mol_type = protein
                        organism = synthetic construct
SEQUENCE: 480
```

```
MRTDNDYMRL AIKEARKAQE LGEVPIGAVI VKDNHVIARA HNLRETLQQP TAHAEHIAIE      60
RASEVIGSWR LEDCTLYVTL EPCVMCAGAI VMSRIPRVVY GAIDPKGGCT GSLMNLLAQP     120
QFNHRAIVES GILENECSTL LREFFKNIRQ QKRSLKQAKI QNDTNLLE                 168

SEQ ID NO: 481          moltype = AA  length = 181
FEATURE                 Location/Qualifiers
REGION                  1..181
                        note = source = /note="Description of Artificial Sequence:
                         Syntheticpolypeptide"
source                  1..181
                        mol_type = protein
                        organism = synthetic construct
SEQUENCE: 481
MDTNEPLTNG AGASEQDLQF MGQAILEAKK AEAIGEVPIG AVIVRDGKVI AASHNLRERD     60
QEATAHAELA AITEACRKTG SWRLEDTVLY VTLEPCPMCA GAILQSRIPR VVYGARDPKA    120
GCVDSLYRLL DDPRFNHRCD VTEGVLADEC GALLTNFFRG IRKRRKAEKQ ARRALESEQG    180
E                                                                   181

SEQ ID NO: 482          moltype = AA  length = 155
FEATURE                 Location/Qualifiers
REGION                  1..155
                        note = source = /note="Description of Artificial Sequence:
                         Syntheticpolypeptide"
source                  1..155
                        mol_type = protein
                        organism = synthetic construct
SEQUENCE: 482
MSRDEYFMDI ALKEAKKAYN KGEVPIGCVI VKDDKIVSRG HNQVLSKKSG VNHAEIIAIN     60
KAGQKLGDFR LEDTELFVTL EPCCMCAGAI VNSRIKRVII GAMDVKRGFC GSIENVLDRQ    120
ELNHRSIIKT GVLEQKCLDI LQDFFKNLRS EKKNK                              155

SEQ ID NO: 483          moltype = AA  length = 174
FEATURE                 Location/Qualifiers
REGION                  1..174
                        note = source = /note="Description of Artificial Sequence:
                         Syntheticpolypeptide"
source                  1..174
                        mol_type = protein
                        organism = synthetic construct
SEQUENCE: 483
MKTSQQLKDE AYMKEALTEA DKAEAIGEVP IGAVIVKDDI IIARGYNERE TKQRATGHAE     60
LVAIEEACRI LKTWRLEGCT LYVTLEPCPM CAGAIVQSRI DRVVYGADDP KGGSCGTVVN    120
LLDEPKFNHA PLVTSGTLKE EAADRLSSFF RALREARKQK KKEGIPHETE SDFT          174

SEQ ID NO: 484          moltype = AA  length = 151
FEATURE                 Location/Qualifiers
REGION                  1..151
                        note = source = /note="Description of Artificial Sequence:
                         Syntheticpolypeptide"
source                  1..151
                        mol_type = protein
                        organism = synthetic construct
SEQUENCE: 484
MNHEYFMKIA IEEAKKCLFL DEVPVGAIIV KDGKIIARAH NLRETLRDAT AHAEILAINE     60
ACMALGGWRL LDCTMYVTLE PCPMCAGALV NSRIKTLIFG TRDPKGGACG SLYNIVADER    120
LNHRIEIIEG VLQDECSKLL KEFFKSKRKK D                                   151

SEQ ID NO: 485          moltype = AA  length = 197
FEATURE                 Location/Qualifiers
REGION                  1..197
                        note = source = /note="Description of Artificial Sequence:
                         Syntheticpolypeptide"
source                  1..197
                        mol_type = protein
                        organism = synthetic construct
SEQUENCE: 485
MIVLERRPVY ASNSSQAERL LRCDCVLNSG YGTLMVRIVH FSMSGAEQME HEKFMREALQ     60
EAEKAIKWGE VPIGAVVVRE GQVIARGHNM RETWKDPTAH AEIVALREAS RVLGGWRLTG    120
CKLYVTLEPC PMCAGAILLA RIDEVIFGAR EPKFGAAGSI VNLIETDRFN HQPQLTSGVL    180
AEECGMILKE FFRQRRK                                                   197

SEQ ID NO: 486          moltype = AA  length = 171
FEATURE                 Location/Qualifiers
REGION                  1..171
                        note = source = /note="Description of Artificial Sequence:
                         Syntheticpolypeptide"
source                  1..171
                        mol_type = protein
                        organism = synthetic construct
```

```
SEQUENCE: 486
MTNLERDEKM MRRALELARQ AALEGEVPVG AVVARGDEII AEGRNRREAC KNALCHAEIE    60
AIDAACRALH GWRLWECDLY VTLEPCPMCT GAILNARIAR VIFGASDPKA GSCGSIVNLF   120
DLPYNHHPQL VSGVLREECG EVLTEFFQRL RDQRAVKKPS EPKSPAKDGT E            171

SEQ ID NO: 487          moltype = AA   length = 157
FEATURE                 Location/Qualifiers
REGION                  1..157
                        note = source = /note="Description of Artificial Sequence:
                          Syntheticpolypeptide"
source                  1..157
                        mol_type = protein
                        organism = synthetic construct
SEQUENCE: 487
MNREHEAWMD LALDEARAAL ATDDVPIGAV VISPDGKLLS TGRNEREALK DPTAHAEVVA    60
IRNAVSALAA RGADDGWRLE DCTLVVTLEP CAMCAGAIVL ARIPRVVFGA WDEKAGACGS   120
VFDIVREPRL NHWVEVYPRV REQECADLLR DFFRSKR                            157

SEQ ID NO: 488          moltype = AA   length = 182
FEATURE                 Location/Qualifiers
REGION                  1..182
                        note = source = /note="Description of Artificial Sequence:
                          Syntheticpolypeptide"
source                  1..182
                        mol_type = protein
                        organism = synthetic construct
SEQUENCE: 488
MEAKVGSTQI TGGACSVLAE ETEKWMEQAM QMAKEALENI EVPVGCLLVY NNEVVGKGRN    60
EVNQTKNATR HAEMVAIDQA LDWCRRHGKS PSEVFEHMVL YVTVEPCIMC AAALRLMKIP   120
LVVYGCQNER FGGCGSVLDI ASADLPNTGR PFQCFEILKK LPIPQASGCC VFYFYLVGLG   180
CG                                                                  182

SEQ ID NO: 489          moltype = AA   length = 155
FEATURE                 Location/Qualifiers
REGION                  1..155
                        note = source = /note="Description of Artificial Sequence:
                          Syntheticpolypeptide"
source                  1..155
                        mol_type = protein
                        organism = synthetic construct
SEQUENCE: 489
MESDRYYMKK AIEEAEKAEA LGEVPIGAVL VHEGEVIARG HNLRETTQKT SSHAECITID    60
RANDVIGSWR LEECTLYVTL EPCPMCAGAI LQSRIPVLVY GAYDRKAGCA GTLMNLLDDD   120
RFNHRTAIRA GVMEEECGEM LSSFFRRIRK KRKDK                              155

SEQ ID NO: 490          moltype = AA   length = 149
FEATURE                 Location/Qualifiers
REGION                  1..149
                        note = source = /note="Description of Artificial Sequence:
                          Syntheticpolypeptide"
source                  1..149
                        mol_type = protein
                        organism = synthetic construct
SEQUENCE: 490
MHIQAEEALH SDEVPVGCVF VKGDTAIARA RNRTNEWRNA TLHAELEAID HLLPDHPAPL    60
SEITLYVTVE PCVMCASALR QIGIGRVVYG CGNERFGGCG SVIDIHASYV LVLTSSGAKA   120
GAGRRVGSHS ESRPSRRESR RNARTEARL                                     149

SEQ ID NO: 491          moltype = AA   length = 167
FEATURE                 Location/Qualifiers
REGION                  1..167
                        note = source = /note="Description of Artificial Sequence:
                          Syntheticpolypeptide"
source                  1..167
                        mol_type = protein
                        organism = synthetic construct
SEQUENCE: 491
MEEEEAATLD WMDQAFDMAK EALECGEVPV GCLLVHNGQA IGRGRNEVNE TKNATRHAEM    60
VAIDRVLDWC KQHNRDYTEV FPQTVLYVTV EPCIMCAAAV RLMSILSCLF MLGNQMLKCY   120
SFGNTGEPFE CVSGYRAKEA VEMLKAFYRQ ENPNAPKSKV RKKDHRN                 167

SEQ ID NO: 492          moltype = AA   length = 162
FEATURE                 Location/Qualifiers
REGION                  1..162
                        note = source = /note="Description of Artificial Sequence:
                          Syntheticpolypeptide"
source                  1..162
                        mol_type = protein
                        organism = synthetic construct
```

```
SEQUENCE: 492
MLPLDDPDTR FMQQALTLAR SAPLIGEVPI AALLVHEGIV IAQAHNLRET RQDPTAHAEV    60
IVIQDAARHM GSWRLINTTL YVTLEPCTMC IGAIVLARIP RLVFAATDPK AGACGSIMNI   120
PPEPRLNHRV EVVGGVCAEE SQALLQDFFQ QLRKDAARRE TT                      162

SEQ ID NO: 493           moltype = AA  length = 182
FEATURE                  Location/Qualifiers
REGION                   1..182
                         note = source = /note="Description of Artificial Sequence:
                           Syntheticpolypeptide"
source                   1..182
                         mol_type = protein
                         organism = synthetic construct
SEQUENCE: 493
MVRPQAEEAF TASEIPVGCV LVHQGRIIAK GRNRTNEGRN ATLHAEFDAL RHLLPDRSHT    60
VTPQLTRPFT PQEGERKIWE TPLEGVVLYV TVEPCIMCAA AMRQVGIEKV IYGCGNDRFG   120
GTGGVQSIHS ESVRFPFDLL DRVANSCLVR SFVALDCCTL RRIQLTAITE EKRRLCCYGD   180
SI                                                                  182

SEQ ID NO: 494           moltype = AA  length = 169
FEATURE                  Location/Qualifiers
REGION                   1..169
                         note = source = /note="Description of Artificial Sequence:
                           Syntheticpolypeptide"
source                   1..169
                         mol_type = protein
                         organism = synthetic construct
SEQUENCE: 494
MQEDAYYMRL ALEEAQKAYD LEEVPIGAVL VDREGEVVAR GHNMREVWHD ATAHAEMIAI    60
REACAKEGRW RLSGLTLYVT IEPCPMCAGA IVMSRVDRVV YGSTDARAGA CESVFNIPGC   120
PALNHRPEMT AGVLQEECAG IMKRFFKERR AKRKALRQQA AGSPETAER               169

SEQ ID NO: 495           moltype = AA  length = 146
FEATURE                  Location/Qualifiers
REGION                   1..146
                         note = source = /note="Description of Artificial Sequence:
                           Syntheticpolypeptide"
source                   1..146
                         mol_type = protein
                         organism = synthetic construct
SEQUENCE: 495
MATRHAELEA IDFILSQHPP KEQDFPISPH SGPSGDNPFA ETTLYVTIEP CIMCASALRQ    60
VGIKRVVFGA GNERFGGNGS VLPVHTDAQL KNAPAYEAVG GYYREDAIML LRRFYLTENV   120
FAPNPRSKAK RVLKTYFQRE SRPFCF                                        146

SEQ ID NO: 496           moltype = AA  length = 150
FEATURE                  Location/Qualifiers
REGION                   1..150
                         note = source = /note="Description of Artificial Sequence:
                           Syntheticpolypeptide"
source                   1..150
                         mol_type = protein
                         organism = synthetic construct
SEQUENCE: 496
MGVARTLAEQ ASAEGEVPVG ALVVKDGEII GRGYNQPIGR HDPSAHAEMQ ALRDAAARLG    60
NYRLDGCDLY VTLEPCPMCS GAILHARIAR VIYGAADAKT GAAGSTVDLF ADARLNHHAA   120
VFGGVEAETC AEQLSAFFRQ RRRSAGDGEE                                    150

SEQ ID NO: 497           moltype = AA  length = 160
FEATURE                  Location/Qualifiers
REGION                   1..160
                         note = source = /note="Description of Artificial Sequence:
                           Syntheticpolypeptide"
source                   1..160
                         mol_type = protein
                         organism = synthetic construct
SEQUENCE: 497
MEQENYMRRA LTLAREAGDA GEVPVGCVIV RDGKVVGEGR NRREELTSAA SHAEMEAIAA    60
ANERLGSWRL EGCALYVTLE PCPMCAGAIL NARVSKVFYG ARDPAFGACG GVTNLFMEDF   120
PNRPALVGGV LAEECREVLR AFFQKLRNDG GTGESPEPKI                         160

SEQ ID NO: 498           moltype = AA  length = 154
FEATURE                  Location/Qualifiers
REGION                   1..154
                         note = source = /note="Description of Artificial Sequence:
                           Syntheticpolypeptide"
source                   1..154
                         mol_type = protein
                         organism = synthetic construct
```

```
SEQUENCE: 498
MEDDIKYMKM ALAEARKAYQ RAEVPIGAVV ICDDKVVGRG FNLREQTQDP TSHAEMIALR    60
EAAKNEASWR LENCQLYVTL EPCPMCAGAI LQSRIKRLVY GASDPKAGAV NSLYQLLNDE   120
RFNHQVEVEA GVMKKEAAQL LKDFFRDLRE RKDG                               154

SEQ ID NO: 499          moltype = AA   length = 159
FEATURE                 Location/Qualifiers
REGION                  1..159
                        note = source = /note="Description of Artificial Sequence:
                        Syntheticpolypeptide"
source                  1..159
                        mol_type = protein
                        organism = synthetic construct
SEQUENCE: 499
MQEALVEASA AARLGEVPVG AVVVKDGMII GRGHNLRETS NDPTTHAEMI AIRQAAAAID    60
SWRLIGCTLY VTLEPCVMCM GAIILARIPR LVFGSRDPRV GAVGSIFDLS RDERFNHQVA   120
VTEGVLALES SDMLSGFFRQ LRAEKKSRKR KAADSEDQT                          159

SEQ ID NO: 500          moltype = AA   length = 151
FEATURE                 Location/Qualifiers
REGION                  1..151
                        note = source = /note="Description of Artificial Sequence:
                        Syntheticpolypeptide"
source                  1..151
                        mol_type = protein
                        organism = synthetic construct
SEQUENCE: 500
MNDNDFMGEA LRLAGCAAER GEVPVGAVVV CDGQIVGTGF NRRETGKNAL AHAELEAIDA    60
ACRRLGGWRL HRCELYVTLE PCPMCAGAII NARIRRLVFG ARDPKSGCFG SVSDFNALAF   120
NHKPQVVCGV RGEECAQILS AFFQKLRRGR Q                                  151

SEQ ID NO: 501          moltype = AA   length = 175
FEATURE                 Location/Qualifiers
REGION                  1..175
                        note = source = /note="Description of Artificial Sequence:
                        Syntheticpolypeptide"
source                  1..175
                        mol_type = protein
                        organism = synthetic construct
SEQUENCE: 501
MEKDIEFMKQ ALIEAEKAFT LDEAPIGAVI VYKEQVIGRG HNRRNTDKNA LAHAEVMAIN    60
EACKHIKDWR LEECTIYITL EPCPMCSGAI VQARLPRVVF GARSPKAGFG GSVLNILQMD   120
ELNHRCEVVE GVCEEEASQL LKSYFKQMRQ KNKIIGGELW QQIQDIRKQE CLEIL        175

SEQ ID NO: 502          moltype = AA   length = 112
FEATURE                 Location/Qualifiers
REGION                  1..112
                        note = source = /note="Description of Artificial Sequence:
                        Syntheticpolypeptide"
source                  1..112
                        mol_type = protein
                        organism = synthetic construct
SEQUENCE: 502
MVYNNEIVGK GRNEVNETKN ATRHAEMVAI DQVLDWCQQH KKQPEDVFTH TVLYVTVEPC    60
IMCAAALRMM NIGEPFQCIA GYRSEEAVEM LKTFYRQENP NAPKSKVRKK EF           112

SEQ ID NO: 503          moltype = AA   length = 155
FEATURE                 Location/Qualifiers
REGION                  1..155
                        note = source = /note="Description of Artificial Sequence:
                        Syntheticpolypeptide"
source                  1..155
                        mol_type = protein
                        organism = synthetic construct
SEQUENCE: 503
MKDHSYYMEM ALEEARRAYA KGEVPIGAVL VVDGEVIAKA HNTREEHQQA LNHAEMLAIK    60
EACEKQGFWR LDNSYLYTTV EPCVMCSGAI VQARVENVIY GASDPKYGCC GSCIDLVGEN   120
KFNHQAEVIS GVLEEECSML MKNFFKELRE KKKKQ                              155

SEQ ID NO: 504          moltype = AA   length = 158
FEATURE                 Location/Qualifiers
REGION                  1..158
                        note = source = /note="Description of Artificial Sequence:
                        Syntheticpolypeptide"
source                  1..158
                        mol_type = protein
                        organism = synthetic construct
SEQUENCE: 504
MKFSEEKNLS FMQMALDQAQ LAQADGEVPI GCLIVDNQTS EIIATGFNER EQTQDAIKHA    60
```

```
EIIAIEKACQ KVGSWRLEHT SLYVTLEPCP MCAGAIINSR IEEVIFGAYD PKAGSVGSIN    120
NLFEEKRYNH HPDFLGGMLA DDSASLLQNF FREIRRKK                            158

SEQ ID NO: 505          moltype = AA  length = 161
FEATURE                 Location/Qualifiers
REGION                  1..161
                        note = source = /note="Description of Artificial Sequence:
                        Syntheticpolypeptide"
source                  1..161
                        mol_type = protein
                        organism = synthetic construct
SEQUENCE: 505
MMEQAADERF MRRALELAEE AARWGEVPVG AVVVENGRIV GEGFNRRETW RDGTAHAEML    60
AIEEASRRLG GWRLTNCVLY VTLEPCPMCA GAIVLSRVQR VVYGATDAKG GAVASKVRLL    120
EPGLWNHAPQ ITSGILADDC AKLLTDFFRK RRLKRRDGEV S                        161

SEQ ID NO: 506          moltype = AA  length = 168
FEATURE                 Location/Qualifiers
REGION                  1..168
                        note = source = /note="Description of Artificial Sequence:
                        Syntheticpolypeptide"
source                  1..168
                        mol_type = protein
                        organism = synthetic construct
SEQUENCE: 506
MEEFNEKWMK VAIELAEKAL AQGEVPVGCI FVRGEEIIAK GRNDVNRTRN ATRHAEMICI    60
DEVFERFKTT DVFKEVTVVV TVEPCIMCAG ALHDLGVRGV VFGCANDRFG GCGSVFDVAA    120
VHHTPVPVHG GVFASKAMEL LKTFYMGVNP NAPPSKVKTR KKTELSMN                 168

SEQ ID NO: 507          moltype = AA  length = 195
FEATURE                 Location/Qualifiers
REGION                  1..195
                        note = source = /note="Description of Artificial Sequence:
                        Syntheticpolypeptide"
source                  1..195
                        mol_type = protein
                        organism = synthetic construct
SEQUENCE: 507
MRQRSKIFMH LRQVLFYSEE LQKCTDQKGG DRMHGEDERY MALAIDEAAK ARAIGEVPIG    60
AVIVREGAVI AQAYNQRETL QEPTAHAELS ALREAGRKLG TWRLTGCTLY VTLEPCPMCA    120
GAVVLSRIDR LVFGAPDPKA GCAGTLMNLV QDSRFNHQAE VAGNVLGEQC GALLTDFFSN    180
LRREKRGRAN DRPEI                                                    195

SEQ ID NO: 508          moltype = AA  length = 177
FEATURE                 Location/Qualifiers
REGION                  1..177
                        note = source = /note="Description of Artificial Sequence:
                        Syntheticpolypeptide"
source                  1..177
                        mol_type = protein
                        organism = synthetic construct
SEQUENCE: 508
MPLLSLECYP LSDAELTHEY WMRHALTLAQ RAWDEGEVPV GAVLVHNNQV IGEGWNRPIG    60
RHDPTAHAEI MALRQGGLVQ QNYRLLDTTL YVTLEPCVMC AGAMVHSRIG RLIFGARDAK    120
TGAAGSLIDV LHHPGMNHRV EVVEGILRDE CAGMLSAFFR QRRAEKKALK KGATDVL       177

SEQ ID NO: 509          moltype = AA  length = 178
FEATURE                 Location/Qualifiers
REGION                  1..178
                        note = source = /note="Description of Artificial Sequence:
                        Syntheticpolypeptide"
source                  1..178
                        mol_type = protein
                        organism = synthetic construct
SEQUENCE: 509
MGEYFMRKYT EDEKFMKEAI KQAKKAEAIG DVPIGCVIVH DGKIIARGYN KRNKDKTVLA    60
HAELLAMKKA CKKLGDWRLE DCTMYITLEP CQMCAGAIVQ ARVTRVVIGS MNAKAGCGGS    120
ILNLLEMQEF NHQAEVERGV LQEECSEMLS AFFRKLREIQ KEKKKKRKLI QEENQTDN     178

SEQ ID NO: 510          moltype = AA  length = 164
FEATURE                 Location/Qualifiers
REGION                  1..164
                        note = source = /note="Description of Artificial Sequence:
                        Syntheticpolypeptide"
source                  1..164
                        mol_type = protein
                        organism = synthetic construct
SEQUENCE: 510
MKTHEEYMEL ALEEARKAEE IDEVPVGCVI VCDGEVISRG HNLKEQLNQA YAHAEMMAIQ   60
```

```
KAAEVKGNWC LNDCDLYVTL EPCMMCTGII NLSRIRTVYY GTQDPKGGCL ETVIDLKKIN    120
RLNHYPNIVG NILQKECSEI LTNYFRKKRE IIKEKKQKNK ANIQ                     164

SEQ ID NO: 511          moltype = AA  length = 152
FEATURE                 Location/Qualifiers
REGION                  1..152
                        note = source = /note="Description of Artificial Sequence:
                        Syntheticpolypeptide"
source                  1..152
                        mol_type = protein
                        organism = synthetic construct
SEQUENCE: 511
MQEKDHEFFM REALKEARKA FEQDEVPVGA VIAYEGSIIA RAHNLRERSQ DATAHAEVLA    60
IKAACEAMGT WRLTGCSLYV TLEPCPMCAG AIILARLDRV VFGAPDPKAG AAGSVVDLFK    120
VERFNHHPEV VSGVLAEECG ILLKDFFRQK RL                                   152

SEQ ID NO: 512          moltype = AA  length = 159
FEATURE                 Location/Qualifiers
REGION                  1..159
                        note = source = /note="Description of Artificial Sequence:
                        Syntheticpolypeptide"
source                  1..159
                        mol_type = protein
                        organism = synthetic construct
SEQUENCE: 512
MVQNAGNSLA GQRDVHFMEM ALEEARQAAR EGEIPVGAVL VRDGQVLARD HNRREQDRDA    60
TAHAEFLVIR QACRLLRRWR LSDTTLYVTL EPCPMCAGAI WNARVGRLVY GAWDSAAGSC    120
GSQFNLPAHP SLNFRTEVTA GVLEEECRKI LQDFLKARR                           159

SEQ ID NO: 513          moltype = AA  length = 214
FEATURE                 Location/Qualifiers
REGION                  1..214
                        note = source = /note="Description of Artificial Sequence:
                        Syntheticpolypeptide"
source                  1..214
                        mol_type = protein
                        organism = synthetic construct
SEQUENCE: 513
MQEVGVDPEK NDFLQPSDSE VQTWMAKAFD MAVEALENGE VPVGCLMVYN NEIIGKGRNE    60
VNETKNATRH AEMVALDQVL DWCRLREKDC KEVCEQTVLY VTVEPCIMCA AALRLLRIPF    120
VVYGCKNERF GGCGSVLDVS SDHLPHTGTS FKCIAGYRAE EAVEMLKTFY KQENPNAPKP    180
KVRKDSINPQ DGAAVIQVMR GPPDEETETI AHLS                                214

SEQ ID NO: 514          moltype = AA  length = 154
FEATURE                 Location/Qualifiers
REGION                  1..154
                        note = source = /note="Description of Artificial Sequence:
                        Syntheticpolypeptide"
source                  1..154
                        mol_type = protein
                        organism = synthetic construct
SEQUENCE: 514
MTEQQYYMTE ALIEAKKAFA LKEVPIGAVM VRKGEIIARG YNLRNSAKNP LCHAEIDVID    60
KSAKIVGDWR LEDCTLYVTV EPCPMCAGAI VQSRIPKIVF GTRNNKAGCA GSILNILQEP    120
RFNHQVEIEE NVLQQECAEL MRAFFKNFRK KSNM                                154

SEQ ID NO: 515          moltype = AA  length = 153
FEATURE                 Location/Qualifiers
REGION                  1..153
                        note = source = /note="Description of Artificial Sequence:
                        Syntheticpolypeptide"
source                  1..153
                        mol_type = protein
                        organism = synthetic construct
SEQUENCE: 515
MELATDEEKM YMEEALKEAA LAALEGEIPV GAILVQDGRV IARNHNRRER AHDATAHAEI    60
LVIREACEKL RRWRLADSTL YVTMEPCPMC AGAIYNARIG RVVFGASDSV AGACGSLFQI    120
PLHPSLHANT IIKAGIEAER CKKILQEFFT RRR                                 153

SEQ ID NO: 516          moltype = AA  length = 161
FEATURE                 Location/Qualifiers
REGION                  1..161
                        note = source = /note="Description of Artificial Sequence:
                        Syntheticpolypeptide"
source                  1..161
                        mol_type = protein
                        organism = synthetic construct
SEQUENCE: 516
MAKVPTFSEQ QIDYFMQEAL NEAKLAGSEG EVPIGAVIVF ENQIIARAHN HRERDQLATA    60
```

```
HAELIAIERA NQALKSWRLE DTALFVTLEP CIMCAGAIIN ARVPAVYYGA QDAKGGGTQS   120
LYQLLEDERL NHRVAVQAGV RAEESTKILQ QFFADIRAKR K                      161

SEQ ID NO: 517          moltype = AA  length = 171
FEATURE                 Location/Qualifiers
REGION                  1..171
                        note = source = /note="Description of Artificial Sequence:
                        Syntheticpolypeptide"
source                  1..171
                        mol_type = protein
                        organism = synthetic construct
SEQUENCE: 517
MCVCVCLQPN MDHFMEQALE QARKAEQLKE VPVGCVFVYR GEIIANGCNL VNETKNATRH   60
VEFICIDQVL EYCKNRSLKH EDVFREVTVV VTVEPCIMCA AALIELNVRE VIYGCKNDRF   120
GGCTVLDVPG LLKTSIPIRG GVRADEAMEL LKEFYKGENP SAPVPKVKSQ K            171

SEQ ID NO: 518          moltype = AA  length = 153
FEATURE                 Location/Qualifiers
REGION                  1..153
                        note = source = /note="Description of Artificial Sequence:
                        Syntheticpolypeptide"
source                  1..153
                        mol_type = protein
                        organism = synthetic construct
SEQUENCE: 518
MDHEKFMAEA LKEAEKAALQ GEVPVGAVVV YNGEIIGRGH NLRETFSDPT AHAEIVALKE   60
AASKLKNWQL KDCTLYVTVE PCMCAGAIY QARIKTLVYG APDLKAGAVD TLFDLVRNPR    120
LNHRVEVISG VLAAEASKII TDFFREKRNR GKF                                153

SEQ ID NO: 519          moltype = AA  length = 150
FEATURE                 Location/Qualifiers
REGION                  1..150
                        note = source = /note="Description of Artificial Sequence:
                        Syntheticpolypeptide"
source                  1..150
                        mol_type = protein
                        organism = synthetic construct
SEQUENCE: 519
MRNNYINLVI ETALNEAEIA LLEGEVPVSC VMKFGNIIIK THNTTNKSCD PLKHCELDAI   60
REYQRFHMSN TNDIIMFITL EPCTMCCRII TDFKERFIKC NLKLFFGVYN DIFGNLKITG   120
NTFGECIYDE RCIEIIKRFY EQQNPNTVNI                                    150

SEQ ID NO: 520          moltype = AA  length = 169
FEATURE                 Location/Qualifiers
REGION                  1..169
                        note = source = /note="Description of Artificial Sequence:
                        Syntheticpolypeptide"
source                  1..169
                        mol_type = protein
                        organism = synthetic construct
SEQUENCE: 520
MYTDQFYMKI ALEEARKASA IGEVPIGAIV VKDNEVISRA HNLRESTQDP TAHAEHIAIQ   60
KAAKQLNSWR LASCKLYVTL EPCVMCSGAI VMSRIPEVIY GAQDLKGGCA GSLMNLLQES   120
RFNHRAKITT GVLAEECSHL LKTFFKDIRQ KKKIIRTEDN TNSETFGKI               169

SEQ ID NO: 521          moltype = AA  length = 169
FEATURE                 Location/Qualifiers
REGION                  1..169
                        note = source = /note="Description of Artificial Sequence:
                        Syntheticpolypeptide"
source                  1..169
                        mol_type = protein
                        organism = synthetic construct
SEQUENCE: 521
MTDEDYMELA LAEAIKAAQL GEVPIGALLV YQDEVVAKAF NLREALQTTA SHAEMLVIDK   60
GNEVINSWRL EDCTLYVTLE PCPMCAGAIL QARIPRVVFG AYDPKAGCAG SILNLLDDKR   120
FNHQVEVTRG VLAEACGHLL KDFFKQLRSR KQEAEVVSLA DYKEENNNG               169

SEQ ID NO: 522          moltype = AA  length = 127
FEATURE                 Location/Qualifiers
REGION                  1..127
                        note = source = /note="Description of Artificial Sequence:
                        Syntheticpolypeptide"
source                  1..127
                        mol_type = protein
                        organism = synthetic construct
SEQUENCE: 522
MAPDLSQHFK FMAVALFVGY KALLKNETPV ACVVTRGCQI ISIGYNHTNI TLNGTKHAEF   60
IALGRLKEPV DYKNLTLYVT VEPCIMCASY LRQLGLKNVI YGCGNDRFGG AGTILPLHND   120
```

```
PKLPHKP                                                                  127

SEQ ID NO: 523          moltype = AA  length = 170
FEATURE                 Location/Qualifiers
REGION                  1..170
                        note = source = /note="Description of Artificial Sequence:
                          Syntheticpolypeptide"
source                  1..170
                        mol_type = protein
                        organism = synthetic construct
SEQUENCE: 523
MVSLSVPLSS HSFPPTLAPS RAKLNDLYAG AQGEEALDVR EIPVGCVLVH EGKIIARGRN   60
RTNEGRNATL HAEFDALRHL LPDRSPSQTP GLVRPYTPQT DDVLAAAGYD SAAGRKVWQT  120
PLKGVVLYVT VEPCLMCASA MRQVGIEKVV YGCANDRFGG NGGVQSIHAE             170

SEQ ID NO: 524          moltype = AA  length = 182
FEATURE                 Location/Qualifiers
REGION                  1..182
                        note = source = /note="Description of Artificial Sequence:
                          Syntheticpolypeptide"
source                  1..182
                        mol_type = protein
                        organism = synthetic construct
SEQUENCE: 524
MTKDLMDSTE LNTMDERSRD EYFMSLAIEE GKKAYALGEI PIGAILVHNN QVISRHHNRR   60
ELDHDATAHA EVLVIREACN SLKRWRLTGC TLYVTIEPCP MCAGAIINSR IDRVVYGASD  120
YKGGAVESLF NVLSHPGLNH EPQLQAGILA DECSQLMKDF FKERRKARRS TQEAEGSALE  180
MR                                                                 182

SEQ ID NO: 525          moltype = AA  length = 147
FEATURE                 Location/Qualifiers
REGION                  1..147
                        note = source = /note="Description of Artificial Sequence:
                          Syntheticpolypeptide"
source                  1..147
                        mol_type = protein
                        organism = synthetic construct
SEQUENCE: 525
MFNKFMAEAI EEAKKALAED EVPVGAVITH RGKIIAAAHN LRETLNRATA HAEILAIEKA   60
CSILNSWYLT DCDLYVTLEP CIMCAGAIVN ARIRSLYFGA FDPKAGACGS VIDVFRLKEL  120
NHRVTVYAGI MEDECASLLT KFFRSKR                                      147

SEQ ID NO: 526          moltype = AA  length = 160
FEATURE                 Location/Qualifiers
REGION                  1..160
                        note = source = /note="Description of Artificial Sequence:
                          Syntheticpolypeptide"
source                  1..160
                        mol_type = protein
                        organism = synthetic construct
SEQUENCE: 526
MTVNTGSMHE TWMRLALEQA ERAGREGEVP IGAVIVKDGA ALAVGRNRRE TDHNALAHAE   60
AEAIRAACAA LGSWRLSGCT LYVTLEPCPM CAGAIINARV DTVVFGAYDP KAGASGSVID  120
LFSCPFNHHP AVMGGVLEED CRRLLQDFFA GLRRPKNDGC                        160

SEQ ID NO: 527          moltype = AA  length = 161
FEATURE                 Location/Qualifiers
REGION                  1..161
                        note = source = /note="Description of Artificial Sequence:
                          Syntheticpolypeptide"
source                  1..161
                        mol_type = protein
                        organism = synthetic construct
SEQUENCE: 527
MNHEIFMQMA IDEAKKAYKI NEVPIGAVVI KHGEVIGRGH NLRESSQNPL MHAEVVAINE   60
ASKNIGSWRL EECVLYVTLE PCVMCSGAIV MSRIPTVVYG AHDAKGGCSG SLMNLLHESR  120
FNHQATVIAG IKHEECSMLL KDFFKSLRNN KLLEKNKKLE E                      161

SEQ ID NO: 528          moltype = AA  length = 160
FEATURE                 Location/Qualifiers
REGION                  1..160
                        note = source = /note="Description of Artificial Sequence:
                          Syntheticpolypeptide"
source                  1..160
                        mol_type = protein
                        organism = synthetic construct
SEQUENCE: 528
MPTLEYQKDD FFFMRQAIQE AKRAMEIDEV PIGAVIVKAD EVIARAHNLR ETLQDATAHA   60
ELLAIRKACE VLGTWRLEGC TLYVTLEPCP MCAGAVILSR VDRLVFGAKD PKGGACGSLM  120
```

```
NLPADERFNH RPKIAAGIMA DECGNILKKF FQDKRMNKKA                          160

SEQ ID NO: 529           moltype = AA   length = 201
FEATURE                  Location/Qualifiers
REGION                   1..201
                         note = source = /note="Description of Artificial Sequence:
                            Syntheticpolypeptide"
source                   1..201
                         mol_type = protein
                         organism = synthetic construct
SEQUENCE: 529
MDEPITEHEI TPAVSENSKH ASWMKQALMM GEQALEHGET PVGCVLVYDN KIVGRGMNDT    60
NRSMNGTRHA EFLAIAEMLQ SYPKSALQST DLYVTVEPCI MCASALRQYG IRSVYFGCAN    120
DRFGGTGGVL NIHSDRSIDP PYPVYGGLFQ KEAIMLLRRF YIQENDKAPK PRPKRNRELN    180
TAFDRVPEIG GANGGNIEQS S                                             201

SEQ ID NO: 530           moltype = AA   length = 184
FEATURE                  Location/Qualifiers
REGION                   1..184
                         note = source = /note="Description of Artificial Sequence:
                            Syntheticpolypeptide"
source                   1..184
                         mol_type = protein
                         organism = synthetic construct
SEQUENCE: 530
MWRGTCGRDK KLTVNKKFME QFMSEAFIEA KSVLEAGEVP VGCIFLYHGD GKNEVIARAG    60
NNVNATKNAT RHAEFLCIDQ TLEFCTRNSL SIKDVFSKIS VVVTVEPCIM CSAALHDLGV    120
KEILYGCAND RFGGKTLVDV PFVTNRRDGQ TQVNGGVCAD EAMALLKDFY KGDNPSAPIT    180
KTKR                                                                184

SEQ ID NO: 531           moltype = AA   length = 155
FEATURE                  Location/Qualifiers
REGION                   1..155
                         note = source = /note="Description of Artificial Sequence:
                            Syntheticpolypeptide"
source                   1..155
                         mol_type = protein
                         organism = synthetic construct
SEQUENCE: 531
MENNDEKFMM KAIEQAKIAY DMDEVPVGCV IVKDGEIIAQ AYNSVEKDKN ATMHAELKAI    60
NQATEFIGNF RLDDCIMYVT LEPCVMCTGA LVYSRIPKVV FGAFDKKRGA CGSLISLNDY    120
EGLNHKIEVK SIMEKECVEL MQSFFRRIRE KNRNK                              155

SEQ ID NO: 532           moltype = AA   length = 97
FEATURE                  Location/Qualifiers
REGION                   1..97
                         note = source = /note="Description of Artificial Sequence:
                            Syntheticpolypeptide"
source                   1..97
                         mol_type = protein
                         organism = synthetic construct
SEQUENCE: 532
MMDLTNEFGF MAIATFVAFR ALKNGETPVA CIFVHEPTHT ILSFGCNDTN GSLNGTMHAE    60
FVAIEKILQG FNLYKKGREE IIEFFMDVTL YVTVEPC                            97

SEQ ID NO: 533           moltype = AA   length = 155
FEATURE                  Location/Qualifiers
REGION                   1..155
                         note = source = /note="Description of Artificial Sequence:
                            Syntheticpolypeptide"
source                   1..155
                         mol_type = protein
                         organism = synthetic construct
SEQUENCE: 533
MSDDIAFMQQ ALELAREAAS LGEVPVGAVA VLDGNVVGTG YNRRECDRNP FAHAEMLALA    60
AAAKARDAWR LSGVTLYVTL EPCAMCAGAL VQSRVTRLVF GTMDPKAGAV GSLYNLVEEP    120
RHNHRLQVTS GILAEDSRQL LKTFFERLRA KRREN                              155

SEQ ID NO: 534           moltype = AA   length = 161
FEATURE                  Location/Qualifiers
REGION                   1..161
                         note = source = /note="Description of Artificial Sequence:
                            Syntheticpolypeptide"
source                   1..161
                         mol_type = protein
                         organism = synthetic construct
SEQUENCE: 534
MVDQMTDEYY MGLALAEAQA AFQIGEVPIG AVIVMDGQVV AAGHNLRETW HDATAHAEII    60
AIRQACERLS RWRLTGATLY VTIEPCPMCA GALIMSRIDR LVYGSSDYKA GAVESIFNIV    120
```

```
QNEALNHQLA VTAGVRAEEC ARIMRDFFRM RRSGEMRSIS E                    161

SEQ ID NO: 535          moltype = AA  length = 159
FEATURE                 Location/Qualifiers
REGION                  1..159
                        note = source = /note="Description of Artificial Sequence:
                         Syntheticpolypeptide"
source                  1..159
                        mol_type = protein
                        organism = synthetic construct
SEQUENCE: 535
MTKDEFYMGK ALEEAKKAAA VGEIPIGAVI VHKKKAVARA HNLRETLPCA TAHAELLAIA  60
EACRVLGRWR LTGCTLYVTV EPCPMCAGAI VNSRLDRVVY GCADTKGGGT RSLYKIVDDE 120
RLNHRAIVTA GIRETECAAL LKDFFRKRRA EEKRKTVSD                       159

SEQ ID NO: 536          moltype = AA  length = 168
FEATURE                 Location/Qualifiers
REGION                  1..168
                        note = source = /note="Description of Artificial Sequence:
                         Syntheticpolypeptide"
source                  1..168
                        mol_type = protein
                        organism = synthetic construct
SEQUENCE: 536
MERHEHYMRL AMQEAKKAEA IGEVPIGCVI VKGDEVIASG YNHRETNRQA TAHAELLAIE  60
AACEKLANWR LEGCELYVTL EPCPMCAGAI MLSRIEHVIF GAVDPKGGCC GTLMNLVQDD 120
RFNHVSQLTG GILEQECGEM LTSFFRELRA KKKQQKRAMG CNATNETV             168

SEQ ID NO: 537          moltype = AA  length = 176
FEATURE                 Location/Qualifiers
REGION                  1..176
                        note = source = /note="Description of Artificial Sequence:
                         Syntheticpolypeptide"
source                  1..176
                        mol_type = protein
                        organism = synthetic construct
SEQUENCE: 537
MHTCIILPNK PTIIKSAVEK DDVWWMGSAI REAEKAAERG EVPIGAVIVR DGKIISRGYN  60
LREGKQDPAA HAELIAIRKA AKKLGNWRLA GTTLYVTLEP CIMCMGAILL ARVEKVVFGC 120
YDPKGGAAGS LYDLSDDKRL NHRVTLVAGI RQAECAALLS GFFAALRAEK KRAKLQ    176

SEQ ID NO: 538          moltype = AA  length = 156
FEATURE                 Location/Qualifiers
REGION                  1..156
                        note = source = /note="Description of Artificial Sequence:
                         Syntheticpolypeptide"
source                  1..156
                        mol_type = protein
                        organism = synthetic construct
SEQUENCE: 538
MEDSTGKHEY FMRQALAEAR KAAEKDEVPI GAVIVYENHI IARAHNQREM LNDPTAHAEM  60
IAITQAAAHL QNWRLTGTTI YVTLEPCAMC AGALVQSRID TLVYGTPDKK AGACASVINL 120
VQEPRFNHRL NVLSNVLADE CKHILQKFFL ENCRTK                          156

SEQ ID NO: 539          moltype = AA  length = 176
FEATURE                 Location/Qualifiers
REGION                  1..176
                        note = source = /note="Description of Artificial Sequence:
                         Syntheticpolypeptide"
source                  1..176
                        mol_type = protein
                        organism = synthetic construct
SEQUENCE: 539
MFSSEEKKHY MELAFAEAEK AEAQDEVPIG AIVVAPDGQV IGRGYNRREL DNIATHHAEI  60
LAINEACKNL NSWRLIDCSL FVTLEPCAMC AGAIINARLK EVFYGAPDHK AGASGSVVDL 120
FAVEKFNHHP QVIRGLYSEK ASNMLTNFFR AIRAKQKEKK LKAKTKENDA SPSQID    176

SEQ ID NO: 540          moltype = AA  length = 172
FEATURE                 Location/Qualifiers
REGION                  1..172
                        note = source = /note="Description of Artificial Sequence:
                         Syntheticpolypeptide"
source                  1..172
                        mol_type = protein
                        organism = synthetic construct
SEQUENCE: 540
MSKGDSDQKY MQQAIQLALQ AQAQGEVPIG ALLVKDDKIV AQAYNLRENN QDATAHAELM  60
VIQAACKQLN SWRLTGCTLY VTLEPCVMCA GALVLSRVER VVYGALDPKA GAVHSLFNIL 120
THPLLNHQIE VQGGVCEAEC RQLLKNFFQQ RRQENKLKKQ MRQNVSLERE VE        172
```

```
SEQ ID NO: 541         moltype = AA  length = 151
FEATURE                Location/Qualifiers
REGION                 1..151
                       note = source = /note="Description of Artificial Sequence:
                       Syntheticpolypeptide"
source                 1..151
                       mol_type = protein
                       organism = synthetic construct
SEQUENCE: 541
MDDFAYMRQA MELAEQAAAL GEIPVGALVV QDATGEVLGR GYNRREVDHD PTAHAEVLAI    60
RQAALAIGSW RLSGCTLYVT LEPCPMCCGT IINARVRRVV FGAYDSKAGS ADSVINLFAL   120
PYNHKPAVTG GLLEDACKEQ LQRFFSGLRE K                                  151

SEQ ID NO: 542         moltype = AA  length = 160
FEATURE                Location/Qualifiers
REGION                 1..160
                       note = source = /note="Description of Artificial Sequence:
                       Syntheticpolypeptide"
source                 1..160
                       mol_type = protein
                       organism = synthetic construct
SEQUENCE: 542
MEDQDHYFME QALAEAKKAE EIGEVPIGAV VVKDGRVIAT AHNLRESKQQ ATAHAEVLAI    60
EQASLETGFW RLDDCALYVT LEPCPMCAGA ILQSRISKLV YGAKDPKAGC VHSLYSLLED   120
PRFNHQVEVI AGVNEEECGE RLTQFFRQLR ANKREKKSES                         160

SEQ ID NO: 543         moltype = AA  length = 180
FEATURE                Location/Qualifiers
REGION                 1..180
                       note = source = /note="Description of Artificial Sequence:
                       Syntheticpolypeptide"
source                 1..180
                       mol_type = protein
                       organism = synthetic construct
SEQUENCE: 543
MVGKKMNITY NDDDYMKEAI EEAKKAGELG EVPIGAVVVL DGKIISRAHN LRESNQNAVA    60
HAELLAIEEA CGMLGTWRLE DAALYVTLEP CAMCSGAIIL SRIKRVVYGA ADPKGGCAGT   120
FMNLLQDERF NHQSEVSAGV LEEECGSLLT DFFRALRERK KEEKRRRKQL LDLQEGIDRP   180

SEQ ID NO: 544         moltype = AA  length = 108
FEATURE                Location/Qualifiers
REGION                 1..108
                       note = source = /note="Description of Artificial Sequence:
                       Syntheticpolypeptide"
source                 1..108
                       mol_type = protein
                       organism = synthetic construct
SEQUENCE: 544
MVGCVFVYQG KIIGRGMNAT NRTLNGTRHA EFMAISHILS PPAYSEDKAY PPTVFHDTDL    60
YVTVEPCIMC ASLLRQFGIR KVYFGASNDK FGGTGGVLNI HADEDIGN               108

SEQ ID NO: 545         moltype = AA  length = 185
FEATURE                Location/Qualifiers
REGION                 1..185
                       note = source = /note="Description of Artificial Sequence:
                       Syntheticpolypeptide"
source                 1..185
                       mol_type = protein
                       organism = synthetic construct
SEQUENCE: 545
MVEAGVTAAS AATAATAASA TSAAAFLPWT EEDARYIRLA LEEAQAAYDI GEVPVGALVV    60
SAKGEILGRG YNRTIIDHDP TAHAEIVALR NAARQLENYR LPGITVYVTL EPCVMCIGAM   120
LHARLARVVF GAYDPKTGAC GSVLDVGAVP KLNHHTSVTG GVLAEPCGDL LRRFFRERRA   180
KESIA                                                               185

SEQ ID NO: 546         moltype = AA  length = 16
FEATURE                Location/Qualifiers
REGION                 1..16
                       note = source = /note="Description of Artificial Sequence:
                       Syntheticpeptide"
source                 1..16
                       mol_type = protein
                       organism = synthetic construct
SEQUENCE: 546
SGSETPGTSE SATPES                                                    16

SEQ ID NO: 547         moltype = AA  length = 1072
FEATURE                Location/Qualifiers
```

```
REGION                  1..1072
                        note = source = /note="Description of Artificial Sequence:
                         Syntheticpolypeptide"
source                  1..1072
                        mol_type = protein
                        organism = synthetic construct
SEQUENCE: 547
MSELDYRIGL AIGTNSIGWG VIELFWNKDR ERYEKVRIVD KGVRMFDKAE IPNKGASLAE    60
PRRIARSSRR RLNRKSQRKK EIRNLLVQHG MITQEELDLL YPLSKKSIDI WDIRLDGLDR   120
LLNHLEWARL LIHLAQRRGF KSNRKSELKD AETGKVLSSI QVNEKRLFLY RTVGEMWIKD   180
AEFSKYDRRR NSPNEYVFSV SRADLEKEIV TLFEAQRKFQ SSYASKNLQE TYLQIWAHQL   240
PFASGNAILN KVGYCSLLKG KERRIPKATY TFQYFSALDQ VNRTRLGPDF QPFTQEQKEI   300
ILDKMFQRTD YYKKKTIPEV SYYDIRKWLE LDETIQFKGL NYDPNEELKK IEKKPFINLK   360
AFYEIKKVVA NYAERTNEAF STLDYDAIAY ALTVYKTDKD IRSYLKKSNN LSKRCYDDQL   420
IEELFTLSYT KFGHLSFKAI NHVLPIMQEG RTYQEAIHQL GYDTTNLKKE NRSMFLPLIP   480
DEITNPIVKR AITQARKVVN AIIRRYGSPN SVHIALAREL SKSHDERKKI MTAHDENYKK   540
NKGAISILIE NGILNPTGYD IVRYKLWKEQ GERCAYSLKE IPPDTFFNEL KKERNGSPIL   600
EVDHILPYSQ SFIDSYHNKV LVYSDENRNK GNRIPYTYFL ETNKDWEAFE RYVRSNKLFS   660
KKKREYLLKK TYLPRESELI KERHLNDTRY ASTFLKNFIE QNLQFKEVEV NLRKKRVQTV   720
NGVITAHLRK RWGLEKNRQE TYLHHAMDAI IVACTDHHMV TRITEYYQIK ESNKSVKKPY   780
FPMPWEGFRD ELLSHLASQP IAKKISEELK AGYQSSDYIF VSRMPKRSVT GAAHDQTIRR   840
KGGIDKKGKT IIIKRVRLKD IKFDENGDFK MVGKEQDLAT YEAIKQRYLE HRKNSKKAFE   900
TPLYKPSKKG TGNLIKRVKI EGQTKAFVRE VNGGVAQNSD LVRVDLFEKD DKYYMVPIYV   960
PDTVCSELPK KVVKSGKGYE QWLTDNSFT FKSSLYPYDL VRLVKGNEDR FLYFGTLDID  1020
SDRLNFKDVN KPSKQNEYRY SLKTIENLEK YEVGVLGDLR LVKQETRRIF NR          1072

SEQ ID NO: 548          moltype = AA   length = 7
FEATURE                 Location/Qualifiers
REGION                  1..7
                        note = source = /note="Description of Artificial Sequence:
                         Syntheticpeptide"
source                  1..7
                        mol_type = protein
                        organism = synthetic construct
SEQUENCE: 548
ENLYFQS                                                                7

SEQ ID NO: 549          moltype = DNA   length = 135
FEATURE                 Location/Qualifiers
misc_feature            1..135
                        note = source = /note="Description of Artificial Sequence:
                         Syntheticpolynucleotide"
source                  1..135
                        mol_type = other DNA
                        organism = synthetic construct
SEQUENCE: 549
aggagcgaag gcatgaaacc atatcgtcat agttccatga aagccaaaag tggctttgat    60
gtttctatga taagggtttc ggcccgtggc gtcgggatc gcctgccat tccgatgggc    120
ttctccccat ttatt                                                    135

SEQ ID NO: 550          moltype = DNA   length = 135
FEATURE                 Location/Qualifiers
misc_feature            1..135
                        note = source = /note="Description of Artificial Sequence:
                         Syntheticpolynucleotide"
source                  1..135
                        mol_type = other DNA
                        organism = synthetic construct
SEQUENCE: 550
acgcacaaac gtcgtatctc cgcacgtcat agttccatga aagccaaaag tggctttgat    60
gtttctatga taagggtttc ggcccgtggc gtcgggatc gcctgccat tccgatgggc    120
ttctccccat ttatt                                                    135

SEQ ID NO: 551          moltype = DNA   length = 135
FEATURE                 Location/Qualifiers
misc_feature            1..135
                        note = source = /note="Description of Artificial Sequence:
                         Syntheticpolynucleotide"
source                  1..135
                        mol_type = other DNA
                        organism = synthetic construct
SEQUENCE: 551
tatctccgca ctcggcccag gcggtgtcat agttccatga aagccaaaag tggctttgat    60
gtttctatga taagggtttc ggcccgtggc gtcgggatc gcctgccat tccgatgggc    120
ttctccccat ttatt                                                    135

SEQ ID NO: 552          moltype = DNA   length = 135
FEATURE                 Location/Qualifiers
misc_feature            1..135
```

```
                        note      source = /note="Description of Artificial Sequence:
                                  Syntheticpolynucleotide"
source                  1..135
                        mol_type = other DNA
                        organism = synthetic construct
SEQUENCE: 552
cagctgtctc agtttatgga ccagagtcat agttccatga aagccaaaag tggctttgat    60
gtttctatga taagggtttc ggcccgtggc gtcggggatc gcctgcccat tccgatgggc   120
ttctccccat ttatt                                                    135

SEQ ID NO: 553          moltype = AA   length = 1071
FEATURE                 Location/Qualifiers
REGION                  1..1071
                        note = source = /note="Description of Artificial Sequence:
                                  Syntheticpolypeptide"
source                  1..1071
                        mol_type = protein
                        organism = synthetic construct
SEQUENCE: 553
MRELDYRIGL AIGTNSIGWG VIELSWNKDR ERYEKVRIVD QGVRMFDRAE MPKTGASLAE    60
PRRIARSSRR RLNRKSQRKK NIRNLLVQHG VITQEELDSL YPLSKKSMDI WGIRLDGLDR   120
LLNHFEWARL LIHLAQRRGF KSNRKSELKD TETGKVLSSI QLNEKRLSLY RTVGEMWMKD   180
PDFSKYDRKR NSPNEYVFSV SRAELEKEIV TLFAAQRRFQ SPYASKDLQE TYLQIWTHQL   240
PPFASGNAILN KVGYCSLLKG KERRIPKATY TFQYFSALDQ VNRTRLGPDF QPFTKEQREI   300
ILNNMFQRTD YYKKKTIPEV TYYDIRKWLE LDETIQFKGL NYDPNEELKK IEKKPFINLK   360
APYEINKVVA NYSERTNETF STLDYDGIGY ALTVYKTDKD IRSYLKSSHN LPKRCYDDQL   420
IEELLSLSYT KFGHLSLKAI NHVLSIMQKG NTYKEAVDQL GYDTSGLKKE KRSKFLPPIS   480
DEITNPIVKR ALTQARKVVN AIIRRHGSPH SVHIELAREL SKNHDERTKI VSAQDENYKK   540
NKGAISILSE HGILNPTGYD IVRYKLWKEQ GERCAYSLKE IPADTFFNEL KKERNGAPIL   600
EVDHILPYSQ SFIDSYHNKV LVYSDENRKK GNRIPYTYPL ETNKDWEAFE RYVRSNKFFS   660
KKKREYLLKR AYLPRESELI KERHLNDTRY ASTFLKNFIE QNLQFKEAED NPRKRRVQTV   720
NGVITAHFRK RWGLEKDRQE TYLHHAMDAI IVACTDHHMV TRVTEYYQIK ESNKSVKKPY   780
FPMPWEGFRD ELLSHLASQP IAKKISEELK AGYQSLDYIF VSRMPKRSIT GAAHKQTIMR   840
KGGIDKKGKT IIIERLHLKD IKFDENGDFK MVGKEQDMAT YEAIKQRYLE HGKNSKKAFE   900
TPLYKPSKKG TGNLIKRVKV EGQAKSFVRE VNGGVAQNGD LVRVDLFEKD DKYYMVPIYV   960
PDTVCSELPK KVVASSKGYE QWLTDNSFT FKFSLYPYDL VRLVKGDEDR FLYFGTLDID   1020
SDRLNFKDVN KPSKKNEYRY SLKTIEDLEK YEVGVLGDLR LVRKETRRNF H           1071

SEQ ID NO: 554          moltype = AA   length = 213
FEATURE                 Location/Qualifiers
REGION                  1..213
                        note = source = /note="Description of Artificial Sequence:
                                  Syntheticpolypeptide"
source                  1..213
                        mol_type = protein
                        organism = synthetic construct
SEQUENCE: 554
MNPQIRNPME GMDRHAFNYN FENEPILYGR SYTWLCYEVK IRKDPSKLPW DTGVFRGQVR    60
PKLQSNRRYE LSNWECRKHV YFQPQYHAEM CFLSWFCGNQ LPAHKRFQIT WFVSWTPCPD   120
CVAKVTEFLA EHPNVTLTIS VARLYYYRGK DWRRALCRLH QAGARVKIMD YEEFAYCWEN   180
FVYNEGQSFM PWDKFDDNYA FLHHKLKEIL RNP                                213

SEQ ID NO: 555          moltype = AA   length = 182
FEATURE                 Location/Qualifiers
REGION                  1..182
                        note = source = /note="Description of Artificial Sequence:
                                  Syntheticpolypeptide"
source                  1..182
                        mol_type = protein
                        organism = synthetic construct
SEQUENCE: 555
MEATYPHIFY FHFKNLRKAY GRNETWLCFT MEIIKQHSTV FWETGVFRNQ VYPESLCHAE    60
RCFLSWFCED ILSPNTDYRV TWYTSWSPCL DCAGEVAEFL ARHSNVKLAI FAARLYYFWD   120
PHYQQGLRSL SEKGASVEIM GYKDFKYCWE NFVYNGDEPF KPWKGLKYNF LFLDSKLQEI   180
LQ                                                                  182

SEQ ID NO: 556          moltype = DNA   length = 130
FEATURE                 Location/Qualifiers
misc_feature            1..130
                        note = source = /note="Description of Artificial Sequence:
                                  Syntheticpolynucleotide"
source                  1..130
                        mol_type = other DNA
                        organism = synthetic construct
SEQUENCE: 556
aggttttaat ggcccagcct gtcatagttc cattaaagcc aaaagtggct ttgatgtttc    60
tatgataagg gtttcgaccc gtggcgtcgg ggatcgcctg cccattgaaa tgggcttctc   120
cccatttatt                                                          130
```

```
SEQ ID NO: 557            moltype = DNA   length = 130
FEATURE                   Location/Qualifiers
misc_feature              1..130
                          note = source = /note="Description of Artificial Sequence:
                          Syntheticpolynucleotide"
source                    1..130
                          mol_type = other DNA
                          organism = synthetic construct
SEQUENCE: 557
catggcagta cattagagca gtcatagttc cattaaagcc aaaagtggct ttgatgtttc    60
tatgataagg gtttcgaccc gtggcgtcgg ggatcgcctg cccattgaaa tgggcttctc   120
cccatttatt                                                          130

SEQ ID NO: 558            moltype = DNA   length = 130
FEATURE                   Location/Qualifiers
misc_feature              1..130
                          note = source = /note="Description of Artificial Sequence:
                          Syntheticpolynucleotide"
source                    1..130
                          mol_type = other DNA
                          organism = synthetic construct
SEQUENCE: 558
cacatctcga gcaagacgtt gtcatagttc cattaaagcc aaaagtggct ttgatgtttc    60
tatgataagg gtttcgaccc gtggcgtcgg ggatcgcctg cccattgaaa tgggcttctc   120
cccatttatt                                                          130

SEQ ID NO: 559            moltype = DNA   length = 130
FEATURE                   Location/Qualifiers
misc_feature              1..130
                          note = source = /note="Description of Artificial Sequence:
                          Syntheticpolynucleotide"
source                    1..130
                          mol_type = other DNA
                          organism = synthetic construct
SEQUENCE: 559
cttctatagc ctccttcccc gtcatagttc cattaaagcc aaaagtggct ttgatgtttc    60
tatgataagg gtttcgaccc gtggcgtcgg ggatcgcctg cccattgaaa tgggcttctc   120
cccatttatt                                                          130

SEQ ID NO: 560            moltype = DNA   length = 130
FEATURE                   Location/Qualifiers
misc_feature              1..130
                          note = source = /note="Description of Artificial Sequence:
                          Syntheticpolynucleotide"
source                    1..130
                          mol_type = other DNA
                          organism = synthetic construct
SEQUENCE: 560
cctgaatgct gtgcggctct gtcatagttc cattaaagcc aaaagtggct ttgatgtttc    60
tatgataagg gtttcgaccc gtggcgtcgg ggatcgcctg cccattgaaa tgggcttctc   120
cccatttatt                                                          130

SEQ ID NO: 561            moltype = DNA   length = 130
FEATURE                   Location/Qualifiers
misc_feature              1..130
                          note = source = /note="Description of Artificial Sequence:
                          Syntheticpolynucleotide"
source                    1..130
                          mol_type = other DNA
                          organism = synthetic construct
SEQUENCE: 561
gccgcacagc attcaggtcg gtcatagttc cattaaagcc aaaagtggct ttgatgtttc    60
tatgataagg gtttcgaccc gtggcgtcgg ggatcgcctg cccattgaaa tgggcttctc   120
cccatttatt                                                          130

SEQ ID NO: 562            moltype = DNA   length = 4923
FEATURE                   Location/Qualifiers
misc_feature              1..4923
                          note = source = /note="Description of Artificial Sequence:
                          Syntheticpolynucleotide"
source                    1..4923
                          mol_type = other DNA
                          organism = synthetic construct
SEQUENCE: 562
gccaccatgg tgtctaaggg cgaggaactg ttcaccggcg tggtgcccat cctggtggaa    60
ctggacgggg atgtgaacgg ccacaagttc agcgtgtccg gcgagggaga gggcgacgcc   120
acatacggca agctgaccct gaaattcatc tgcaccacag gaaagctccc cgtgccttgg   180
cctaccctgt tcaccaccct gacgcatggc gtcaatgttt cagccgctac ccccgaccac   240
atgaaacagc acgacttttt caaaagcgcc atgcctgagg gctacgtgca agagcggacc   300
```

```
atcttcttca aggacgacgg aaattacaag accagagccg aggtgaagtt cgagggcgac  360
accctggtga atagaatcga gctgaagggc atcgacttca aggaagatgg caacatcctg  420
ggccacaagc tggaatacaa ctacaacagc cacaacgtgt acatcatggc cgacaagcag  480
aagaacggca tcaaggtgaa cttcaagatc agacacaaca tcgaggacgg cagcgtgcaa  540
ctggccgatc attaccagca gaacacccct atcggcgatg gtcctgtgct gctgcctgac  600
aaccactacc tgagcaccca gagcgccctg tctaaagatc ctaacgagaa gcgggaccac  660
atggtcctgc tggaattcgt gaccgccgct ggcataacac tcggcatgga cgagctgtac  720
aagtaaggat ccgcaggcct ctgctagctt gactgactga gatacagcgt accttcagct  780
cacagacatg ataagataca ttgatgagtt tggacaaacc acaactagaa tgcagtgaaa  840
aaaatgcttt atttgtgaaa tttgatgatgc tattgcttta tttgtaacca ttataagctg  900
caataaacaa gttaacaaca acaattgcat tcatttatg tttcaggttc aggggaggt    960
gtgggaggtt ttttaaagca agtaaaacct ctacaaatgt ggtattggcc catctctatc  1020
ggtatcgtag cataacccct tggggcctct aaacgggtct tgaggggttt tttgtgcccc  1080
tcgggccgga ttgctatcta ccggcattgg cgcagaaaaa aatgcctgat gcgacgctgc  1140
gcgtcttata ctcccacata tgccagattc agcaacggat acggcttccc caacttgccc  1200
acttccatac gtgtcctcct taccagaaat ttatccttaa ggtcgtcagc tatcctgcag  1260
gcgatctctc gatttcgatc aagacattcc tttaatggtc ttttctgac accactaggg   1320
gtcagaagta gttcatcaaa cttcttccc tcctaatct cattggttac cttgggctat     1380
cgaaacttaa ttaaccagtc aagtcagcta cttggcgaga tcgacttgtc tgggtttcga  1440
ctacgctcag aattgcgtca gtcaagttcg atctggtcct tgctattgca cccgttctcc  1500
gattacgagt ttcatttaaa tcatgtgagc aaaaggccag caaaaggcca ggaaccgtaa  1560
aaaggccgcg ttgctggcgt ttttccatag gctccgcccc cctgacgagc atcacaaaaa  1620
tcgacgctca agtcagaggt ggcgaaaccc gacaggacta taaagatacc aggcgtttcc  1680
ccctggaagc tccctcgtgc gctctcctgt tccgaccctg ccgcttaccg gatacctgtc  1740
cgcctttctc ccttcgggaa gcgtggcgct ttctcatagc tcacgctgta ggtatctcag  1800
ttcggtgtag gtcgttcgct ccaagctggg ctgtgtgcac gaacccccg ttcagcccga   1860
ccgctgcgcc ttatccggta actatcgtct tgagtccaac ccggtaagac acgacttatc  1920
gccactggca gcagccactg gtaacaggat tagcagagcg aggtatgtag gcggtgctac  1980
agagttcttg aagtggtggc ctaactacgg ctacactaga agaacagtat ttggtatctg  2040
cgtctgctcg aagccagtta ccttcggaaa aagagttggt agctcttgat ccggcaaaca  2100
aaccaccgct ggtagcggtg gtttttttgt ttgcaagcag cagattacgc gcagaaaaaa  2160
aggatctcaa gaagatcctt tgatcttttc tacggggtct gacgctcagt ggaacgaaaa  2220
ctcacgttaa gggattttgg tcatgagatt atcaaaagg atcttcacct agatcctttt    2280
aaattaaaaa tgaagtttta aatcaatcta aagtatatat gagtaaactt ggtctgacag  2340
ttaccaatgc ttaatcagtg aggcacctat ctcagcgatc tgtctatttc gttcatccat  2400
agttgcattt aaatttccga actctccaag gccctcgtcg gaaaatcttc aaacctttcg  2460
tccgatccat cttgcaggct acctctcgaa cgaactatcg caagtctctt ggccggcctt  2520
gcgccttggc tattgcttgg cagcgcctat cgccaggtat tactccactc ccgaatatcc  2580
gagatcggga tcacccgaga gaagttcaac ctacatcctc aatcccgatc tatccgagat  2640
ccgaggaata tcgaaatcgg ggcgcgcctg tgtaccgag aacgatcctc tcagtgcgag    2700
tctcgacgat ccatatcgtt gcttggcagt cagccagtcg gaatccagct tgggaccag    2760
gaagtccaat cgtcagatat tgtactcaag cctggtcacg cagcgtacc gatctgttta    2820
aacctagata ttgatagtct gatcggtcaa cgtataatcg agtcctagct tttgcaaaca  2880
tctatcaaga gacaggatca gcaggaggct ttcgcatgag tattcaacat ttccgtgtcg  2940
cccttattcc cttttttgcg gcattttgcc ttcctgtttt tgctcacccca gaaacgctgg  3000
tgaaagtaaa agatgctgaa gatcagttgg gtgcgcgagt gggttacatc gaactggatc  3060
tcaacagcgg taagatcctt gagagttttc gccccgaaga acgcttttcca atgatgagca  3120
cttttaaagt tctgctatgt ggcgcggtat tatcccgtat tgacgccggg caagagcaac  3180
tcggtcgccg catacactat tctcagaatg acttggttga gtattcacca gtcacagaaa  3240
agcatcttac ggatggcatg acagtaagag aattatgcag tgctgccata accatgagtg  3300
ataacactgc ggccaactta cttctgacaa cgattggag accgaaggag ctaaccgctt   3360
ttttgcacaa catgggggat catgtaactc gccttgatcg ttgggaaccg gagctgaatg  3420
aagccatacc aaacgacgag cgtgacacca cgatgcctgt agcaatggca acaaccttgc  3480
gtaaactatt aactggcgaa ctacttactc tagcttcccg gcaacagttg atagactgga  3540
tggaggcgga taaagttgca ggaccacttc tgcgctcggc ccttccggct ggctggttta  3600
ttgctgataa atctggagcc ggtgagcgtg gtctcgcgg tatcattgca cgactggggc     3660
cagatggtaa gccctcccgt atcgtagtta ctacacgac ggggagtcag gcaactatgg    3720
atgaacgaaa tagacagatc gctgagatag gtgcctcact gattaagcat tggtaaccga  3780
ttctaggtgc attggcgcag aaaaaaatgc ctgatgcgac gctgcgcgtc ttatactccc  3840
acatatgcca gattcagcaa cggatacggc ttccccaact tgcccacttc catacgtgtc  3900
ctccttacca gaaatttatc cttaagatcc cgaatcgttt aaactcgact ctggctctat  3960
cgaatctccg tcgtttcgag cttacgcgaa cagccgtggc gctcatttgc tcgtcgggca  4020
tcgaatctcg tcagctatcg tcagcttacc tttttggcag cgatcgcggc tcccgacatc  4080
ttggaccatt agctccacag gtatcttctt ccctctgtta gtcataacga cagctcagcc  4140
tacctctcaa ttcaaaaaac ccctcaagac ccgtttagag ccccaagggg ttatgctat   4200
caatcgttgc gttacacaca caaaaaacca acacacatcc atcttcgatg gatagcgatt  4260
ttattatcta actgctgatc gagtgtagcc agatctagta atcaattacg gggtcattag  4320
ttcatagccc atatatggag ttccgcgtta cataacttac ggtaaatggc ccgcctggct  4380
gaccgcccaa cgacccccgc ccattgacgt caataatgac gtatgttccc atagtaacgc  4440
caatagggac tttccattga cgtcaatggg tggagtattt acggtaaact gcccacttgg  4500
cagtacatca agtgtatcat atgccaagta cgccccctat tgacgtcaat gacggtaaat  4560
ggcccgcctg gcattatgcc cagtacatga ccttatggga ctttcctact ggcagtaca   4620
tctacgtatt agtcatcgct attaccatgc tgatgcggtt ttggcagtac atcaatgggc  4680
gtggatagcg gtttgactca cggggatttc caagtctcca ccccattgac gtcaatggga  4740
gtttgttttg gcaccaaaat caacgggact ttccaaaatg tcgtaacaac tccgccccat  4800
tgacgcaaat gggcggtagg cgtgtacggt gggaggtcta tataagcaga ctgtttag    4860
tgaaccgtca gatcagatct ttgtcgatcc taccatccac tcgacacacc cgccagcggc  4920
cgc                                                                 4923
```

| SEQ ID NO: 563 | moltype = DNA length = 140 |
|---|---|
| FEATURE | Location/Qualifiers |
| misc_feature | 1..140 |
| | note = source = /note="Description of Artificial Sequence: Syntheticpolynucleotide" |
| source | 1..140 |
| | mol_type = other DNA |
| | organism = synthetic construct |

SEQUENCE: 563

```
accctgacgc atggcgtgca atgttgtcat agttccatga aagccaaaag tggctttgat   60
gtttctatga taagggtttc ggcccgtggc gtcgggatcg cctgcccat tccgatgggc   120
ttctccccat ttattttttt                                              140
```

| SEQ ID NO: 564 | moltype = DNA length = 4923 |
|---|---|
| FEATURE | Location/Qualifiers |
| misc_feature | 1..4923 |
| | note = source = /note="Description of Artificial Sequence: Syntheticpolynucleotide" |
| source | 1..4923 |
| | mol_type = other DNA |
| | organism = synthetic construct |

SEQUENCE: 564

```
cgctcatttg ctcgtcgggc atcgaatctc gtcagctatc gtcagcttac cttttttggca  60
gcgatcgcgg ctcccgacat cttggaccat tagctccaca ggtatcttct tccctctagt  120
ggtcataaca gcagcttcag ctacctctca attcaaaaaa cccctcaaga cccgtttaga  180
ggccccaagg ggttatgcta tcaatcgttg cgttacacac aaaaaaaacc aacacacatc  240
catcttcgat ggatagcgat tttattatct aactgctgat cgagtgtagc cagatctagt  300
aatcaattac ggggtcatta gttcatagcc catatatgga gttccgcgtt acataactta  360
cggtaaatgg cccgcctggc tgaccgccca acgaccccg cccattgacg tcaataatga  420
cgtatgttcc catagtaacg ccaataggga ctttccattg acgtcaatgg tggagtatt  480
tacggtaaac tgcccacttg gcagtacatc aagtgtatca tatgccaagt acgccccta  540
ttgacgtcaa tgacggtaaa tggcccgcct ggcattatgc ccagtacatg accttatggg  600
actttcctac ttggcagtac atctacgtat tagtcatcgc tattaccatg ctgatgcggt  660
tttggcagta catcaatggg cgtggatagc ggtttgactc acggggattt ccaagtctcc  720
accccattga cgtcaatggg agtttgtttt ggcaccaaaa tcaacgggac tttccaaaat  780
gtcgtaacaa ctccgcccca ttgacgcaaa tgggcggtag gcgtgtacgg tgggaggtct  840
atataagcag agctggttta gtgaaccgtc agatcagatc tttgtcgatc ctaccatcca  900
ctcgacacac ccgccagcgg ccgcgccacc atggtgtcta agggcgagga actgttcacc  960
ggcgtggtgc ccatcctggt ggaactggac ggggatgtga acggccacaa gttcagcgtg 1020
tccggcgagg gagagggcga cgccacatac ggcaagctga ccctgaaatt catctgcacc 1080
acaggaaagc tccccgtgcc ttgacctacc ctggtcacca ccctgacgta cggcgtgcaa 1140
tgtttcagcc gctaccccga ccacatgaaa cagcacgact ttttcaaaag cgccatgcct 1200
gagggctacg tgcaagagcg gaccatcttc ttcaaggacg acggaaatta caagaccaga 1260
gccgaggtga agttcgaggg cgacaccctg tgaatagaa tcgagctgaa gggcatcgac 1320
ttcaaggaag atggcaacat cctgggccac aagctggaat acaactacaa cagccacaac 1380
gtgtacatca tggccgacaa gcagaagaac ggcatcaagg tgaacttcaa gatcagacac 1440
aacatcgagg acggcagcgt gcaactggcc gatcattacc agcagaacac ccctatcggc 1500
gatggtcctg tgctgctgcc tgacaaccac tacctgagca cccagagcgc cctgtctaaa 1560
gatcctaacg agaagcggga ccacatggtc tgctgtgaat tcgtgaccgc cgctggcata 1620
acactcggca tggacgagct gtacaagtaa ggatccgcag gcctctgcta gcttgactga 1680
ctgagataca gcgtaccttc agctcacaga catgataaga tacattgatg agtttggaca 1740
aaccacaact agaatgcagt gaaaaaaatg ctttatttgt gaaatttgtg atgctattgc 1800
tttatttgta accattataa gctgcaataa acaagttaac aacaacaatt gcattcattt 1860
tatgtttcag gttcaggggg aggtgtggga ggttttttaa agcaagtaaa acctctacaa 1920
atgtggtatt ggcccatctc tatcggtatc gtagcataac ccctgggcc ctctaaacgg 1980
gtcttgaggg gttttttgtg cccctcgggc cggattgcta tctaccggca ttggcgcaga 2040
aaaaaatgcc tgatgcgacg ctgcgcgtct tatactccca catatgccag attcagcaac 2100
ggatacggct tccccaactt gcccacttcc atacgtgtcc tccttaccag aaatttatcc 2160
ttaagctcgt cagctatcct gcaggcgatc tctcgatttc gatcaagaca ttcctttaat 2220
ggtcttttct ggacaccact aggggtcaga agtagttcat caaactttct tccctccta  2280
atctcattgg ttaccttggg ctatcgaaac ttaattaacc agtcaagtca gctacttggc 2340
gagatcgact tgtctgggtt tcgactacgc tcagaattgc gtcagtcaag ttcgatctgg 2400
tccttgctat tgcacccgtt ctccgattac gagtttcatt taaatcatgt gagcaaaagg 2460
ccagcaaaag gccaggaacc gtaaaaaggc cgcgttgctg gcgtttttcc ataggctccg 2520
ccccctgac gagcatcaca aaaatcgacg ctcaagtcag aggtggcgaa acccgacagg 2580
actataaaga taccaggcgt ttccccctgg aagctccctc gtgcgctctc ctgttccgac 2640
cctgccgctt accggatacc tgtccgcctt tctcccttcg ggaagcgtgg cgctttctca 2700
tagctcacgc tgtaggtatc tcagttcggt gtaggtcgtt cgctccaagc tgggctgtgt 2760
gcacgaaccc cccgttcagc ccgaccgctg cgccttatcc ggtaactatc gtcttgagtc 2820
caacccggta agacacgact tatcgccact ggcagcagcc actggtaaca ggattagcag 2880
agcgaggtat gtaggcggtg ctacagagtt cttgaagtgg tggcctaact acggctacac 2940
tagaagaaca gtatttggta tctgcgctct gctgaagcca gttaccttcg gaaaagagt  3000
tggtagctct tgatccggca acaaaccacc gctggtagc ggtggttttt tgtttgcaa  3060
gcagcagatt acgcgcagaa aaaaaggatc tcaagaagat cctttgatct tttctacggg 3120
gtctgacgct cagtggaacg aaaactcacg ttaagggatt ttggtcatga gattatcaaa 3180
aaggatcttc acctagatcc ttttaaatta aaaatgaagt tttaaatcaa tctaaagtat 3240
atatgagtaa acttggtctg acagttacca atgcttaatc agtgaggcac ctatctcagc 3300
gatctgtcta tttcgttcat ccatagttgc atttaaattt ccgaactctc caaggccctc 3360
gtcggaaaat cttcaaacct ttcgtccgat ccatcttgca ggctacctct cgaacgaact 3420
```

```
atcgcaagtc tcttggccgg ccttgcgcct tggctattgc ttggcagcgc ctatcgccag    3480
gtattactcc aatcccgaat atccgagatc gggatcaccc gagagaagtt caacctacat    3540
cctcaatccc gatctatccg agatccgagg aatatcgaaa tcggggcgcg cctggtgtac    3600
cgagaacgat cctctcagtg cgagtctcga cgatccatat cgttgcttgg cagtcagcca    3660
gtcggaatcc agcttgggac ccaggaagtc caatcgtcag atattgtact caagcctggt    3720
cacggcagcg taccgatctg tttaaaccta gatattgata gtctgatcgg tcaacgtata    3780
atcgagtcct agcttttgca aacatctatc aagagacagg atcagcagga ggctttcgca    3840
tgagtattca acatttccgt gtcgccctta ttccctttt tgcggcattt tgccttcctg    3900
tttttgctca cccagaaacg ctggtgaaag taaaagatgc tgaagatcga ttgggtgcgc    3960
gagtgggtta catcgaactg gatctcaaca gcggtaagat ccttgagagt tttcgccccg    4020
aagaacgctt tccaatgatg agcactttta aagttctgct atgtggcgcg gtattatccc    4080
gtattgacgc cgggcaagag caactcggtc gccgcataca ctattctcag aatgacttgg    4140
ttgagtattc accagtcaca gaaaagcatc ttacggatgg catgacagta agagaattat    4200
gcagtgctgc cataaccatg agtgataaca ctgcggccaa cttacttctg acaacgattg    4260
gaggaccgaa ggagctaacc gcttttttgc acaacatggg ggatcatgta actcgccttg    4320
atcgttggga accggagctg aatgaagcca taccaaacga cgagcgtgac accacgatgc    4380
ctgtagcaat ggcaacaacc ttgcgtaaac tattaactgg cgaactactt actctagctt    4440
cccggcaaca gttgatagac tggatggagg cggataaagt tgcaggacca cttctgcgct    4500
cggcccttcc ggctggctgg tttattgctg ataaatctgg agccggtgag cgtgggtctc    4560
gcggtatcat tgcagcactg gggccagatg gtaagccctc ccgtatcgta gttatctaca    4620
cgacggggag tcaggcaact atggatgaac gaaatagaca gatcgctgag ataggtgcct    4680
cactgattaa gcattggtaa ccgattctag gtgcattggc gcagaaaaaa atgcctgatg    4740
cgacgctgcg cgtcttatac tcccacatat gccagattca gcaacggata cggcttcccc    4800
aacttgccca cttccatacg tgtcctcctt accagaaatt tatccttaag atcccgaatc    4860
gtttaaactc gactctggct ctatcgaatc tccgtcgttt cgagcttacg cgaacagccg    4920
tgg                                                                  4923

SEQ ID NO: 565          moltype = DNA   length = 2714
FEATURE                 Location/Qualifiers
misc_feature            1..2714
                        note = source = /note="Description of Artificial Sequence:
                        Syntheticpolynucleotide"
source                  1..2714
                        mol_type = other DNA
                        organism = synthetic construct
SEQUENCE: 565
ctccaataac tgtgatccac cacaagcgcc agggttttcc cagtcacgac gttgtaaaac     60
gacggccagt catgcataat ccgcacgcat ctggaataag gaagtgccat tccgcctgac    120
cttgtacaaa aaagcaggct ttaaaggaac caattcagtc gactggatcc ggtaccaagg    180
tcggcagga agagggccta tttcccatga ttccttcata tttgcatata cgatacaagg    240
ctgttagaga gataattaga attaatttga ctgtaaacac aaagatatta gtacaaaata    300
cgtgacgtag aaagtaataa tttcttgggt agtttgcagt tttaaatta tgttttaaaa    360
tggactatca tatgcttacc gtaacttgaa agtatttcga tttattatct ttatatatct    420
tgtggaaagg acgaaacacc gcccgtgcct tgacctaccc tggtcagtca tagttccatg    480
aaagccaaaa gtggctttga tgtttctatg ataagggttt cggcccgtgg cgtcggggat    540
cgcctgccca ttccgatggg cttctcccca ttattttt tctagaccca gctttcttgt    600
acaaagttgg cattaaggct aggtggaggc tcagtgatga taagtctgcg atggtggatg    660
catgtgtcat ggtcatagct gtttcctgtg tgaaattgtt atccgctcag agggcacaat    720
cctattccgc gctatccgac aatctccaag acattaggtg gagttcagtt cggcgtatgg    780
catatgtcgc tggaagaac atgtgagcaa aaggccagca aaaggccagg aaccgtaaaa    840
aggccgcgtt gctggcgttt ttccatagg ccgcccccc tgacgagcat cacaaaaatc    900
gacgctcaag tcagaggtgg cgaaacccga caggactata agataccag gcgtttcccc    960
ctggaagctc cctcgtgcgc tctcctgttc cgacctgcc gcttaccgga tacctgtccg   1020
cctttctccc ttcgggaagc gtggcgcttt ctcatagctc acgctgtagg tatctcagtt   1080
cggtgtaggt cgttcgctcc aagctgggct gtgtgcacga acccccccgtt cagcccgacc   1140
gctgcgcctt atccggtaac tatcgtcttg agtccaaccc ggtaagacac gacttatcgc   1200
cactggcagc agccactggt aacaggatta gcagagcgag gtatgtaggc ggtgctacag   1260
agttcttgaa gtggtggcct aactacggct acactagaag aacagtattt ggtatctgcg   1320
ctctgctgaa gccagttacc ttcggaaaaa gagttggtag ctcttgatcc ggcaaacaaa   1380
ccaccgctgg tagcggtggt tttttttgtt gcaagcagca gattacgcgc agaaaaaaag   1440
gatctcaaga agatcctttg atcttttcta cggggtctga cgctcattc aacaaagccg   1500
ccgtcccgtc aagtcagcgt aaatgggtag ggggcttcaa atcgtcctcg tgataccaat   1560
tcggagcctg ctttttgta caaacttgtt gataatggca attcaaggat cttcacctag   1620
atccttttaa attaaaaatg aagttttaaa tcaatctaaa gtatatatga gtaaacttgg   1680
tctgacagtt accaatgctt aatcagtgag gcacctatct cagcgatctg tctatttcgt   1740
tcatccatag ttgcctgact ccccgtcgtg tagataacta cgatacggga gggcttacca   1800
tctggcccca gtgctgcaat gataccgcga gagccacgct caccggctcc agatttatca   1860
gcaataaacc agccagccgg aagggccgag cgcagaagtg gtcctgcaac tttatccgcc   1920
tccatccagt ctattaattg ttgccgggaa gctagagtaa gtagttcgcc agttaatagt   1980
ttgcgcaacg ttgttgccat tgctacaggc atcgtggtgt cacgctcgtc gtttggtatg   2040
gcttcattca gctccggttc ccaacgatca aggcgagtta catgatcccc catgttgtgc   2100
aaaaaagcgg ttagctcctt cggtcctccg atcgttgtca gaagtaagtt ggccgcagtg   2160
ttatcactca tggttatggc agcactgcat aattctctta ctgtcatgcc atccgtaaga   2220
tgcttttctg tgactggtga gtactcaacc aagtcattct gagaatagtg tatgcggcga   2280
ccgagttgct cttgcccggc gtcaatacgg gataataccg cgccacatag cagaacttta   2340
aaagtgctca tcattggaaa acgttcttcg gggcgaaaac tctcaaggat cttaccgctg   2400
ttgagatcca gttcgatgta acccactcgt gcacccaact gatcttcagc atcttttact   2460
ttcaccagcg tttctgggtg agcaaaaaca ggaaggcaaa atgccgcaaa aaagggaata   2520
agggcgacac ggaaatgttg aatactcata ctcttccttt ttcaatatta ttgaagcatt   2580
```

-continued

```
tatcagggtt attgtctcat gagcggatac atatttgaat gtatttagaa aaataaacaa   2640
ataggggttc cgcgcacatt tccccgaaaa gtgccagata cctgaaacaa aacccatcgt   2700
acggccaagg aagt                                                     2714

SEQ ID NO: 566          moltype = DNA   length = 663
FEATURE                 Location/Qualifiers
misc_feature            1..663
                        note = source = /note="Description of Artificial Sequence:
                        Syntheticpolynucleotide"
source                  1..663
                        mol_type = other DNA
                        organism = synthetic construct
SEQUENCE: 566
atgggtgaga aaaaaatcac cggatatacc accgttgata tatcccaatg gcatcgtaaa   60
gaacattttg aggcatttca gtcagttgct caatgtacct ataaccagac cgttcagctg   120
gatattacgg ccttttttaaa gaccgtaaag aaaaataagc acaagtttta tccggccttt   180
attcacattc ttgcccgcct gatgaatgct catccggaat tcgtatggc aatgaaagac    240
ggtgagctgg tgatatggga tagtgttcac ccttgttaca ccgttttcca tgagcaaact   300
gaaacgtttt catcgctctg gagtgaatac cacgacgatt tccggcagtt tctacacata   360
tattcgcaag atgtggcgtg ttacggtgaa aacctggcct atttccctaa agggtttatt   420
gagaatatgt ttttcgtctc agccaatccc tgggtgagtt tcaccagttt tgatttaaac   480
gtggccaata tggacaactt cttcgccccc gttttcacca tgggcaaata ttatacgcaa   540
ggcgacaagg tgctgatgcc gctggcgatt caggttcatc gcgccgtttg tgatggcttc   600
catgtcggca gaatgcttaa tgaattacaa cagtactgcg atgagtggca gggcggggcg   660
taa                                                                 663

SEQ ID NO: 567          moltype = DNA   length = 663
FEATURE                 Location/Qualifiers
misc_feature            1..663
                        note = source = /note="Description of Artificial Sequence:
                        Syntheticpolynucleotide"
source                  1..663
                        mol_type = other DNA
                        organism = synthetic construct
SEQUENCE: 567
atgggtgaga aaaaaatcac cggatatacc accgttgata tatcccaatg gcatcgtaaa   60
gaacattttg aggcatttca gtcagttgct caatgtacct ataaccagac cgttcagctg   120
gatattacgg ccttttttaaa gaccgtaaag aaaaataagc acaagtttta tccggccttt   180
attcacattc ttgcccgcct gatgaatgct catccggaat tcgtatggc aatgaaagac    240
ggtgagctgg tgatatggga tagtgttcac ccttgttaca ccgttttcca tgagcaaact   300
gaaacgtttt catcgctctg gagtgaatac cacgacgatt tccggcagtt tctacacata   360
tattcgcaag atgtggcgtg ttacggtgaa aacctggcct atttccctaa agggtttatt   420
gagaatatgt ttttcgtctc agccaatccc tgggtgagtt tcaccagttt tgatttaaac   480
gtggccaata tggacaactt cttcgccccc gttttcacca tgggcaaata ttatacgcaa   540
ggcgacaagg tgctgatgcc gctggcgatt caggttcact cgccgtttg tgatggcttc    600
catgtcggca gaatgcttaa tgaattacaa cagtactgcg atgagtggca gggcggggcg   660
taa                                                                 663

SEQ ID NO: 568          moltype = AA    length = 1368
FEATURE                 Location/Qualifiers
REGION                  1..1368
                        note = source = /note="Description of Artificial Sequence:
                        Syntheticpolypeptide"
source                  1..1368
                        mol_type = protein
                        organism = synthetic construct
SEQUENCE: 568
MDKKYSIGLA IGTNSVGWAV ITDEYKVPSK KFKVLGNTDR HSIKKNLIGA LLFDSGETAE   60
ATRLKRTARR RYTRRKNRIC YLQEIFSNEM AKVDDSFFHR LEESFLVEED KKHERHPIFG   120
NIVDEVAYHE KYPTIYHLRK KLVDSTDKAD LRLIYLALAH MIKFRGHFLI EGDLNPDNSD   180
VDKLFIQLVQ TYNQLFEENP INASGVDAKA ILSARLSKSR RLENLIAQLP GEKKNGLFGN   240
LIALSLGLTP NFKSNFDLAE DAKLQLSKDT YDDDLDNLLA QIGDQYADLF LAAKNLSDAI   300
LLSDILRVNT EITKAPLSAS MIKRYDEHHQ DLTLLKALVR QQLPEKYKEI FFDQSKNGYA   360
GYIDGGASQE EFYKFIKPIL EKMDGTEELL VKLNREDLLR KQRTFDNGSI PHQIHLGELH   420
AILRRQEDFY PFLKDNREKI EKILTFRIPY YVGPLARGNS RFAWMTRKSE ETITPWNFEE   480
VVDKGASAQS FIERMTNFDK NLPNEKVLPK HSLLYEYFTV YNELTKVKYV TEGMRKPAFL   540
SGEQKKAIVD LLFKTNRKVT VKQLKEDYFK KIECFDSVEI SGVEDRFNAS LGTYHDLLKI   600
IKDKDFLDNE ENEDILEDIV LTLTLFEDRE MIEERLKTYA HLFDDKVMKQ LKRRRYTGWG   660
RLSRKLINGI RDKQSGKTIL DFLKSDGFAN RNFMQLIHDD SLTFKEDIQK AQVSGQGDSL   720
HEHIANLAGS PAIKKGILQT VKVVDELVKV MGRHKPENIV IEMARENQTT QKGQKNSRER   780
MKRIEEGIKE LGSQILKEHP VENTQLQNEK LYLYYLQNGR DMYVDQELDI NRLSDYDVDA   840
IVPQSFLKDD SIDNKVLTRS DKNRGKSDNV PSEEVVKKMK NYWRQLLNAK LITQRKFDNL   900
TKAERGGLSE LDKAGFIKRQ LVETRQITKH VAQILDSRMN TKYDENDKLI REVKVITLKS   960
KLVSDFRKDF QFYKVREINN YHHAHDAYLN AVVGTALIKK YPKLESEFVY GDYKVYDVRK   1020
MIAKSEQEIG KATAKYFFYS NIMNFFKTEI TLANGEIRKR PLIETNGETG EIVWDKGRDF   1080
ATVRKVLSMP QVNIVKKTEV QTGGFSKESI LPKRNSDKLI ARKKDWDPKK YGGFDSPTVA   1140
YSVLVVAKVE KGKSKKLKSV KELLGITIME RSSFEKNPID FLEAKGYKEV KKDLIIKLPK   1200
YSLFELENGR KRMLASAGEL QKGNELALPS KYVNFLYLAS HYEKLKGSPE DNEQKQLFVE   1260
QHKHYLDEII EQISEFSKRV ILADANLDKV LSAYNKHRDK PIREQAENII HLFTLTNLGA   1320
```

```
PAAFKYFDTT IDRKRYTSTK EVLDATLIHQ SITGLYETRI DLSQLGGD            1368

SEQ ID NO: 569          moltype = AA  length = 1368
FEATURE                 Location/Qualifiers
REGION                  1..1368
                        note = source = /note="Description of Artificial Sequence:
                          Syntheticpolypeptide"
source                  1..1368
                        mol_type = protein
                        organism = synthetic construct
SEQUENCE: 569
MDKKYSIGLA IGTNSVGWAV ITDEYKVPSK KFKVLGNTDR HSIKKNLIGA LLFDSGETAE  60
ATRLKRTARR RYTRRKNRIC YLQEIFSNEM AKVDDSFFHR LEESFLVEED KKHERHPIFG 120
NIVDEVAYHE KYPTIYHLRK KLVDSTDKAD LRLIYLALAH MIKFRGHFLI EGDLNPDNSD 180
VDKLFIQLVQ TYNQLFEENP INASGVDAKA ILSARLSKSR RLENLIAQLP GEKKNGLFGN 240
LIALSLGLTP NFKSNFDLAE DAKLQLSKDT YDDDLDNLLA QIGDQYADLF LAAKNLSDAI 300
LLSDILRVNT EITKAPLSAS MIKRYDEHHQ DLTLLKALVR QQLPEKYKEI FFDQSKNGYA 360
GYIDGGASQE EFYKFIKPIL EKMDGTEELL VKLNREDLLR KQRTFDNGSI PHQIHLGELH 420
AILRRQEDFY PFLKDNREKI EKILTFRIPY YVGPLARGNS RFAWMTRKSE ETITPWNFEE 480
VVDKGASAQS FIERMTNFDK NLPNEKVLPK HSLLYEYFTV YNELTKVKYV TEGMRKPAFL 540
SGEQKKAIVD LLFKTNRKVT VKQLKEDYFK KIECFDSVEI SGVEDRFNAS LGTYHDLLKI 600
IKDKDFLDNE ENEDILEDIV LTLTLFEDRE MIEERLKTYA HLFDDKVMKQ LKRRRYTGWG 660
RLSRKLINGI RDKQSGKTIL DFLKSDGFAN RNFMQLIHDD SLTFKEDIQK AQVSGQGDSL 720
HEHIANLAGS PAIKKGILQT VKVVDELVKV MGRHKPENIV IEMARENQTT QKGQKNSRER 780
MKRIEEGIKE LGSQILKEHP VENTQLQNEK LYLYYLQNGR DMYVDQELDI NRLSDYDVDH 840
IVPQSFLKDD SIDNKVLTRS DKNRGKSDNV PSEEVVKKMK NYWRQLLNAK LITQRKFDNL 900
TKAERGGLSE LDKAGFIKRQ LVETRQITKH VAQILDSRMN TKYDENDKLI REVKVITLKS 960
KLVSDFRKDF QFYKVREINN YHHAHDAYLN AVVGTALIKK YPKLESEFVY GDYKVYDVRK 1020
MIAKSEQEIG KATAKYFFYS NIMNFFKTEI TLANGEIRKR PLIETNGETG EIVWDKGRDF 1080
ATVRKVLSMP QVNIVKKTEV QTGGFSKESI LPKRNSDKLI ARKKDWDPKK YGGFDSPTVA 1140
YSVLVVAKVE KGKSKKLKSV KELLGITIME RSSFEKNPID FLEAKGYKEV KKDLIIKLPK 1200
YSLFELENGR KRMLASAGEL QKGNELALPS KYVNFLYLAS HYEKLKGSPE DNEQKQLFVE 1260
QHKYLDEII  EQISEFSKRV ILADANLDKV LSAYNKHRDK PIREQAENII HLFTLTNLGA 1320
PAAFKYFDTT IDRKRYTSTK EVLDATLIHQ SITGLYETRI DLSQLGGD            1368

SEQ ID NO: 570          moltype = AA  length = 82
FEATURE                 Location/Qualifiers
REGION                  1..82
                        note = source = /note="Description of Artificial Sequence:
                          Syntheticpolypeptide"
source                  1..82
                        mol_type = protein
                        organism = synthetic construct
SEQUENCE: 570
TNLSDHEKET GKQLVIQESI LMLPEEVEEV IGNKPESDIL VHTAYDESTD ENVMLLTSDA  60
PEYKPWALVI QDSNGENKIK ML                                          82

SEQ ID NO: 571          moltype = AA  length = 199
FEATURE                 Location/Qualifiers
REGION                  1..199
                        note = source = /note="Description of Artificial Sequence:
                          Syntheticpolypeptide"
source                  1..199
                        mol_type = protein
                        organism = synthetic construct
SEQUENCE: 571
MEASPASGPR HLMDPHIFTS NFNNGIGRHK TYLCYEVERL DNGTSVKMDQ HRGFLHNQAK  60
NLLCGFYGRH AELRFLDLVP SLQLDPAQIY RVTWFISWSP CFSWGCAGEV RAFLQENTHV 120
RLRIFAARIY DYDPLYKEAL QMLRDAGAQV SIMTYDEFKH CWDTFVDHQG CPFQPWDGLD 180
EHSQALSGRL RAILQNQGN                                             199

SEQ ID NO: 572          moltype = AA  length = 164
FEATURE                 Location/Qualifiers
REGION                  1..164
                        note = source = /note="Description of Artificial Sequence:
                          Syntheticpolypeptide"
source                  1..164
                        mol_type = protein
                        organism = synthetic construct
SEQUENCE: 572
MKTHEEYMEL ALEEARKAEE IDEVPVGCVI VCDGEVISRG HNLKEQLNQA YAHAEMMAIQ  60
KAAEVKGNWC LNDCDLYVTL EPCMMCTGII NLSRIRTVYY GKQYPTGGCL ETVIDLKKIN 120
RLNHYPNIVG NILQKECSEI LTNYFRKKRE IIKEKKQKNK ANIQ                 164

SEQ ID NO: 573          moltype = AA  length = 154
FEATURE                 Location/Qualifiers
REGION                  1..154
                        note = source = /note="Description of Artificial Sequence:
                          Syntheticpolypeptide"
```

```
source                    1..154
                          mol_type = protein
                          organism = synthetic construct
SEQUENCE: 573
MLEDFMRVAL EEAKKAYKQG EVPVGAVIVK NGKVISKAHN ETRQKKNAVA HAEILAIDKA      60
CKKLENERLV DTEMYVTLEP CAMCAGAILQ ARIPRLLFGA ENPKAGFCGS VLDILQLSAL     120
NHRVELLPPV LREDCKRLMT DFFGRLRAHS DSEE                                 154

SEQ ID NO: 574            moltype = AA   length = 160
FEATURE                   Location/Qualifiers
REGION                    1..160
                          note = source = /note="Description of Artificial Sequence:
                            Syntheticpolypeptide"
source                    1..160
                          mol_type = protein
                          organism = synthetic construct
SEQUENCE: 574
MEQENYMRRA LTLAREAGDA GEVPVGCVIV RDGKVVGEGR NRREELTSAA SHAEMEAIAA      60
ANERLGSWRL EGCALYVTLE PCPMCAGAIL NARVSKVFYG ERSPKFGACG GVTNLFMEDF     120
PNRPALVGGV LAEECREVLR AFFQKLRNDG GTGESPEPKI                            160

SEQ ID NO: 575            moltype = AA   length = 152
FEATURE                   Location/Qualifiers
REGION                    1..152
                          note = source = /note="Description of Artificial Sequence:
                            Syntheticpolypeptide"
source                    1..152
                          mol_type = protein
                          organism = synthetic construct
SEQUENCE: 575
MDRYMTRALE LARLAFDEGE VPVGAVVVKK TTGEIIGEGR NMREGAKNAL AHAEIIAIDQ      60
ACRTLGGWRL PECAIYVTLE PCPMCCGAII NARIDNVIFG KYLLESGSAA SVQKMFELPY     120
NYRPEVTGGI MEQECADILS EFFRQLRIRK KT                                   152

SEQ ID NO: 576            moltype = AA   length = 155
FEATURE                   Location/Qualifiers
REGION                    1..155
                          note = source = /note="Description of Artificial Sequence:
                            Syntheticpolypeptide"
source                    1..155
                          mol_type = protein
                          organism = synthetic construct
SEQUENCE: 576
MENNDEKFMM KAIEQAKIAY DMDEVPVGCV IVKDGEIIAQ AYNSVEKDKN ATMHAELKAI      60
NQATEFIGNF RLDDCIMYVT LEPCVMCTGA LVYSRIPKVV FGAFAKRRGA CGSLISLNDY     120
EGLNHKIEVK SIMEKECVEL MQSFFRRIRE KNRNK                                155

SEQ ID NO: 577            moltype = AA   length = 169
FEATURE                   Location/Qualifiers
REGION                    1..169
                          note = source = /note="Description of Artificial Sequence:
                            Syntheticpolypeptide"
source                    1..169
                          mol_type = protein
                          organism = synthetic construct
SEQUENCE: 577
MTEHEKFMNA ALKLARKAAA EGEVPVGCVV VRDGVIVGRG RNRRETKKDA LGHAEIEAIH      60
KACKKLGGWR LHQCDLYVTL EPCPMCTGAI INARIKTVYY GGPSLRAGSC GSVVNLFDLP     120
YNHKPELVSG LMEQECTEEL QKFFRQLRER KKLEKQLRKQ AQMNDLNEI                 169

SEQ ID NO: 578            moltype = AA   length = 151
FEATURE                   Location/Qualifiers
REGION                    1..151
                          note = source = /note="Description of Artificial Sequence:
                            Syntheticpolypeptide"
source                    1..151
                          mol_type = protein
                          organism = synthetic construct
SEQUENCE: 578
MDDFAYMRQA MELAEQAAAL GEIPVGALVV QDATGEVLGR GYNRREVDHD PTAHAEVLAI      60
RQAALAIGSW RLSGCTLYVT LEPCPMCCGT IINARVRRVV FGAYSSTAGS ADSVINLFAL     120
PYNHKPAVTG GLLEDACKEQ LQRFFSGLRE K                                    151

SEQ ID NO: 579            moltype = AA   length = 169
FEATURE                   Location/Qualifiers
REGION                    1..169
                          note = source = /note="Description of Artificial Sequence:
                            Syntheticpolypeptide"
source                    1..169
```

```
                        mol_type = protein
                        organism = synthetic construct
SEQUENCE: 579
MTEHEKFMNA ALKLARKAAA EGEVPVGCVV VRDGVIVGRG RNRRETKKDA LGHAEIEAIH    60
KACKKLGGWR LHQCDLYVTL EPCPMCTGAI INARIKTVYY GSPQLGAGSC GSVVNLFDLP   120
YNHKPELVSG LMEQECTEEL QKFFRQLRER KKLEKQLRKQ AQMNDLNEI              169

SEQ ID NO: 580          moltype = AA   length = 168
FEATURE                 Location/Qualifiers
REGION                  1..168
                        note = source = /note="Description of Artificial Sequence:
                         Syntheticpolypeptide"
source                  1..168
                        mol_type = protein
                        organism = synthetic construct
SEQUENCE: 580
MEKEEASLQG IHERWMRQAL EEADKAEQLN EVPIGAIIVK DQQIIGRGYN VRETQHQATG    60
HAEIQAIEDA NRHQQAWRLE GATMYVTLEP CPMCAGALIN SRIQTVVYGA SGLKAGCAGT   120
LMNLLQDDRF NHQVEVISGV LAEECGDKLS YFFRKLRQRK GKNIDRAE               168

SEQ ID NO: 581          moltype = AA   length = 158
FEATURE                 Location/Qualifiers
REGION                  1..158
                        note = source = /note="Description of Artificial Sequence:
                         Syntheticpolypeptide"
source                  1..158
                        mol_type = protein
                        organism = synthetic construct
SEQUENCE: 581
MTRDEMYMRK ALELAALAAD EDEVPVGAVV VKKSTGEIVG RGFNRREYGR SPLTHAEIVA    60
IDEASRKLGG WRLIDCELFV TLEPCPMCAG AVINSRVERV VFGQYGKRAG SCGSVVDLFG   120
LPYNHKPECI GGVLEEECAA VLTEFFKGLR KRKVKVNE                          158

SEQ ID NO: 582          moltype = AA   length = 164
FEATURE                 Location/Qualifiers
REGION                  1..164
                        note = source = /note="Description of Artificial Sequence:
                         Syntheticpolypeptide"
source                  1..164
                        mol_type = protein
                        organism = synthetic construct
SEQUENCE: 582
MKTHEEYMEL ALEEARKAEE IDEVPVGCVI VCDGEVISRG HNLKEQLNQA YAHAEMMAIQ    60
KAAEVKGNWC LNDCDLYVTL EPCMMCTGII NLSRIRTVYY GRQWPEGGCL ETVIDLKKIN   120
RLNHYPNIVG NILQKECSEI LTNYFRKKRE IIKEKKQKNK ANIQ                   164

SEQ ID NO: 583          moltype = AA   length = 169
FEATURE                 Location/Qualifiers
REGION                  1..169
                        note = source = /note="Description of Artificial Sequence:
                         Syntheticpolypeptide"
source                  1..169
                        mol_type = protein
                        organism = synthetic construct
SEQUENCE: 583
MTEHEKFMNA ALKLARKAAA EGEVPVGCVV VRDGVIVGRG RNRRETKKDA LGHAEIEAIH    60
KACKKLGGWR LHQCDLYVTL EPCPMCTGAI INARIKTVYY GAPRLSAGSC GSVVNLFDLP   120
YNHKPELVSG LMEQECTEEL QKFFRQLRER KKLEKQLRKQ AQMNDLNEI              169

SEQ ID NO: 584          moltype = AA   length = 168
FEATURE                 Location/Qualifiers
REGION                  1..168
                        note = source = /note="Description of Artificial Sequence:
                         Syntheticpolypeptide"
source                  1..168
                        mol_type = protein
                        organism = synthetic construct
SEQUENCE: 584
MEKEEASLQG IHERWMRQAL EEADKAEQLN EVPIGAIIVK DQQIIGRGYN VRETQHQATG    60
HAEIQAIEDA NRHQQAWRLE GATMYVTLEP CPMCAGALIN SRIQTVVYGF SSLTAGCAGT   120
LMNLLQDDRF NHQVEVISGV LAEECGDKLS YFFRKLRQRK GKNIDRAE               168

SEQ ID NO: 585          moltype = AA   length = 150
FEATURE                 Location/Qualifiers
SITE                    1..150
                        note = /note="This sequence may encompass 1-30 'Gly Gly Gly
                         Gly Ser' repeating units"
REGION                  1..150
                        note = source = /note="Description of Artificial Sequence:
```

```
                        Syntheticpolypeptide"
source                  1..150
                        mol_type = protein
                        organism = synthetic construct
SEQUENCE: 585
GGGGSGGGGS GGGGSGGGGS GGGGSGGGGS GGGGSGGGGS GGGGSGGGGS GGGGSGGGGS    60
GGGGSGGGGS GGGGSGGGGS GGGGSGGGGS GGGGSGGGGS GGGGSGGGGS GGGGSGGGGS   120
GGGGSGGGGS GGGGSGGGGS GGGGSGGGGS                                    150

SEQ ID NO: 586          moltype = AA  length = 30
FEATURE                 Location/Qualifiers
SITE                    1..30
                        note = /note="This sequence may encompass 1-30 residues"
REGION                  1..30
                        note = source = /note="Description of Artificial Sequence:
                        Syntheticpolypeptide"
source                  1..30
                        mol_type = protein
                        organism = synthetic construct
SEQUENCE: 586
GGGGGGGGGG GGGGGGGGGG GGGGGGGGGG                                     30

SEQ ID NO: 587          moltype = AA  length = 150
FEATURE                 Location/Qualifiers
SITE                    1..150
                        note = /note="This sequence may encompass 1-30 'Glu Ala Ala
                        Ala Lys'repeating units"
REGION                  1..150
                        note = source = /note="Description of Artificial Sequence:
                        Syntheticpolypeptide"
source                  1..150
                        mol_type = protein
                        organism = synthetic construct
SEQUENCE: 587
EAAAKEAAAK EAAAKEAAAK EAAAKEAAAK EAAAKEAAAK EAAAKEAAAK EAAAKEAAAK    60
EAAAKEAAAK EAAAKEAAAK EAAAKEAAAK EAAAKEAAAK EAAAKEAAAK EAAAKEAAAK   120
EAAAKEAAAK EAAAKEAAAK EAAAKEAAAK                                    150

SEQ ID NO: 588          moltype = AA  length = 60
FEATURE                 Location/Qualifiers
SITE                    1..60
                        note = /note="This sequence may encompass 1-30 'Xaa
                        Pro'repeating units"
MOD_RES                 1
                        note = Any amino acid
MOD_RES                 3
                        note = Any amino acid
MOD_RES                 5
                        note = Any amino acid
MOD_RES                 7
                        note = Any amino acid
MOD_RES                 9
                        note = Any amino acid
MOD_RES                 11
                        note = Any amino acid
MOD_RES                 13
                        note = Any amino acid
MOD_RES                 15
                        note = Any amino acid
MOD_RES                 17
                        note = Any amino acid
MOD_RES                 19
                        note = Any amino acid
MOD_RES                 21
                        note = Any amino acid
MOD_RES                 23
                        note = Any amino acid
MOD_RES                 25
                        note = Any amino acid
MOD_RES                 27
                        note = Any amino acid
MOD_RES                 29
                        note = Any amino acid
MOD_RES                 31
                        note = Any amino acid
MOD_RES                 33
                        note = Any amino acid
MOD_RES                 35
                        note = Any amino acid
```

```
MOD_RES            37
                   note = Any amino acid
MOD_RES            39
                   note = Any amino acid
MOD_RES            41
                   note = Any amino acid
MOD_RES            43
                   note = Any amino acid
MOD_RES            45
                   note = Any amino acid
MOD_RES            47
                   note = Any amino acid
MOD_RES            49
                   note = Any amino acid
MOD_RES            51
                   note = Any amino acid
MOD_RES            53
                   note = Any amino acid
MOD_RES            55
                   note = Any amino acid
MOD_RES            57
                   note = Any amino acid
MOD_RES            59
                   note = Any amino acid
REGION             1..60
                   note = source = /note="Description of Artificial Sequence:
                    Syntheticpolypeptide"
source             1..60
                   mol_type = protein
                   organism = synthetic construct
SEQUENCE: 588
XPXPXPXPXP XPXPXPXPXP XPXPXPXPXP XPXPXPXPXP XPXPXPXPXP XPXPXPXPXP    60

SEQ ID NO: 589     moltype = AA   length = 36
FEATURE            Location/Qualifiers
MOD_RES            2
                   note = Any amino acid
MOD_RES            4..29
                   note = Any amino acid
SITE               4..29
                   note = /note="This region may encompass 23-26 residues"
MOD_RES            32..35
                   note = Any amino acid
SITE               32..35
                   note = /note="This region may encompass 2-4 residues"
REGION             1..36
                   note = source = /note="Description of Artificial Sequence:
                    Syntheticpolypeptide"
source             1..36
                   mol_type = protein
                   organism = synthetic construct
SEQUENCE: 589
HXEXXXXXXX XXXXXXXXX XXXXXXXXXP CXXXXC                               36

SEQ ID NO: 590     moltype = AA   length = 5
FEATURE            Location/Qualifiers
REGION             1..5
                   note = source = /note="Description of Artificial Sequence:
                    Syntheticpeptide"
source             1..5
                   mol_type = protein
                   organism = synthetic construct
SEQUENCE: 590
GGGGS                                                                 5

SEQ ID NO: 591     moltype = AA   length = 5
FEATURE            Location/Qualifiers
REGION             1..5
                   note = source = /note="Description of Artificial Sequence:
                    Syntheticpeptide"
source             1..5
                   mol_type = protein
                   organism = synthetic construct
SEQUENCE: 591
EAAAK                                                                 5

SEQ ID NO: 592     moltype = AA   length = 80
FEATURE            Location/Qualifiers
SITE               1..80
```

```
                        note = /note="This sequence may encompass 1-20 'Ser Gly Gly
                              Ser'repeating units"
REGION                  1..80
                        note = source = /note="Description of Artificial Sequence:
                              Syntheticpolypeptide"
source                  1..80
                        mol_type = protein
                        organism = synthetic construct
SEQUENCE: 592
SGGSSGGSSG GSSGGSSGGS SGGSSGGSSG GSSGGSSGGS SGGSSGGSSG GSSGGSSGGS    60
SGGSSGGSSG GSSGGSSGGS                                                80

SEQ ID NO: 593          moltype = AA   length = 6
FEATURE                 Location/Qualifiers
REGION                  1..6
                        note = source = /note="Description of Artificial Sequence:
                              Synthetic6xHis tag"
source                  1..6
                        mol_type = protein
                        organism = synthetic construct
SEQUENCE: 593
HHHHHH                                                                6

SEQ ID NO: 594          moltype = AA   length = 10
FEATURE                 Location/Qualifiers
REGION                  1..10
                        note = source = /note="Description of Artificial Sequence:
                              Synthetic10xHis tag"
source                  1..10
                        mol_type = protein
                        organism = synthetic construct
SEQUENCE: 594
HHHHHHHHHH                                                           10

SEQ ID NO: 595          moltype = DNA   length = 41
FEATURE                 Location/Qualifiers
misc_feature            1..41
                        note = source = /note="Description of Artificial Sequence:
                              Syntheticoligonucleotide"
source                  1..41
                        mol_type = other DNA
                        organism = synthetic construct
SEQUENCE: 595
gtctgattgc ctgtcgttgc ccctcccaag gagttggcag a                        41

SEQ ID NO: 596          moltype = DNA   length = 69
FEATURE                 Location/Qualifiers
misc_feature            1..69
                        note = source = /note="Description of Artificial Sequence:
                              Syntheticoligonucleotide"
source                  1..69
                        mol_type = other DNA
                        organism = synthetic construct
SEQUENCE: 596
gtctgattgc ctgtcgttgc ccctaagtgt attaagcatt gtctcagaga ttttggagga    60
gttggcaga                                                            69

SEQ ID NO: 597          moltype = DNA   length = 39
FEATURE                 Location/Qualifiers
misc_feature            1..39
                        note = source = /note="Description of Artificial Sequence:
                              Syntheticoligonucleotide"
source                  1..39
                        mol_type = other DNA
                        organism = synthetic construct
SEQUENCE: 597
gtctgattgc ctgtcgttgc ccctggagga gttggcaga                           39

SEQ ID NO: 598          moltype = DNA   length = 47
FEATURE                 Location/Qualifiers
misc_feature            1..47
                        note = source = /note="Description of Artificial Sequence:
                              Syntheticoligonucleotide"
source                  1..47
                        mol_type = other DNA
                        organism = synthetic construct
SEQUENCE: 598
gtctgattgc ctgtcgttgc ccctcccaga tcggaggagt tggcaga                  47
```

```
SEQ ID NO: 599          moltype = DNA  length = 44
FEATURE                 Location/Qualifiers
misc_feature            1..44
                        note = source = /note="Description of Artificial Sequence:
                        Syntheticoligonucleotide"
source                  1..44
                        mol_type = other DNA
                        organism = synthetic construct
SEQUENCE: 599
gtctgattgc ctgtcgttgc ccctcccaga taggagttgg caga                            44

SEQ ID NO: 600          moltype = DNA  length = 39
FEATURE                 Location/Qualifiers
misc_feature            1..39
                        note = source = /note="Description of Artificial Sequence:
                        Syntheticoligonucleotide"
source                  1..39
                        mol_type = other DNA
                        organism = synthetic construct
SEQUENCE: 600
gtctgattgc ctgtcgttgc ccatctggga gttggcaga                                  39

SEQ ID NO: 601          moltype = DNA  length = 41
FEATURE                 Location/Qualifiers
misc_feature            1..41
                        note = source = /note="Description of Artificial Sequence:
                        Syntheticoligonucleotide"
source                  1..41
                        mol_type = other DNA
                        organism = synthetic construct
SEQUENCE: 601
gtctgattgc ctgtcgttgc ccctctggag gagttggcag a                               41

SEQ ID NO: 602          moltype = DNA  length = 23
FEATURE                 Location/Qualifiers
misc_feature            1..23
                        note = source = /note="Description of Artificial Sequence:
                        Syntheticoligonucleotide"
source                  1..23
                        mol_type = other DNA
                        organism = synthetic construct
SEQUENCE: 602
gtctgattgg aggagttggc aga                                                   23

SEQ ID NO: 603          moltype = DNA  length = 40
FEATURE                 Location/Qualifiers
misc_feature            1..40
                        note = source = /note="Description of Artificial Sequence:
                        Syntheticoligonucleotide"
source                  1..40
                        mol_type = other DNA
                        organism = synthetic construct
SEQUENCE: 603
gtctgattgc ctgtcgttgc ccctcggagg agttggcaga                                 40

SEQ ID NO: 604          moltype = DNA  length = 42
FEATURE                 Location/Qualifiers
misc_feature            1..42
                        note = source = /note="Description of Artificial Sequence:
                        Syntheticoligonucleotide"
source                  1..42
                        mol_type = other DNA
                        organism = synthetic construct
SEQUENCE: 604
gtctgattgc ctgtcgttgc ccctccagga ggagttggca ga                              42

SEQ ID NO: 605          moltype = DNA  length = 34
FEATURE                 Location/Qualifiers
misc_feature            1..34
                        note = source = /note="Description of Artificial Sequence:
                        Syntheticoligonucleotide"
source                  1..34
                        mol_type = other DNA
                        organism = synthetic construct
SEQUENCE: 605
gtctgattgc ctgtcgttgc ccggagttgg caga                                       34

SEQ ID NO: 606          moltype = DNA  length = 42
FEATURE                 Location/Qualifiers
```

-continued

```
misc_feature            1..42
                        note = source = /note="Description of Artificial Sequence:
                        Syntheticoligonucleotide"
source                  1..42
                        mol_type = other DNA
                        organism = synthetic construct
SEQUENCE: 606
gtctgattgc ctgtcgttgc ccatcatgga ggagttggca ga                              42

SEQ ID NO: 607          moltype = DNA   length = 43
FEATURE                 Location/Qualifiers
misc_feature            1..43
                        note = source = /note="Description of Artificial Sequence:
                        Syntheticoligonucleotide"
source                  1..43
                        mol_type = other DNA
                        organism = synthetic construct
SEQUENCE: 607
gtctgattgc ctgtcgttgc ccctccatgg aggagttggc aga                             43

SEQ ID NO: 608          moltype = DNA   length = 33
FEATURE                 Location/Qualifiers
misc_feature            1..33
                        note = source = /note="Description of Artificial Sequence:
                        Syntheticoligonucleotide"
source                  1..33
                        mol_type = other DNA
                        organism = synthetic construct
SEQUENCE: 608
gtctgattgc ctgtcgttgc ccctcccagt act                                        33

SEQ ID NO: 609          moltype = DNA   length = 44
FEATURE                 Location/Qualifiers
misc_feature            1..44
                        note = source = /note="Description of Artificial Sequence:
                        Syntheticoligonucleotide"
source                  1..44
                        mol_type = other DNA
                        organism = synthetic construct
SEQUENCE: 609
gtctgattgc ctgtcgttgc cccaatcttg gaggagttgg caga                            44

SEQ ID NO: 610          moltype = DNA   length = 43
FEATURE                 Location/Qualifiers
misc_feature            1..43
                        note = source = /note="Description of Artificial Sequence:
                        Syntheticoligonucleotide"
source                  1..43
                        mol_type = other DNA
                        organism = synthetic construct
SEQUENCE: 610
gtctgattgc ctgtcgttgc cctgggatgg aggagttggc aga                             43

SEQ ID NO: 611          moltype = DNA   length = 35
FEATURE                 Location/Qualifiers
misc_feature            1..35
                        note = source = /note="Description of Artificial Sequence:
                        Syntheticoligonucleotide"
source                  1..35
                        mol_type = other DNA
                        organism = synthetic construct
SEQUENCE: 611
gtctgattgc ctgtcgttgc ccctcagttg gcaga                                      35

SEQ ID NO: 612          moltype = DNA   length = 42
FEATURE                 Location/Qualifiers
misc_feature            1..42
                        note = source = /note="Description of Artificial Sequence:
                        Syntheticoligonucleotide"
source                  1..42
                        mol_type = other DNA
                        organism = synthetic construct
SEQUENCE: 612
gtctgattgc ctgtcgttgc ccctcatgga ggagttggca ga                              42

SEQ ID NO: 613          moltype = AA    length = 53
FEATURE                 Location/Qualifiers
VARIANT                 1
                        note = /replace="His" or "Cys"
```

| | |
|---|---|
| MOD_RES | 2<br>note = Any amino acid |
| MOD_RES | 4..48<br>note = Any amino acid |
| SITE | 4..48<br>note = /note="This region may encompass 15-45 residues" |
| MOD_RES | 51..52<br>note = Any amino acid |
| SITE | 1..53<br>note = /note="Variant residues given in the sequence have nopreference with respect to those in the annotationsfor variant positions" |
| REGION | 1..53<br>note = source = /note="Description of Artificial Sequence: Syntheticpolypeptide" |
| source | 1..53<br>mol_type = protein<br>organism = synthetic construct |

SEQUENCE: 613
DXEXXXXXXX XXXXXXXXXX XXXXXXXXXX XXXXXXXXXX XXXXXXXXPC XXC         53

| | |
|---|---|
| SEQ ID NO: 614 | moltype = AA length = 4 |
| FEATURE | Location/Qualifiers |
| REGION | 1..4<br>note = source = /note="Description of Artificial Sequence: Syntheticpeptide" |
| source | 1..4<br>mol_type = protein<br>organism = synthetic construct |

SEQUENCE: 614
EEQL                                                              4

| | |
|---|---|
| SEQ ID NO: 615 | moltype = AA length = 6 |
| FEATURE | Location/Qualifiers |
| REGION | 1..6<br>note = source = /note="Description of Artificial Sequence: Syntheticpeptide" |
| source | 1..6<br>mol_type = protein<br>organism = synthetic construct |

SEQUENCE: 615
AEVSQA                                                            6

| | |
|---|---|
| SEQ ID NO: 616 | moltype = AA length = 4 |
| FEATURE | Location/Qualifiers |
| REGION | 1..4<br>note = source = /note="Description of Artificial Sequence: Syntheticpeptide" |
| source | 1..4<br>mol_type = protein<br>organism = synthetic construct |

SEQUENCE: 616
GEQL                                                              4

| | |
|---|---|
| SEQ ID NO: 617 | moltype = AA length = 6 |
| FEATURE | Location/Qualifiers |
| REGION | 1..6<br>note = source = /note="Description of Artificial Sequence: Syntheticpeptide" |
| source | 1..6<br>mol_type = protein<br>organism = synthetic construct |

SEQUENCE: 617
AEVSKA                                                            6

That which is claimed:

1. A fusion protein comprising:
   a) a DNA-binding polypeptide that binds to a target polynucleotide; and
   b) a deaminase polypeptide, wherein said deaminase polypeptide comprises an amino acid sequence having at least 90% sequence identity to SEQ ID NOs: 399 or 420, and wherein said deaminase polypeptide deaminates at least one nucleotide in said target polynucleotide.

2. The fusion protein of claim 1, wherein the DNA-binding polypeptide is a meganuclease, zinc finger fusion protein, or a TALEN.

3. The fusion protein of claim 1, wherein the DNA-binding polypeptide is an RNA-guided nuclease polypeptide.

4. The fusion protein of claim 3, wherein the RNA-guided nuclease polypeptide is a Type II CRISPR-Cas polypeptide.

5. The fusion protein of claim 3, wherein the RNA-guided nuclease polypeptide is a Type V CRISPR-Cas polypeptide.

6. The fusion protein of claim 3, wherein the RNA-guided nuclease polypeptide has nickase activity or is nuclease inactive.

7. A method for modifying a target polynucleotide, said method comprising contacting said target polynucleotide with the fusion protein of claim 6, and introducing one or more guide RNAs (gRNAs) or one or more nucleotide sequences encoding the one or more gRNAs;
wherein the one or more gRNAs hybridize to said target polynucleotide and form a complex with the RNA-guided nuclease polypeptide of the fusion protein, thereby directing said fusion protein to bind to said target polynucleotide sequence and said deaminase polypeptide of the fusion protein deaminates at least one nucleotide in said target polynucleotide, thereby modifying said target polynucleotide.

8. The method of claim 7, wherein the modification of the target polynucleotide comprises a C to T point mutation.

9. The fusion protein of claim 6, wherein the RNA-guided nuclease polypeptide comprises an amino acid sequence having at least 90% sequence identity to any one of SEQ ID NOs: 547, 553, 568, and 569.

10. The fusion protein of claim 3, wherein the RNA-guided nuclease polypeptide has at least 95% sequence identity to SEQ ID NOs: 1, 16, 24, 35, 43, or 50.

11. A system for modifying a target polynucleotide sequence, said system comprising:
a) one or more guide RNAs (gRNAs) capable of hybridizing to said target polynucleotide sequence or one or more nucleotide sequences encoding the one or more gRNAs; and
b) the fusion protein of claim 3 or a nucleotide sequence encoding said fusion protein;
wherein said nucleotide sequences encoding the one or more guide RNAs and encoding the fusion protein are each operably linked to a promoter heterologous to said nucleotide sequence;
wherein the one or more gRNAs hybridize to the target polynucleotide sequence, and
wherein the one or more gRNAs form a complex with the RNA-guided nuclease polypeptide of the fusion protein, thereby directing said fusion protein to bind to and modify said target polynucleotide sequence.

12. The system of claim 11, wherein the one or more gRNAs is a single guide RNA.

13. The system of claim 11, wherein the one or more gRNAs is a dual guide RNA.

14. The system of claim 11, wherein said target polynucleotide sequence is located adjacent to a protospacer adjacent motif (PAM).

15. The system of claim 11, wherein the target polynucleotide sequence is within a cell.

16. The system of claim 15, wherein the cell is a eukaryotic cell.

17. The system of claim 16, wherein the eukaryotic cell is a mammalian cell.

18. The system of claim 15, wherein the cell is a prokaryotic cell.

19. The fusion protein of claim 1, wherein said deaminase polypeptide comprises the amino acid sequence set forth as SEQ ID NO: 399 or 420.

20. The fusion protein of claim 3, wherein the RNA-guided nuclease polypeptide has at least 90% sequence identity to SEQ ID NOs: 1, 16, 24, 35, 43, or 50.

21. The fusion protein of claim 3, wherein said deaminase polypeptide comprises an amino acid sequence having at least 95% sequence identity to SEQ ID NOs: 399 or 420.

22. The fusion protein of claim 17, wherein said deaminase polypeptide comprises the amino acid sequence set forth as SEQ ID NO: 399 or 420.

23. The fusion protein of claim 1, wherein the fusion protein further comprises a uracil glycosylase inhibitor (UGI) polypeptide.

24. The fusion protein of claim 23, wherein the UGI polypeptide comprises an amino acid sequence having at least 85% sequence identity to SEQ ID NO: 570.

25. The fusion protein of claim 1, wherein the fusion protein further comprises a nuclear localization signal (NLS).

26. A method for deaminating a target polynucleotide, said method comprising contacting said target polynucleotide with the fusion protein of claim 1, wherein said deaminase polypeptide deaminates at least one nucleotide in said target polynucleotide.

27. A method for modifying a target polynucleotide, said method comprising contacting said target polynucleotide with the fusion protein of claim 1, wherein said DNA-binding polypeptide binds to said target polynucleotide and said deaminase deaminates at least one nucleotide in said target polynucleotide.

28. The fusion protein of claim 1, wherein said deaminase polypeptide comprises an amino acid sequence having at least 95% sequence identity to SEQ ID NOs: 399 or 420.

* * * * *